United States Patent
Ast et al.

(10) Patent No.: US 12,287,344 B2
(45) Date of Patent: Apr. 29, 2025

(54) FRET-BASED METHOD TO MEASURE SEEDING ACTIVITY OF MISFOLDED PROTEIN SPECIES IN BIOLOGICAL SAMPLES

(71) Applicant: MAX-DELBRÜCK-CENTRUM FÜR MOLEKULARE MEDIZIN IN DER HELMHOLTZ-GEMEINSCHAFT, Berlin (DE)

(72) Inventors: Anne Ast, Berlin (DE); Alexander Buntru, Hamburg (DE); Erich Wanker, Berlin (DE)

(73) Assignee: MAX-DELBRÜCK-CENTRUM FÜR MOLEKULARE MEDIZIN IN DER HELMHOLTZ-GEMEINSCHAFT, Berlin (DE)

( * ) Notice: Subject to any disclaimer, the term of this patent is extended or adjusted under 35 U.S.C. 154(b) by 1055 days.

(21) Appl. No.: 17/266,257

(22) PCT Filed: Aug. 7, 2019

(86) PCT No.: PCT/EP2019/071205
§ 371 (c)(1),
(2) Date: Feb. 5, 2021

(87) PCT Pub. No.: WO2020/030687
PCT Pub. Date: Feb. 13, 2020

(65) Prior Publication Data
US 2021/0302442 A1    Sep. 30, 2021

(30) Foreign Application Priority Data
Aug. 7, 2018 (EP) .................................... 18187782

(51) Int. Cl.
*G01N 33/68* (2006.01)
*C07K 14/47* (2006.01)
*G01N 33/542* (2006.01)

(52) U.S. Cl.
CPC ...... *G01N 33/6896* (2013.01); *C07K 14/4711* (2013.01); *G01N 33/542* (2013.01); *G01N 2500/20* (2013.01); *G01N 2800/2835* (2013.01); *G01N 2800/50* (2013.01)

(58) Field of Classification Search
CPC ............ G01N 33/6896; G01N 33/542; G01N 2500/20; G01N 2800/2835; G01N 2800/50; C07K 14/4711
See application file for complete search history.

(56) References Cited

PUBLICATIONS

Warner (JACS 2017 139:14456-14469). (Year: 2017).*
Arrasate et al., "Inclusion Body Formation Reduces Levels of Mutant Huntingtin and the Risk of Neuronal Death", Nature, vol. 431, No. 7010, Oct. 14, 2004, pp. 805-810.
Atarashi et al., "Ultrasensitive Detection of Scrapie Prion Protein Using Seeded Conversion of Recombinant Prion Protein", Nature Methods, vol. 4, No. 8, Aug. 2007, pp. 645-650.
Atarashi et al., "Ultrasensitive Human Prion Detection in Cerebrospinal Fluid by Real-time Quaking-induced Conversion", Nature Medicine, vol. 17, No. 2, Feb. 2011, pp. 175-178.
Babcock et al., "Transcellular Spreading of Huntingtin Aggregates in the *Drosophila* Brain", Proceedings of the National Academy of Sciences of the United States of America, vol. 112, No. 39, Sep. 29, 2015, pp. E5427-E5433.
Baldo et al., "Maintenance of Basal Levels of Autophagy in Huntington's Disease Mouse Models Displaying Metabolic Dysfunction", PLOS One, vol. 8, No. 12, Dec. 20, 2013, 15 pages.
Bhattacharyya et al., "Oligoproline Effects on Polyglutamine Conformation and Aggregation", Journal of Molecular Biology, vol. 355, No. 3, Jan. 20, 2006, pp. 524-535.
Biancalana et al., "Molecular Mechanism of Thioflavin-T Binding to Amyloid Fibrils", Biochimica et Biophysica Acta, vol. 1804, No. 7, Jul. 2010, pp. 1405-1412.
Brehme et al., "A Chaperome Subnetwork Safeguards Proteostasis in Aging and Neurodegenerative Disease", Cell Reports, vol. 9, No. 3, Nov. 6, 2014, pp. 1135-1150.
Brundin et al., "Prion-like Transmission of Protein Aggregates in Neurodegenerative Diseases", Nature Reviews Molecular Cell Biology, vol. 11, No. 4, Apr. 2010, pp. 301-307.
Carter et al., "Characterization of Progressive Motor Deficits in Mice Transgenic for the Human Huntington's Disease Mutation", Journal of Neuroscience, vol. 19, No. 8, Apr. 15, 1999, pp. 3248-3257.
Castilla et al., "Detection of Prions in Blood", Nature Medicine, vol. 11, No. 9, Sep. 2005, pp. 982-985.
Chan et al., "Mechanisms of Chaperone Suppression of Polyglutamine Disease: Selectivity, Synergy and Modulation of Protein Solubility in *Drosophila*", Human Molecular Genetics, vol. 9, No. 19, Nov. 22, 2000, pp. 2811-2820.
Chiti et al., "Protein Misfolding, Amyloid Formation, and Human Disease: A Summary of Progress Over the Last Decade", Annual Review of Biochemistry, vol. 86, Jun. 20, 2017, pp. 27-68.
Ciamei et al., "Progression of Behavioural Despair in R6/2 and HDH Knock-in Mouse Models Recapitulates Depression in Huntington's Disease", Behavioural Brain Research, vol. 291, Sep. 15, 2015, pp. 140-146.
Cohen et al., "From Macroscopic Measurements to Microscopic Mechanisms of Protein Aggregation", Journal of Molecular Biology, vol. 421, No. 2-3, Aug. 10, 2012, pp. 160-171.

(Continued)

*Primary Examiner* — Changhwa J Cheu
(74) *Attorney, Agent, or Firm* — Kilpatrick Townsend & Stockton LLP

(57) ABSTRACT

The present invention relates to a method for the quantification of seeding ($\Delta t_{50}$) of an amyloidogenic aggregate, methods for assessing the risk for development, predicting the onset or assessing the progression of a polyQ disease, and a method for identifying compounds that inhibit mHTT seeding activity (HSA) in vitro. Further, uses of fluorophore-bearing polyQ proteins, particularly mutant N-terminal huntingtin fragments comprising exon-1 and related soluble protein constructs are provided.

21 Claims, 36 Drawing Sheets

Figure 1:
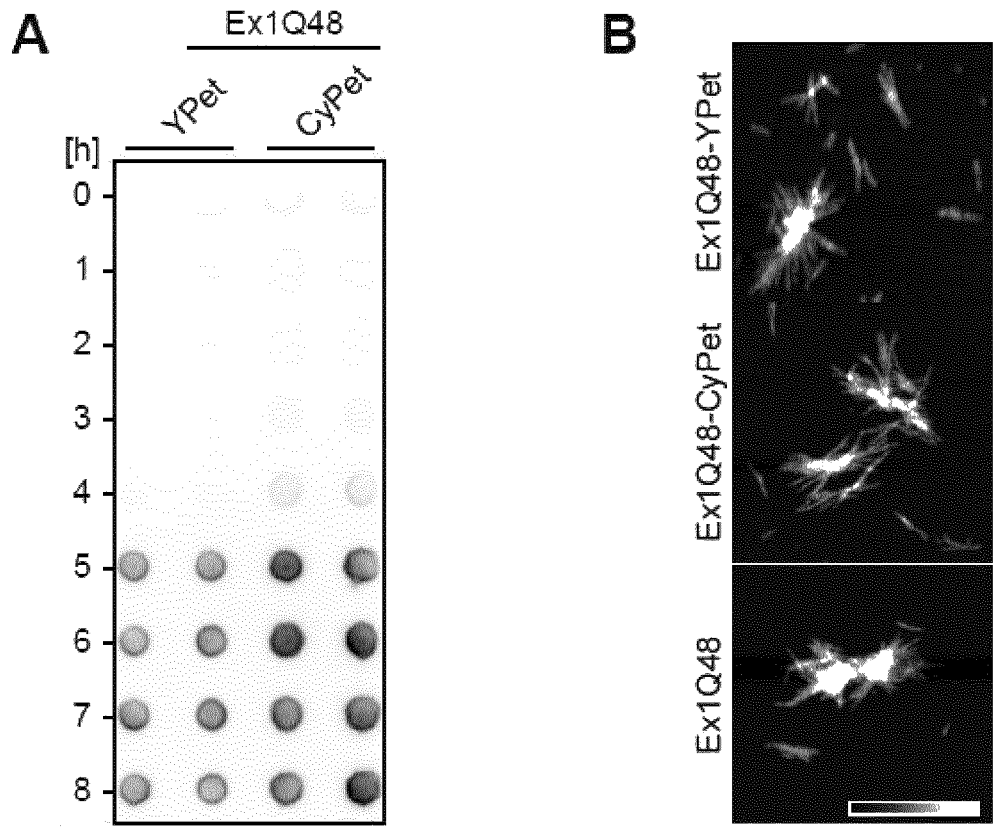
Figure 1:
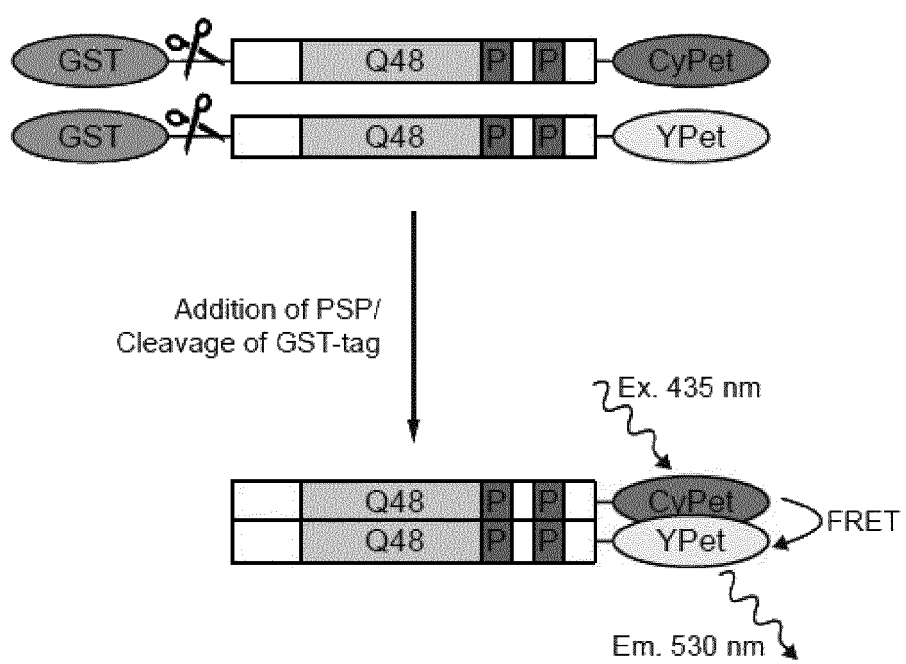
Figure 1:
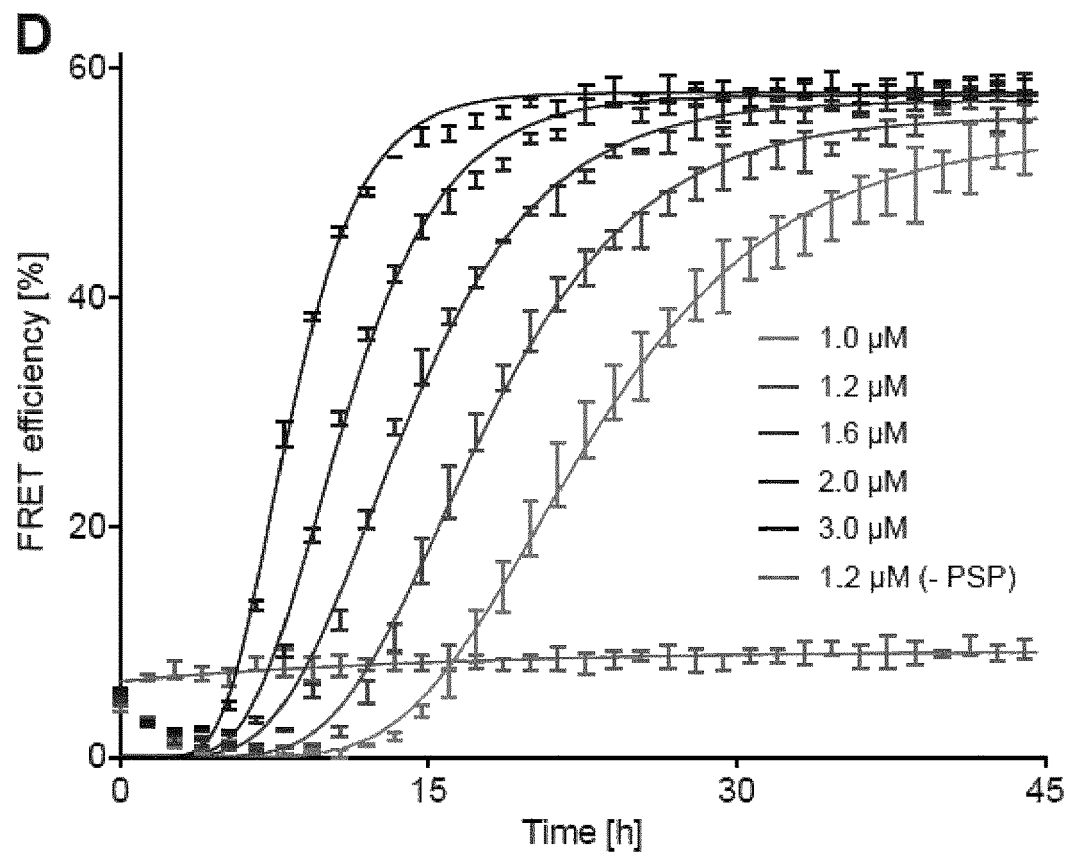
Figure 1:
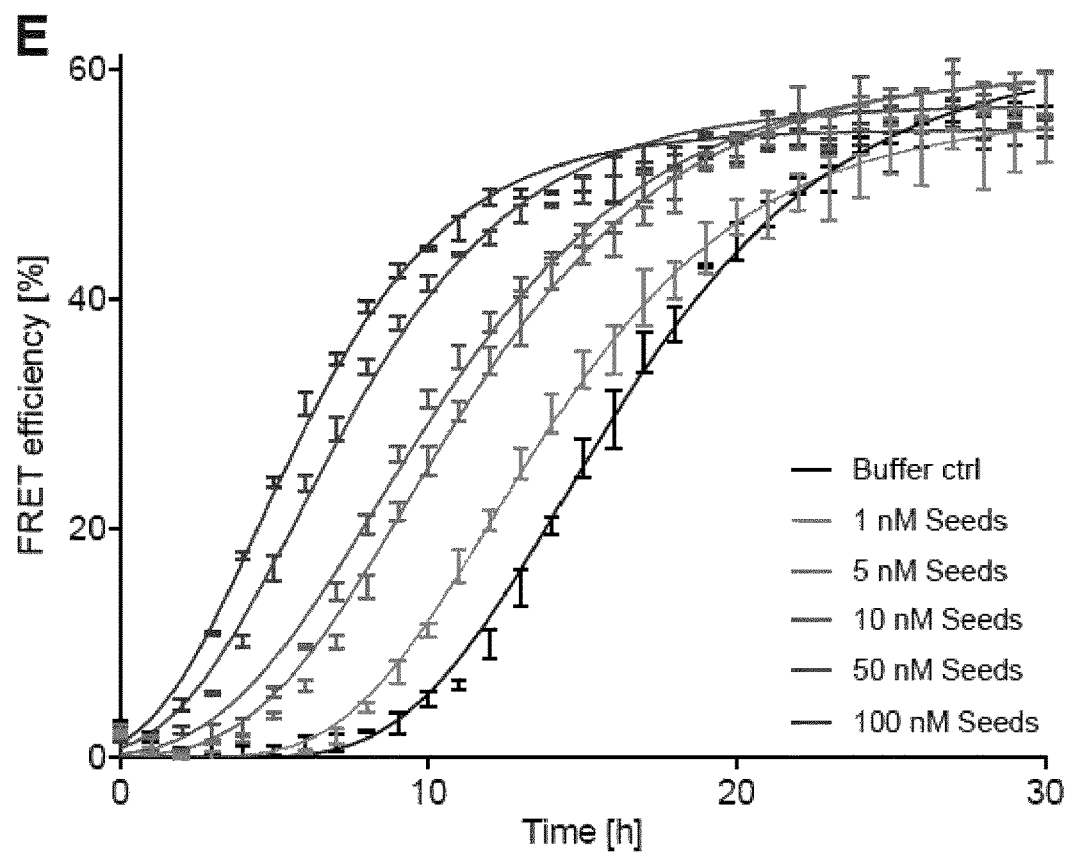
Figure 1:
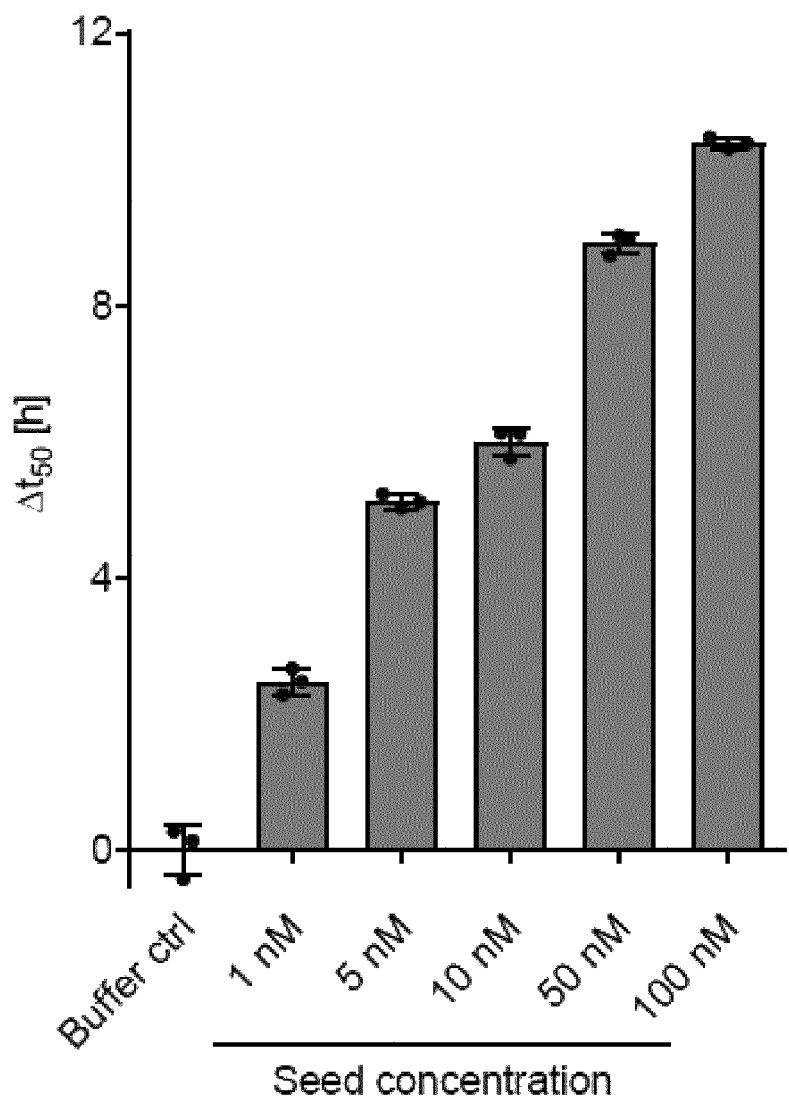

Specification includes a Sequence Listing.

(56) References Cited

PUBLICATIONS

Crick et al., "Unmasking the Roles of N- and C-terminal Flanking Sequences From Exon 1 of Huntingtin as Modulators of Polyglutamine Aggregation", Proceedings of the National Academy of Sciences of the United States of America, vol. 110, No. 50, Dec. 10, 2013, pp. 20075-20080.

Davies et al., "Formation of Neuronal Intranuclear Inclusions Underlies the Neurological Dysfunction in Mice Transgenic for the HD Mutation", Cell, vol. 90, No., 3, Aug. 8, 1997, pp. 537-548.

Difiglia et al., "Aggregation of Huntingtin in Neuronal Intranuclear Inclusions and Dystrophic Neurites in Brain", Science, vol. 277, No. 5334, Sep. 26, 1997, pp. 1990-1993.

Du et al., "A Kinetic Aggregation Assay Allowing Selective and Sensitive Amyloid-beta Quantification in Cells and Tissues", Biochemistry, vol. 50, No. 10, Mar. 15, 2011, pp. 1607-1617.

Gao et al., "Modulation of Human IAPP Fibrillation: Cosolutes, Crowders and Chaperones", Physical Chemistry Chemical Physics, vol. 17, No. 13, Apr. 7, 2015, pp. 8338-8348.

Guo et al., "Cell-to-cell Transmission of Pathogenic Proteins in Neurodegenerative Diseases", Nature Medicine, vol. 20, No. 2, Feb. 2014, pp. 130-138.

Gupta et al., "Protein Misfolding Detected Early in Pathogenesis of Transgenic Mouse Model of Huntington Disease Using Amyloid Seeding Assay", Journal of Biological Chemistry, vol. 287, No. 13, Mar. 23, 2012, pp. 9982-9989.

Herva et al., "Anti-amyloid Compounds Inhibit Alpha-synuclein Aggregation Induced by Protein Misfolding Cyclic Amplification (PMCA)", Journal of Biological Chemistry, vol. 289, No. 17, Apr. 25, 2014, pp. 11897-11905.

Hockly et al., "Standardization and Statistical Approaches to Therapeutic Trials in the R6/2 Mouse", Brain Research Bulletin, vol. 61, No. 5, Sep. 30, 2003, pp. 469-479.

Holmes et al., "Proteopathic Tau Seeding Predicts Tauopathy in Vivo", Proceedings of the National Academy of Sciences of the United States of America, vol. 111, No. 41, Oct. 14, 2014, pp. E4376-E4385.

Hult et al., "Mutant Huntingtin Causes Metabolic Imbalance by Disruption of Hypothalamic Neurocircuits", Cell Metabolism, vol. 13, No. 4, Apr. 6, 2011, pp. 428-439.

Jarrett et al., "Seeding "One-dimensional Crystallization" of Amyloid: A Pathogenic Mechanism in Alzheimer's Disease and Scrapie?", Cell, vol. 73, No. 6, Jun. 18, 1993, pp. 1055-1058.

Jeon et al., "Human-to-mouse Prion-like Propagation of Mutant Huntingtin Protein", Acta Neuropathologica Communications, vol. 132, No. 4, Oct. 2016, pp. 577-592.

Jiang et al., "Coordinated Traffic of Grb2 and Ras During Epidermal Growth Factor Receptor Endocytosis Visualized in Living Cells", Molecular Biology of the Cell, vol. 13, No. 5, May 2002, pp. 1522-1535.

Jucker et al., "Self-propagation of Pathogenic Protein Aggregates in Neurodegenerative Diseases", Nature, vol. 501, Sep. 5, 2013, pp. 45-51.

Kayed et al., "Common Structure of Soluble Amyloid Oligomers Implies Common Mechanism of Pathogenesis", Science, vol. 300, No. 5618, Apr. 18, 2003, pp. 486-489.

Ko et al., "New Anti-huntingtin Monoclonal Antibodies: Implications for Huntingtin Conformation and Its Binding Proteins", Brain Research Bulletin, vol. 56, No. 3-4, Nov. 1, 2001, pp. 319-329.

Kuemmerle et al., "Huntington Aggregates May Not Predict Neuronal Death in Huntington's Disease", Annals of Neurology, vol. 46, No. 6, Dec. 1999, pp. 842-849.

Larson et al., "Age-, Tissue- and Length-dependent Bidirectional Somatic CAG*CTG Repeat Instability in an Allelic Series of R6/2 Huntington Disease Mice", Neurobiology of Disease, vol. 76, Apr. 2015, pp. 98-111.

Latouche et al., "A Conditional Pan-neuronal Drosophila Model of Spinocerebellar Ataxia 7 With a Reversible Adult Phenotype Suitable for Identifying Modifier Genes", Journal of Neuroscience, vol. 27, No. 10, Mar. 7, 2007, pp. 2483-2492.

Laue, "Electron Microscopy of Viruses", Methods in Cell Biology, vol. 96, 2010, pp. 1-20.

Leitman et al., "Soluble Forms of PolyQ-expanded Huntingtin Rather Than Large Aggregates Cause Endoplasmic Reticulum Stress", Nature Communications, vol. 4, No. 1, Nov. 2013, 10 pages.

Levine et al., "Thioflavine T Interaction With Synthetic Alzheimer's Disease Beta-amyloid Peptides: Detection of Amyloid Aggregation in Solution", Protein Science, vol. 2, No. 3, Mar. 1993, pp. 404-410.

Li et al., "Aggregation of N-terminal Huntingtin Is Dependent on the Length of Its Glutamine Repeats", Human Molecular Genetics, vol. 7, No. 5, May 1998, pp. 777-782.

Li et al., "Ultrastructural Localization and Progressive Formation of Neuropil Aggregates in Huntington's Disease Transgenic Mice", Human Molecular Genetics, vol. 8, No. 7, Jul. 1999, pp. 1227-1236.

Lin et al., "Neurological Abnormalities in a Knock-in Mouse Model of Huntington's Disease", Human Molecular Genetics, vol. 10, No. 2, Jan. 15, 2001, pp. 137-144.

Liu et al., "RIM-Binding Protein, a Central Part of the Active Zone, Is Essential for Neurotransmitter Release", Science, vol. 334, No. 6062, Dec. 16, 2011, pp. 1565-1569.

Mangiarini et al., "Exon 1 of the HD Gene With an Expanded CAG Repeat Is Sufficient to Cause a Progressive Neurological Phenotype in Transgenic Mice", Cell, vol. 87, No. 3, Nov. 1, 1996, pp. 493-506.

Mishra et al., "Inhibiting the Nucleation of Amyloid Structure in a Huntingtin Fragment by Targeting α-Helix-Rich Oligomeric Intermediates", Journal of Molecular Biology, vol. 415, No. 5, Feb. 3, 2012, pp. 900-917.

Nguyen et al., "Evolutionary Optimization of Fluorescent Proteins for Intracellular FRET", Nature Biotechnology, vol. 23, No. 3, Mar. 2005, pp. 355-360.

Nucifora et al., "Identification of Novel Potentially Toxic Oligomers Formed in Vitro From Mammalian-derived Expanded Huntingtin Exon-1 Protein", Journal of Biological Chemistry, vol. 287, No. 19, May 4, 2012, pp. 16017-16028.

Osterwalder et al., "A Conditional Tissue-specific Transgene Expression System Using Inducible GAL4", Proceedings of the National Academy of Sciences of the United States of America, vol. 98, No. 22, Oct. 23, 2001, pp. 12596-12601.

Pecho-Vrieseling et al., "Transneuronal Propagation of Mutant Huntingtin Contributes to Non-cell Autonomous Pathology in Neurons", Nature Neuroscience, vol. 17, No. 8, Aug. 2014, pp. 1064-1072.

Pieri et al., "Fibrillar Alpha-synuclein and Huntingtin Exon 1 Assemblies Are Toxic to the Cells", Biophysical Journal, vol. 102, No. 12, Jun. 20, 2012, pp. 2894-2905.

Rosenblatt et al., "Predictors of Neuropathological Severity in 100 Patients With Huntington's Disease", Annals of Neurology, vol. 54, No., 4, Oct. 2003, pp. 488-493.

Ryan et al., "High-Affinity Amphipathic Modulators of Amyloid Firbril Nucleation and Elongation", Journal of Molecular Biology, vol. 406, No. 3, Feb. 25, 2011, pp. 416-429.

Saborio et al., "Sensitive Detection of Pathological Prion Protein by Cyclic Amplification of Protein Misfolding", Nature, vol. 411, No. 6839, Jun. 2001, pp. 810-813.

Sahl et al., "Cellular Inclusion Bodies of Mutant Huntingtin Exon 1 Obscure Small Fibrillar Aggregate Species", Scientific Reports, vol. 2, Article No. 895, 2012, 7 page.

Sathasivam et al., "Aberrant Splicing of HTT Generates the Pathogenic Exon 1 Protein in Huntington Disease", Proceedings of the National Academy of Sciences of the United States of America, vol. 110, No. 6, Feb. 5, 2013, pp. 2366-2370.

Scherzinger et al., "Huntingtin-encoded Polyglutamine Expansions Form Amyloid-like Protein Aggregates in Vitro and in Vivo", Cell, vol. 90, No. 3, Aug. 8, 1997, pp. 549-558.

Scherzinger et al., "Self-assembly of Polyglutamine-containing Huntingtin Fragments Into Amyloid-like Fibrils: Implications for Huntington's Disease Pathology", Proceedings of the National Academy of Sciences of the United States of America, vol. 96, No. 8, Apr. 13, 1999, pp. 4604-4609.

(56) References Cited

PUBLICATIONS

Schindelin et al., "Fiji: An Open-source Platform for Biological-image Analysis", Nature Methods, vol. 9, No. 7, Jun. 28, 2012, pp. 676-882.

Scior et al., "Complete Suppression of HTT Fibrilization and Disaggregation of TTT Fibrils by a Trimeric Chaperone Complex", The EMBO Journal, vol. 37, No. 2, Jan. 17, 2018, pp. 282-299.

Stewart et al., "Improved Stability of *Drosophila* Larval Neuromuscular Preparations in Hemolymph-Like Physiological Solutions", Journal of Comparative Physiology A, vol. 175, No. 2, Aug. 1, 1994, pp. 179-191.

Tan et al., "Huntington's Disease Cerebrospinal Fluid Seeds Aggregation of Mutant Huntingtin", Molecular Psychiatry, vol. 20, No. 11, Nov. 2015, pp. 1286-1293.

Theillet et al., "Structural Disorder of Monomeric Alpha-synuclein Persists in Mammalian Cells", Nature, vol. 530, No. 7588, Feb. 4, 2016, pp. 45-50.

Vonsattel et al., "Neuropathological Classification of Huntington's Disease", Journal of Neuropathology & Experimental Neurology, vol. 44, No. 6, Nov. 1985, pp. 559-577.

Wagner et al., "Self-assembly of Mutant Huntingtin Exon-1 Fragments into Large Complex Fibrillar Structures Involves Nucleated Branching", Journal of Molecular Biology, vol. 430, No. 12, Jun. 8, 2018, pp. 1725-1744.

Wanker et al., "Membrane Filter Assay for Detection of Amyloid-like Polyglutamine-containing Protein Aggregates", Methods in Enzymology, vol. 309, 1999, pp. 375-386.

Warrick et al., "Suppression of Polyglutamine-mediated Neurodegeneration in *Drosophila* by the Molecular Chaperone HSP70", Nature Genetics, vol. 23, No. 4, Dec. 1999, pp. 425-428.

Woodman et al., "The Hdh(Q150/Q150) Knock-in Mouse Model of HD and the R6/2 Exon 1 Model Develop Comparable and Widespread Molecular Phenotypes", Brain Research Bulletin, vol. 72, No. 2-3, Apr. 30, 2007, pp. 83-97.

Zhang et al., "A simple statistical parameter for use in evaluation and validation of high Throughput Screening Assays", Journal of Biomolecular Screening, vol. 4, No. 2, Apr. 1999, pp. 67-73.

Zuccato et al., "Molecular Mechanisms and Potential Therapeutical Targets in Huntington's Disease", Physiological Reviews, vol. 90, No. 3, Jul. 2010, pp. 905-981.

\* cited by examiner

A

B

E

A

D

A

B

A

B

G

GS;HSPA1L;HTTex1Q97 6d-ON

A

B

C

D

E

FRET-BASED METHOD TO MEASURE SEEDING ACTIVITY OF MISFOLDED PROTEIN SPECIES IN BIOLOGICAL SAMPLES

FIELD OF THE INVENTION

The present invention relates to a method for the quantification of seeding activity ($\Delta t_{50}$) of an amyloidogenic aggregate, methods for assessing the risk for development, predicting the onset or assessing the progression of a polyQ disease, and a method for identifying compounds that inhibit mHTT seeding activity (HSA) in vitro. Further, uses of fluorophore-bearing polyQ proteins, particularly mutant N-terminal huntingtin fragments comprising exon-1 and related soluble protein constructs are provided.

BACKGROUND OF THE INVENTION

Self-propagating protein aggregates are a pathological hallmark of a large number of neurodegenerative diseases (NDs) including Huntington's disease (HD) (Chiti and Dobson, 2017; Jucker and Walker, 2013). Recent studies indicate that aggregate pathology and associated tissue atrophy do not appear randomly throughout the brain but instead progress along distinct neuronal networks (Brundin et al., 2010). Evidence was provided that amyloidogenic protein assemblies spread from cell to cell, converting free molecules of the same protein into aggregated species. This transcellular propagation may drive pathogenesis in NDs (Guo and Lee, 2014; Pecho-Vrieseling et al., 2014). To understand the mechanisms of disease development and progression, it is of critical importance to specifically monitor the activity of self-propagating protein aggregates in complex biosamples.

A number of assays have been established that allow the quantification of seeding activity of amyloidogenic aggregates in crude protein homogenates (Atarashi et al., 2007; Holmes et al., 2014; Tan et al., 2015). These methods take advantage of the phenomenon that ordered protein aggregates are formed from monomers by a nucleation-dependent process (Jarrett and Lansbury, 1993; Scherzinger et al., 1999), a relatively slow process in vitro. However, spontaneous amyloid formation can be accelerated by addition of preformed aggregates that function as seeds for the conversion of monomers from a soluble into an aggregated state (Cohen et al., 2012; Jarrett and Lansbury, 1993). Biosamples that contain seeding-competent protein aggregates might therefore stimulate the polymerization of soluble amyloidogenic proteins with related amino acid sequences in cell-free or cell-based seeding assays.

Based on this premise, the protein misfolding cyclic amplification (PMCA) technology and related methods (Atarashi et al., 2007; Atarashi et al., 2011; Saborio et al., 2001) have been developed, which allow the detection of minute quantities of seeding-competent PrP$^{Sc}$ aggregates in various biomaterials prepared from patients or rodent models with prion disease (Castilla et al., 2005). Variants of the PMCA technology have also been applied for the amplification of amyloid-β and α-synuclein aggregates from biosamples (Du et al., 2011; Herva et al., 2014). A key feature of PMCA methods is that seed-mediated amyloid polymerization is indirectly monitored through the reporter dye Thioflavin T (ThT), which changes its fluorescence emission upon binding to ordered amyloid fibrils (Biancalana and Koide, 2010). Also cell-based amyloid polymerization assays have been developed (Holmes et al., 2014; Tan et al., 2015). In these assays, ectopically expressed aggregation-prone reporter proteins with fluorescent tags are utilized as biosensors for detecting amyloidogenic aggregates.

Recent studies with brain slices, fly and mouse models provide evidence that mHTT aggregates with pathogenic polyQ tracts indeed possess seeding activity and spread from cell to cell (Pecho-Vrieseling et al., 2014; Babcock and Ganetzky, 2015; Pearce et al., 2015), suggesting that proteopathic mHTT seeding in HD patient brains or mouse models drives pathogenesis (Brundin et al., 2010; Jeon et al., 2016). Several mHTT aggregate species, i.e. small oligomers and fibrils, have been described as potentially pathogenic (Nucifora et al., 2012; Pieri et al., 2012; Scherzinger et al., 1997).

To be regarded as disease relevant, the inventors propose that seeding-competent aggregates, e.g. mHTT aggregates, need to be detectable in affected brain regions in patients and transgenic HD models, e.g. mouse models. To promote disease development, such structures should be present in model systems prior to the appearance of a disease phenotype. Also, their abundance in affected tissues should increase with the severity of disease symptoms. Finally, perturbation of seeding activity through genetic manipulation should influence the disease phenotype in model systems. In summary, to elucidate the potential importance of seeding in disease, it is crucial to detect seeding-competent structures in relevant biosamples, and to investigate their potential impact on biological functions and phenotypes.

BRIEF SUMMARY OF THE INVENTION

The present inventors surprisingly found that quantification of seeding activity of amyloidogenic proteins like mHTT is possible with high sensitivity and specificity even in complex biosamples with FRET-based assay.

Accordingly, the present invention provides methods involving FRET-based determination of seeding activity ($\Delta t_{50}$) in a variety of biological samples.

In a first aspect, a method for the quantification of seeding activity ($\Delta t_{50}$) of an amyloidogenic aggregate is provided, which comprises the steps of:
(i) providing, in a solution, a mixture of an amyloidogenic protein A which is N-terminally or C-terminally fused to a donor fluorophore molecule, e.g. a cyan fluorescent protein (CFP), and an amyloidogenic protein B which is N-terminally or C-terminally fused to an acceptor fluorophore molecule, e.g. a yellow fluorescent protein (YFP), wherein the amyloidogenic proteins A and B are preferably identical and wherein the donor fluorophore molecule and the acceptor fluorophore molecule are capable of Förster Resonance Energy Transfer (FRET) if they are in close proximity to each other;
(ii) adding a sample containing an amyloidogenic protein aggregate C to the mixture of step (i), wherein the amyloidogenic protein aggregate C preferably comprises or consists of amyloidogenic proteins A and/or B;
(iii) shaking the mixture of step (ii);
(iv) measuring fluorescence signals in the donor, e.g. cyan, channel, the acceptor, e.g. yellow, channel and the Förster Resonance Energy Transfer (FRET) channel at predetermined intervals after completion of step (iii);
(v) calculating FRET efficiency (E) from the signals obtained in step (iv); and
(vi) quantifying seeding activity ($\Delta t_{50}$) by subtracting the time at half-maximal FRET efficiency of a sample ($t_{50}$(S)) from the time at half-maximal FRET efficiency of a negative control ($t_{50}$(0)).

In a further aspect, a method for assessing the risk for development of a polyglutamine (polyQ) disease in a subject is provided, which comprises the steps of:
(i) quantification of seeding activity ($\Delta t_{50}$) of a polyQ-containing protein in a sample;
(ii) correlating that the subject is at risk for development of the polyQ disease when the seeding activity in the sample is increased as compared to a reference sample.

In a further aspect, a method for predicting the onset of a polyglutamine (polyQ) disease in a subject is provided, which comprises the steps of:
(i) quantification of seeding activity ($\Delta t_{50}$) of a polyQ-containing protein in a sample;
(ii) correlating that the onset of the polyQ disease has occurred or will occur soon when the seeding activity in the sample is increased as compared to a reference sample.

In a further aspect, a method for assessing the progression of a polyglutamine (polyQ) disease in a subject is provided, which comprises the steps of:
(i) quantification of seeding activity ($\Delta t_{50}$) of a polyQ-containing protein in a sample collected at a timepoint $t_1$;
(ii) quantification of seeding activity ($\Delta t_{50}$) of a polyQ-containing protein in a sample collected at a timepoint $t_2$, wherein $t_2$ is later than $t_1$, comprising the steps (a) to (f) as defined in (i); and
(iii) correlating that the polyQ disease has progressed when the seeding activity in the sample taken at $t_2$ is increased as compared to the sample taken at $t_1$.

In yet a further aspect, a method for identifying compounds that inhibit mHTT seeding activity (HSA) in vitro is provided, which comprises the steps of:
(i) determining HSA in a test sample;
(ii) determining HSA in a control sample without the compound or mixture of compounds to be tested for inhibiting HSA in vitro; and
(iii) selecting compounds or mixtures of compounds which show decreased seeding activity as compared to control samples.

In yet a further aspect, the use of soluble glutathione S-transferase HTT exon-1 fusion proteins in an aggregation assay is provided, wherein a first fusion protein comprises from about 35 to about 75, particularly about 40 to about 55, e.g. 40 or 48 or 49 glutamine residues which is C-terminally fused to a donor fluorophore molecule, e.g. a CFP such as CyPet, and a second fusion protein comprises from about 35 to about 75, particularly about 40 to about 55, e.g. 40 or 48 or 49 glutamine residues which is C-terminally fused to an acceptor fluorophore molecule, e.g. a YFP such as YPet.

Likewise, the use of soluble HTT exon-1 fusion proteins in an aggregation assay is provided, wherein a first fusion protein comprises from about 35 to about 75, particularly about 40 to about 55, e.g. 40 or 48 or 49 glutamine residues which is C-terminally fused to a donor fluorophore molecule, e.g. a CFP such as CyPet, and a second fusion protein comprises from about 35 to about 75, particularly about 40 to about 55, e.g. 40 or 48 or 49 glutamine residues which is C-terminally fused to an acceptor fluorophore molecule, e.g. a YFP such as YPet.

In a further aspect, a soluble protein is provided, which comprises, from N- to C-terminus: (i) optionally glutathione S-transferase (GST), particularly of SEQ ID NO.: 6; (ii) exon 1 of huntingtin with 48 glutamine residues (HTTEx1Q48), particularly of SEQ ID NO.: 2; and (iii) CyPet, particularly of SEQ ID NO.: 23, or YPet, particularly of SEQ ID NO.: 21.

DETAILED DESCRIPTION OF THE INVENTION

There is increasing experimental evidence that self-propagating aggregates, or seeds, of proteins like mHTT, play an important role in model organisms, e.g. HD model organisms (Babcock and Ganetzky, 2015; Pecho-Vrieseling et al., 2014.

The fluorescent dye Thioflavin T (ThT) is currently utilized in a large number of cell-free assays as a reporter molecule to monitor the seeding activity of amyloidogenic protein aggregates (Gupta et al., 2012). ThT exhibits enhanced fluorescence when it is bound to β-sheet-rich amyloid structures (LeVine, 1993). However, its binding to such structures is significantly decreased, when competing proteins are present in complex amyloid polymerization reactions (Biancalana and Koide, 2010). Therefore, previously established ThT-based seeding assays are relatively insensitive when complex biosamples such as brain homogenates are analyzed (Gupta et al., 2012).

To overcome these limitations, the present inventors have developed a sensitive FRET-based biosensor assay, which in the context of HD has been termed FRET-based mHTT aggregate seeding (FRASE) assay, which does not require ThT reporter molecules for the quantification of HSA in biosamples. Two fluorescently tagged aggregation-prone fusion proteins are used as reporter molecules to monitor seeding activity. This assay is highly robust and affected by contaminating proteins in complex biosamples only to a very small extent. Therefore, the assay can be employed without the need for upstream purification of seeds, which would complicate the protocol and decrease accuracy of quantification.

For example, the present inventors surprisingly found that the FRASE assay enables the quantification of mHTT seeding activity (HSA) in complex biosamples.

Accordingly, the present invention provides a method for the quantification of seeding activity ($\Delta t_{50}$) of an amyloidogenic aggregate, comprising the steps of:
(i) providing, in a solution, a mixture of an amyloidogenic protein A which is N-terminally or C-terminally fused to a donor fluorophore molecule, e.g. a cyan fluorescent protein (CFP), and an amyloidogenic protein B which is N-terminally or C-terminally fused to an acceptor fluorophore molecule, e.g. a yellow fluorescent protein (YFP), wherein the amyloidogenic proteins A and B are preferably identical and wherein the donor fluorophore molecule and the acceptor fluorophore molecule are capable of Förster Resonance Energy Transfer (FRET) if they are in close proximity to each other;
(ii) adding a sample containing an amyloidogenic protein aggregate C to the mixture of step (i), wherein the amyloidogenic protein aggregate C preferably comprises or consists of amyloidogenic proteins A and/or B;
(iii) shaking the mixture of step (ii);
(iv) measuring fluorescence signals in the donor, e.g. cyan, channel, the acceptor, e.g. yellow, channel and the Förster Resonance Energy Transfer (FRET) channel at predetermined intervals after completion of step (iii);
(v) calculating FRET efficiency (E) from the signals obtained in step (iv); and (vi) quantifying seeding activity ($\Delta t_{50}$) by subtracting the time at half-maximal FRET efficiency of a sample ($t_{50}(S)$) from the time at half-maximal FRET efficiency of a negative control ($t_{50}(0)$).

Amyloidogenic proteins are proteins that undergo non-native cross-β-assembly to form linear polymers (fibrils), which is a central feature of diseases of toxic misfolding. In the context of the present invention, an amyloidogenic protein is a protein which can, in vivo or in vitro, self-assemble into amyloid fibrils. A particular group of amyloidogenic proteins, from which proteins A and B may be selected from, are wild-type or mutant forms of the group consisting of proteins comprising repeats of at least 15 consecutive glutamine residues in their amino acid sequence, and amyloidogenic fragments thereof. These proteins are also referred to as polyQ proteins.

Specific examples of polyQ proteins according to the invention are wild-type or mutant forms of the group consisting of huntingtin (HTT), androgen receptor (AR), atrophin 1 (ATN1), ataxin 1 (ATXN1), ataxin 2 (ATXN1), ataxin 3 (ATXN1), ataxin 7 (ATXN1), TATA-box binding protein (TBP), $\alpha_{1A}$-voltage dependent calcium channel subunit (CACNA1A), and polyglutamine repeat containing fragments thereof. An exemplary polyQ containing fragment of HTT is exon 1.

A "mutant form" in the context of the invention is particularly a protein that contains at least one, e.g. from 1 to 100 such as from 1 to 20, insertions, deletions (such as a truncation) or substitutions of amino acids in its primary sequence that increase its amyloidogenic properties, e.g. leads to facilitated amyloid formation. In particular, mutant forms of amyloidogenic proteins, such as polyQ proteins, are characterized by an increased number of glutamine residues as compared to the corresponding wild-type form, i.e. additional glutamine residues are inserted into the wild-type sequence. The number of glutamine residues may be increased by e.g. 5-75 glutamines.

In another embodiment, mutant forms of amyloidogenic proteins, such as polyQ proteins, are characterized by an increased number of glutamine residues and proline residues as compared to the corresponding wild-type form, i.e. additional glutamine and proline residues are inserted into the wild-type sequence. The number of glutamine residues may be increased by e.g. 5-75 glutamines. The number of proline residues may be increased by e.g. 1-20 prolines. Additionally, these mutant forms may optionally have 1-75 deletions (such as a truncation) of amino acids in their primary sequence that increase the amyloidogenic properties, e.g. lead to facilitated amyloid formation. Such truncation may e.g. concern the N17 region and/or the proline-rich domain (PRD) region of a polyQ protein, such as a HTT protein. In a preferred embodiment, the truncation concerns the N17 region of a polyQ protein, such as a HTT protein. In another preferred embodiment, the truncation concerns the N17 region and the PRD region of a polyQ protein, such as a HTT protein.

Other exemplary amyloidogenic proteins according to the invention are wild-type or mutant forms of the group consisting of Tau protein, TAR DNA-binding protein 43 (TDP-43), Fused in Sarcoma (FUS) protein, Suppressor 35 (SUP35) protein, alpha-synuclein (α-Syn), and amyloidogenic fragments thereof.

Huntingtin is a large cytoplasmic protein (348 kDa in humans) that is widely expressed in the body. The first exon (exon 1) of the HTT gene contains a naturally polymorphic CAG repeat, leading to variable numbers of glutamine residues in the huntingtin protein. The amino acid sequence of wild-type human huntingtin (with 21 consecutive glutamine residues in exon 1), accessible via UniProtKB (accession no. P42858) is shown in SEQ ID NO.:1. A number of up to 35 glutamine residues (within exon 1, which is always referred to herein with regard to polyQ repeats unless indicated otherwise) is considered wild-type. Conversely, HTT with 36 glutamine residues or more in exon 1 is classified as mutant huntingtin (mHTT) herein.

In certain preferred embodiments of the invention, the amyloidogenic proteins A and B are mutant huntingtin (mHTT), particularly N-terminal fragments of mHTT, more particularly N-terminal fragments of mHTT comprising mHTT exon 1, more particularly N-terminal fragments of mHTT consisting of mHTT exon 1. In the context of the invention, mHTT exon 1 is also referred to as mHTTex1. Exemplary nucleotide and amino acid sequences of human wild-type exon 1 with 23 consecutive glutamine residues (Ex1Q23) and mutant huntingtin exon 1 with 48 or 49 consecutive glutamine residues (Ex1Q48, Ex1Q49) are shown in SEQ ID NOs.: 2-5. Further mutant huntingtin exon 1 sequences according to the invention with 48 or 40 consecutive glutamine residues and an adjacent modified proline rich domain (PRD) comprising 6 or more consecutive proline residues are e.g. K2Q48P6 (SEQ ID NO: 71), ΔN17Q48+6PRD (SEQ ID NO: 72) and ΔN17Q40+6PRD (SEQ ID NO: 73).

Of particular interest in the present invention are amyloidogenic proteins of human origin and of genetic model organisms, e.g. *Caenorhabditis elegans*, fruit fly, zebrafish and *Xenopus laevis*. According to some embodiments, the amyloidogenic proteins A and B are *Homo sapiens* proteins or *Drosophila melanogaster* proteins.

The amyloidogenic proteins A and B may be different proteins or may be isoforms of the same protein, but preferably share a high degree of amino acid sequence identity, e.g. at least 80%, at least 90%, at least 95%, or at least 98%. Particularly, amyloidogenic proteins A and B have an amino acid sequence identity of at least 95%, more particularly at least 98%. In some embodiments, the amino acid sequence identity of proteins A and B is 100%, i.e. amyloidogenic proteins A and B are identical.

The percent sequence identity may be determined according to the following formula:

$$I = n:L$$

wherein I is the identity in percent, n is the number of identical amino acids between a given sequence and a comparative sequence, and L is the length of the comparative sequence. Importantly, when calculating the percent sequence identity according to this formula, an alignment of the two sequences shall be carried out without gaps between complementary portions and over the whole length of the comparative sequence.

Each of the amyloidogenic proteins A and B fused to the fluorophore may be prepared synthetically, e.g. by solid phase peptide synthesis, or it may be prepared recombinantly, e.g. from expression of suitable vectors in bacteria, yeast, or expression cell lines known to the skilled person. Accordingly, in preferred embodiments, each of the amyloidogenic proteins A and B is independently a synthetically produced protein or a recombinantly produced protein.

The amyloidogenic protein aggregate C by definition comprises at least one amyloidogenic protein, which has or which have self-aggregated. For example, protein aggregate C may comprise mutant huntingtin. In particular embodiments, aggregate C comprises amyloidogenic proteins A and/or B. In other embodiments, aggregate C consists of amyloidogenic proteins A and/or B, i.e. it is constituted exclusively by protein A or by protein B or by a mixture of both protein A and B.

The aggregate may be formed in the presence of one or more other compounds, e.g. chaperones, which may still be present in the aggregate C used in the inventive method. Also, it is possible that preformed aggregate C has subsequently (i.e. after formation) been brought into contact with a further compound, which may for instance positively or negatively influence its seeding properties.

The protein aggregate C may be synthetically produced or recombinantly produced, e.g. from synthetic or recombinantly expressed proteins A and/or B. In some embodiments, the synthetically or recombinantly produced aggregate C may optionally be sonicated before being added to the mixture of step (i) as defined above.

Alternatively, it is possible that protein aggregate C is present in a sample, e.g. a biological sample. Such samples can be tissue samples or body fluid samples or culture samples, e.g. cell culture samples. Any of these samples may optionally be pretreated. Pretreatment can be effected by at least one of centrifugation, cell lysis, protein extraction, dialysis, sonication and similar procedures used in protein purification known to the skilled person. Accordingly, the sample containing aggregate C may be selected from the group consisting of an optionally pretreated tissue sample, an optionally pretreated body fluid sample and an optionally pretreated cell culture sample.

In exemplary embodiments, the sample is pretreated. Such a pretreated tissue, body fluid or cell culture sample may be selected from the group consisting of a homogenate, an extract, a pellet and a lysate. As indicated above, the pretreated sample may, in some embodiments and in addition to previous pretreatment steps, be sonicated. A "homogenate" particularly is a cell suspension or animal tissue that has been ground in an all-glass homogenizer (douncer) to disrupt cells. An "extract" is particularly a cell suspension or animal tissue, wherein cells have been chemically or physically lysed, and the cell debris has subsequently been removed, e.g. by centrifugation (e.g. at 30,000 g or 100,000 g). A "pellet" may be obtained, e.g., by centrifugation of a cell suspension etc., which is then washed with suitable buffers or further purified, as is known to the skilled person. A "lysate" is the material that remains when cells are lysed by enzymes, inorganic chemicals, or physical means.

In some preferred embodiments, the tissue used in the inventive method is muscle tissue. Exemplary pretreated tissue samples are selected from the group consisting of brain homogenates, brain extracts, and protein extracts from post-mortem tissue such as cerebral cortex, caudate nucleus and cerebellum.

Body fluids suitable for use in the inventive method are, inter alia, blood, preferably full blood, or cerebrospinal fluid. An exemplary pretreated body fluid sample is blood plasma.

Suitable cell culture samples according to the invention include cell line samples, e.g. from a fibroblast cell line or iPSC-derived neurons, stem cell samples, e.g. induced pluripotent stem cells (iPSC), and primary cell culture samples. The sources of primary cultures comprise excised animal tissue that is cultured either as an explant culture, suspension or as monolayer and maintained in vitro. The excised tissue is subjected to enzyme treatment and the dissociated cells are cultured under the appropriate conditions in culture medium until they reach adequate numbers.

The solution in which the mixture of amyloidogenic proteins A and B is provided preferably is a buffer, e.g. an aggregation buffer. For example, an aggregation buffer may be made up of a buffering agent (e.g. Tris-HCl, HEPES-KOH, etc.), particularly at a pH of from 7 to 8 and concentration of 25-100 mM, at least one salt (e.g. NaCl, $(NH_4)_2SO_4$, $MgCl_2$, KCl), preferably at a total concentration of 50-200 mM, a chelator (e.g. EDTA) and a reducing agent (e.g. β-mercaptoethanol or dithiothreitol (DTT)). A specific example of a buffer for use according to the invention consists of an aqueous solution of 50 mM Tris-HCl pH 7.4, 150 mM NaCl, 1 mM EDTA and 1 mM DTT.

Within the context of the above-described method for the quantification of seeding activity ($\Delta t_{50}$) of an amyloidogenic aggregate, it is also encompassed by the invention that the preformed aggregate may be used to screen for compounds that influence seeding competence of the aggregate. For example, a given amyloidogenic aggregate C may be pretreated with a compound of interest (D) before being used in the described screening method. Then, seeding activity is determined once with a sample containing aggregate C without pretreatment, and once with a sample containing aggregate C pretreated with the compound D. Compound D may be e.g. a protein, peptide or small molecule as defined hereinbelow.

Alternatively, a given amyloidogenic aggregate C may be formed in the presence of a compound D. Then, seeding activity is determined once with a sample containing aggregate C formed in the absence of compound D, and once with a sample containing aggregate C formed in the presence of compound D. Compound D may be e.g. a protein, peptide or small molecule as defined hereinbelow.

Accordingly, the invention provides a method for identifying compounds that inhibit seeding activity of amyloidogenic aggregates, comprising the steps of:
(i) quantifying seeding activity ($\Delta t_{50}$) in a first test sample, comprising the steps of:
  (a) providing, in a solution, a mixture of an amyloidogenic protein A which is N-terminally or C-terminally fused to a donor fluorophore molecule, e.g. a CFP, and an amyloidogenic protein B which is N-terminally or C-terminally fused to an acceptor fluorophore molecule, e.g. a YFP, wherein the amyloidogenic proteins A and B are preferably identical and wherein the donor fluorophore molecule and the acceptor fluorophore molecule are capable of FRET if they are in close proximity to each other;
  (b) adding a sample containing an amyloidogenic protein aggregate C to the mixture of step (a), wherein the amyloidogenic protein aggregate C preferably comprises or consists of amyloidogenic proteins A and/or B;
  (c) shaking the mixture of step (b);
  (d) measuring fluorescence signals in the donor, e.g. cyan, channel, the acceptor, e.g. yellow, channel and the FRET channel at predetermined intervals after completion of step (c);
  (e) calculating FRET efficiency (E) from the signals obtained in step (d); and
  (f) quantifying seeding activity ($\Delta t_{50}$) by subtracting the time at half-maximal FRET efficiency of a sample ($t_{50}(S)$) from the time at half-maximal FRET efficiency of a negative control ($t_{50}(0)$);
(ii) quantifying seeding activity ($\Delta t_{50}$) in a second test sample, comprising the steps (a) to (f) as described in (i), wherein the aggregate C further has been pretreated with a compound D or has been formed in the presence of a compound D;
(iii) correlating that the compound of interest has an inhibitory effect on the seeding activity of aggregate C, if the seeding activity obtained in step (ii) is lower than the seeding activity obtained in step (i).

Preferably, the amyloidogenic proteins A and B are mutant huntingtin (mHTT), particularly N-terminal fragments of mHTT, more particularly N-terminal fragments of mHTT comprising mHTT exon 1, more particularly N-terminal fragments of mHTT consisting of mHTT exon 1. In the context of the invention, mHTT exon 1 is also referred to as mHTTex1. Exemplary nucleotide and amino acid sequences of human wild-type exon 1 with 23 consecutive glutamine residues (Ex1Q23) and mutant huntingtin exon 1 with 48 or 49 consecutive glutamine residues (Ex1Q48, Ex1Q49) are shown in SEQ ID NOs.: 2-5. Further mutant huntingtin exon 1 sequences according to the invention with 48 or 40 consecutive glutamine residues and an adjacent modified proline rich domain (PRD) comprising 6 or more consecutive proline residues are e.g. K2Q48P6 (SEQ ID NO: 71), ΔN17Q48+6PRD (SEQ ID NO: 72) and ΔN17Q40+6PRD (SEQ ID NO: 73).

The present invention further provides a method for assessing the risk for development of a polyglutamine (polyQ) disease in a subject, comprising
  (i) quantification of seeding activity ($\Delta t_{50}$) of a polyQ-containing protein in a sample, comprising the steps of:
    (a) providing, in a solution, a mixture of a first, preferably recombinant, polyQ-containing protein which is C-terminally fused to a donor fluorophore molecule, e.g. a CFP, and a second, preferably recombinant, polyQ-containing protein which is C-terminally fused to an acceptor fluorophore molecule, e.g. a YFP, wherein the first and second proteins are the same polyQ-containing protein and wherein the donor fluorophore molecule and the acceptor fluorophore molecule are capable of FRET if they are in close proximity to each other;
    (b) adding a sample collected from the subject to the mixture of step (a);
    (c) shaking the mixture of step (b);
    (d) measuring fluorescence signals in the donor, e.g. cyan, channel, the acceptor, e.g. yellow, channel and the FRET channel at predetermined intervals after completion of step (c);
    (e) calculating FRET efficiency (E) from the signals obtained in step (d); and
    (f) quantifying seeding activity ($\Delta t_{50}$) by subtracting the time at half-maximal FRET efficiency of a sample ($t_{50}(S)$) from the time at half-maximal FRET efficiency of a negative control ($t_{50}(0)$); and
  (ii) correlating that the subject is at risk for development of the polyQ disease when the seeding activity in the sample is increased as compared to a reference sample.

In some embodiments, a $\Delta t_{50}$ of the collected sample which is significantly higher than $\Delta t_{50}$ of a reference sample indicates that the subject is at risk for developing a polyQ disease.

Typically, $\Delta t_{50}$ of the reference sample will be about 0 with standard error of the mean (SEM). $\Delta t_{50}$ of the collected sample to be analyzed may be of about the same value (i.e. about 0±SEM) if the subject is not at risk for developing the polyQ disease of interest. However, if the subject is at risk for developing the polyQ disease of interest, $\Delta t_{50}$ of the collected sample to be analyzed may be significantly higher.

Of course, it should be verified that the reference sample is obtained from a source which is not at risk of developing the polyQ disease of interest (i.e., a healthy subject or cell culture).

The present invention further provides a method for predicting the onset of a polyglutamine (polyQ) disease in a subject, comprising
  (i) quantification of seeding activity ($\Delta t_{50}$) of a polyQ-containing protein in a sample, comprising the steps of:
    (a) providing, in a solution, a mixture of a first, preferably recombinant, polyQ-containing protein which is C-terminally fused to a donor fluorophore molecule, e.g. a CFP, and a second, preferably recombinant, polyQ-containing protein which is C-terminally fused to an acceptor fluorophore molecule, e.g. a YFP, wherein the first and second proteins are the same polyQ-containing protein and wherein the donor fluorophore molecule and the acceptor fluorophore molecule are capable of FRET if they are in close proximity to each other;
    (b) adding a sample collected from the subject to the mixture of step (a);
    (c) shaking the mixture of step (b);
    (d) measuring fluorescence signals in the donor, e.g. cyan, channel, the acceptor, e.g. yellow, channel and the FRET channel at predetermined intervals after completion of step (c);
    (e) calculating FRET efficiency (E) from the signals obtained in step (d); and
    (f) quantifying seeding activity ($\Delta t_{50}$) by subtracting the time at half-maximal FRET efficiency of a sample ($t_{50}(S)$) from the time at half-maximal FRET efficiency of a negative control ($t_{50}(0)$); and
  (ii) correlating that the onset of the polyQ disease has occurred or will occur soon when the seeding activity in the sample is increased as compared to a reference sample.

In some embodiments, a $\Delta t_{50}$ of the collected sample which is significantly higher than $\Delta t_{50}$ of a reference sample indicates that onset of the analyzed polyQ disease will occur soon (i.e. is imminent). In other embodiments, a $\Delta t_{50}$ of the collected sample which is significantly higher than $\Delta t_{50}$ of a reference sample indicates that onset of the analyzed polyQ disease has already occurred.

Typically, $\Delta t_{50}$ of the reference sample will be from about 0 to about 1. $\Delta t_{50}$ of the collected sample to be analyzed may be of about the same value (i.e. about 0±SEM to about 1±SEM) if there is no imminent onset of the polyQ disease of interest. If onset of the polyQ disease of interest will occur soon (e.g. within a time interval of between 3 and 9 months), $\Delta t_{50}$ of the collected sample to be analyzed may be at least about 2, e.g. from about 2 to about 3, particularly 2.5 to 3.5. If onset of the polyQ disease of interest has occurred already, $\Delta t_{50}$ of the collected sample to be analyzed may be at least about 4, e.g. from about 4 to about 6, particularly 3.6 to 6.0. In the context of the invention, the "onset" of a disease is the timepoint, from which onwards established clinical signs or symptoms can be detected.

Of course, it should be verified that the reference sample is obtained from a source where there is at least no imminent onset of the polyQ disease of interest, or even better, which is not at all developing the polyQ disease of interest (i.e., a healthy subject or cell culture).

In general, the reference sample in the above-described method for assessing the risk for development of a polyQ disease and method for predicting the onset of a polyglutamine (polyQ) disease should be a sample that is closely related to the sample collected from the subject to be analyzed; typically, it may be derived from the same organism and from the same tissue or a cell culture of the respective tissue or the same body fluid as the sample of step (i)(b). If the sample of step (i)(b) is pretreated, the reference sample should be subjected to the same pretreatment. Seeding activity ($\Delta t_{50}$) is quantified in the reference sample according to steps (i)(a)-(f), using the reference sample instead of the sample collected from the subject to be analyzed. The obtained value can be compared with the seeding activity ($\Delta t_{50}$) value of the sample collected from the subject to be analyzed.

Alternatively, it is possible to rely on known values of reference samples (of corresponding origin) obtained according to a standardized procedure analogous to the method steps (i)(a)-(f) described above.

The present invention further provides a method for assessing the progression of a polyglutamine (polyQ) disease in a subject, comprising (i) quantification of seeding activity ($\Delta t_{50}$) of a polyQ-containing protein in a sample collected at a timepoint $t_1$, comprising the steps of:
  (a) providing, in a solution, a mixture of a first, preferably recombinant, polyQ-containing protein which is C-terminally fused to a donor fluorophore molecule, e.g. a CFP, and a second, preferably recombinant, polyQ-containing protein which is C-terminally fused to an acceptor fluorophore molecule, e.g. a YFP, wherein the first and second proteins are the same polyQ-containing protein and wherein the donor fluorophore molecule and the acceptor fluorophore molecule are capable of FRET if they are in close proximity to each other;
  (b) adding a sample collected from the subject to the mixture of step (a);
  (c) shaking the mixture of step (b);
  (d) measuring fluorescence signals in the donor, e.g. cyan, channel, the acceptor, e.g. yellow, channel and the FRET channel at predetermined intervals after completion of step (c);
  (e) calculating FRET efficiency (E) from the signals obtained in step (d);
  (f) quantifying seeding activity ($\Delta t_{50}$) by subtracting the time at half-maximal FRET efficiency of a sample ($t_{50}(S)$) from the time at half-maximal FRET efficiency of a negative control ($t_{50}(0)$);
(ii) quantification of seeding activity ($\Delta t_{50}$) of a polyQ-containing protein in a sample collected at a timepoint $t_2$, wherein $t_2$ is later than $t_1$, comprising the steps (a) to (f) as defined in (i); and
(iii) correlating that the polyQ disease has progressed when the seeding activity in the sample taken at $t_2$ is increased as compared to the sample taken at $t_1$.

PolyQ diseases according to the invention are particularly selected from the group consisting of Huntington's disease (HD), Machado-Joseph disease (MJD/SCA3), dentatorubral pallidoluysian atrophy (DRPLA), spinocerebellar ataxia (SCA) type 1, SCA type 2, SCA type 6, SCA type 7, SCA type 17 and spinal and bulbar muscular atrophy, X-linked 1 (SMAX1/SBMA).

A polyQ disease of particular interest in preferred embodiments of the invention is Huntington's disease (HD).

In the above-described methods for assessing the risk for development, predicting the onset or assessing the progression of a polyQ disease, the polyQ protein of the respective step (i)(a) may be a synthetically produced or recombinant protein. Preferably, it is recombinantly produced. The polyQ protein is particularly selected from wild-type or mutant forms of the group consisting of huntingtin (HTT), androgen receptor (AR), atrophin 1 (ATN1), ataxin 1 (ATXN1), ataxin 2 (ATXN1), ataxin 3 (ATXN1), ataxin 7 (ATXN1), TATA-box binding protein (TBP), $\alpha_{1A}$-voltage dependent calcium channel subunit (CACNA1A), and polyglutamine repeat containing fragments thereof. In certain preferred embodiments, the polyQ protein is mutant huntingtin (mHTT) or an N-terminal fragment thereof, characterized by an increased number of glutamine residues as compared to the corresponding wild-type form. More preferably, the polyQ protein is selected from N-terminal fragments of mHTT comprising mHTT exon 1, particularly N-terminal fragments of mHTT consisting of mHTT exon 1 (mHTTex1). Specific examples of mHTTex1 according to the invention include mHTT Ex1Q48 (SEQ ID NO.: 2), Ex1Q49 (SEQ ID NO.: 4), K2Q48P6 (SEQ ID NO: 71), ΔN17Q48+6PRD (SEQ ID NO: 72) and ΔN17Q40+6PRD (SEQ ID NO: 73).

In the above-described methods for assessing the risk for development, predicting the onset or assessing the progression of a polyQ disease, the subject may be a mammalian subject, particularly a subject selected from the group consisting of mouse, rat, monkey, sheep, pig and human. In preferred embodiments, the subject is a human. The subject may also be a non-mammalian model organism for studying a polyQ disease, e.g. a model organism used to study HD. In particular, the model organism may be selected from the group consisting of yeast, *Caenorhabditis elegans*, fruit fly, zebrafish and *Xenopus laevis*. Alternatively, the subject is a population of cells from cell culture. The cell population may, for example, be stem cells, including pluripotent stem cells, such as induced pluripotent stem cells (iPSC), fibroblasts, or iPSC-derived neurons. Also, cells from established cell lines or primary cell culture may be suitable.

The sample used in step (i)(b) of the above-described methods for assessing the risk for development, predicting the onset or assessing the progression of a polyQ disease may be obtained from a variety of tissues, body fluids, whole organisms and cultured cells from a number of different organisms. The sample may be collected from a living organism, or it may be collected post mortem.

In some embodiments, the sample is a tissue sample, which is optionally pretreated as described above. For example, the sample may be selected from the group consisting of muscle tissue, protein extracts from muscle tissue, homogenated muscle tissue, nasal brushing and nasal epithelial tissue. Among samples that can only be obtained post mortem are mammalian, e.g. human, brain samples. In some embodiments, the sample is a human brain sample.

In other embodiments, the sample is a body fluid sample. Suitable body fluids include blood, sputum and cerebrospinal fluid. For example, the sample may be selected from the group consisting of full blood, homogenated blood, blood plasma and cerebrospinal fluid.

The solution in which the mixture of the first and second polyQ proteins is provided preferably is a buffer, e.g. an aggregation buffer. For example, an aggregation buffer may be made up of a buffering agent (e.g. Tris-HCl, HEPES-KOH, etc.), particularly at a pH of from 7 to 8 and concentration of 25-100 mM, at least one salt (e.g. NaCl, $(NH_4)_2SO_4$, $MgCl_2$, KCl), preferably at a total concentration of 50-200 mM, a chelator (e.g. EDTA) and a reducing agent (e.g. β-mercaptoethanol or dithiothreitol (DTT)). A specific example of a buffer for use according to the invention consists of an aqueous solution of 50 mM Tris-HCl pH 7.4, 150 mM NaCl, 1 mM EDTA and 1 mM DTT.

The present invention further provides a method for identifying compounds that inhibit mHTT seeding activity (HSA) in vitro, comprising the steps of:
  (i) determining HSA in a test sample, comprising the steps of:

(a) providing, in a solution, a mixture of a purified, preferably recombinant, mutant form of an N-terminal huntingtin fragment comprising exon 1 (mHTTex1) characterized by an increased number of glutamine residues as compared to the corresponding wild-type form, which is (1) N-terminally fused to a globular peptide comprising a protease recognition sequence at its C-terminus, and (2) C-terminally fused to a donor fluorophore molecule, e.g. a CFP, and a purified, preferably recombinant, mutant form of an N-terminal huntingtin fragment comprising exon 1 (mHTTex1) characterized by an increased number of glutamine residues as compared to the corresponding wild-type form, which is (1) N-terminally fused to a globular peptide comprising a protease recognition sequence at its C-terminus, and (2) C-terminally fused to an acceptor fluorophore molecule, e.g. a YFP;

(b) adding a compound or a mixture of compounds to be tested for inhibiting HSA in vitro to the mixture of step (a);

(c) adding a protease specifically recognizing the protease recognition sequence within the globular peptide to the mixture of step (b);

(d) optionally adding preformed aggregates of mHTT or N-terminal fragments thereof to the mixture of step (c);

(e) shaking the mixture of step (c) or step (d);

(f) measuring fluorescence signals in the donor, e.g. cyan, channel, the acceptor, e.g. yellow, channel and the FRET channel at predetermined intervals after completion of step (e);

(g) calculating FRET efficiency (E) from the signals obtained in step (f); and (h) quantifying seeding activity ($\Delta t_{50}$) by subtracting the time at half-maximal FRET efficiency of a sample ($t_{50}(S)$) from the time at half-maximal FRET efficiency of a negative control ($t_{50}(0)$);

(ii) determining HSA in a control sample without the compound or mixture of compounds to be tested for inhibiting HSA in vitro, comprising steps (a), (c), optionally (d), (e), (f), (g) and (h) as defined in (i); and (iii) selecting compounds or mixtures of compounds which show decreased seeding activity as compared to control samples.

With the above-described method, it is possible to screen for compounds directly targeting mHTT seeding in vitro, which may have therapeutic potential. A "compound" in the context of this screening method includes small molecules (i.e. naturally occurring, modified or synthetic organic molecules with a molecular weight of about 900 Da or less) as well as peptides (up to 100 amino acids) and proteins (more than 100 amino acids), which may be further modified, e.g. by attaching moieties like polyethylene glycol (PEG) to increase half-life. It is also possible to test a mixture of compounds, e.g. of two or three compounds, which only in combination inhibit mHTT seeding activity in vitro.

The fusion protein comprising the donor fluorophore molecule and the fusion protein comprising the acceptor fluorophore molecule comprise, each independently, a purified mutant form of an N-terminal huntingtin fragment comprising exon 1 (mHTTex1). This mutant form is characterized by an increased number of glutamine residues as compared to the corresponding wild-type form. In certain embodiments, the N-terminal huntingtin fragment consists of exon 1 (mHTTex1). The N-terminal huntingtin fragment may have, e.g., from 35 to 75 glutamines in exon 1 (mHTT Ex1Q35-mHTT Ex1Q75). Specific examples of mHTTex1 for use in this screening method include mHTT Ex1Q48 (SEQ ID NO.: 2), Ex1Q49 (SEQ ID NO.: 4), K2Q48P6 (ID NO: 71), ΔN17Q48+6PRD (SEQ ID NO: 72) and ΔN17Q40+6PRD (SEQ ID NO: 73).

The N-terminal huntingtin fragments of step (i)(a) of the above-described screening method are N-terminally fused to a globular peptide. The globular peptide comprises a protease recognition sequence at its C-terminus. Suitable globular peptide tags include glutathione-S-transferase (GST) and maltose binding protein (MBP). In preferred embodiments, the globular peptide is GST, particularly GST as shown in SEQ ID NO.: 6. Suitable protease recognition sequences are known to the skilled person. An exemplary protease recognition sequence, which is recognized by the commercially available PreScission® Protease (or PSP; GE Healthcare), is LEVLFQGP (SEQ ID NO.: 8).

Further, the N-terminal huntingtin fragments of step (i)(a) of the above-described screening method is C-terminally fused to a donor fluorophore molecule and an acceptor fluorophore molecule, respectively. The fluorophore molecules are selected from suitable FRET pairs, for instance those described below.

The protease used for cleaving off the globular protein at the N-terminus of the mHTT fragments (step (i)(c) of the above-described screening method), starts the aggregation reaction. It will be selected according to the used protease recognition sequence. A number of recognition sequence/protease combinations are known to the skilled person. For example, when the protease recognition sequence LEVLFQGP (SEQ ID NO.: 8) is used, a suitable protease is PreScission® Protease (or PSP; GE Healthcare).

The preformed aggregate of step (i)(d) of the above-described screening method may optionally be added to the reaction as an aggregation seed. Such a seed can increase aggregation rate of the mHTT fragments fused to the fluorophore molecules. The preformed aggregate may be obtained from various sources. According to some embodiments the preformed aggregate may be obtained ex vivo, e.g. from a subject suffering from HD or from a HD model. According to other embodiments, it may be obtained in vitro, e.g. from recombinantly expressed or chemically synthesized and subsequently aggregated mHTT or N-terminal fragment thereof.

When obtained in vitro, the aggregated mHTT or N-terminal fragment thereof is characterized by an increased number of glutamine residues as compared to the corresponding wild-type form. The aggregate of N-terminal huntingtin fragment may consist of exon 1 (mHTTex1). In certain preferred embodiments, the preformed aggregates of mHTT or N-terminal fragment thereof consist of mHTT exon 1 having from 35 to 75 glutamines in exon 1 (Ex1Q35-Ex1Q75). Specific examples of mHTTex1 aggregates for use in this screening method include aggregates consisting of Ex1Q48 (SEQ ID NO.: 2), Ex1Q49 (SEQ ID NO.: 4), K2Q48P6 (SEQ ID NO.: 71), ΔN17Q48+6PRD (SEQ ID NO.: 72) or ΔN17Q40+6PRD (SEQ ID NO.: 73). It is possible to use a similar recombinant construct, but without fusion to fluorophore molecules, for obtaining the preformed aggregates. For example, the preformed aggregates of mHTT or an N-terminal fragment thereof may be obtained by adding a suitable protease to purified mHTT GST-Ex1Q48 (SEQ ID NO.: 9), purified mHTT GST-Ex1Q49 (SEQ ID NO.: 11), purified GST-K2Q48P6 (SEQ ID NO: 60), purified GST-ΔN17Q48+6PRD (SEQ ID NO: 62) or purified GST-ΔN17Q40+6PRD (SEQ ID NO: 64). As mentioned above, selection of a suitable protease depends on the protease recognition sequence in the fusion protein. A number of recognition sequence/protease combinations are known to the skilled person. For example, when the protease recognition sequence LEVLFQGP (SEQ ID NO.: 8) is used, a suitable protease is PreScission® Protease (or PSP; GE Healthcare).

The solution in which the mixture of the purified mutant N-terminal huntingtin fragments comprising exon 1 (mHTTex1) fused to the FRET pair fluorophores is provided preferably is a buffer, e.g. an aggregation buffer. For example, an aggregation buffer may be made up of a buffering agent (e.g. Tris-HCl, HEPES-KOH, etc.), particularly at a pH of from 7 to 8 and concentration of 25-100 mM, at least one salt (e.g. NaCl, $(NH_4)_2SO_4$, $MgCl_2$, KCl), preferably at a total concentration of 50-200 mM, a chelator (e.g. EDTA) and a reducing agent (e.g. β-mercaptoethanol or dithiothreitol (DTT)). A specific example of a buffer for use according to the invention consists of an aqueous solution of 50 mM Tris-HCl pH 7.4, 150 mM NaCl, 1 mM EDTA and 1 mM DTT.

In all methods described herein, advantage is taken of the capability of certain fluorophore molecules to effect an energy transfer. This phenomenon is termed Förster or fluorescence resonance energy transfer (FRET) and is characterized in that a donor fluorophore molecule is excited, and in its excited state transfers (non-radiatively) excitation energy to a fluorophore molecule in close proximity. Close proximity is usually given when the distance between donor and acceptor fluorophore is in the range of 1-10 nm. A number of optical methods is known to measure FRET and to calculate FRET efficiency therefrom.

The donor and acceptor molecules capable of FRET are also termed FRET pairs. Nowadays, a variety of FRET pairs is available. Within the scope of the invention, it is encompassed to use, e.g., blue/yellow FRET pairs, green/red FRET pairs, and far-red/infra-red FRET pairs. Specific examples of FRET pairs that may in principle be used are ECFP/EYFP, mTurquoise2/sEYFP, SCFP/SYFP, CyPet/YPet, ECFP/mVenus, mCerulean/mCitrine, EGFP/mCherry, mNeonGreen/mRuby3, EGFP/mRFP1, mCerulean/mVenus and mTurquoise/mVenus.

Particularly, the acceptor fluorophore molecule according to the present invention is a yellow fluorescent protein (YFP). A number of YFPs are presently known, and it is encompassed by the invention that the YFP may, e.g., be selected from the group consisting of EYFP, Venus (e.g. mVenus), Citrine (e.g. mCitrine) and YPet. A preferred YFP according to the invention is YPet. A specific example of YPet used according to the invention is shown in SEQ ID NO.: 21.

The donor fluorophore molecule according to the invention is particularly a cyan fluorescent protein (CFP), which may, e.g., be selected from the group consisting of ECFP, SCFP, Cerulean (e.g. Cerulean, mCerulean2, mCerulean3), Turquoise (e.g. mTurquoise, mTurquoise2) and CyPet. A preferred CFP according to the invention is CyPet. A specific example of CyPet used according to the invention is shown in SEQ ID NO.: 23.

According to some embodiments of the invention, the donor fluorophore molecule is a CFP, which is preferably selected from the group consisting of ECFP, SCFP and CyPet, more preferably CyPet, and the acceptor fluorophore molecule is a YFP, which is preferably selected from the group consisting of EYFP, Venus, Citrine and YPet, more preferably YPet. In certain preferred embodiments of the invention, CyPet/YPet is used as the FRET pair.

Thus, in some preferred embodiments of the method for the quantification of seeding activity ($\Delta t_{50}$) of an amyloidogenic aggregate described herein, the amyloidogenic proteins A and B are mHTT Ex1Q48-YPet (SEQ ID NO.: 13) and mHTT Ex1Q48-CyPet (SEQ ID NO.: 15).

In some preferred embodiments of the method for the quantification of seeding activity ($\Delta t_{50}$) of an amyloidogenic aggregate described herein, the amyloidogenic proteins A and B are K2Q48P6-YPet (SEQ ID NO.: 66) and K2Q48P6-CyPet (SEQ ID NO.: 65).

In some preferred embodiments of the method for the quantification of seeding activity ($\Delta t_{50}$) of an amyloidogenic aggregate described herein, the amyloidogenic proteins A and B are ΔN17Q48+6PRD-YPet (SEQ ID NO.: 68) and ΔN17Q48+6PRD-CyPet (SEQ ID NO.: 67).

In some preferred embodiments of the method for the quantification of seeding activity ($\Delta t_{50}$) of an amyloidogenic aggregate described herein, the amyloidogenic proteins A and B are ΔN17Q40+6PRD-YPet (SEQ ID NO.: 70) and ΔN17Q40+6PRD-CyPet (SEQ ID NO.: 69).

Likewise, in some preferred embodiments of the methods for assessing the risk for development, predicting the onset or assessing the progression of a polyQ disease, the first and second recombinant polyQ-containing proteins of step (a) are mHTT Ex1Q48-YPet (SEQ ID NO.: 13) and mHTT Ex1Q48-CyPet (SEQ ID NO.: 15).

In some preferred embodiments of the methods for assessing the risk for development, predicting the onset or assessing the progression of a polyQ disease, the first and second recombinant polyQ-containing proteins of step (a) are K2Q48P6-YPet (SEQ ID NO.: 66) and K2Q48P6-CyPet (SEQ ID NO.: 65).

In some preferred embodiments of the methods for assessing the risk for development, predicting the onset or assessing the progression of a polyQ disease, the first and second recombinant polyQ-containing proteins of step (a) are ΔN17Q48+6PRD-YPet (SEQ ID NO.: 68) and ΔN17Q48+6PRD-CyPet (SEQ ID NO.: 67).

In some preferred embodiments of the methods for assessing the risk for development, predicting the onset or assessing the progression of a polyQ disease, the first and second recombinant polyQ-containing proteins of step (a) are ΔN17Q40+6PRD-YPet (SEQ ID NO.: 70) and ΔN17Q40+6PRD-CyPet (SEQ ID NO.: 69).

In some preferred embodiments of the method for identifying compounds that inhibit mHTT seeding activity (HSA) in vitro, the purified recombinant mutant forms of huntingtin (mHTT) in step (i)(a) and step (ii)(a) are mHTT GST-Ex1Q48-YPet (SEQ ID NO.: 17) and mHTT GST-Ex1Q48-CyPet (SEQ ID NO.: 19).

In some preferred embodiments of the method for identifying compounds that inhibit mHTT seeding activity (HSA) in vitro, the purified recombinant mutant forms of huntingtin (mHTT) in step (i)(a) and step (ii)(a) are mHTT GST-K2Q48P6-CyPet (SEQ ID NO.: 48) and mHTT GST-K2Q48P6-YPet (SEQ ID NO.: 50).

In some preferred embodiments of the method for identifying compounds that inhibit mHTT seeding activity (HSA) in vitro, the purified recombinant mutant forms of huntingtin (mHTT) in step (i)(a) and step (ii)(a) are mHTT GST-ΔN17Q48+6PRD-CyPet (SEQ ID NO.: 52) and mHTT GST-ΔN17Q48+6PRD-YPet (SEQ ID NO.: 54).

In some preferred embodiments of the method for identifying compounds that inhibit mHTT seeding activity (HSA) in vitro, the purified recombinant mutant forms of huntingtin (mHTT) in step (i)(a) and step (ii)(a) are mHTT GST-ΔN17Q40+6PRD-CyPet (SEQ ID NO.: 56) and mHTT GST-ΔN17Q40+6PRD-YPet (SEQ ID NO.: 58).

The ratio in which the protein fused to the donor fluorophore molecule and the protein fused to the acceptor fluorophore molecule (both of which are also referred to herein as "the fluorophore fusion proteins") are provided will typically be selected in order to provide the best FRET results. In the context of the present invention, it is preferred that the ratio of the protein fused to the donor fluorophore molecule to the protein fused to the acceptor fluorophore molecule ranges from 2:3 to 3:2, e.g. 2:3, 4:5, 7:8, 1:1, 8:7, 5:4, 3:2. In certain preferred embodiments, the ratio is about 1:1 or exactly 1:1, i.e. the fluorophore fusion proteins are provided as an equimolar mixture. Suitable concentrations of the fluorophore fusion proteins in the reaction mixture are typically in the low micromolar range. For example, the fluorophore fusion proteins can be provided in a concentration of from about 0.1 µM to about 2.0 µM each (i.e. when using an equimolar mixture, the final concentration of both fluorophore fusion proteins will be from about 0.2 µM to about 4.0 µM). Specific examples of fluorophore fusion protein concentrations, e.g. of GST-Ex1Q48-YPet and GST-Ex1Q48-CyPet, are 0.5 µM each, 0.6 µM each, 0.7 µM each, 0.75 µM each or 0.8 µM each, particularly in an equimolar mixture (i.e. final concentrations 1.0 µM, 1.2 µM, 1.4 µM, 1.5 µM or 1.6 µM).

In this context it is noted that the sample added to the mixture of fluorophore fusion proteins may be in the range of from about 1% (v/v) to about 30% (v/v), particularly 1% (v/v) to 10% (v/v).

Measurement of fluorescence signals is performed as known in the field of FRET, for instance in a fluorescence plate reader. Fluorescence signals in the donor channel are usually measured at the peak excitation (Ex) wavelength and the peak emission (Em) wavelength. For cyan fluorescent proteins, signals may e.g. be recorded at the following wavelengths:

| cyan fluorescent protein | Ex/nm | Em/nm |
|---|---|---|
| ECFP | 439 | 476 |
| SCFP | 433 | 474 |
| Cerulean | 433 | 475 |
| Turquoise | 434 | 474 |
| CyPet | 435 | 475 |

In certain preferred embodiments of the invention, fluorescence signals in the donor channel are measured at 435 nm (excitation) and 475 nm (emission).

Likewise, fluorescence signals in the acceptor channel are usually measured at the peak excitation (Ex) wavelength and the peak emission (Em) wavelength. For yellow fluorescent proteins, signals may e.g. be recorded at the following wavelengths:

| yellow fluorescent protein | Ex/nm | Em/nm |
|---|---|---|
| EYFP | 514 | 527 |
| Venus | 515 | 528 |
| Citrine | 516 | 529 |
| YPet | 500 | 530 |

In certain preferred embodiments of the invention, fluorescence signals in the acceptor channel are measured at 500 nm (excitation) and 530 nm (emission).

Fluorescence signals in the FRET channel (also referred to as DA) are typically recorded at the excitation wavelength of the donor fluorophore and the acceptor wavelength of the acceptor fluorophore. In certain preferred embodiments of the invention, fluorescence signals in the FRET channel are measured at 435 nm (excitation) and 530 nm (emission).

The raw signals obtained are then processed to calculate FRET efficiency. To this end, raw signals were processed by subtracting the background fluorescence of unlabeled Ex1Q48, or unlabeled K2Q48P6, or unlabeled ΔN17Q48+6PRD or unlabeled ΔN17Q40+6PRD, respectively, in all channels. Signals in the FRET channel were corrected for donor bleed-through (c$_D$) and acceptor cross excitation (c$_A$) using donor- and acceptor-only samples to obtain sensitized emission. Finally, sensitized emission was normalized to the acceptor signals (Jiang and Sorkin, 2002). In preferred embodiments of the invention, FRET efficiency (E) is calculated according to formula (1)

$$E = (DA - c_D \cdot DD - c_A AA)/AA \qquad (1),$$

wherein
DA is the FRET channel signal
c$_D$ is the donor bleed-through
DD is the donor channel signal
c$_A$ is the acceptor cross-excitation
AA is the acceptor channel signal.

Measurement of fluorescence signals can be performed at a predetermined timepoint or, preferably, it can be measured at certain intervals after the assay where FRET signals are expected has been started. This intervals will typically be in the range of minutes, e.g. from 1 minute to 50 minutes, particularly 10 to 30 minutes. A specific example according to the invention is an interval of 20 minutes. Measurement is usually stopped when FRET efficiency has reached saturation. This can be after, e.g., 12 hours, 24 hours, 48 hours or even longer, depending on the experimental conditions. A specific endpoint for fluorescence measurement in the methods according to the invention is 48 hours.

Accordingly, in some embodiments, the fluorescence signals are measured at intervals of 20 minutes for up to 48 h.

The FRET efficiency results can be further used to quantify seeding activity ($\Delta t_{50}$ in hours), which in the case of mutant huntingtin, is referred to as mHTT seeding activity (HSA). To this end, the $t_{50}$ values (time at half-maximal FRET efficiency) of the respective sample are subtracted from the negative control. To obtain the $t_{50}$ values, the aggregation kinetics are preferably curve fitted by Richard's five-parameter dose-response curve (Formula (2) below), e.g. using the software GraphPad Prism (GraphPad Software, La Jolla, USA).

$$y = y_0 + \left( \frac{y_\infty - y_0}{\left[1 + 10^{(Log x b - x) \times HillSlope}\right]^S} \right) \qquad (2)$$

wherein
y$_0$=minimum asymptote
y$_{ab}$=maximum asymptote
Logxb=LogEC50+(1/HillSlope)*Log((2^(1/S))−1)
LogEC50=concentrations that give half-maximal effects, in
the same units as X
x=time
HillSlope=unitless slope factor or Hill slope
S=asymmetry factor All methods involving quantification of seeding activity described herein comprise a step of shaking, in order to properly mix the fluorophore containing molecules with the added sample to be analyzed. Shaking can be performed, e.g., manually or automatically, e.g. in vertical direction, in a fluorescence reader, for instance from about 3 seconds to about 10 seconds. In certain preferred embodiments, shaking the mixture is performed by 5 seconds vertical shaking.

The present invention further provides the use of certain constructs in an aggregation assay. For example, these constructs may be used in the methods involving quantification of seeding activity described herein. In some embodiments, the invention provides the use of a soluble glutathione S-transferase HTT exon-1 fusion protein comprising from about 35 to about 75, particularly about 40 to about 55, e.g. 40 or 48 or 49 glutamine residues which is C-terminally fused to a donor fluorophore molecule, e.g. a CFP such as CyPet, and of a soluble glutathione S-transferase HTT exon-1 fusion protein comprising from about 35 to about 75, particularly about 40 to about 55, e.g. 40 or 48 or 49 glutamine residues which is C-terminally fused to an acceptor fluorophore molecule, e.g. a YFP such as YPet in an aggregation assay.

In preferred embodiments of the described use, the donor fluorophore fusion protein comprises 48 glutamine residues and/or the donor fluorophore is CyPet. In other preferred embodiments of the described use, the donor fluorophore fusion protein comprises 40 glutamine residues and/or the donor fluorophore is CyPet. Between GST and the HTT sequence, a protease recognition sequence as described herein is typically present. Preferably, the donor fluorophore fusion protein consists of mHTT GST-Ex1Q48-CyPet. A specific example of such a fusion protein has the amino acid sequence as shown in SEQ ID NO.: 19. In other preferred embodiment, the donor fluorophore fusion protein consists of mHTT GST-K2Q48P6-CyPet. A specific example of such a fusion protein has the amino acid sequence as shown in SEQ ID NO.: 48. In another preferred embodiment, the donor fluorophore fusion protein consists of mHTT GST-ΔN17Q48+6PRD-CyPet. A specific example of such a fusion protein has the amino acid sequence as shown in SEQ ID NO.: 52. In another preferred embodiment, the donor fluorophore fusion protein consists of mHTT GST-ΔN17Q40+6PRD-CyPet. A specific example of such a fusion protein has the amino acid sequence as shown in SEQ ID NO.: 56.

Also, in preferred embodiments of the described use, the acceptor fluorophore fusion protein comprises 48 glutamine residues and/or the acceptor fluorophore is YPet. In other preferred embodiments of the described use, the acceptor fluorophore fusion protein comprises 40 glutamine residues and/or the acceptor fluorophore is YPet. Between GST and the HTT sequence, a protease recognition sequence as described herein is typically present. Preferably, the acceptor fluorophore fusion protein consists of mHTT GST-Ex1Q48-YPet. A specific example of such a fusion protein has the amino acid sequence as shown in SEQ ID NO.: 17. In another preferred embodiment, the acceptor fluorophore fusion protein consists of mHTT GST-K2Q48P6-YPet. A specific example of such a fusion protein has the amino acid sequence as shown in SEQ ID NO.: 50. In another preferred embodiment, the acceptor fluorophore fusion protein consists of mHTT GST-ΔN17Q48+6PRD-YPet. A specific example of such a fusion protein has the amino acid sequence as shown in SEQ ID NO.: 54. In another preferred embodiment, the acceptor fluorophore fusion protein consists of mHTT GST-ΔN17Q40+6PRD-YPet. A specific example of such a fusion protein has the amino acid sequence as shown in SEQ ID NO.: 58.

In yet further embodiments of the invention, the use of a soluble HTT exon-1 fusion protein comprising from about 35 to about 75, particularly about 40 to about 55, e.g. 40 or 48 or 49 glutamine residues which is C-terminally fused to a donor fluorophore molecule, e.g. a CFP such as CyPet, and of a soluble HTT exon-1 fusion protein comprising from about 35 to about 75, particularly about 40 to about 55, e.g. 40 or 48 or 49 glutamine residues which is C-terminally fused to an acceptor fluorophore molecule, e.g. a YFP such as YPet in an aggregation assay is provided.

In preferred embodiments of the described use, the donor fluorophore fusion protein comprises 48 glutamine residues and/or the donor fluorophore is CyPet. Preferably, the donor fluorophore fusion protein consists of mHTT Ex1Q48-CyPet. A specific example of such a fusion protein has the amino acid sequence as shown in SEQ ID NO.: 15. In another preferred embodiment, the donor fluorophore fusion protein consists of K2Q48P6-CyPet. A specific example of such a fusion protein has the amino acid sequence as shown in SEQ ID NO.: 65. In another preferred embodiment, the donor fluorophore fusion protein consists of ΔN17Q48+6PRD-CyPet. A specific example of such a fusion protein has the amino acid sequence as shown in SEQ ID NO.: 67. In another preferred embodiment, the donor fluorophore fusion protein consists of ΔN17Q40+6PRD-CyPet. A specific example of such a fusion protein has the amino acid sequence as shown in SEQ ID NO.: 69.

Also, in preferred embodiments of the described use, the acceptor fluorophore fusion protein comprises 48 glutamine residues and/or the acceptor fluorophore is YPet. Preferably, the acceptor fluorophore fusion protein consists of mHTT Ex1Q48-YPet. A specific example of such a fusion protein has the amino acid sequence as shown in SEQ ID NO.: 13. In another preferred embodiment, the acceptor fluorophore fusion protein consists of K2Q48P6-YPet. A specific example of such a fusion protein has the amino acid sequence as shown in SEQ ID NO.: 66. In another preferred embodiment, the acceptor fluorophore fusion protein consists of ΔN17Q48+6PRD-YPet. A specific example of such a fusion protein has the amino acid sequence as shown in SEQ ID NO.: 68. In another preferred embodiment, the acceptor fluorophore fusion protein consists of ΔN17Q40+6PRD-YPet. A specific example of such a fusion protein has the amino acid sequence as shown in SEQ ID NO.: 70.

The aggregation assays mentioned above are preferably cell-free aggregation assays, i.e. no intact living cells are present in the assay.

Within the above-described uses, the inventors have surprisingly found that it is possible to obtain good results even when the sample to be assayed is a complex biosample. Thus, according to preferred embodiments, the above-described fusion proteins are used in an aggregation assay, wherein the aggregation assay involves monitoring mHTT seeding activity (HSA) in a complex biosample.

A "complex biosample" according to the invention is a sample that may comprise a variety of proteins and other factors. In particular, a complex biosample within the context of the invention is selected from the group consisting of optionally pretreated tissue samples, optionally pretreated body fluid samples and optionally pretreated cell culture samples. As described above, pretreatment can be effected by at least one of centrifugation, cell lysis, protein extraction, dialysis, sonication and similar procedures used in protein purification known to the skilled person. Pretreated tissue, body fluid or cell culture samples may, e.g., be selected from the group consisting of a homogenate, an extract, a pellet and a lysate. As indicated above, the pretreated sample may, in some embodiments and in addition to previous pretreatment steps, be sonicated.

More particularly, the complex biosample is selected from muscle tissue, homogenated muscle tissue, protein extracts from muscle tissue, nasal brushing, nasal epithelial tissue, full blood, homogenated blood, blood plasma, cerebrospinal fluid, cells, cell extracts, cell pellets, cell lysates, e.g. from a cell line, from stem cells, or from primary cell culture, brain homogenates, brain extracts that are optionally sonicated, and protein extracts from post-mortem tissue such as cerebral cortex, caudate nucleus and cerebellum.

The present invention further provides soluble protein constructs, which find application, e.g., in the methods and uses described herein. These protein constructs mandatorily comprise exon 1 of huntingtin with 48 glutamine residues (HTTEx1Q48), and, fused to the C-terminus of the HTTEx1Q48 sequence, a fluorophore, i.e. either CyPet or YPet. Optionally, glutathione S-transferase (GST) may be fused to the N-terminus of the HTTEx1Q48 sequence. HTTEx1Q48 particularly has the sequence shown in SEQ ID NO.: 2. CyPet particularly has the sequence as shown in SEQ ID NO.: 23. YPet particularly has the sequence as shown in SEQ ID NO.: 21. GST, if present, particularly has the sequence as shown in SEQ ID NO.: 6. Specific examples of these soluble protein constructs are mHTT Ex1Q48-YPet (SEQ ID NO.: 13), mHTT Ex1Q48-CyPet (SEQ ID NO.: 15), mHTT GST-Ex1Q48-YPet (SEQ ID NO.: 17) and mHTT GST-Ex1Q48-CyPet (SEQ ID NO.: 19).

The present invention further provides soluble protein constructs, which find application, e.g., in the methods and uses described herein, comprising mutant exon 1 of huntingtin with 40 or 48 glutamine residues and an adjacent modified PRD comprising 6 or more, preferably 6-20, consecutive proline residues (Q40Pn and Q48Pn proteins, respectively, with n representing the number of consecutive proline residues), and, fused to the C-terminus of the mutant exon sequence, a fluorophore, i.e. either CyPet or YPet. Optionally, glutathione S-transferase (GST) may be fused to the N-terminus of the mutant exon 1 sequence. A Q40P17 protein particularly has the sequence shown in SEQ ID NO.: 73 (ΔN17Q40+6PRD); a Q48P6 protein particularly has the sequence shown in SEQ ID NO.: 72 (ΔN17Q48+6PRD); a Q48P17 protein particularly has the sequence shown in SEQ ID NO: 71 (K2Q48P6). CyPet particularly has the sequence as shown in SEQ ID NO.: 23. YPet particularly has the sequence as shown in SEQ ID NO.: 21. GST, if present, particularly has the sequence as shown in SEQ ID NO.: 6. Specific examples of these soluble protein constructs are mHTT K2Q48P6-YPet (SEQ ID NO.: 66), mHTT K2Q48P6-CyPet (SEQ ID NO.: 65), mHTT GST-K2Q48P6-YPet (SEQ ID NO.: 50), mHTT GST-K2Q48P6-CyPet (SEQ ID NO.: 48), mHTT ΔN17Q48+6PRD-YPet (SEQ ID NO.: 68), mHTT ΔN17Q48+6PRD-CyPet (SEQ ID NO.: 67), mHTT GST-ΔN17Q48+6PRD-YPet (SEQ ID NO.: 54), mHTT GST-ΔN17Q48+6PRD-CyPet (SEQ ID NO.: 52), mHTT ΔN17Q40+6PRD-YPet (SEQ ID NO.: 70), mHTT ΔN17Q40+6PRD-CyPet (SEQ ID NO.: 69), mHTT GST-ΔN17Q40+6PRD-YPet (SEQ ID NO.: 58) and mHTT GST-ΔN17Q40+6PRD-CyPet (SEQ ID NO.: 56).

FIGURE LEGENDS

FIG. 1. Establishment of a FRET-based mutant HTT aggregate seeding assay (A) Time-dependent aggregation of Ex1Q48-CyPet and -YPet fusion proteins (3 μM) monitored by FRA (500 ng protein per dot). Immunblot, anti-GFP antibody.

(B) Analysis of spontaneously formed Ex1Q48-CyPet, Ex1Q48-YPet and Ex1Q48 aggregates by AFM (3 μM) after 24 h. Scale bars: 1 μm; color gradient represents 0-20 nm height.

(C) Schematic model of FRET-inducing co-aggregating Ex1Q48-CyPet and -YPet upon cleavage of GST fusion proteins with PSP.

(D) Spontaneous time-dependent co-aggregation of Ex1Q48-CyPet and -YPet sensor proteins (1:1 mixture) upon incubation of GST fusion proteins with PSP at 25° C. FRET efficiency is displayed as mean±SD of technical triplicates.

(E) Fibrillar Ex1Q48 aggregates (seeds) induce a concentration-dependent shortening of the lag phase in Ex1Q48-CyPet and -YPet (1:1 mixture, total conc. 1.2 μM) co-polymerization reactions. Seed concentrations are equivalent to monomer concentrations. FRET efficiency is displayed as mean±SD of technical triplicates.

(F) Quantification of mHTT seeding activities (HSAs, $\Delta t_{50}$ values) from aggregation profiles in E. $\Delta t_{50}$ is displayed as individual values (•) and mean±SD of technical triplicates.

Figure 2:
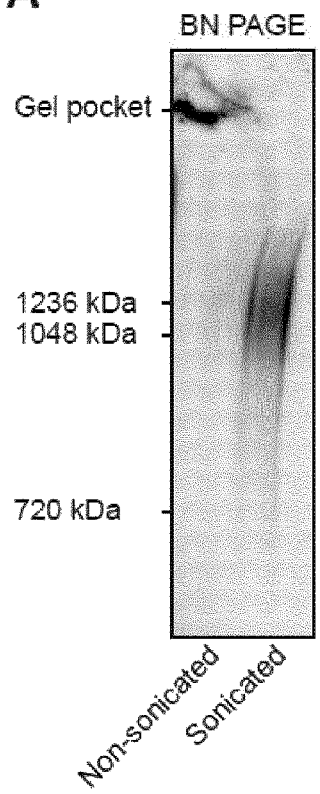
Figure 2:
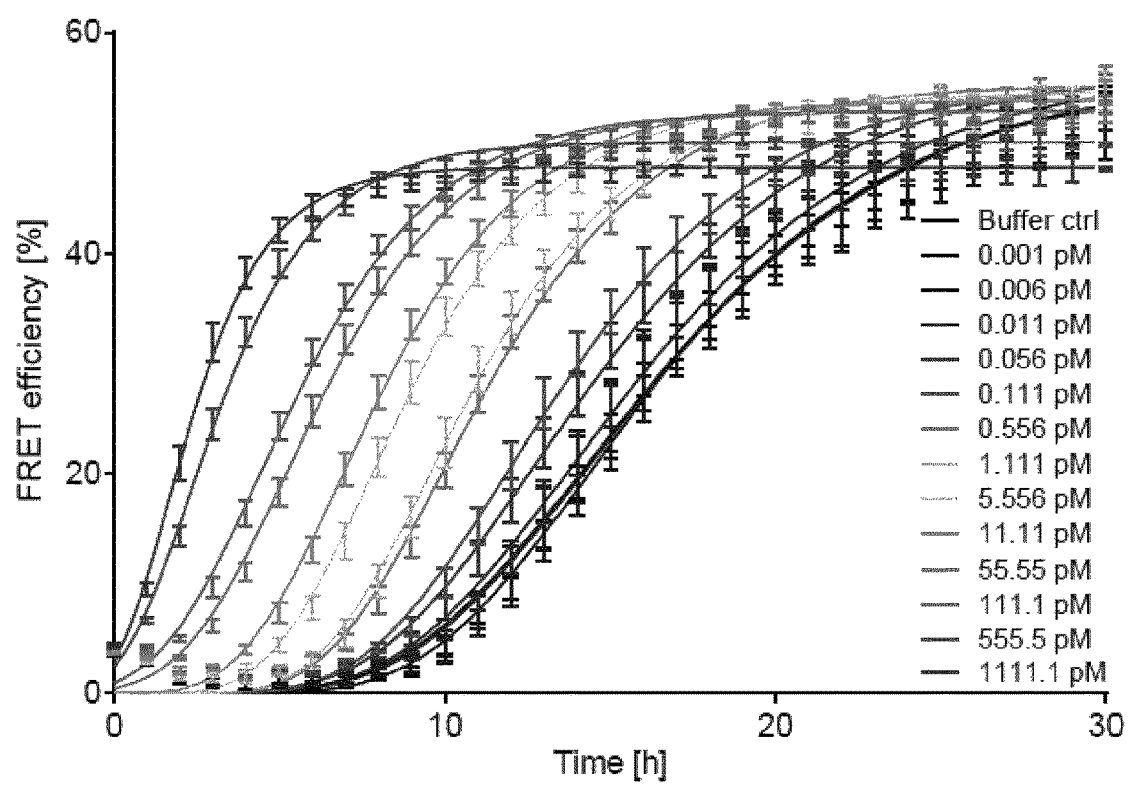
Figure 2:
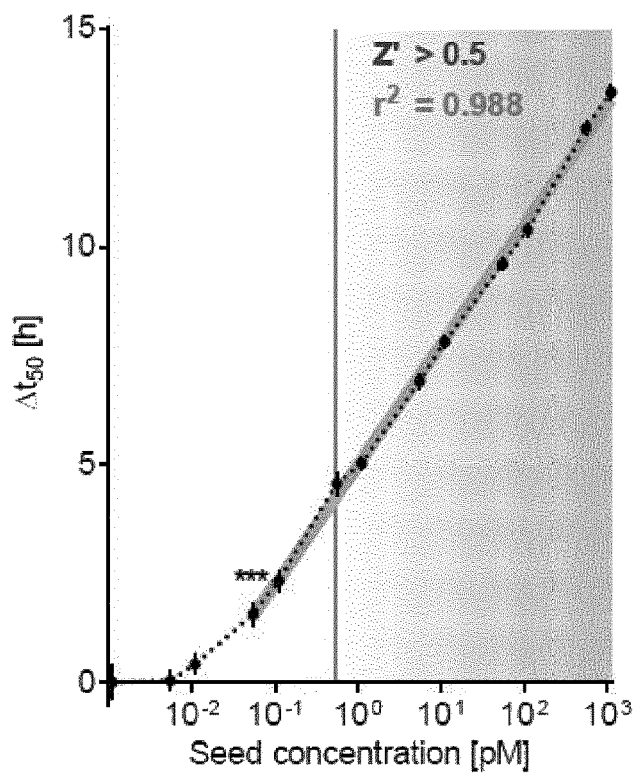
Figure 2:
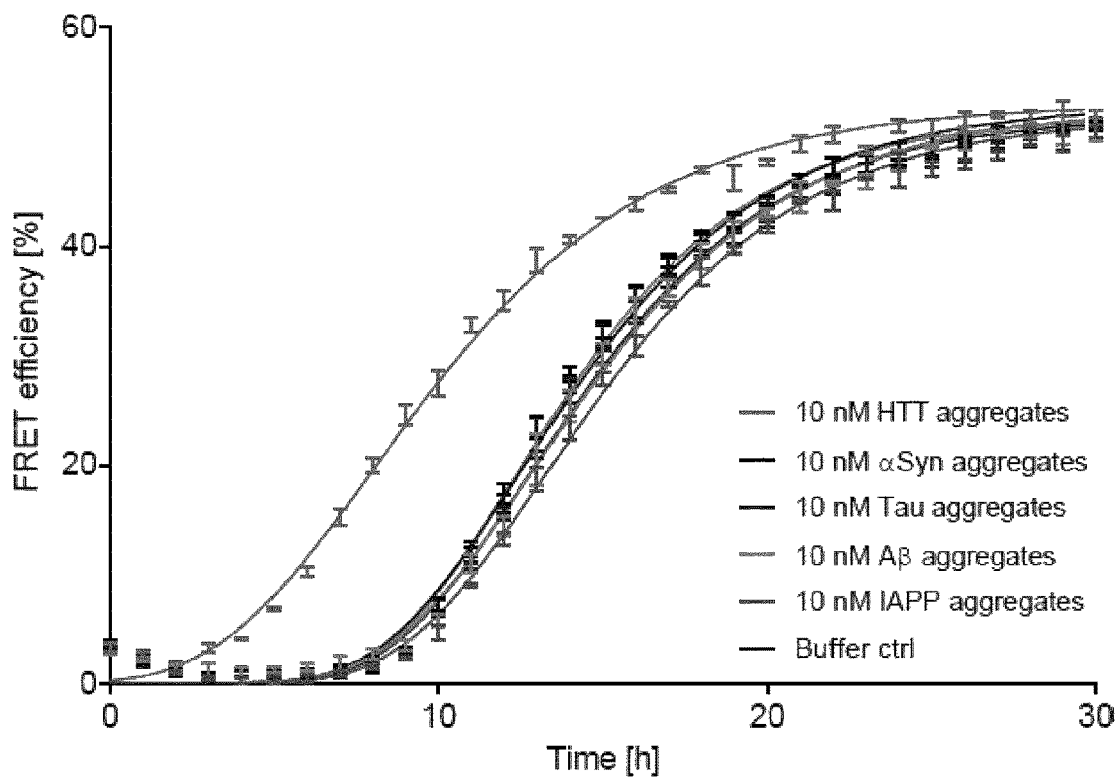
Figure 2:
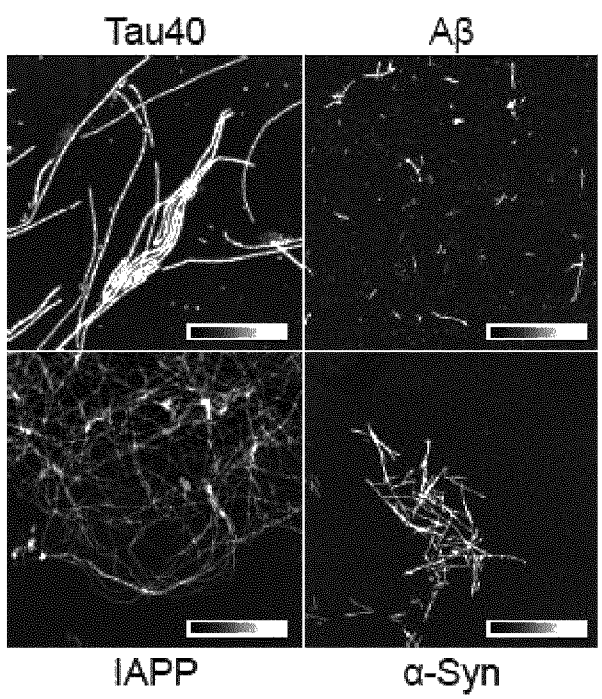

FIG. 2. FRASE assays facilitate detection of HSA with high specificity and sensitivity (A) Analysis of sonicated (1 min) and non-sonicated fibrillar Ex1Q48 aggregates by blue native (BN) PAGE and immunoblotting using HD1 antibody.

(B) Effects of small, preformed Ex1Q48 seeds (1250 kDa) on Ex1Q48-CyPet and -YPet (1:1 mixture, total conc. 1.2 μM) co-aggregation. Data are mean±SEM (n=5).

(C) Calculation of HSAs ($\Delta t_{50}$ values) from aggregation profiles in B. Data are mean±SEM (n=5).

(D) Effects of non-polyQ fibrils on Ex1Q48-CyPet and -YPet (1:1 mixture, total conc. 1.2 μM) co-aggregation. Data are mean±SD of triplicates.

(E) Analysis of α-synuclein (α-Syn), amyloid-β42 (Aβ), islet amyloid polypeptide (IAPP) and Tau (Tau40) fibrils by AFM. Scale bars: 1 μm; Height of color gradients: 0-10 nm (α-Syn), 0-5 nm (Aβ), 0-30 nm (IAPP) and 0-10 nm (Tau40).

Figure 3:
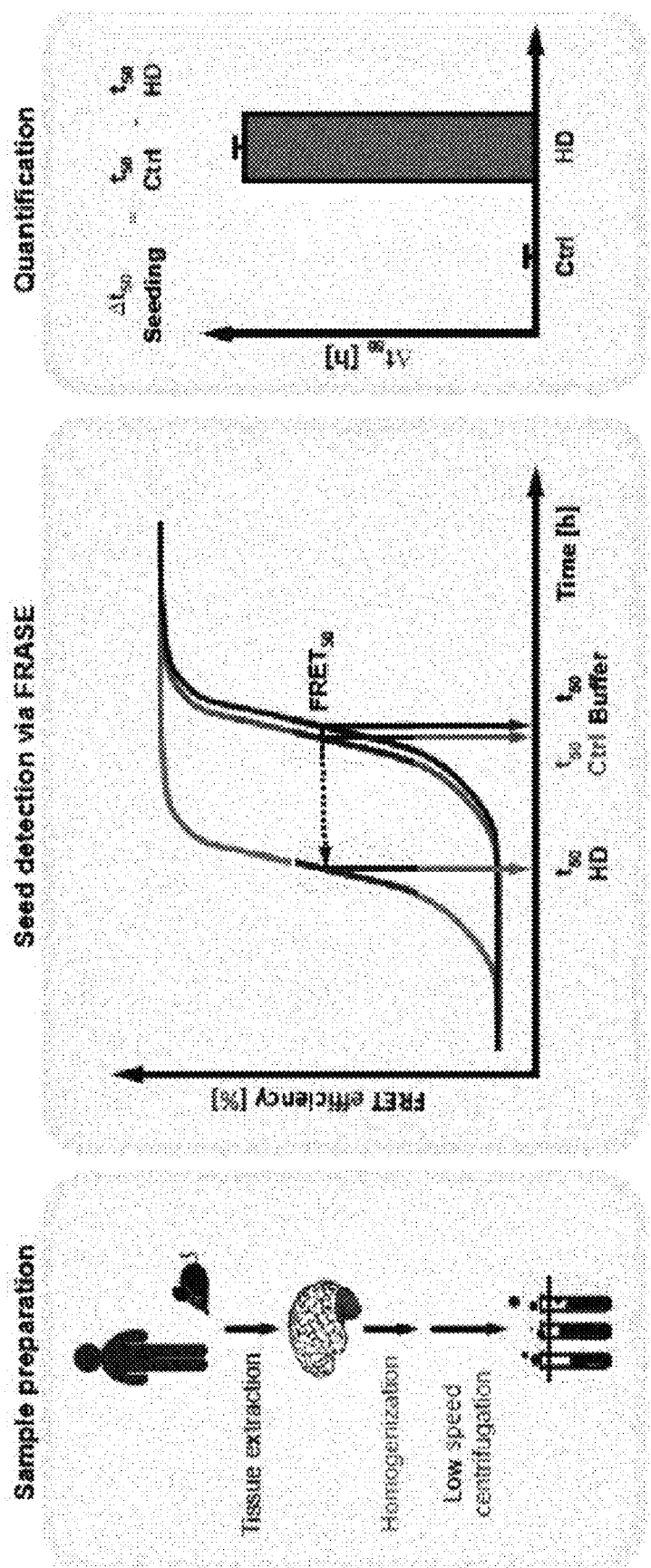
Figure 3:
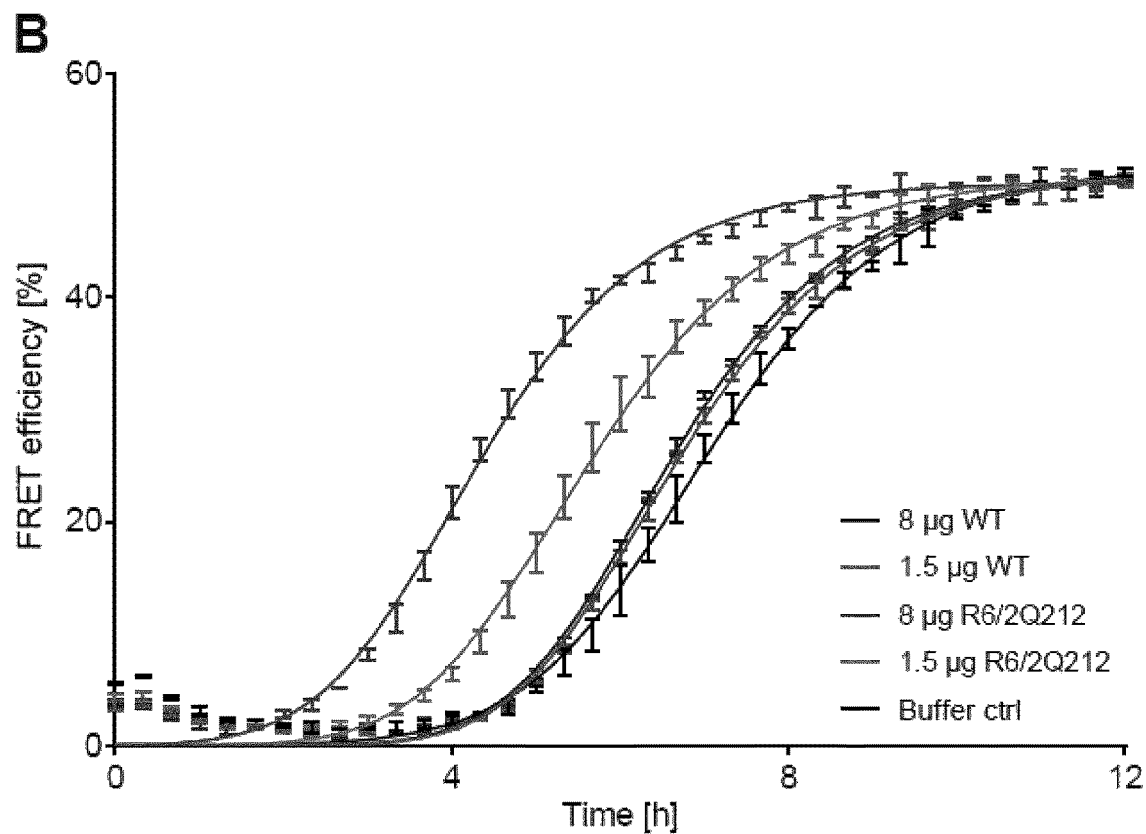
Figure 3:
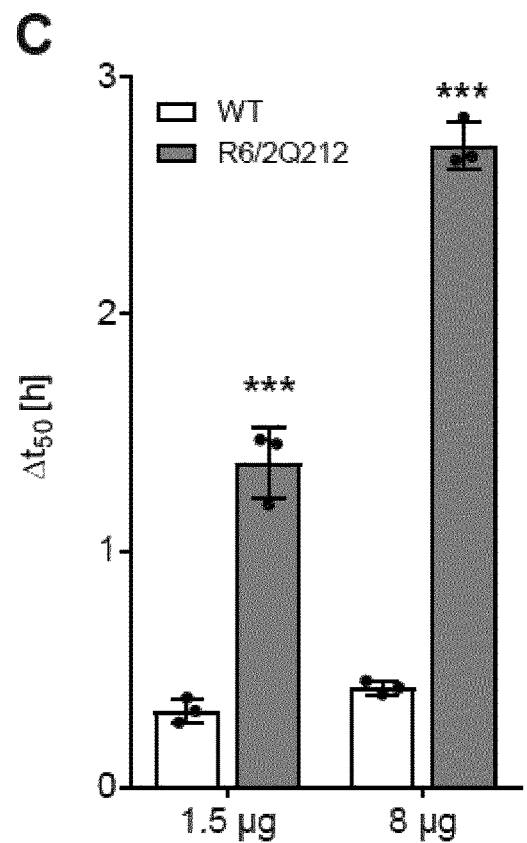
Figure 3:
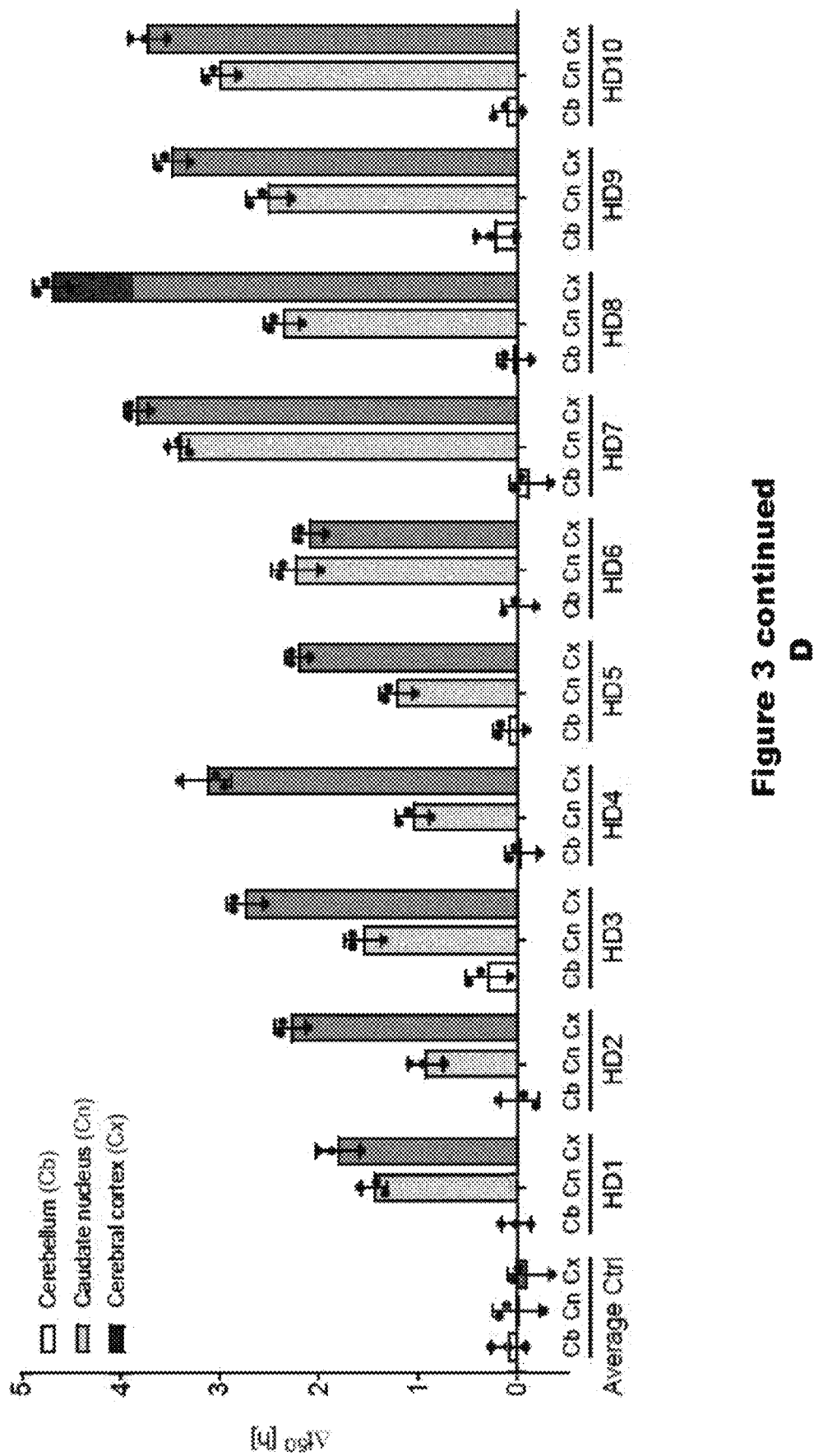
Figure 3:
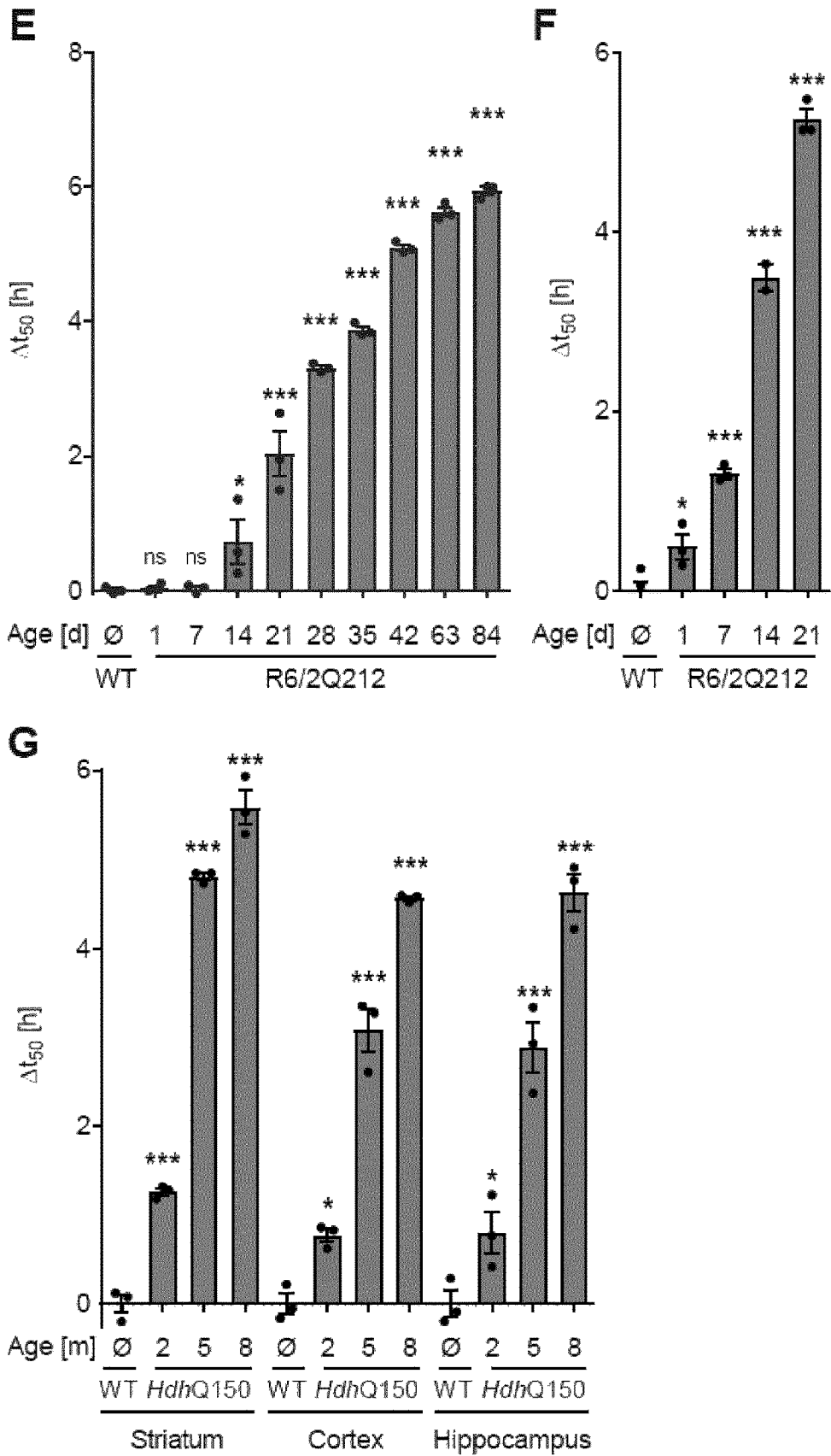

FIG. 3. Quantification of HSA in brain extracts of patients and HD mice (A) Schematic workflow for quantifying HSA in brain tissue homogenates.

(B) Effects of mouse brain homogenates on Ex1Q48-CyPet and -YPet (1:1 mixture, total conc. 3 μM) co-aggregation. Data are mean±SD of technical triplicates.

(C) HSA ($\Delta t_{50}$ values) of mouse brain extracts investigated in B. Statistical analysis: two-way ANOVA followed by Bonferroni's multiple comparison post hoc test against the respective WT controls. $\Delta t_{50}$ is displayed as individual values (•) and as mean±SD of technical triplicates.

(D) Quantification of HSA in brain homogenates prepared from HD patients and controls. For clarity, the average $\Delta t_{50}$ values obtained from 3 healthy control samples are depicted (Average Ctrl). Individual values of $\Delta t_{50}$ (•) and mean±SD of triplicates are displayed.

(E) Quantification of HSA in brain extracts of presymptomatic R6/2Q212 and wild-type (WT) control mice (3 mice per age). Results from WT mice are shown as an average $\Delta t_{50}$ value.

(F) Quantification of HSA in brain extracts of presymptomatic R6/2Q212 and wild-type (WT) control mice after sonication. Results from WT mice are shown as an average $\Delta t_{50}$ value.

(G) Quantification of HSA in brain tissue extracts of HdhQ150 heterozygous knock-in and WT mice. Data are mean±SEM (n=3). One-Way ANOVA followed by Dunnett's multiple comparisons test.

Figure 4:
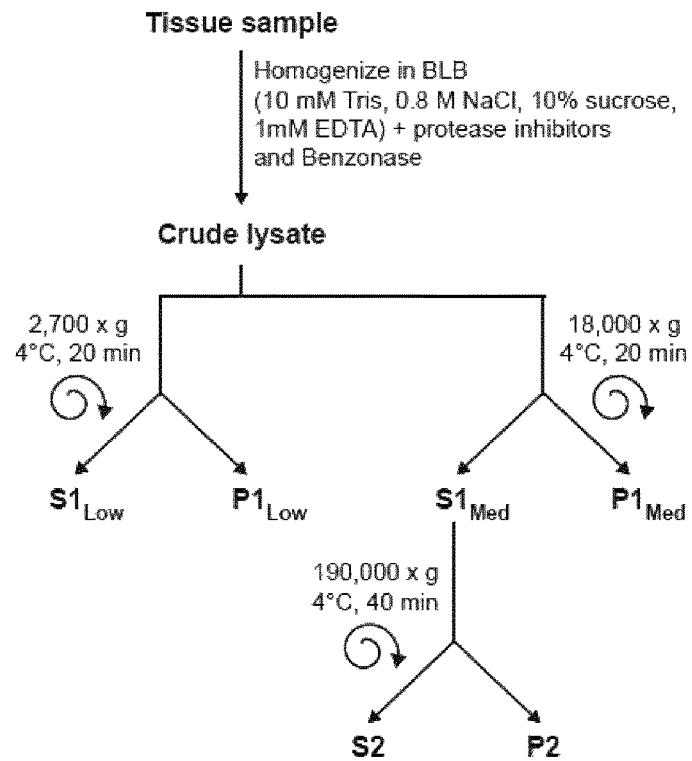
Figure 4:
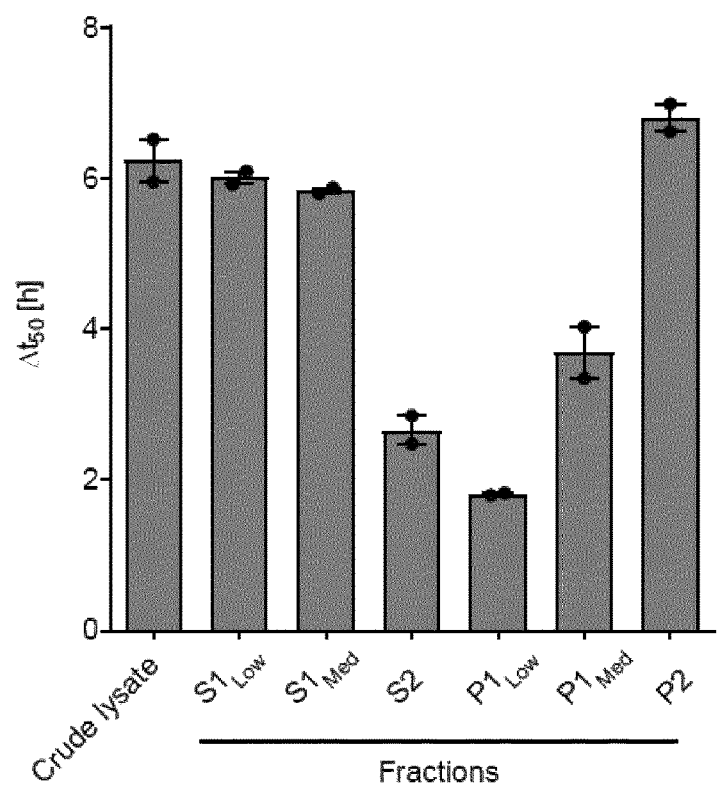
Figure 4:
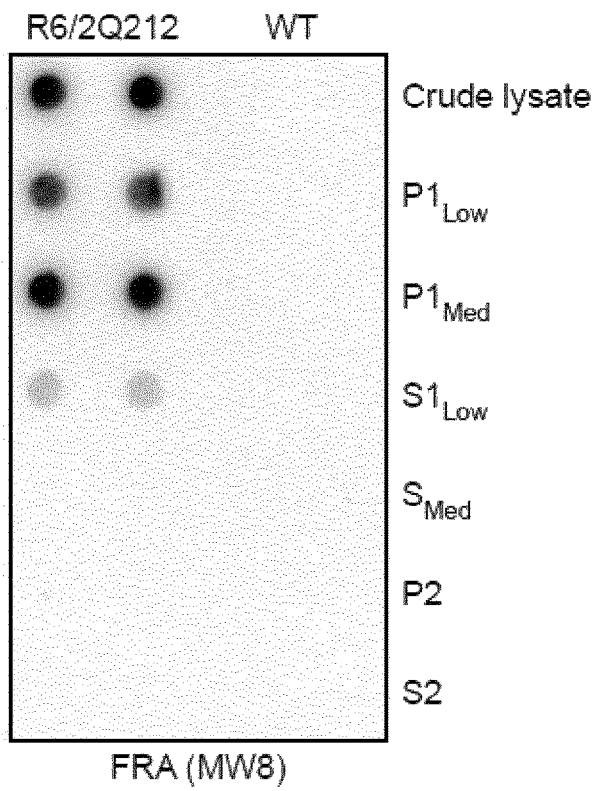
Figure 4:
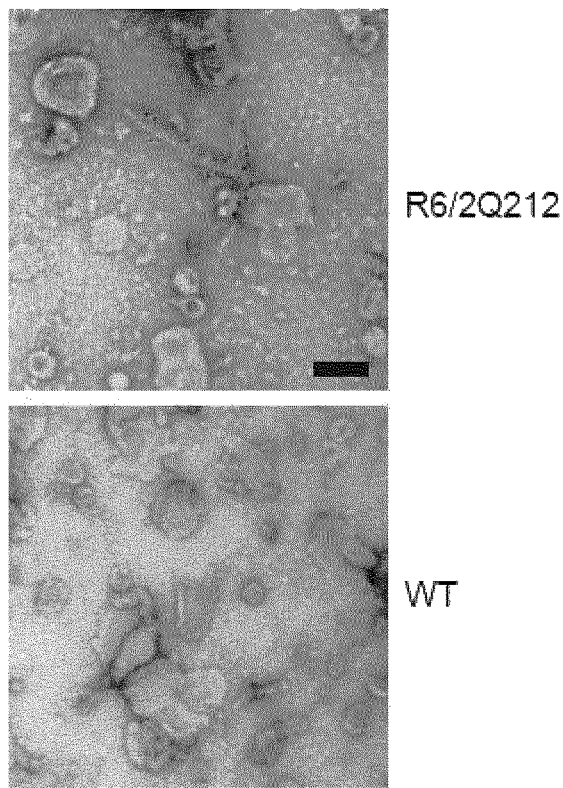

FIG. 4. Detection of small HTTex1 fibrils in soluble brain fractions with high HSA (A) Schematic workflow for preparing soluble and insoluble protein fractions from crude tissue homogenates by centrifugation.

(B) Quantification of HSA in soluble and insoluble fractions prepared from brains of R6/2Q212 transgenic mice. In all cases, data were normalized to average $\Delta t_{50}$ values of age-matched WT control mice. Bars are mean±SEM (n=2). HSAs measured for individual mice are displayed as black dots (•).

(C) Detection of large, SDS-stable fibrillar mHTTex1 aggregates in prepared protein fractions by FRA.

(D) Detection of small, fibrillar HTTex1 aggregates in P2 fractions of R6/2Q212 mice by immunoelectron microscopy using the anti-HTT antibody Agg53. Scale bar: 100 nm.

Figure 5:
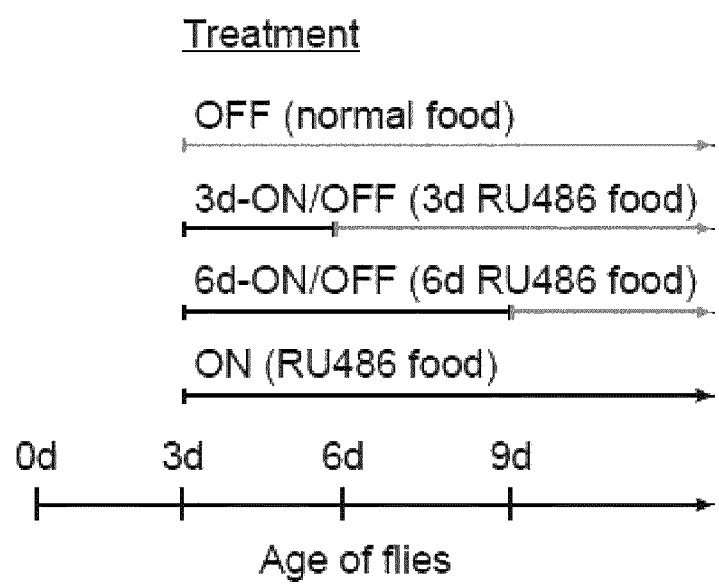
Figure 5:
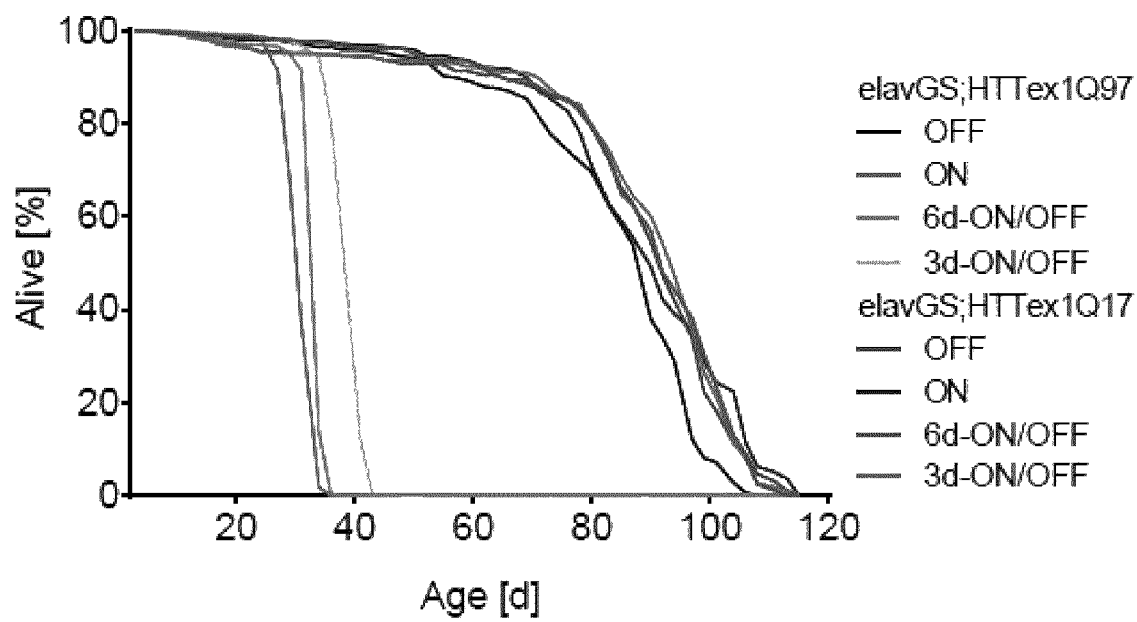
Figure 5:
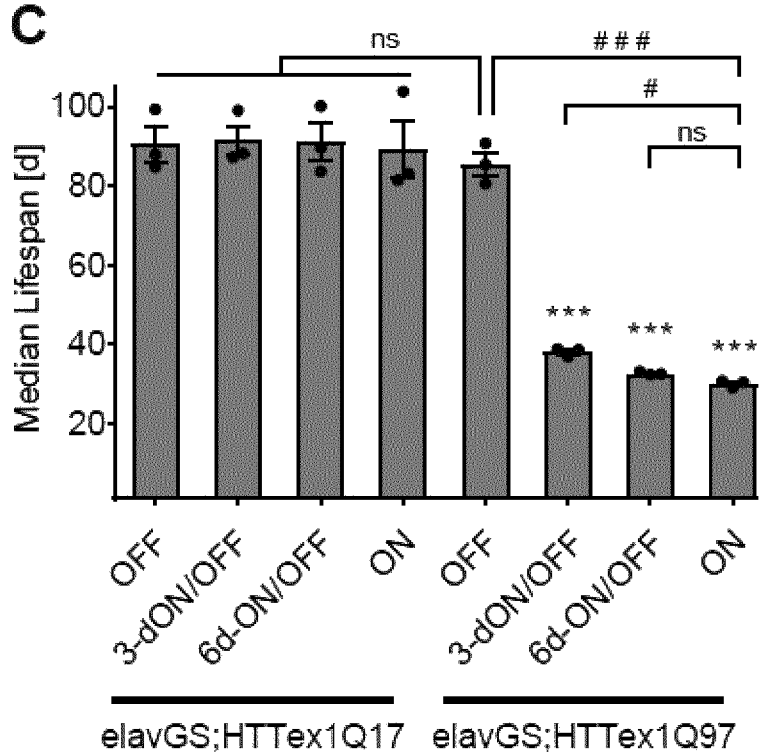
Figure 5:
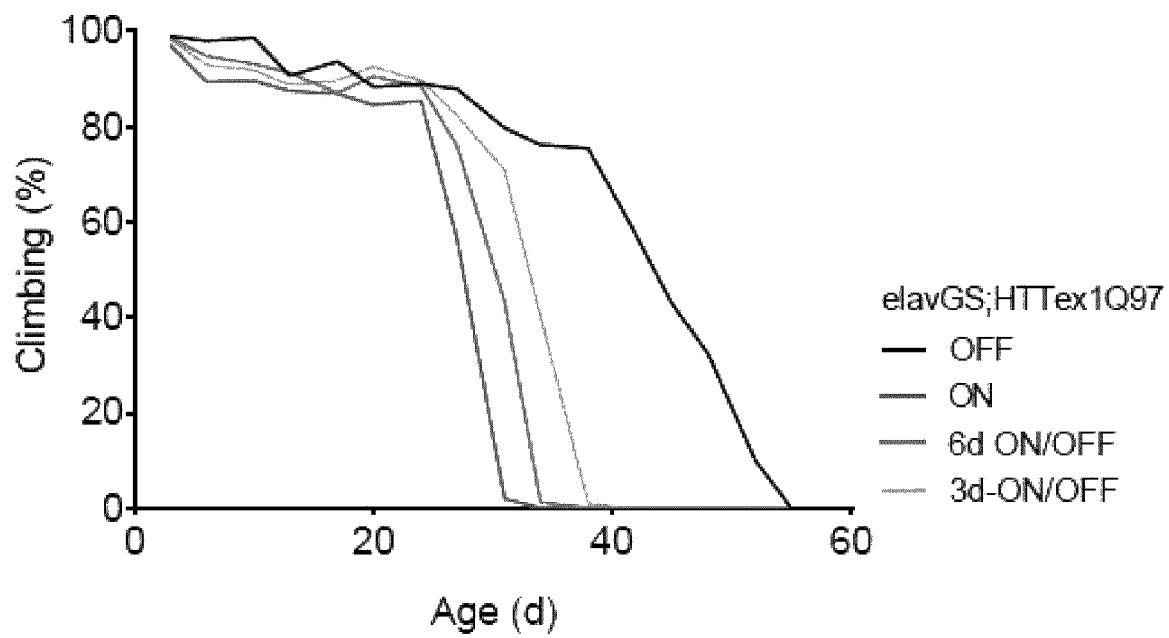
Figure 5:
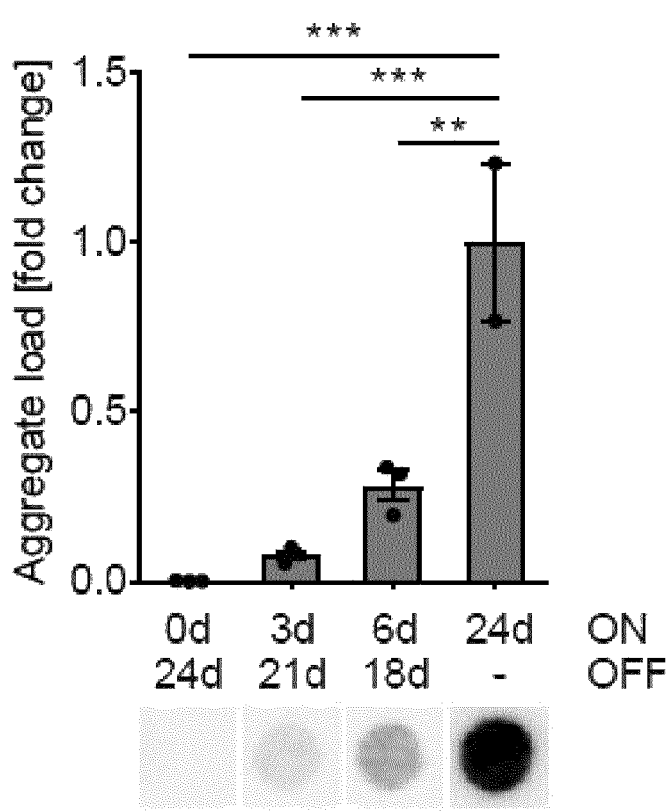
Figure 5:
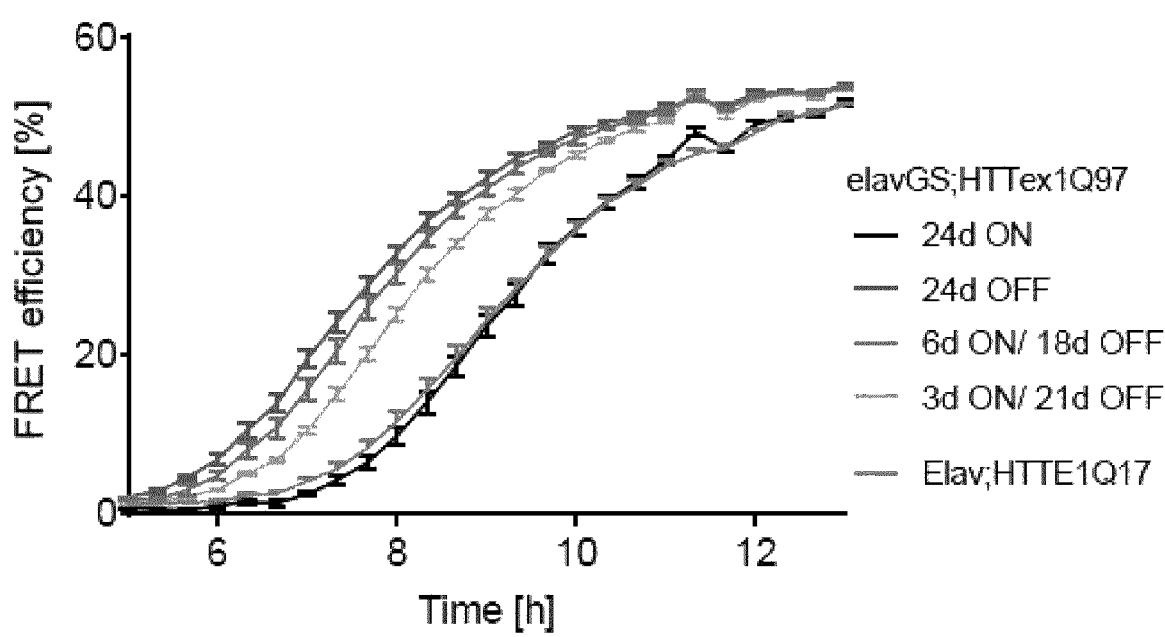
Figure 5:
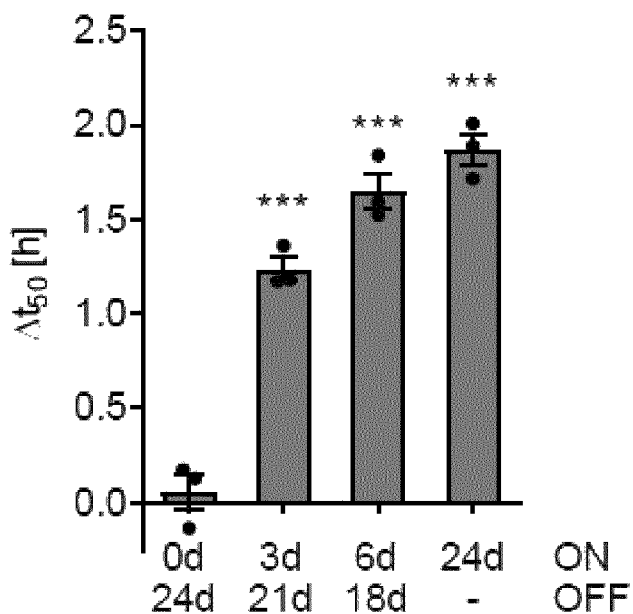
Figure 5:
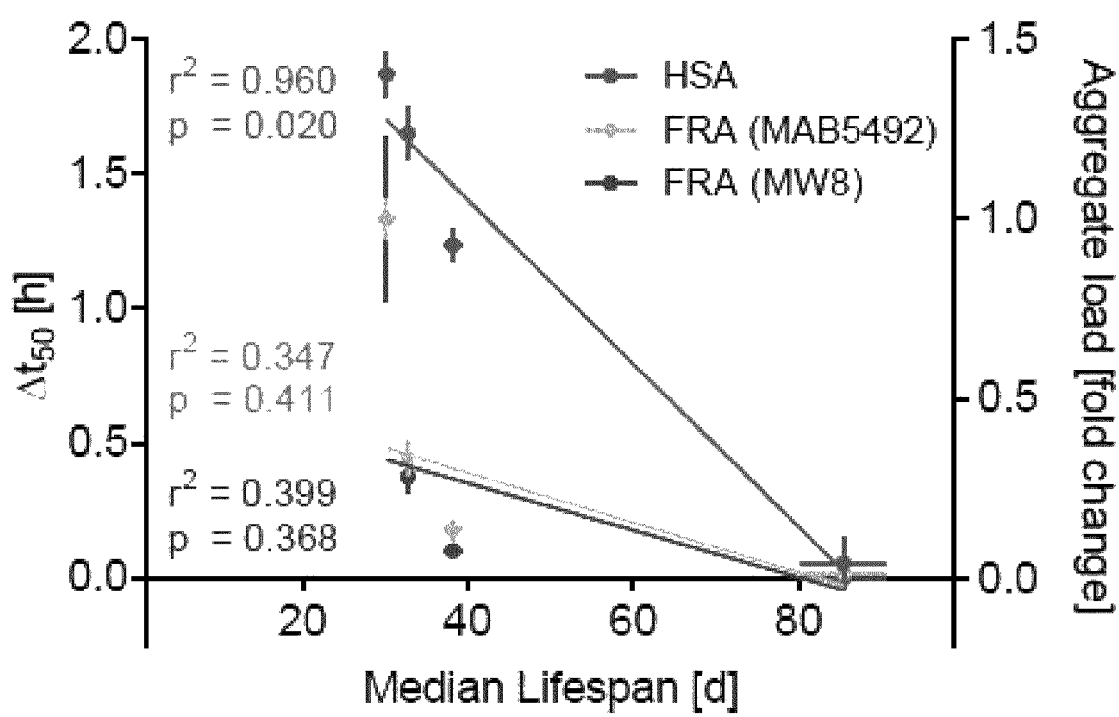

FIG. 5. The short-term HTTex1Q97 expression-induced decrease in *Drosophila* lifespan correlates with HSA but not with aggregate load in general (A) Scheme for short- and long-time RU486 treatment of adult HD transgenic flies.

(B) Survival of RU486 treated and untreated elavGS; HTTex1Q97 and elavGS;HTTex1Q17 flies (n=~100 flies/group). Survival was plotted as the percentage of surviving flies of 3 biological replicates.

(C) Median life span calculated from survival curves in B. Average survival of each experiment (n=~100 flies/group) is presented as black dots (•). Bars are mean±SEM from 3 independent experiments; One-way ANOVA Dunnett's post-hoc test; data were compared to elavGS; HTTex1Q97$^{OFF}$ transgenic flies [statistically significant differences are indicated by asterisks (*)] or to elavGS; HTTex1Q97$^{ON}$ flies [statistically significant differences are indicated by hashtags (#)].

(D) Analysis of motor performance of RU486 treated and untreated elavGS;HTTex1Q97 flies (n=~100 flies/group; three independent experiments).

(E) Detection of large, SDS-stable fibrillar HTTex1 aggregates in heads of RU486 treated and untreated elavGS; HTTex1Q97 flies by FRA using the MW8 antibody. Representative images for each condition are shown. Data are mean±SEM of individual measurements (•); One-way ANOVA Dunnett's post hoc test.

(F) FRASE analysis of head lysates analyzed in E. Values are means±SEM of three biological replicates each performed in triplicates.

(G) Quantification of HSA ($\Delta t_{50}$ values) from FRET-based aggregation profiles depicted in F. Results are displayed as mean±SEM; individual measurements (•); One-way ANOVA Dunnett's post hoc test compared to elavGS;HTTex1Q97$^{OFF}$ flies.

(H) Pearson correlation analysis shows a significant linear relationship between the survival of RU486 treated and untreated elavGS;HTTex1Q97 flies and the HSA measured by FRASE assays (p=0.020). No such correlation was observed between fly survival and the abundance of large, fibrillar HTTex1Q97 aggregates detected by FRAs [p=0.368 (FRA, MAB5492), p=0.411 (FRA, MW8)]. Data are presented as mean±SEM of the three independent experiments.

Figure 6:
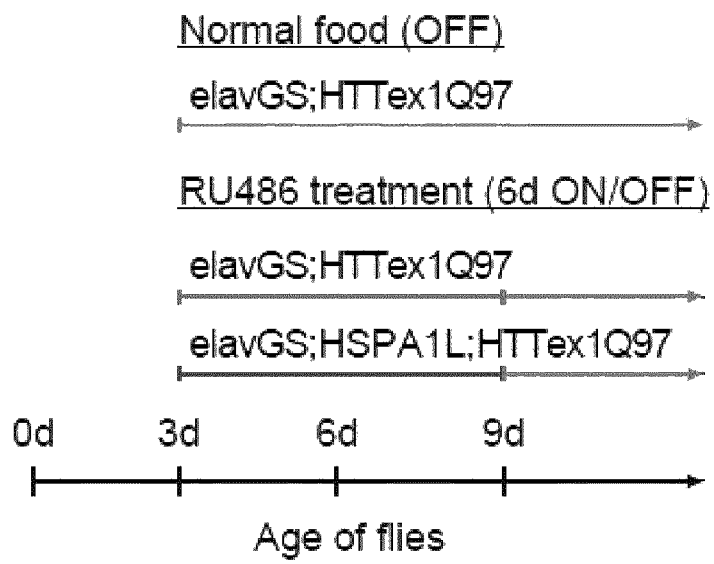
Figure 6:
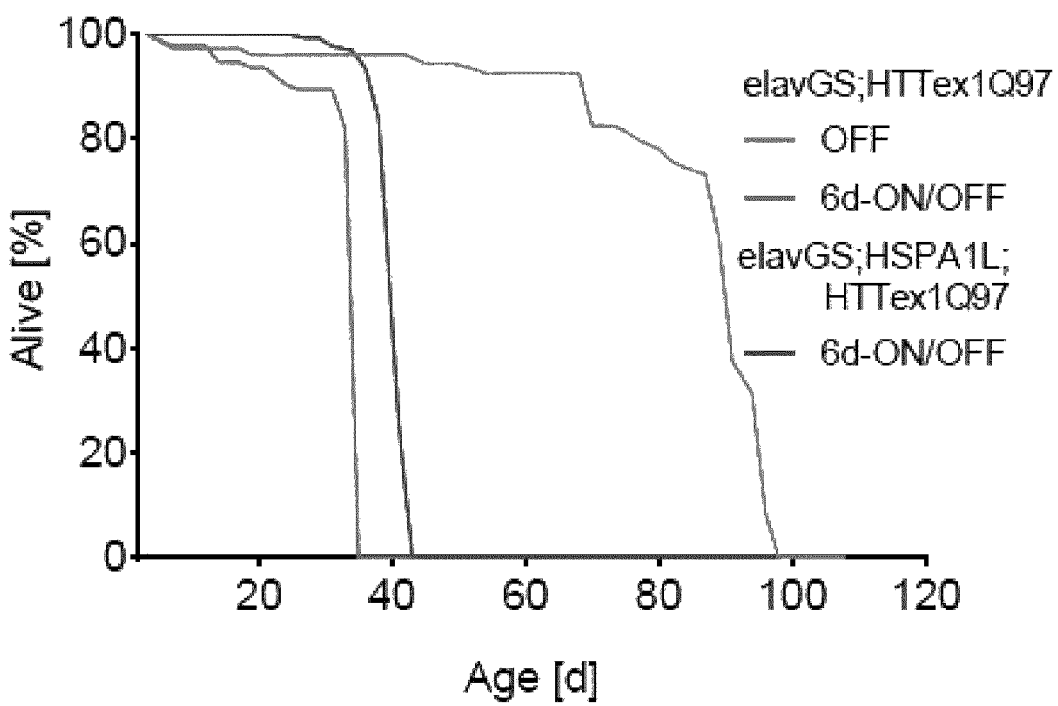
Figure 6:
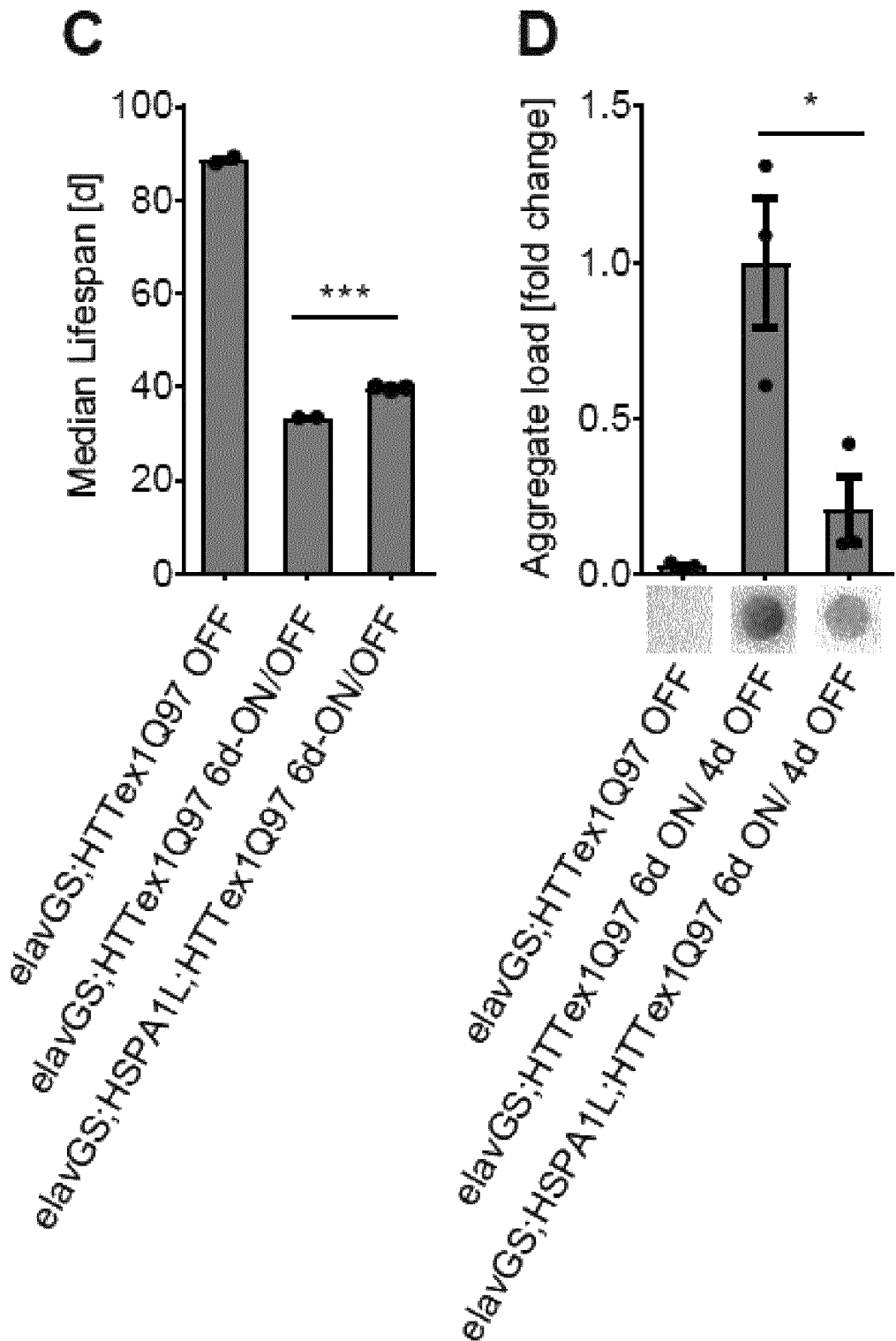
Figure 6:
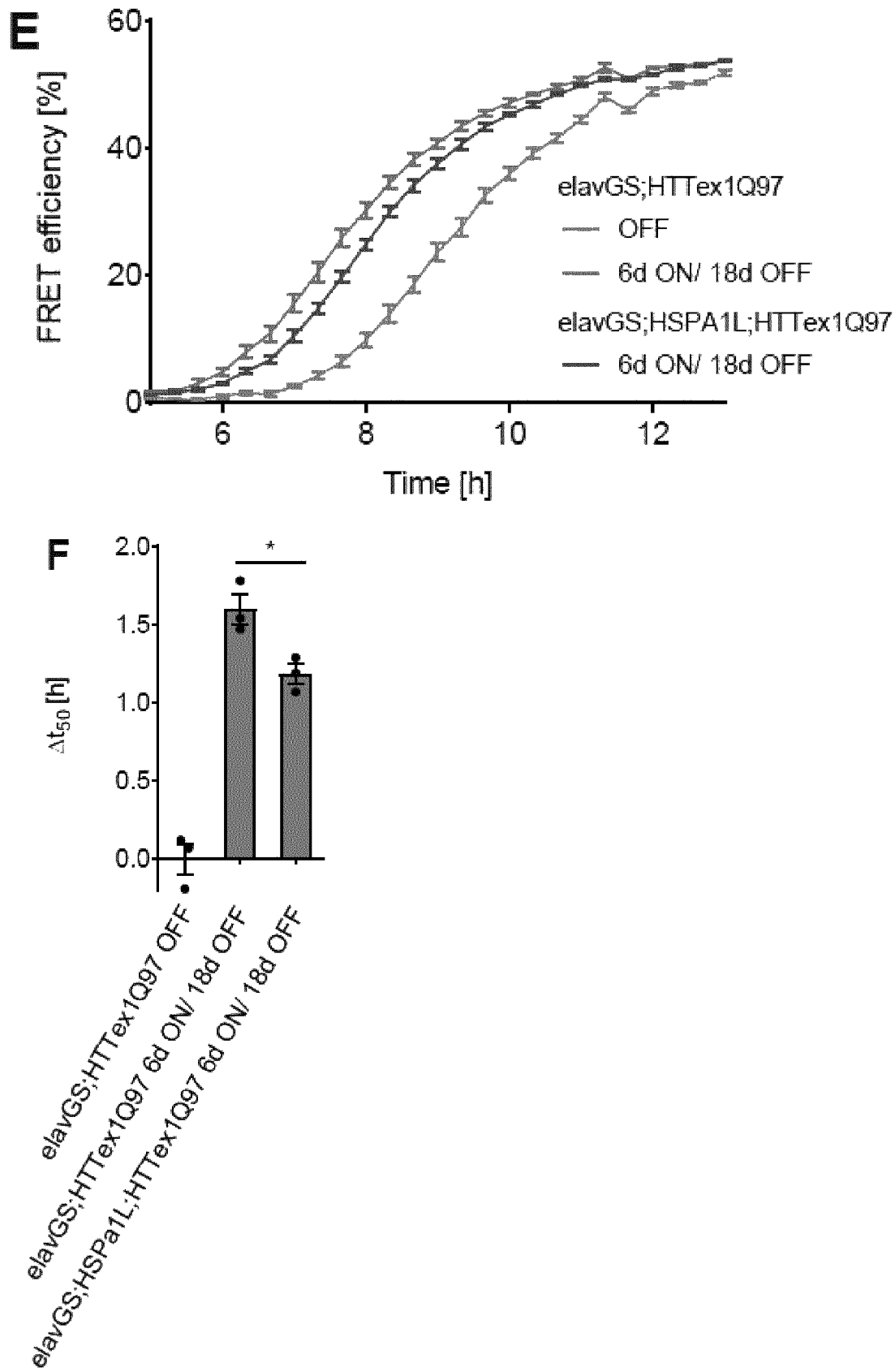
Figure 6:
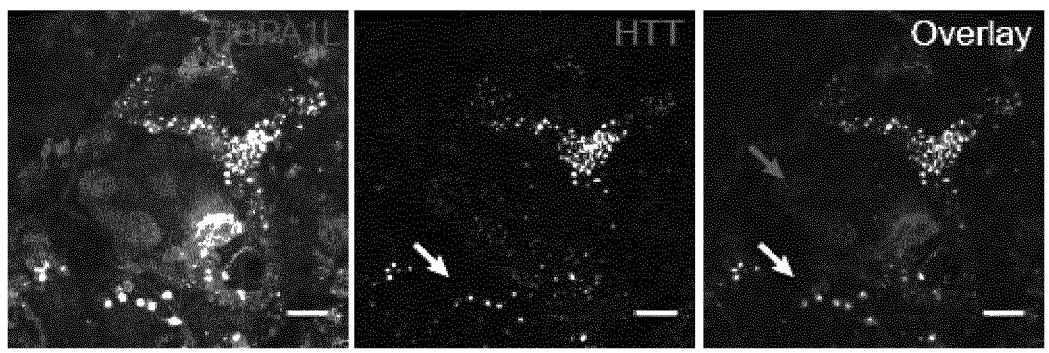

FIG. 6. Co-production of Hsp70 extends survival of HD flies (A) Scheme depicting the workflow for the temporary treatment of HD transgenic flies with RU486.

(B) Life span analysis of short-time RU486 treated elavGS;HSPA1L;HTTex1Q97 flies (n=~90 flies/group). In control experiments, hormone-treated and untreated elavGS; HTTex1Q97 (n=~40 flies/group) were analyzed. The percentage of surviving flies of three biological replicates are shown.

(C) Median life span calculated from survival curves in B. Bars are mean±SEM from three independent replicates; Unpaired t test.

(D) Quantification of large, SDS-stable HTTex1Q97 aggregates in fly heads by FRAs using the MW8 antibody. Representative images for each condition are shown. Data are mean±SEM; Individual measurements are presented as dots (•); Unpaired t-test.

(E) FRASE analysis of fly head lysates. Values are plotted as mean±SEM of 3 biological replicates each performed in triplicates.

(F) Quantification of HSA from FRET-based aggregation profiles in E. Data are mean±SEM; Individual measurements (•); Unpaired t test.

(G) Representative confocal images of the right central brain region of elavGS;HSPA1L;HTTex1Q97 flies treated for 6 days with RU486 and immunostained for HTT (Mab5492, green) and Hsp70 (anti-HSP70/HSP72, red). White arrows indicate co-localization of Hsp70 with HTTex1 aggregates; grey arrow indicates areas with no co-localization. Scale bars: 20 µm.

Figure 7:
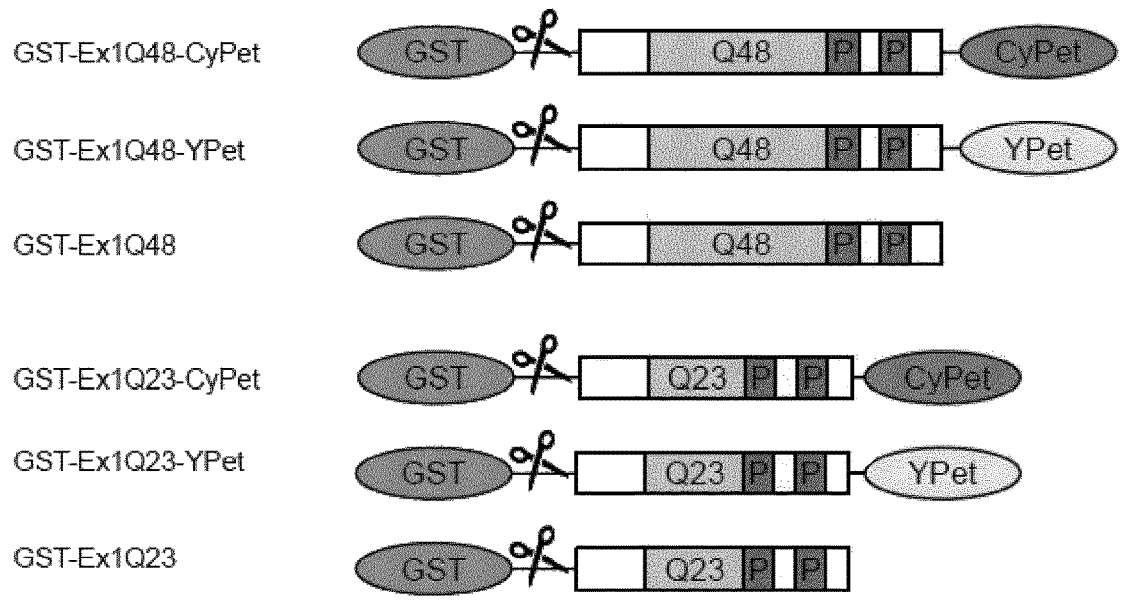
Figure 7:
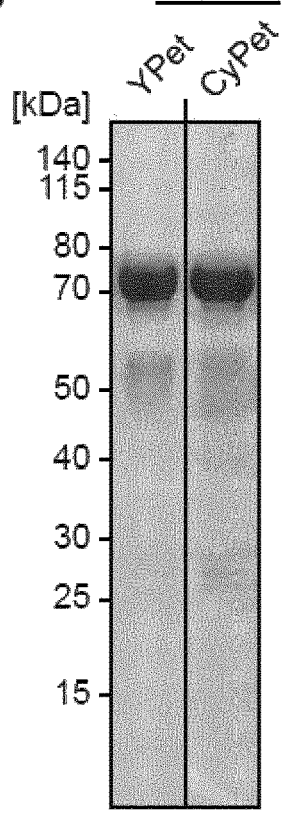
Figure 7:
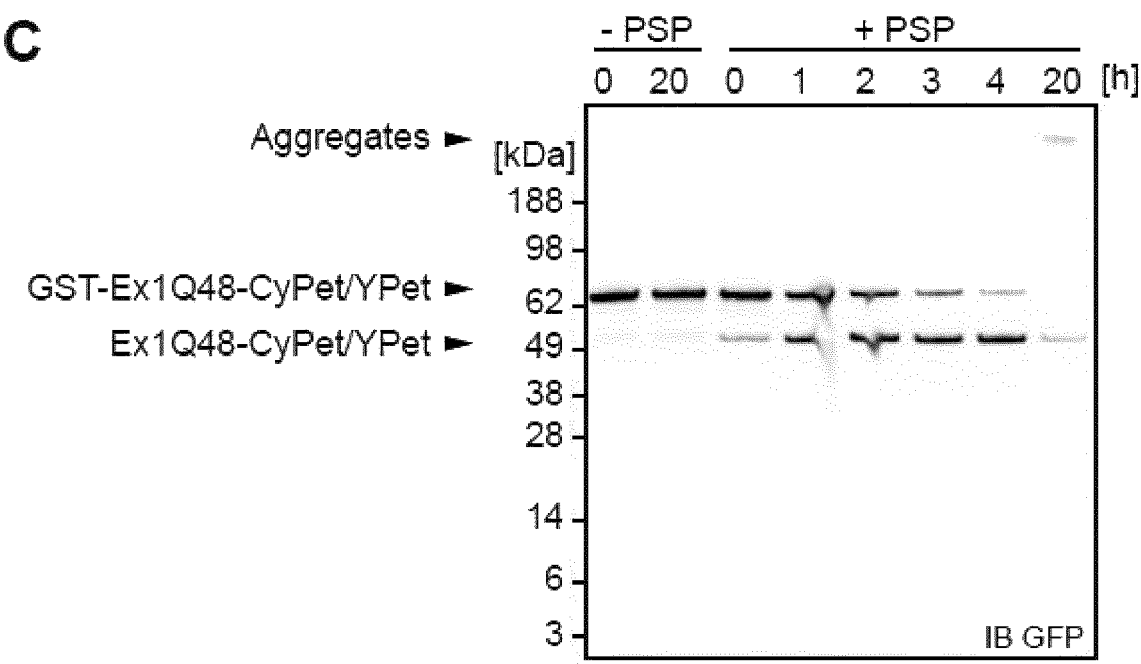
Figure 7:
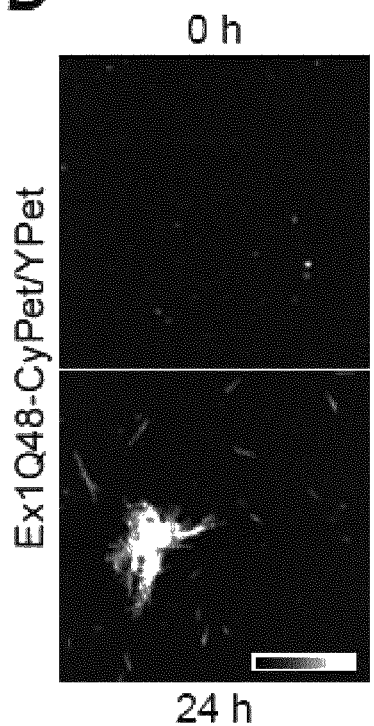
Figure 7:
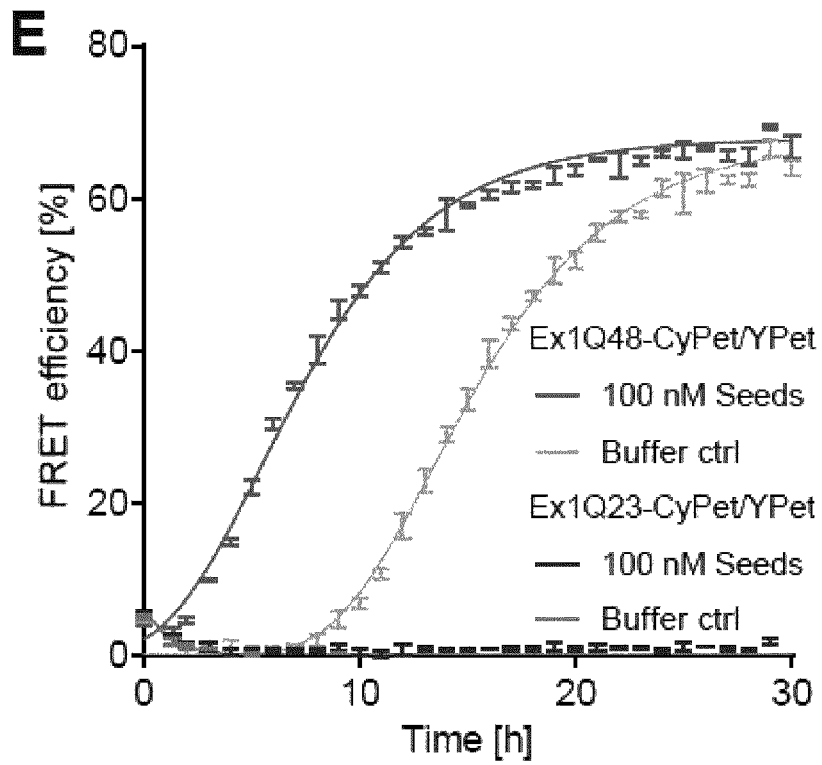
Figure 7:
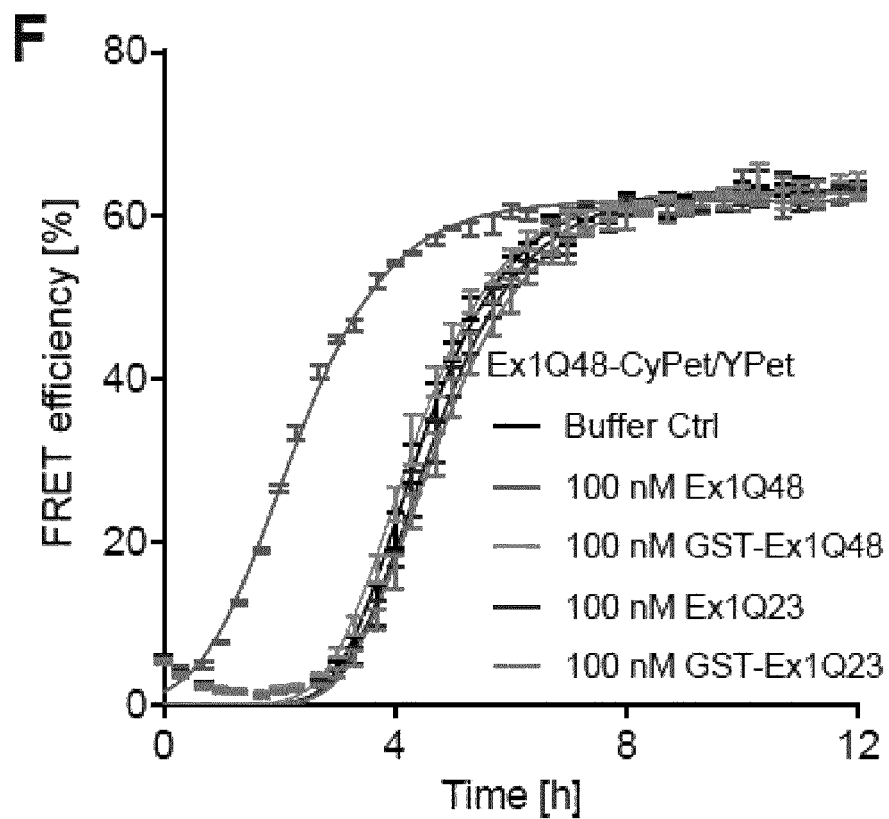

FIG. 7. Characterization of HTTex1 sensor proteins (A) Schematic representation of the applied GST-tagged HTTex1 fusion proteins with pathogenic and non-pathogenic polyQ tracts. P, proline-rich regions. (B) The recombinant GST-Ex1Q48-CyPet and -YPet fusion proteins were affinity purified using glutathione-coated sepharose beads. Purity was assessed by SDS-PAGE and subsequent Coomassie blue staining. (C) Investigation of PreScission protease (PSP)-mediated cleavage of GST-Ex1Q48-CyPet and -YPet fusion proteins. 3 µM of GST fusion proteins were incubated in the presence or absence of PSP. Aliquots were taken at the indicated time points; cleavage was confirmed by SDS-PAGE and immunoblotting with a polyclonal anti-GFP antibody. (D) AFM analysis of co-aggregated sensor proteins Ex1Q48-CyPet/-YPet (3 µM). Scale bar: 1 µm; color gradient represents 0-20 nm height. (E) Preformed, fibrillar Ex1Q48 aggregates (seeds) shorten the lag phase of Ex1Q48-CyPet/-YPet polymerization; no seeding effect was observed with the sensor proteins Ex1Q23-CyPet/-YPet. Seeds were produced by incubating GST-Ex1048 fusion protein with PSP for 24 h at 25° C. Indicated seed concentrations are equivalent to monomer concentrations. Co-aggregation of the sensor proteins (1:1 mixture; 1.2 µM) was monitored by quantification of FRET; the resulting aggregation kinetics were curve fitted by non-linear regression. FRET efficiency is plotted as means±SD of 3 technical replicates. (F) Ex1Q48-CyPet/-YPet (1:1 mixture; 3 µM) sensor protein co-aggregation was accelerated by addition of preformed fibrillary Ex1Q48 seeds. Ex1Q23 protein was prepared under identical conditions (no fibrillar aggregates observed; data not shown). Co-aggregation of sensor proteins was not influenced by the addition of uncleaved GST-Ex1Q48 or GST-Ex1Q23 fusion proteins, respectively. Co-aggregation of the fluorescence sensor proteins was monitored by quantification of FRET; the resulting aggregation kinetics were curve fitted by non-linear regression.

Indicated seed concentrations are equivalent to monomer concentrations. Data is shown as means±SD of 3 technical replicates.

Figure 8:
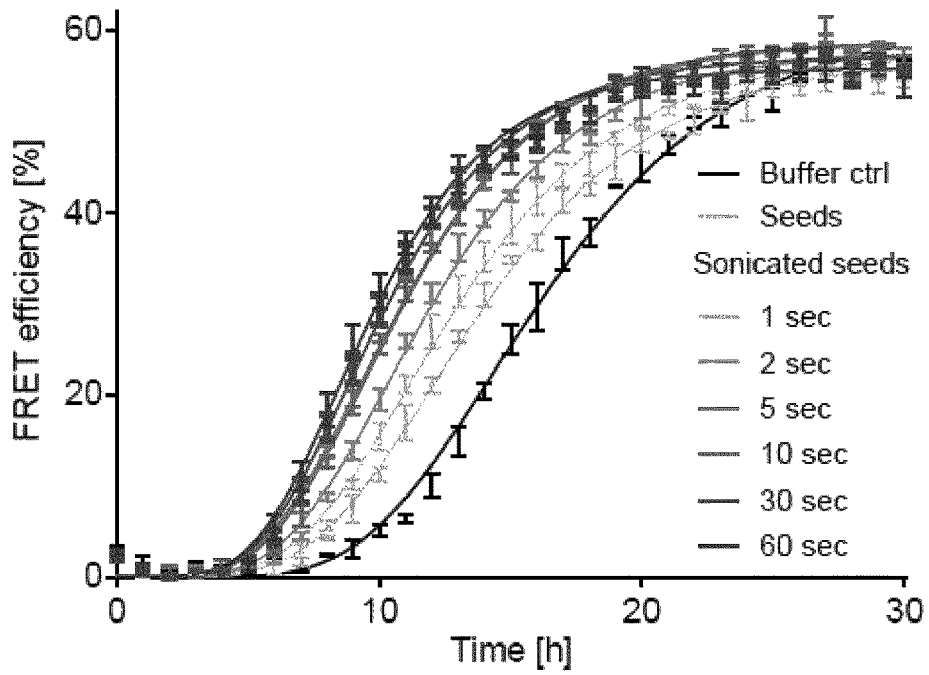
Figure 8:
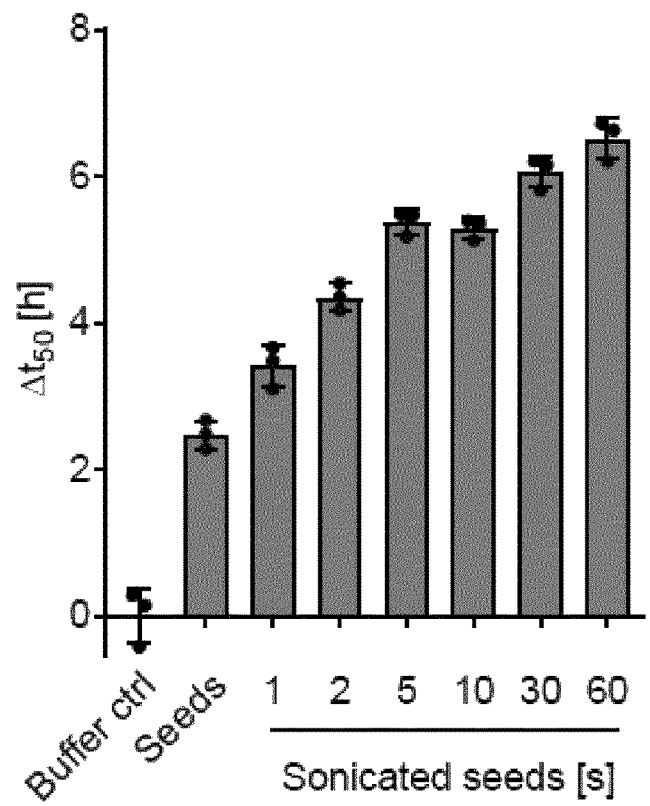
Figure 8:
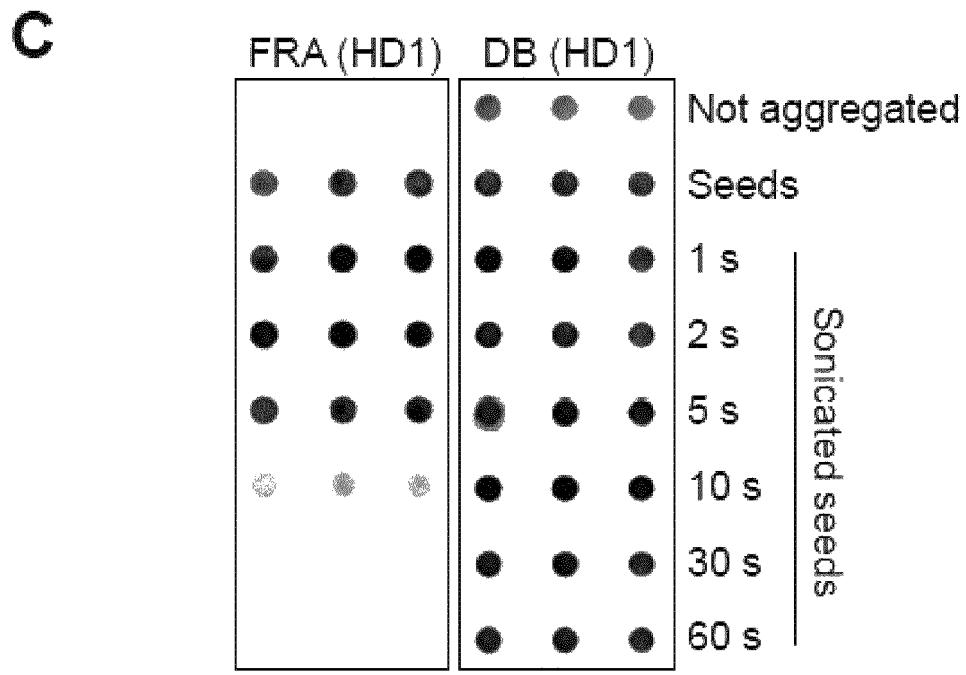
Figure 8:
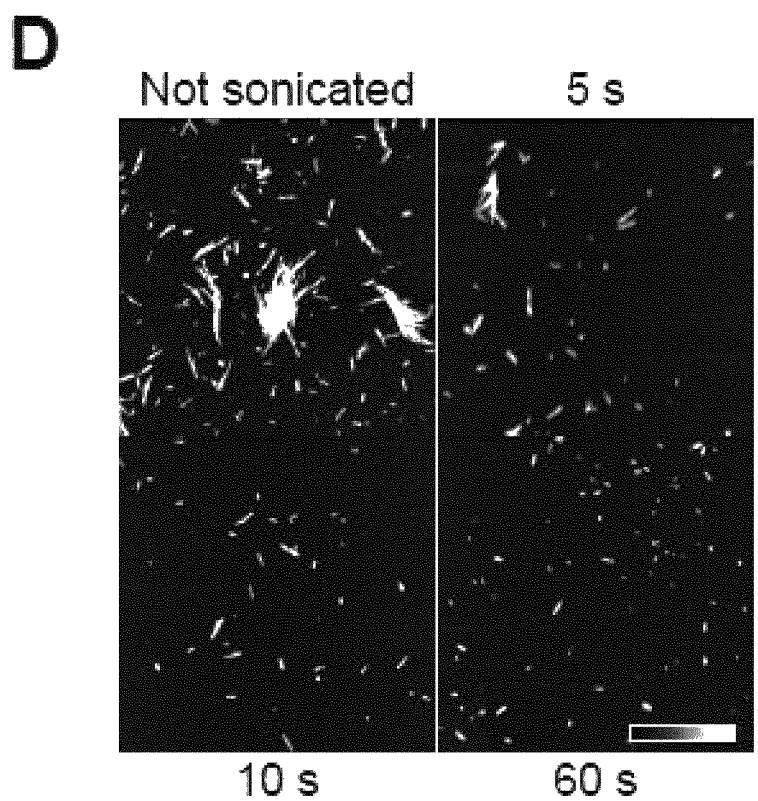

FIG. 8. Both small and large fibrillar Ex1Q48 aggregates exhibit seeding activity in FRASE assays (A) Sonication of preformed, fibrillar Ex1Q48 aggregates reveals protein fractions with high HSA in FRASE assays. Fibrillar Ex1Q48 aggregates were produced by incubating GST-Ex1Q48 fusion protein (2 µM) for 24 h at 25° C. 1 nM preformed Ex1Q48 aggregates (seeds) were added to Ex1Q48-CyPet/-YPet (1:1 mixture; 1.2 µM) co-aggregation reactions. The added seed concentration is equivalent to the monomer concentration. Data is shown as means±SD of 3 technical replicates. (B) Quantification of HSA. Calculated $\Delta t_{50}$ values from Ex1Q48-CyPet/-YPet aggregation profiles in A. $\Delta t_{50}$ is displayed as individual values (•) and mean±SD of technical triplicates. (C) Analysis of sonicated and non-sonicated Ex1Q48 seeds by denaturing filter retardation (FRA, left panel) and dot blot (DB, right panel) assays. Fragmentation of large fibrillar Ex1Q48 aggregates by sonication prevents their detection by FRAs. (D) Preformed Ex1Q48 fibrils were sonicated for the indicated times and visualized by AFM. Sonication reduces the size of preformed Ex1Q48 fibrils. Scale bar: 1 µm; color gradient represents 0-20 nm height.

Figure 9:
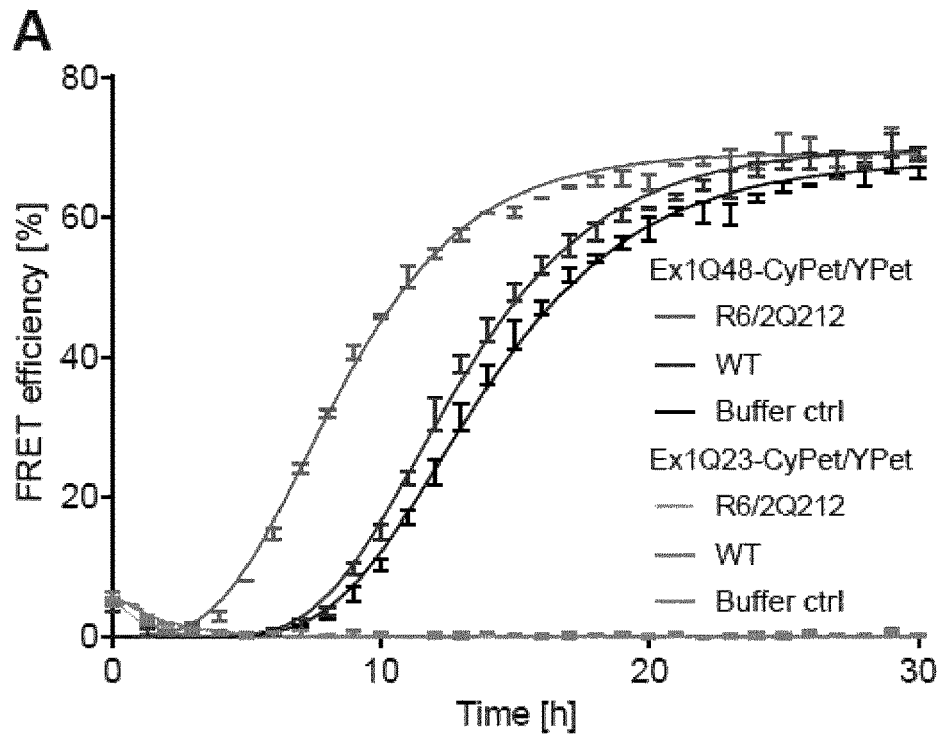
Figure 9:
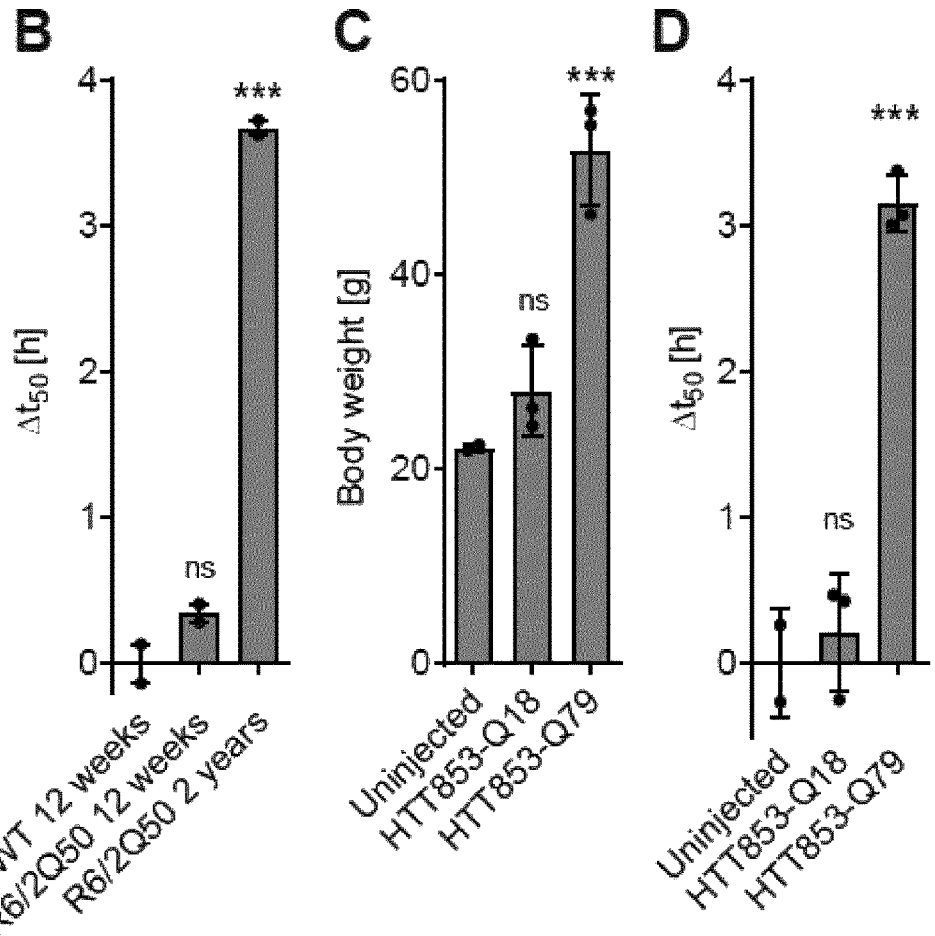
Figure 9:
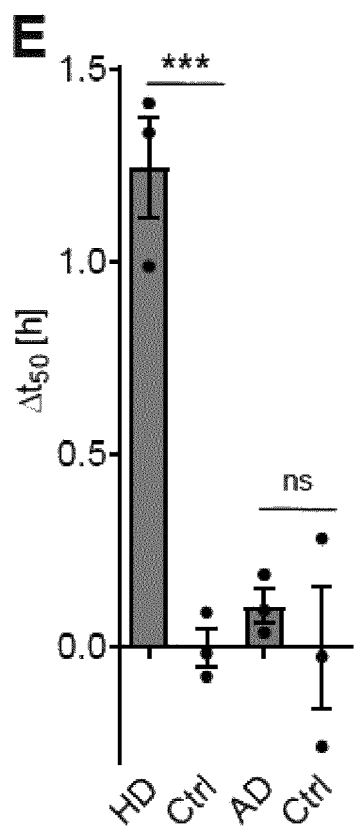
Figure 9:
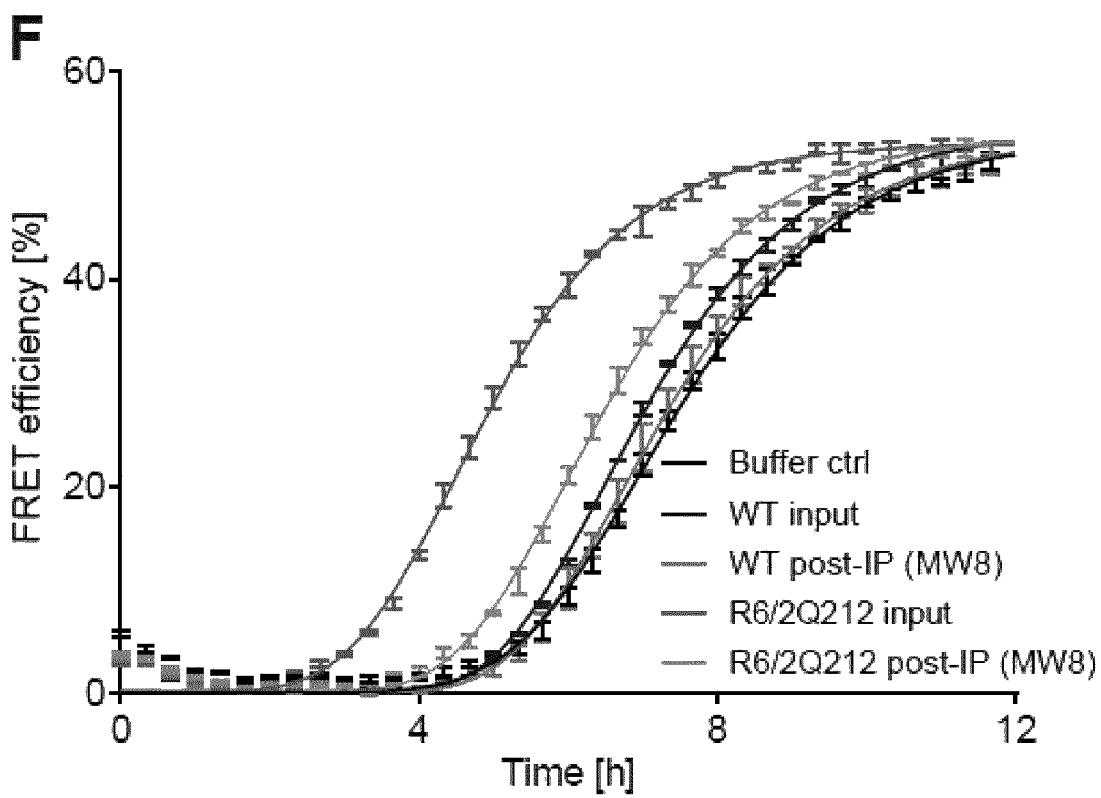
Figure 9:
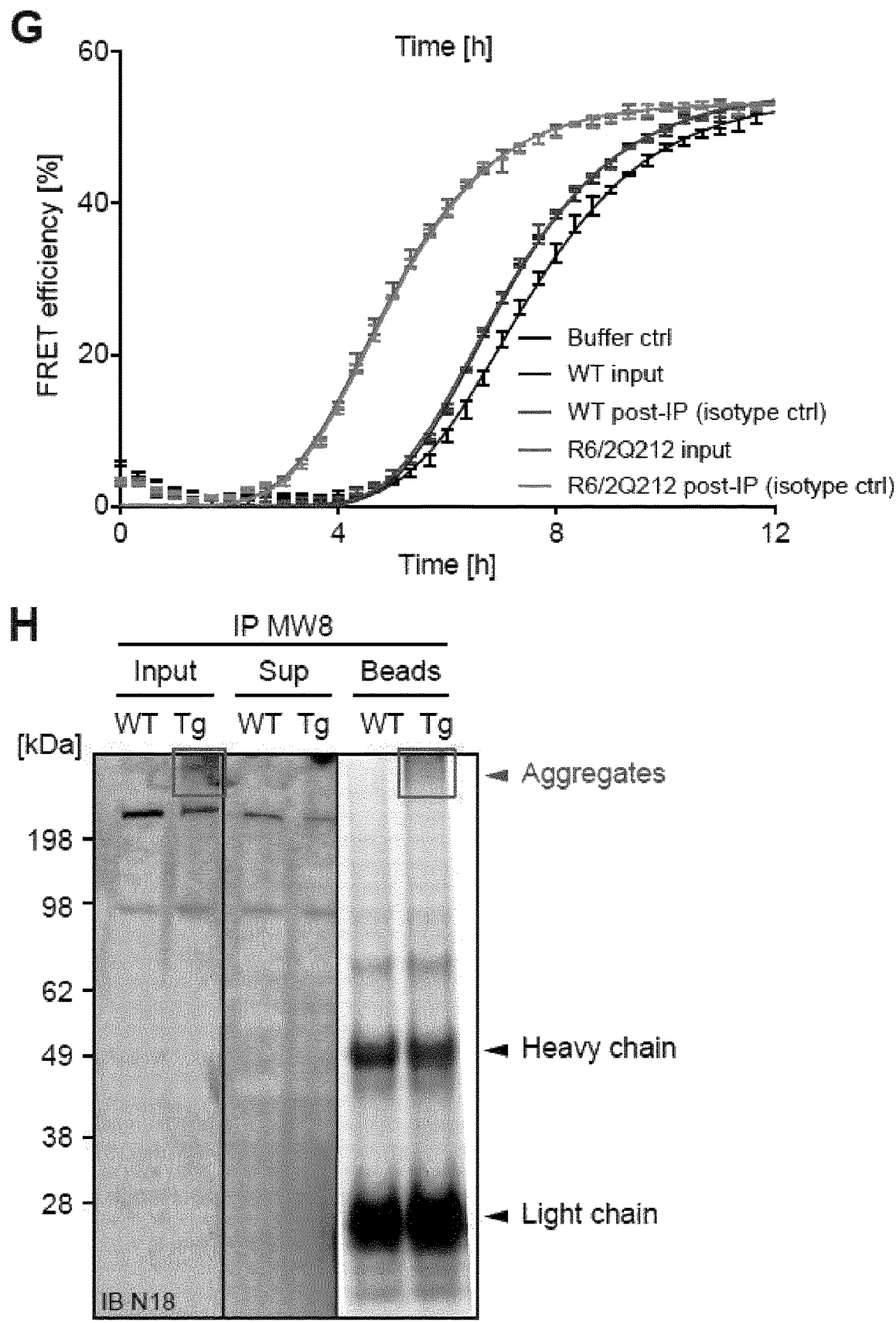
Figure 9:
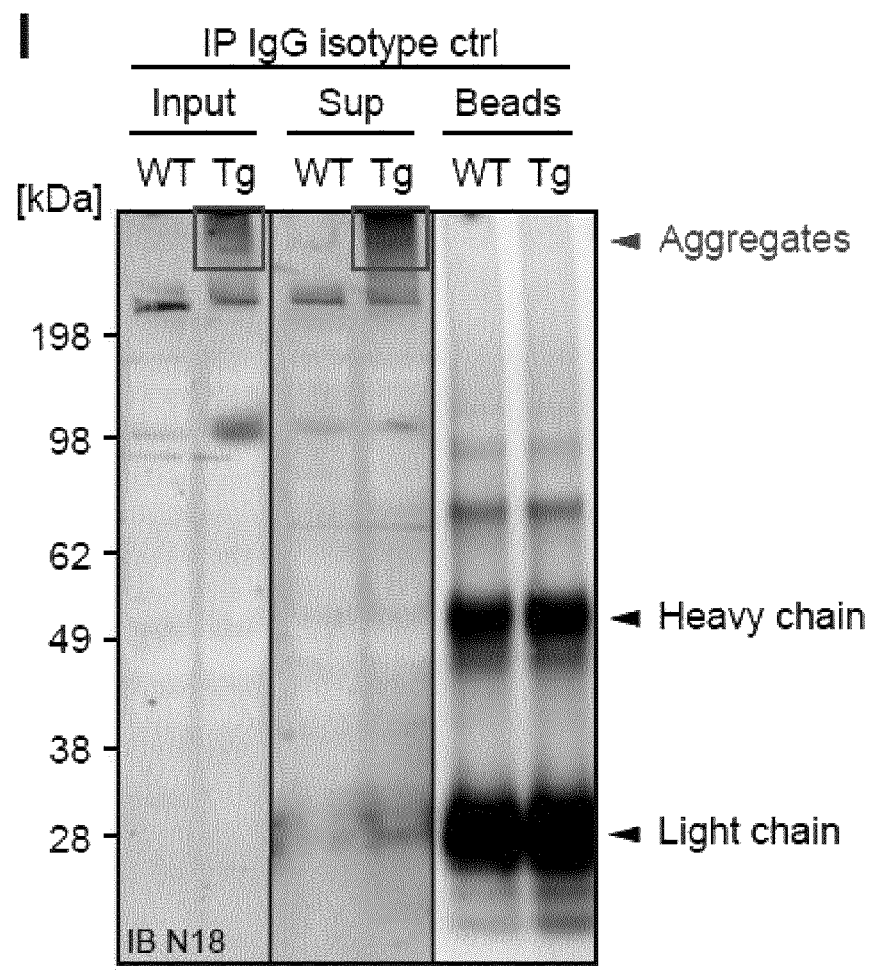

FIG. 9. Detection of mHTT seeding activity in brain extracts of various HD mouse models (A) Brain homogenates (7.5 µg) prepared from R6/2Q212 and WT mice were added to Ex1Q48-CyPet/-YPet or Ex1Q23-CyPet/-YPet sensor proteins. Brain homogenates prepared from R6/2Q212 mice accelerated Ex1Q48-CyPet/-YPet polymerization but do not induce co-aggregation of Ex1Q23-CyPet/-YPet sensor proteins. Co-aggregation of sensor proteins (1:1 mixture; 1.2 µM) was monitored by quantification of FRET and displayed as mean±SD of technical triplicates; the resulting aggregation kinetics were curve fitted by non-linear regression. (B) Quantification of HSA in brain extracts prepared from R6/2Q51 transgenic mice and controls using FRASE assays (1.2 µM Ex1Q48-CyPet/-YPet). HSA measured for each mouse is displayed as dots (•). Bars are mean±SEM. Statistical significance was assessed by One-Way ANOVA followed by Dunnett's multiple comparisons test (n=2). (C) Analysis of body weight of FVB/N mice expressing the proteins HTT853Q18 or HTT853Q79 for 8 weeks. Body weight of individual mice is displayed as dots (•). Bars are mean±SEM. Statistical significance was assessed by One-Way ANOVA followed by Dunnett's multiple comparisons test (n=3). (D) Quantification of HSA in hypothalamic brain homogenates of FVB/N mice expressing the proteins HTT853Q18 or HTT853Q79. The total concentration of sensor proteins was 3 µM. Data are mean±SEM (n=3). Individual measurements are displayed as dots (•). Statistical significance was assessed by One-Way ANOVA followed by Dunnett's multiple comparisons test. (E) Brain homogenates prepared from tissues of HD (caudate nucleus) and AD (temporal cortex) patients were analyzed by FRASE assays and compared to corresponding brain tissue of control individuals. HSA values are plotted individually as dots (•) and as mean±SEM (n=3); caudate tissue from HD patients (Grade 4, CAG repeat length: 52.3±1.2, Age 42.3±2.1), caudate tissue from controls (Age 60.3±1.2), cortical tissue from AD patients (Braak 6, Age 73.3±4.6), cortical tissue from controls (Braak 0, Age 66.3±7). Statistical significance was assessed by unpaired t test. (F) Immunodepletion of mHTTex1 aggregates from R6/2Q212 mouse brain homogenates decreases their seeding activity in FRASE assays. Brain homogenates prepared from transgenic mice and littermate controls (12 weeks) were incubated with MW8 antibody-coated protein G beads; supernatant (post-IP) and input samples were applied to FRASE analysis using 3 µM of sensor proteins. FRET efficiency is plotted as mean±SD of technical triplicates. (G) Same procedure as in F but with an IgG isotype control antibody. (H and 1) Immunoblots of samples analyzed in F and G. mHTTex1 aggregates appear as a smear at the upper edge of the blot (red rectangles). Input, brain extract before immunodepletion; Sup, supernatant after immunodepletion; Beads, antibody-coated protein G beads after immunodepletion. mHTTex1 aggregates are depleted from mouse brain homogenates with the anti-HTT antibody MW8 but not with an IgG isotype control antibody.

Figure 10:
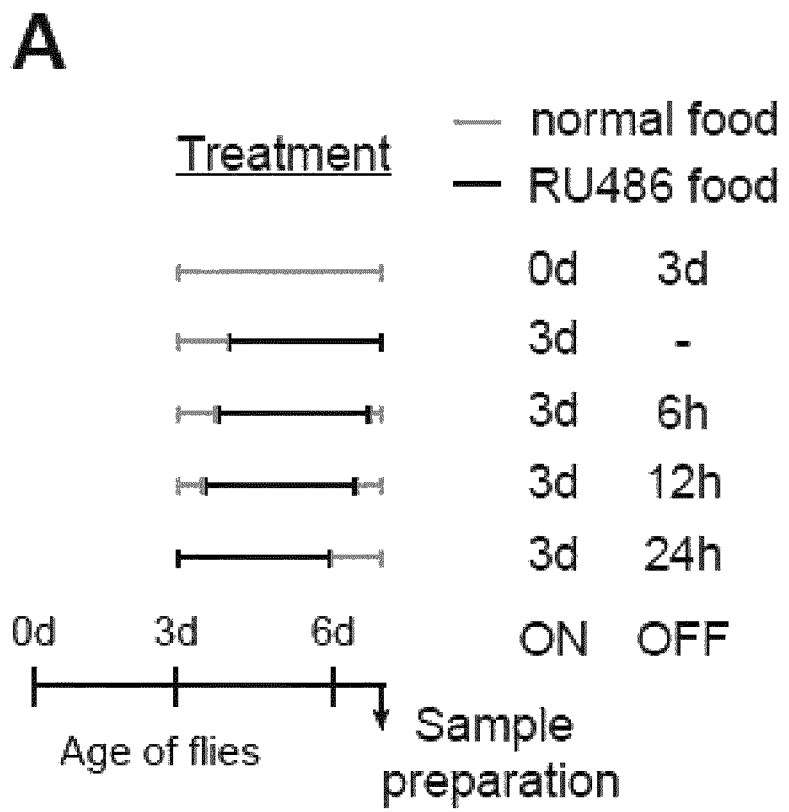
Figure 10:
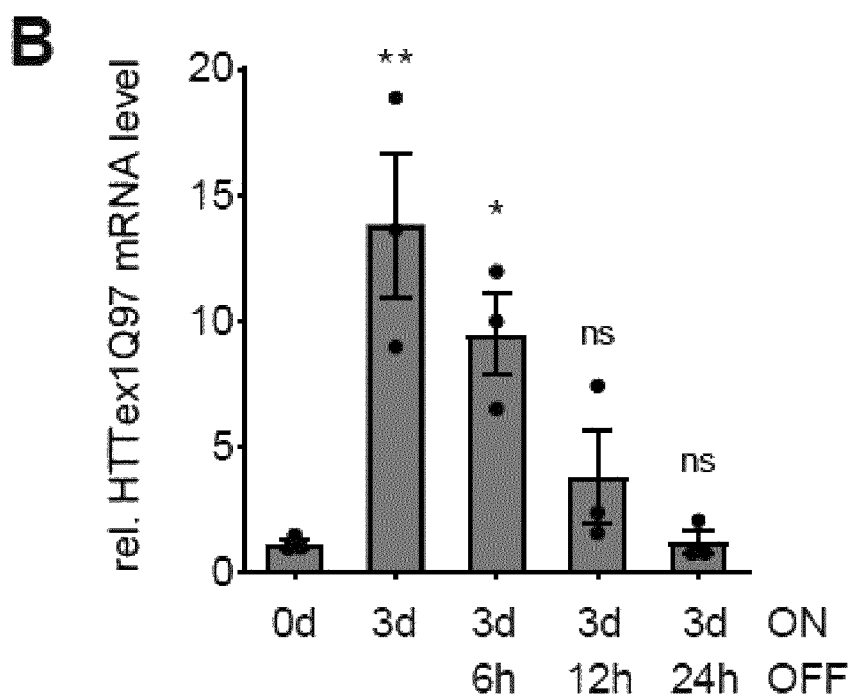
Figure 10:
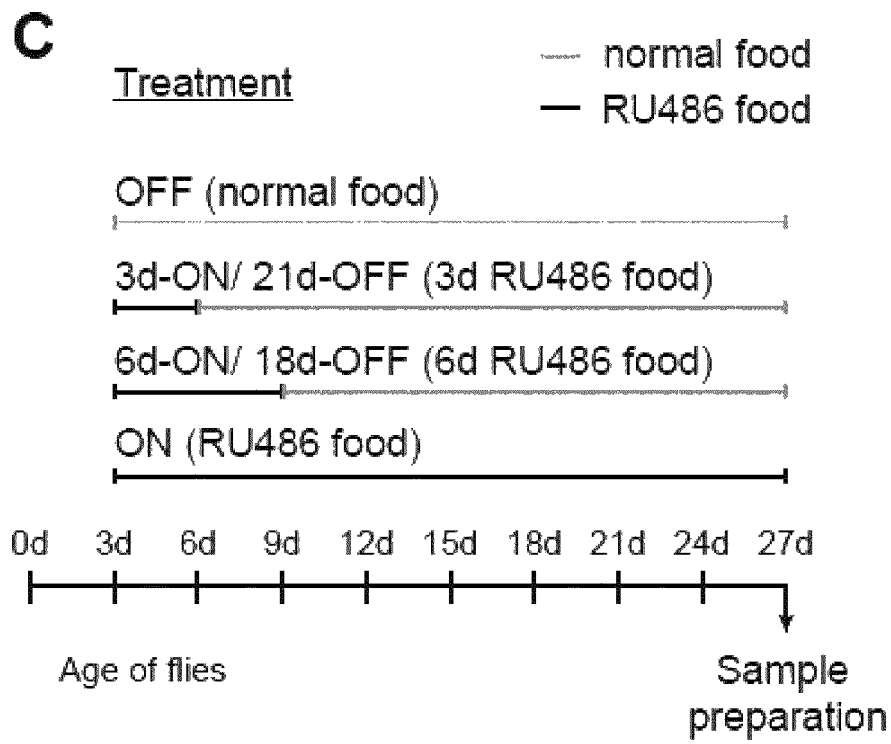
Figure 10:
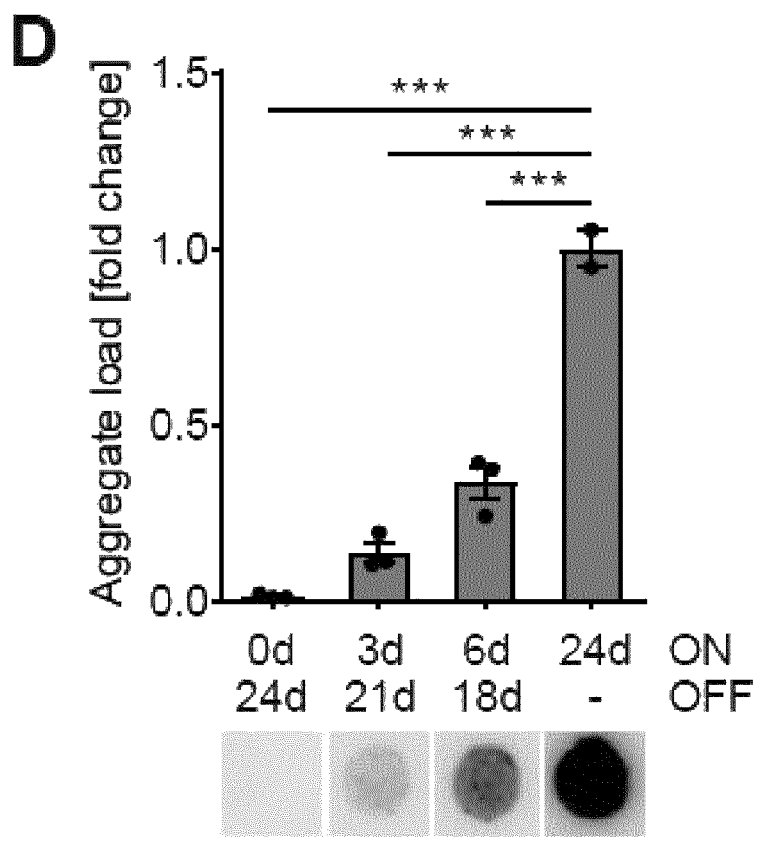
Figure 10:
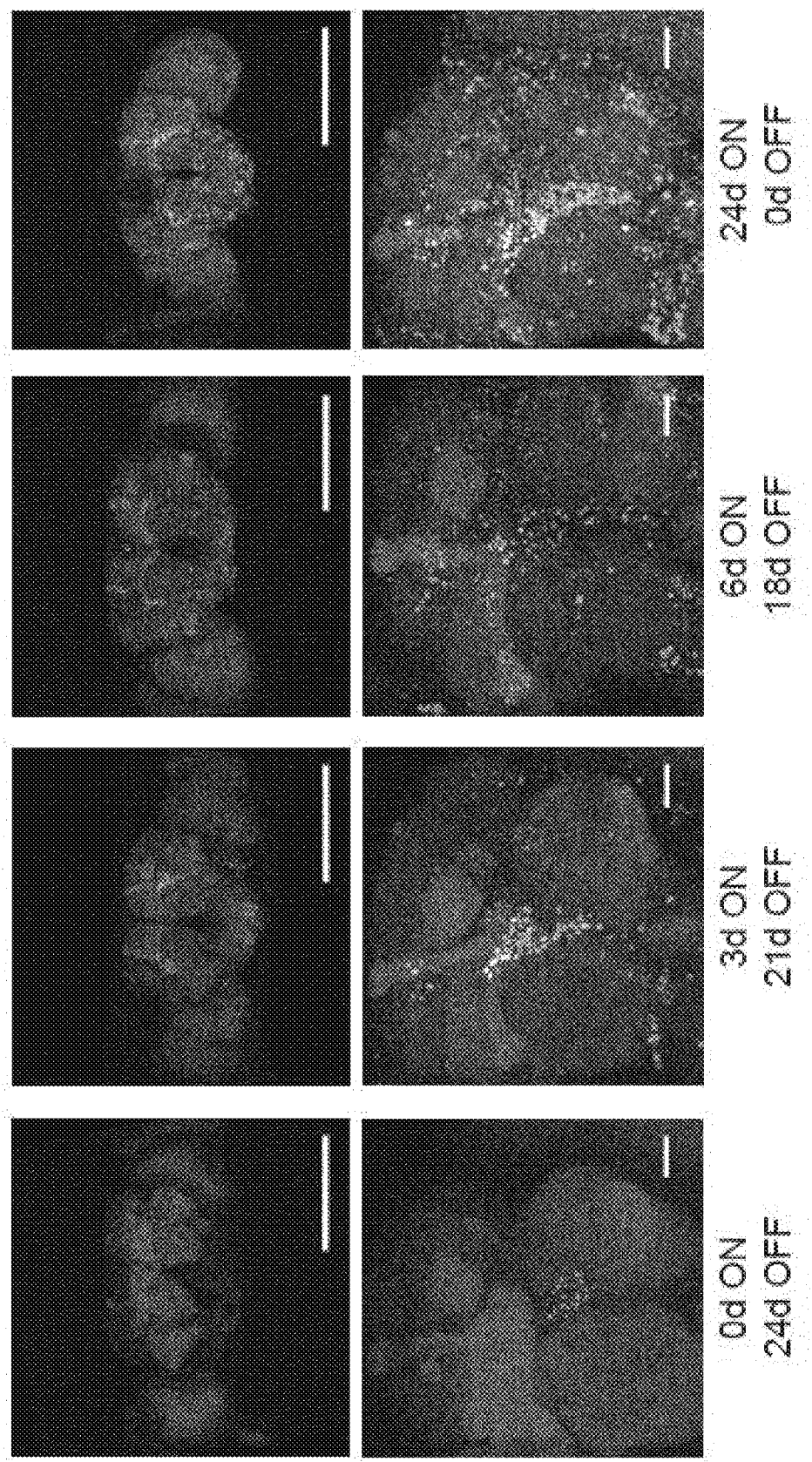

FIG. 10. Detection of mHTTex1 aggregates in *Drosophila* HD models (A) Illustration of hormone treatment utilized to assess the dynamics of HTTex1Q97 transcriptional repression upon hormone removal. Grey lines indicate time periods without RU486 treatment; black lines indicate time periods of exposure to RU486. (B) Relative mRNA levels assessed by qPCR show transcriptional repression of HTTex1Q97 upon removal of RU486. Values are depicted as mean±SEM of 3 biological replicates; individual measurements (•); significance assessment with One-way ANOVA Dunnett's post-hoc test. (C) Treatment scheme for the preparation of *Drosophila* samples for FRA and FRASE analyses. (D) Analysis of mHTTex1 aggregate load in fly head lysates by FRAs (75 µg protein) using the MAB5492 antibody. Data is displayed as mean±SEM of 3 biological replicates; individual measurements (•); statistical significance was assessed by One-way ANOVA Dunnett's post-hoc test. (E) Representative confocal images of elavGS;HTTex1Q97 whole fly brains (hormone treatment as in C. The RBP staining is shown in magenta and the MAB5492 staining in green (Scale bars: 200 µm). Magnifications are shown below (Scale bars: 20 µm).

Figure 11:
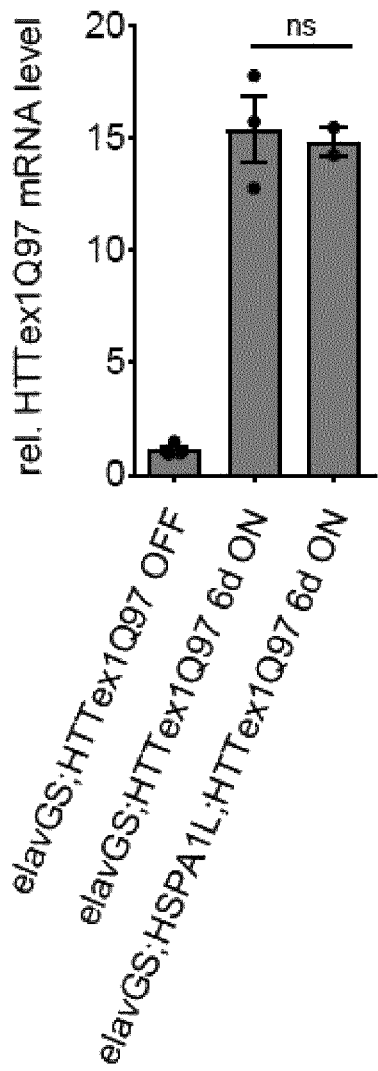
Figure 11:
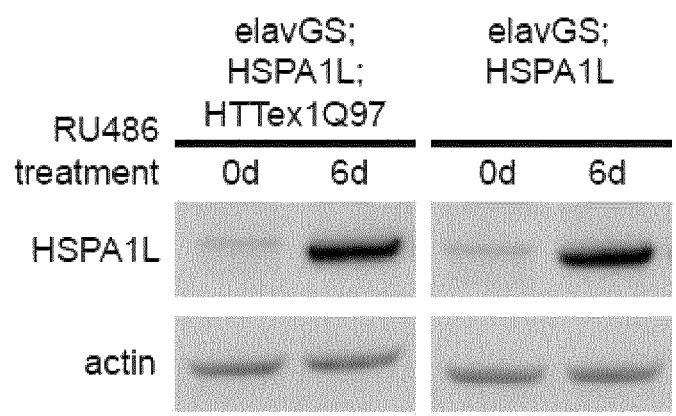
Figure 11:
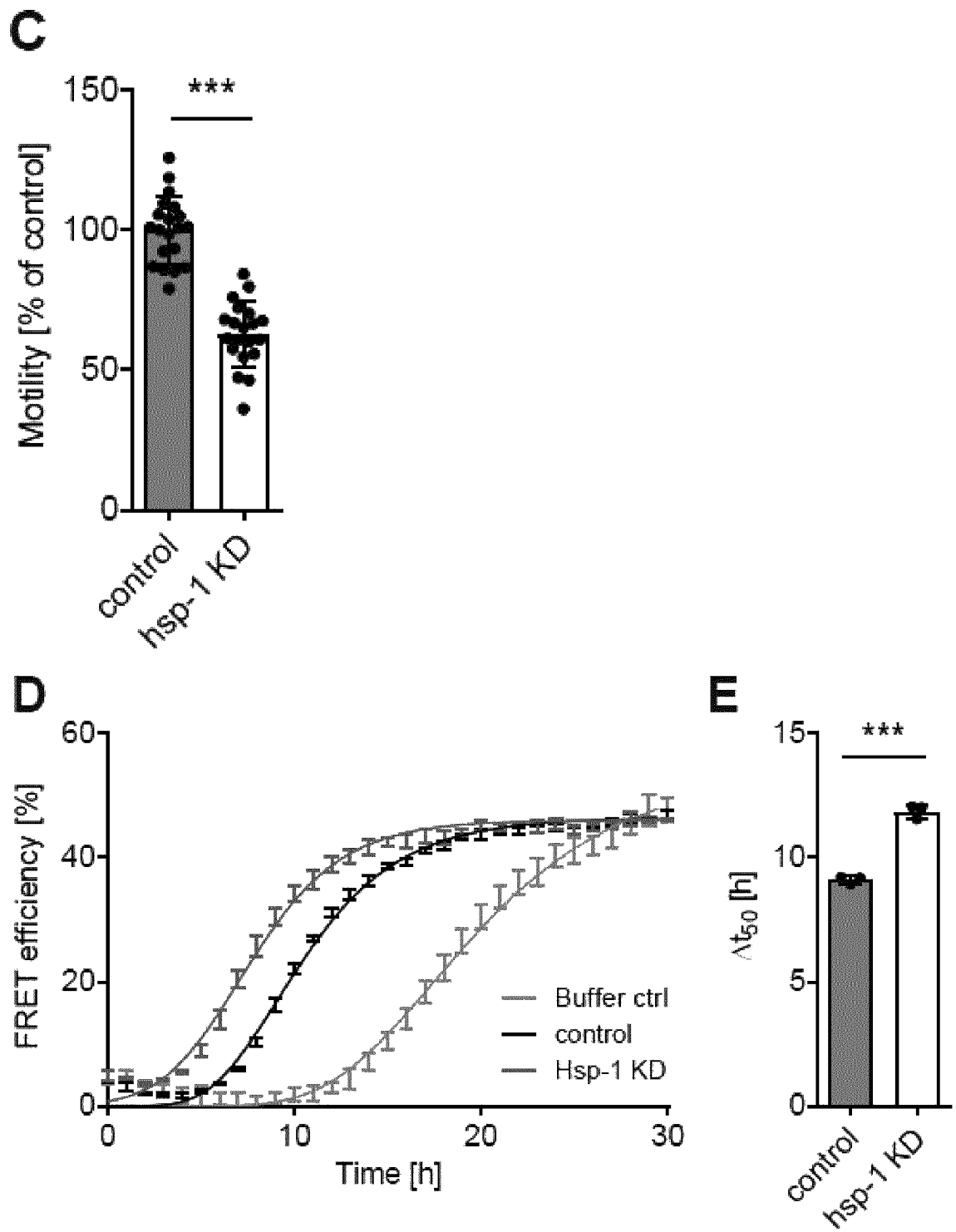

FIG. 11. Effects of chaperone levels on HSA in transgenic flies and worms (A) Relative mRNA levels assessed by qPCR show similar expression of HTTex1Q97 in elavGS;HTTex1Q97 and elavGS;HSPA1L;HTTex1Q97 flies. Bars are mean±SEM of three biological replicates and individual measurements are displayed as dots (•); significance assessment with unpaired t-test. (B) Comparison of Hsp70 protein levels in elavGS; HSPA1L;HTTex1Q97 and elavGS;HSPA1L flies untreated and treatment with RU486. Protein extracts prepared from fly heads were analyzed by SDS-PAGE and immunoblotting (20 µg of total protein). (C) Motility phenotype (% motility) of RNAi-treated and untreated Q35-YFP expressing transgenic worms at day 5. In all cases, data were normalized to age-matched control worms. Data are mean±SEM (n=20). Significance assessment with unpaired t test. (D) FRASE analysis of Q35-YFP seeding activity in RNAi-treated and untreated worms after 5 days. FRET efficiency is displayed as mean±SD. (E) Quantification of results shown in D. HSA values are plotted individually as dots (•) and as mean±SD.

Figure 12:
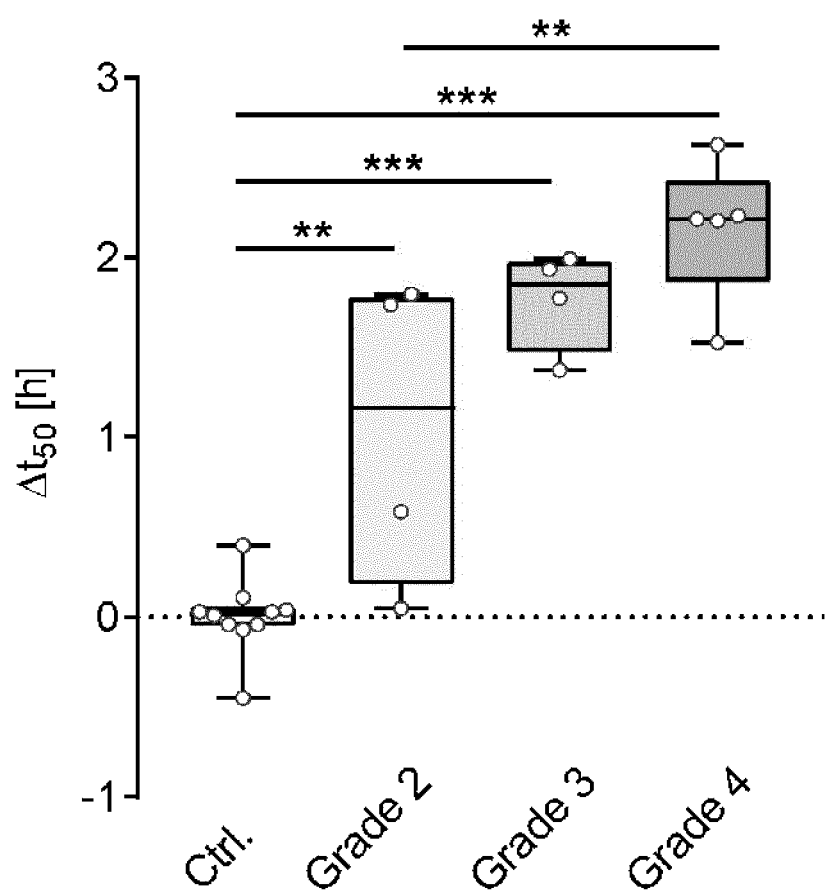

FIG. 12. HSA detected in the putamen of HD patients increases with the advancement of neuropathological changes Assessment of HSA in homogenates prepared from putamen of control individuals and HD patients at different disease stages. $\Delta t_{50}$ values for each individual are plotted as circles; Boxes show first and third quartiles, the central band shows the median, and the whiskers show data within 1.5 IQR of the median; putamen tissue from HD patients (Grade 2 (n=4), CAG repeat length 45.8±0.96, Age 60.25±12.1;

Grade 3 (n=4), CAG repeat length 47.5±1.7, Age 54.5±6.6; Grade 4 (n=5), CAG repeat length 52.0±1.0, Age 44.6±4.9), caudate tissue from controls (n=10, Age 60.6±9.1); statistical significance was assessed by One Way ANOVA followed by Dunnett's multiple comparisons test.

Figure 13:
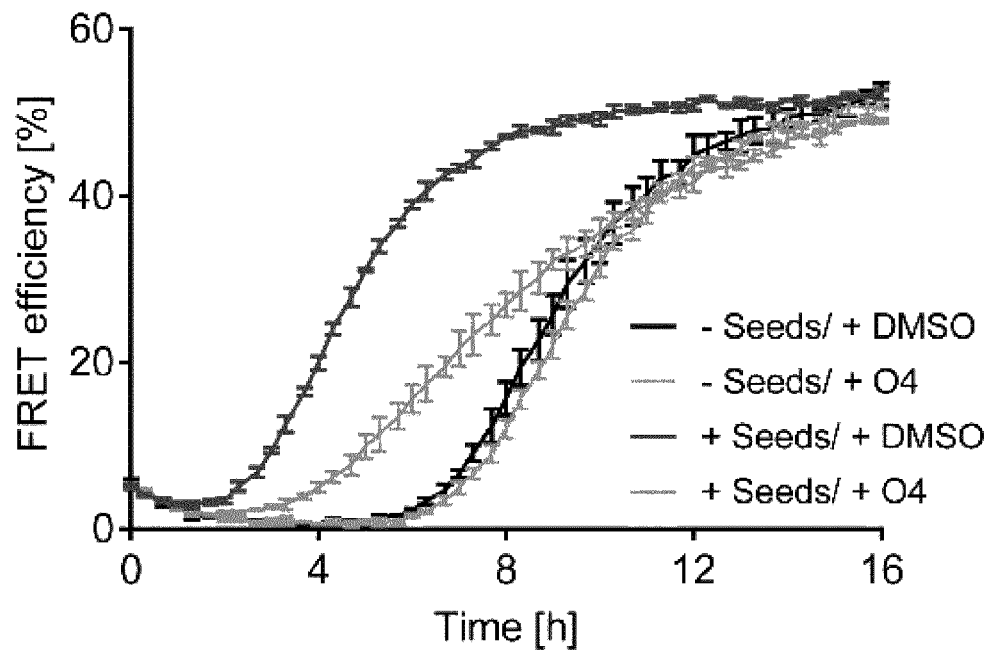
Figure 13:
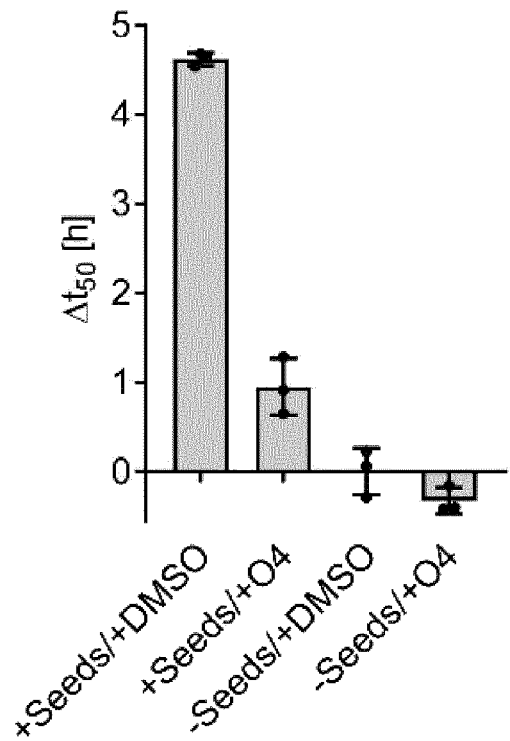

FIG. 13. Modulation of mHTT seeding activity by small molecule compounds

Httex1Q48 seeds were pre-incubated with O4 in 200-fold molar excess at 25° C. for 20 h and subsequently analyzed for their seeding activity using FRASE assays. (A) Aggregation profiles of sensor proteins in the presence or absence of O4 treated seeds and respective controls. Data are mean±SD of technical triplicates. (B) Calculation of $\Delta t_{50}$ values from aggregation profiles in A. $\Delta t_{50}$ is displayed as individual values (black •) and as mean±SD of technical triplicates.

METHODS

Experimental Model and Subject Details
HD Mouse Models

Hemizygous R6/2Q212 mice (Mangiarini et al., 1996) were bred by backcrossing R6/2Q212 males to (CBA/Ca× C57Bl/6J) F1 females (B6CBAF1/OlaHsd, Harlan Olac, Bicester, UK). HdhQ150 heterozygous knock-in mice (Lin et al., 2001; Woodman et al., 2007) on a (CBA/Ca×C57Bl/6J) F1 background were generated by intercrossing HdhQ150 heterozygous CBA/Ca and C57BL/6J congenic lines (inbred lines from Harlan Olac, Bicester, UK). All animals were subject to a 12 h light/dark cycle with unlimited access to drinking water and breeding chow (Special Diet Services, Witham, UK). Housing conditions and environmental enrichment were described previously (Hockly et al., 2003). R6/2 mice were always housed with wild-type mice. The CAG repeat size of the R6/2Q212 mice used in this study was 212±5.27 (s.d.) and that of the HdhQ150 heterozygotes was 160±2.86 (s.d.). Hemizygous R6/2Q51 mice were derived from R6/2 parent lines by selective breeding (Larson et al., 2015) and bred by backcrossing R6/2Q51 males to (CBA×C57Bl/6) F1 females (Charles Rivers, UK). R6/2Q51 mice were maintained and bred as described previously (Larson et al., 2015). Female mice from the FVB/N strain (Charles River Laboratories, Germany) were injected at eight to ten weeks of age with recombinant adeno-associated viral (AAV) vectors of serotype 5 encoding the first 853 amino acids of either the WT form of HTT with 18Q (HTT853-Q18) or the mutant form of the protein with 79Q (HTT853-Q97) (Baldo et al., 2013). All mice were housed in groups at a 12 h light/dark cycle. At 8 weeks post-injection, FVB/N mice were sacrificed. Overall, mice were sacrificed at different ages from 1 day up to 2 years. Tissues were strictly stored at −80° C. until use.

All animal work with R6/2Q212 and HdhQ150 mice was approved by the King's College London Ethical Review panel and performed under a Home Office project license in accordance with the United Kingdom 1986 Animals (Scientific procedures) Act. All animal work with R6/2Q51 mice was approved by the University of Cambridge Ethical Review panel and performed under a Home Office project license in accordance with the United Kingdom 1986 Animals (Scientific procedures) Act. All experimental procedures with FVB/N mice were approved by the Regional Ethical Committee in Lund, Sweden.

Human Brain Tissue

Post mortem brain tissues from human HD and AD patients and unaffected control individuals (both male and female) were obtained from the Newcastle Brain Tissue Resource (NBTR, Newcastle University, UK). Experiments were performed in accordance with the approval of the joint Ethics Committee of Newcastle and North Tyneside Health Authority and following NBTR brain banking procedures. Tissues were collected at 34.5±21.0 h post-mortem from HD patients and controls with an average age of 57.8±10.7 years.

Generation and Maintenance of *Drosophila* Strains

ElavGS-GAL4, Elav-GAL4 and HSPA1L lines were obtained from the Bloomington *Drosophila* Stock Center. Transgenic flies were generated through cloning of cDNAs encoding HTTex1Q17 and HTTex1Q97 into pUAST-attB-rfA (provided by Prof. S. Sigrist, Freie Universität, Berlin) and subsequent site-directed insertion on the third chromosome (68E) using the PhiC31 integrase [Rainbow Transgenic Flies Inc. (Camarillo, Calif., USA)]. All *Drosophila* strains were cultured on standard medium at 25° C. and 65% humidity with a 12 h light-dark cycle. Expression of transgenes was induced by culturing flies on standard medium containing 400 µM RU486.

*C. elegans* Strains and Maintenance

*C. elegans* Q35 AM140 (rmls132 (unc-54p::Q35::YFP)) were grown on NGM plates seeded with the *E. coli* OP50 strain at 20° C. Nematodes were transferred to fresh wells or plates every day in the course of the experiment to separate them from their progeny.

Method Details
Cloning of Expression Vectors

For the construction of plasmids encoding CyPet- and YPet-tagged HTTEx1Q48 fusion proteins, the coding sequence of HTTEx1Q48 was PCR-amplified from pGEX-6P1-HTTEx1Q48 using the primers 5'-gacgacgaatt-catgcgaccctg-3' (SEQ ID NO.: 37) and 5'-gacgacctcgag tggtcggtgcagcgg-3' (SEQ ID NO.: 38). The resulting PCR product was digested with the restriction enzymes EcoRI and NotI. Additionally, CyPet cDNA was PCR amplified from pBAD33-CyPet-His (Addgene plasmid #14030) (Nguyen and Daugherty, 2005) with the primers 5'-acgacctcgagggtggcggtggcggtatgtctaaaggtgaagaattattcgg-3' (SEQ ID NO.: 39) and 5'-gacgacgcggccgcttatttgtacaatt-catccataccatg-3' (SEQ ID NO.: 40). YPet cDNA was amplified from pBAD33-YPet-His (Addgene plasmid #14031) (Nguyen and Daugherty, 2005) with the primers 5'-gacgacctcgagggtggcggtggcggtatgtctaaaggtgaagaattatt-cactgg-3' (SEQ ID NO.: 41) and 5'-gacgacgcggccgcttatttgta-caattcattcataccctcg-3' (SEQ ID NO.: 42). The resulting PCR fragments were cloned into the plasmids pGEX-6P1 using the EcoRI/XhoI/NotI restriction sites to obtain plasmids pGEX-6P1-HTTEx1Q48-CyPet and -YPet, respectively. To generate the plasmids encoding GST-Ex1Q23-CyPet and -YPet or GST-Ex1Q23 the coding sequence of HTTEx1Q23 was PCR-amplified from pDONR221-HTTEx1Q23 using the primers 5'-gacgacgaattcatggcgaccctg-3' (SEQ ID NO.: 43) and 5'-gacgacgcggccgcct cgagtggtcggtgcagcgg-3' (SEQ ID NO.: 44) (GST-Ex1Q23-CyPet and -YPet) or 5'-gacgacgaattcatggcgaccctg-3' (SEQ ID NO.: 45) and 5'-gacgacgcggccgcct cgagttatggtcggtgcagcgg-3' (SEQ ID NO.: 46). The resulting PCR products were digested using EcoRI and XhoI endonucleases and cloned into the plasmids pGEX-6P1-HTTEx1Q48-CyPet, -YPet or pGEX-6P1-HTTEx1Q48 after excision of HTTEx1Q48 fragments by EcoRI/XhoI endonucleases.

To generate the plasmids encoding GST-K2Q48P6-CyPet and -YPet the cDNA 5'-GGgatccAAgAAAcag cagcagca gcagcagcagcagcagcagcagcagcagcagcagcagcagc agcagcagca gcagcagcagcagcagcagcagcagcagcagcagcagcagcagcagcag cagcagcagcagcagcagcagcagcaacagccgccaccgccgcc gcc gctcgag-3' was generated by gene synthesis and subcloned into the plasmids pGEX-6P1-HTTEx1Q48-CyPet, -YPet using endonucleases BamH1 and Xho1.

To generate the plasmids encoding GST-ΔN17Q48+ 6PRD-CyPet and -YPet the cDNA 5'-GGgatccca gcagcagcagcagcagcagcagcagcagcagcagcagcagcag cagca gcagcagcagcagcagcagcagcagcagcagcagcagcagcagc-agcagcagca gcagcagcagcagcagcagcagcagcaacagccgccac cgccgccgccgccgccgccgcctcctccac cgccgccgccgccacagct tc ctcagccgccgccgcaggcacagccgctgctgcctcagctgcagccgcc cc cgc c gccgcccccgccgccaccggcccggccgcggctgaggagccgc tgcaccgaccactcgag-3' was generated by gene synthesis and subcloned into the plasmids pGEX-6P1-HTTEx1Q48-CyPet, -YPet using endonucleases BamH1 and Xho1.

To generate the plasmids encoding GST-ΔN17Q40+ 6PRD-CyPet and -YPet the cDNA 5'-GGgatcccagca gcagcagcagcagcagcagcagcagcagcagcagcagcag cagcag cagcagcagcagcagcagcagcagcagcagcagcagcagcagcagca-gcagcagca gcaacagccgccaccgccgccgccgccgccgccgcctcctc-caccgccgccgccgccacagcttcctcag ccgccgccgcaggcacag cc-gctgctgcctcagctgcagccgcccccgccgccgccccgccgccaccc ggc ccggccgcggctgaggagccgctgcaccgaccactcgag-3' was generated by gene synthesis and subcloned into the plasmids pGEX-6P1-HTTEx1Q48-CyPet, -YPet using endonucleases BamH1 and Xho1.

Recombinant Protein Expression

The proteins GST-Ex1Q23, -Ex1Q48, -Ex1Q23-CyPet, -Ex1Q23-YPet, -Ex1Q48-CyPet, -Ex1Q48-YPet, -K2Q 48P6, -K2Q48P6-CyPet, -K2Q48P6-YPet, –ΔN17Q48+ 6PRD, -ΔN17Q48+6PRD-CyPet, -ΔN17Q48+6PRD-YPet, -ΔN17Q40+6PRD, -ΔN17Q40+6PRD-CyPet, and -ΔN17Q40+6PRD-YPet were produced in *E. coli* BL21-CodonPlus-RP and affinity-purified on glutathione-sepharose beads. Purified proteins were dialyzed over night at 4° C. against 50 mM Tris-HCl pH 7.4, 150 mM NaCl, 1 mM EDTA and 5% glycerol, snap-frozen in liquid $N_2$ and stored at −80° C. Protein concentrations were determined with a NanoDrop spectrophotometer. Prior to use, protein solutions were ultra-centrifuged at 190,000×g for 40 min to remove aggregated material. α-Synuclein (α-Syn) was produced in *E. coli* BL21 (DE3) and monomeric α-Syn was purified as described elsewhere (Theillet et al., 2016). Expression of Tau40 protein was performed in *E. coli* BL21 using a 50 l bioreactor. After cell disruption using a French press, Tau40 protein was purified via cation exchange chromatography and gel filtration. Expression and purification of Tau were performed by InVivo BioTech Services (Hennigsdorf, Germany) using proprietary company protocols.

Preparation of In Vitro Seeds

Spontaneous Ex1Q48 aggregation was initiated by addition of 14 U PreScission protease (GE Healthcare) per nmol purified GST-Ex1Q48 fusion protein (2 µM). The aggregation reaction was performed in 50 mM Tris-HCl pH 7.4, 150 mM NaCl, 1 mM EDTA and 1 mM DTT at 25° C. and constant agitation (450 rpm) for 24 h. Ex1Q23 protein for seeding experiments was prepared from GST-Ex1Q23 fusion protein using the same protocol. K2Q48P6 protein for seeding experiments was prepared from GST-K2Q48P6 fusion protein using the same protocol. ΔN17Q48+6PRD protein for seeding experiments was prepared from GST-ΔN17Q48+6PRD fusion protein using the same protocol. ΔN17Q40+6PRD protein for seeding experiments was prepared from GST-ΔN17Q40+6PRD fusion protein using the same protocol. Synthetic human IAPP was aggregated as described previously (Gao et al., 2015). Lyophilized α-Syn was dissolved in PBS at 500 µM and centrifuged (4° C., 265.000×g) after a 5 min sonication step to remove aggregated material. The supernatant was incubated for 7 d at 37° C. under constant shaking in the presence of a single glass bead. Tau40 was aggregated for 6 d at 37° C. under constant shaking in 100 mM sodium acetate, pH 7.4, and 1 mM DTT in the presence of heparin. Synthetic human $\Delta\beta_{1-42}$ was dissolved in 100 mM NaOH and diluted to 200 µM in low salt buffer (10 mM $K_3PO_4$, pH 7.4, 10 mM NaCl). Aggregation was performed for 6 h at 37° C. under constant agitation.

Atomic Force Microscopy

Aliquots of 15 µl aggregation reactions (24 h) were spotted onto freshly cleaved mica glued to a microscope slide. After incubation for 30 min to allow adsorption, samples were rinsed 4 times with 40 µl distilled water and dried over night at RT. Samples were imaged with a digital multimode Nanowizard II (JPK, Germany) atomic force microscope operating in intermittent-contact mode.

Filter Retardation Assays

FRAs were essentially performed as described previously (Wanker et al., 1999). Briefly, equal volumes of 500 ng of Ex1048 aggregates and 4% SDS solution with 100 mM DTT were mixed and boiled at 95° C. for 5 min. By applying vacuum, samples were filtered through a cellulose acetate membrane with 0.2 µm pores (Schleicher and Schuell, Germany) and washed twice with 100 µl 0.1% SDS. For analysis of tissue homogenates, 60 µg of total protein for mouse brain and 75 µg of total protein for *Drosophila* heads were filtered per dot. Membranes were blocked with 5% skim milk in PBS/0.05% Tween20 (PBS-T) for at least 30 min. Aggregates retained on the membrane were detected using GFP, N18, MW8, Mab5492 or HD1 antibody followed by an appropriate peroxidase-coupled secondary antibody. Signals were quantified using the AIDA image analysis software (Raytest, Germany).

Dot Blot Assays

To estimate total HTT protein, native dot blot (DB) assays were performed as described previously (Kayed et al., 2003). Briefly, 250 ng of Ex1Q48 protein were filtered onto a nitrocellulose membrane and blocked with 5% skim milk in PBS-T. For detection, the membrane was incubated with HD1 antibody followed by an appropriate peroxidase-coupled secondary antibody. Signals were quantified using the AIDA image analysis software (Raytest, Germany).

Native Gels

Protein solutions were mixed with sample buffer and loaded onto a Novex NativePAGE 3-12% Bis-Tris gradient gel (Life Technologies). NativePAGE and immunoblotting were performed according to manufacturer recommendations. Ex1Q48 aggregates were visualized as for SDS-PAGE.

SDS-PAGE and Western Blotting

Samples of aggregation reactions were mixed with loading buffer (50 mM Tris-HCl pH 6.8, 2% SDS, 10% glycerol and 0.1% bromophenol blue) and boiled at 95° C. for 5 min. Samples were loaded onto Novex NuPAGE 4-12% Bis-Tris gradient gels (Life Technologies). SDS-PAGE and immunoblotting were performed according to manufacturer recommendations. Ex1Q48 distribution was visualized by N18 antibody (Santa Cruz) or Ex1Q48-CyPet/-YPet with a GFP antibody (Abcam) followed by appropriate peroxidase labeled secondary antibodies.

Genotyping of *Drosophila* Strains

Total genomic DNA from transgenic flies was extracted using the DNeasy® Blood & Tissue Kit (Qiagen). cDNAs encoding HTTex1Q17 and HTTex1Q97 were PCR amplified using the Pwo DNA polymerase (Roche) and the primers 5'-aaccccgtaaatcaactgc-3' and 5'-atctctgtaggtagtttgtc-3'). The sizes of the resulting PCR products were analyzed by agarose gel electrophoresis.

Quantitative Polymerase Chain Reaction (qPCR)

RNA was extracted from *Drosophila* heads using TRIzol™ Reagent (Invitrogen). cDNA was synthesized using M-MLV Reverse Transcriptase (Thermo Scientific) and qPCR was performed using the SYBR Green PCR Master Mix (Thermo Scientific). Primer pairs for HTT (sense, 5'-gacctggaaaagctgatga-3' and antisense 5'-tcatggtcggtgcagcggct-3'), and control primers for rp49 (sense 5'-tacaggcccaagatcgtgaa-3', and antisense 5'-acgttgtgcaccaggaactt-3') were utilized. SYBR Green analysis was performed using the ViiA7 Real-time PCR system (Thermo Scientific). The amount of mRNA detected was normalized to control rp49 mRNA values.

Viability Analysis of Adult *Drosophila melanogaster*

Viability assays were performed with elavGS; HTTex1Q17, elavGS;HTTex1Q97 and elavGS;HSPA1L; HTTex1Q97 transgenic flies by quantification of lethality of at least 100 females of each genotype and expression condition in three independent biological replicates. Flies were aged at 25° C., with 10 flies per vial and were transferred every 3-4 days. Median lifespan (age at which half of the tested population has died) was calculated by fitting survival curves to the log(inhibitor) vs. normalized response (variable slope) equation using GraphPad Prism. Statistical significance was assessed by one-way ANOVA followed by Dunnett's multiple comparison post hoc test. *, $p \leq 0.05$; , $p:0.01$; *, $p \leq 0.001$.

Analysis of Motor Performance (Climbing Assay)

Ten female flies were placed in a closed empty vial and gently tapped to the bottom of the vial. The percentage of flies that climbed 8 cm within 15 s was recorded. Flies were aged at 25° C. (10 flies per vial) and were monitored and transferred twice a week. Motor performance was assessed for elavGS;HTTex1Q17 and elavGS;HTTex1Q97 flies expressing the HTT transgenes for the indicated times. 100 females of each genotype and expression condition in each of the three biological replicates were investigated.

Preparation of *Drosophila* Head Lysates for FRAs

*Drosophila* head lysates were produced by homogenizing fly heads in 2% SDS and complete protease inhibitor cocktail using a micro pestle. Lysates were centrifuged for 10 min at 8,000 rpm (4° C.). The supernatant was transferred to a new tube and total protein concentration was determined with a Pierce™ BCA assay using BSA as a standard.

Dissection and Immunostaining of *Drosophila* Adult Brain

The whole brains of adult flies were dissected in ice-cold haemolymph-like saline (HL3) solution (Stewart et al., 1994), fixed for 20 min in 4% paraformaldehyde (PFA) in PBS and permeabilized in PBS-T (1% Triton™ X-100) for 20 min at RT. Samples were blocked in 10% normal goat serum (NGS) in PBS-T (0.3% Triton™ X-100) for at least two hours. Brains were incubated with the indicated primary antibody (1:500) in brain staining buffer (5% NGS, 0.1% NaN$_3$ in PBS-T (0.3% Triton™ X-100)) for 48 hours at 4° C. Subsequently, brains were washed in PBS-T (0.3% Triton™ X-100) for 24 hours at 4° C. with multiple buffer exchanges. Next, samples were incubated with appropriate secondary antibody in brain staining buffer for 24 hours at 4° C., washed six times for 30 min in PBS-T (0.3% Triton™ X-100) at RT and stored in VectaShield H-1000 (Vector Laboratories) at least for one day at −20° C. Brains were mounted and imaged using the Leica TCS SP8 Confocal Microscope. Images were analyzed using Fiji.

RNA Interference

For synchronization, gravid adults from one 10 cm NGM plate were collected in a canonical tube and treated with 20% alkaline hypochlorite solution under vigorous agitation for 4 min. The eggs were then washed three times with cold 0.1 M NaCl solution. The eggs were allowed to hatch in M9 medium at 20° C. for 22 h. Animals were then placed as L1 larvae onto RNAi plates that were seeded with *E. coli* expressing dsRNAi against hsp-1 or the empty vector L4440 (control).

Fluorescence Microscopy

The aggregation propensities of Q35-YFP were analyzed throughout adulthood. Animals were subjected to RNAi treatment from the first larval stage on and maintained on RNAi plates throughout the experiment. For imaging, nematodes were mounted onto 2% agarose (Sigma) pads on glass slides and immobilized with 2 mM Levamisole (Sigma). Images were taken on a Zeiss LSM780 confocal microscope at 20× magnification. The Q35-YFP expressing nematodes were analyzed as whole nematode for quantification of the aggregates and an image was taken of the head region of every animal. 20 animals were analyzed for each condition.

Motility Assay

Nematodes were transferred from liquid culture onto a blank (unseeded) NGM plate and allowed to acclimate for 15 min. The movement of the animals was digitally recorded at 20° C. using a Leica M165FC microscope with a DFC3000G digital camera and the Leica LASX Software. Movies of 10 s were captured at 10 frames/s. Animals that crossed each other or those that escaped from the field of view were excluded from analysis. 20 animals were analyzed for each condition. Captured frames were merged into *.avi format, imported into Fiji (Schindelin et al., 2012) and analyzed using the wrMTrck plugin (http://www.phage.dk/plugins). The average speed of each animal was calculated by dividing its body length by the duration of each track (body length per second).

Tissue Homogenization

Frozen brain tissue was cut on dry ice, weighed and homogenized in a 10-fold excess (w/v) of ice-cold 10 mM Tris-HCl pH 7.4, 0.8 M NaCl, 1 mM EDTA, 10% sucrose, 0.25 U/µl benzonase and complete protease inhibitor cocktail with a dounce homogenizer. The homogenate was incubated for 1 h at 4° C. on a rotating wheel and centrifuged for 20 min at 2,700×g (4° C.) to remove cell debris. *Drosophila* heads were processed comparably using 10 µl of ice-cold 10 mM Tris-HCl pH 7.4, 0.8 M NaCl, 1 mM EDTA, 10% sucrose and a complete protease inhibitor cocktail per fly head. Homogenates were centrifuged for 10 min at 8,000 rpm (4° C.). After centrifugation, supernatants were transferred to a new tube and total protein concentration was determined with a Pierce™ BCA assay using BSA as a standard. For FRASE analysis, 0.8-5 µg total protein per replicate were applied.

Electron Microscopy

Total brain homogenate was centrifuged at 18,000×g at 4° C. for 20 min; the resulting supernatant was pelleted by ultra-centrifugation at 190,000×g for 40 min and resuspended in 10 mM Tris-HCl (pH 7.4). Immunolabeling was performed with minor modifications as described (Laue, 2010). Briefly, samples were incubated on formvar-coated copper grids (Plano) for 10 min before immunolabeling. Grids were blocked and washed in PBS supplemented with 1% BSA and 0.1% glycine. Labeling was performed with the anti-HTT aggregate antibody AGG and an appropriate 12 nm colloidal gold-labeled secondary antibody (Jackson ImmunoResearch). Samples were stained with 2% uranyl acetate and imaged with a Zeiss EM 910 transmission electron microscope at 80 kV. Acquisition was performed with a CDD camera (Quemesa, Olympus Viewing System).

Immunodepletion of HTTex1 Aggregates from Mouse Brain Extracts

Protein G-coupled magnetic beads (Life Technologies) were incubated with 4 µg MW8 (Developmental Studies Hybridoma Bank, DSHB) or IgG isotype control (Invitrogen) antibody, respectively, for 10 min at RT to allow antibody binding. Free binding sites were saturated with Pierce protein-free blocking solution according to manufacturer recommendations. 500 µg brain homogenate in brain lysis buffer were incubated with antibody coupled beads for 3 h at 4° C. under constant overhead rotation. Subsequently, aliquots from the supernatants were taken and analyzed with the FRASE assay.

FRASE Assay

Purified GST-Ex1Q48-CyPet and GST-Ex1Q48-YPet were diluted in aggregation buffer at an equimolar ratio to a final concentration of 1.2 µM (0.6 µM each) with 14 U PSP per nmol sensor proteins if not stated otherwise. The solution was then mixed with preformed aggregates of Ex1Q48 (seeds) at varying concentrations with or without prior sonication and transferred to a black 384-well plate (with a final reaction volume of 30 µl per well and a sensor protein concentration of 1.2 µM). For quantification of seeding-competent HTT species in tissue samples, the sensor-protein mixture was supplemented with up to 10% (v/v) tissue homogenate. Fluorescence signals were measured every 20 min following a 5 s pulse of vertical shaking with a Tecan M200 fluorescence plate reader at 25° C. for up to 48 h. CyPet donor fluorescence was measured at excitation (Ex): 435 nm/emission (Em): 475 nm; YPet acceptor fluorescence at Ex: 500 nm/Em: 530 nm; the FRET channel (DA) was recorded at Ex: 435 nm/Em: 530 nm. Raw signals were processed by subtracting the background fluorescence of unlabeled Ex1Q48 in all channels. Signals in the FRET channel were corrected for donor bleed-through ($c_D$) and acceptor cross excitation ($c_A$) using donor- and acceptor-only samples to obtain sensitized emission. Finally, sensitized emission was normalized to the acceptor signals (Jiang and Sorkin, 2002). In brief, the FRET efficiency E (in %) was calculated as follows: $E=(DA-c_D \times DD-c_A \times AA)/AA$ with DD=donor channel signal and AA=acceptor channel signal.

Quantification of Mutant HTT Seeding Activity (HSA)

Seeding effects ($\Delta t_{50}$ [h]) were quantified by subtracting the $t_{50}$ values (time at half-maximal FRET efficiency) of the respective sample from the negative control. To obtain the $t_{50}$ values, the aggregation kinetics were curve fitted by Richard's five-parameter dose-response curve using GraphPad Prism.

$$y = y_0 + \left( \frac{y_\infty - y_0}{\left[1 + 10^{(Logxb-x) \times HillSlope}\right]^S} \right) \quad \text{(Formula (2))}$$

Quantification and Statistical Analysis

Statistical parameters including the exact value of n, the definition of center, dispersion and precision measures (mean±SEM or mean±SD) as well as the statistical analysis chosen and statistical significance are reported in the figures and figure legends. Data is judged to be statistically significant when p<0.05 by the indicated statistical test. In figures, asterisks denote statistical significance as calculated by Student's t test (*, p<0.05; , p<0.01; *, p<0.001). Statistical analysis was performed in GraphPad PRISM 7.

The invention is further illustrated by the following examples.

EXAMPLES

Self-propagating, amyloidogenic mutant huntingtin (mHTT) aggregates may drive progression of Huntington's disease (HD). Here, we report the development of a FRET-based mHTT aggregate seeding (FRASE) biosensor assay that enables the quantification of mHTT seeding activity (HSA) in complex biosamples from HD patients and disease models with high sensitivity and specificity. Application of the FRASE assay revealed HSA in disease-affected brain tissues of HD patients and mouse models, e.g. brain homogenates of presymptomatic HD transgenic and knock-in mice, and its progressive increase with phenotypic changes, suggesting that HSA quantitatively tracks disease progression. Biochemical investigations of mouse brain homogenates demonstrated that small rather than large mHTT structures are responsible for the HSA measured in FRASE assays. Finally, we assessed the neurotoxicity of mHTT seeds in an inducible *Drosophila* model transgenic for HTTex1. We found a strong correlation between HSA measured in adult neurons and the increased mortality of transgenic HD flies, indicating that FRASE assays detect disease-relevant, neurotoxic, mHTT structures with severe phenotypic consequences in vivo.

Example 1: Establishment of a FRET-Based mHTT Aggregate Seeding Assay

To monitor mHTT seeding activity, we first developed a cell-free aggregation assay with recombinant fluorescent reporter proteins (FIG. 7A). Two soluble glutathione S-transferase HTT exon-1 (HTTex1) fusion proteins with 48 glutamines C-terminally fused to CyPet or YPet (GST-Ex1Q48-CyPet or -YPet) were produced in *E. coli* and purified to ~90% homogeneity using glutathione sepharose chromatography (FIG. 7B).

Recombinant proteins were cleaved with PreScission protease (PSP) to release GST and to initiate the spontaneous aggregation of the fusion proteins Ex1Q48-CyPet and -YPet. The assembly of the tagged Ex1Q48 proteins into insoluble aggregates over time was monitored using an established filter retardation assay (FRA), which specifically detects large SDS-stable mHTT aggregates (Wanker et al., 1999). We found that the proteins Ex1Q48-CyPet and -YPet rapidly self-assemble into SDS-stable aggregates in vitro (FIG. 1A), confirming recently reported results (Wagner et al., 2018). To investigate the morphology of spontaneously formed Ex1Q48-CyPet and -YPet aggregates, we analyzed the aggregation reactions with atomic force microscopy (AFM). We observed that the tagged Ex1Q48 fusion proteins, similar to the untagged Ex1Q48 protein (Wagner et al., 2018), form large fibrillar protein aggregates (FIG. 1B).

We hypothesized that co-aggregation of CyPet- and YPet-tagged HTTex1 fragments should lead to a time-dependent increase of FRET as the fluorescent tags are brought in close proximity when fibrillar aggregates are formed (FIG. 1C). We treated mixtures of fusion proteins (1:1 molar ratio; 1-3 µM concentrations) with PSP and quantified the spontaneous formation of Ex1Q48-CyPet/-YPet co-aggregates by repeated FRET measurements. We observed a time- and concentration-dependent increase of FRET efficiency (FIG. 1D), indicating that FRET measurements are suitable to quantify HTTex1 co-aggregation. In contrast, no time-dependent increase of FRET efficiency was observed in samples that were not treated with PSP, underlining that the removal of the GST tag from CyPet- and YPet-tagged Ex1Q48 fragments is critical for the self-assembly of co-aggregates. Proteolytic cleavage of the GST fusion proteins with PSP was confirmed by SDS-PAGE and immunoblotting (FIG. 7C). Finally, AFM analysis confirmed that the samples indeed contain typical fibrillar HTTex1 co-aggregates (FIG. 7D).

In order to assess whether preformed Ex1Q48 fibrils can seed the co-aggregation of Ex1Q48-CyPet/-YPet, we incubated a 1:1 mixture of the GST fusion proteins with PSP and different amounts of preformed Ex1Q48 fibrils as seeds. We observed that addition of fibrils shortens the lag phase of Ex1Q48-CyPet/-YPet polymerization in a concentration-dependent manner (FIGS. 1E and 1F), indicating that they possess seeding activity. We termed the established method, which permits the quantification of in samples of interest, (FRASE) assay.

In independent control experiments, we also investigated whether a mixture of fusion proteins with non-pathogenic polyQ tracts, GST-Ex1Q23-CyPet/-YPet (FIG. 7A), can be applied as reporter molecules to monitor HSA. We found that preformed, fibrillar Ex1Q48 seeds do not induce FRET when they are added to PSP treated GST-Ex1Q23-CyPet/-YPet fusion proteins (FIG. 7E). Finally, we confirmed that addition of proteolytically cleaved GST-Ex1Q23 fusion protein as well as of uncleaved GST-Ex1Q23 or GST-Ex1Q48 fusion proteins do not shorten the lag phase of Ex1Q48-CyPet/-YPet polymerization (FIG. 7F).

Example 2: Both Small and Large Ex1Q48 Fibrils Exhibit HSA in FRASE Assays

Our initial experiments indicate that large bundles of Ex1Q48 fibrils (~1-2 μm in length; FIG. 1B) possess HSA (FIGS. 1E and 1F). We next investigated whether such an activity can also be detected, when small fibrillar Ex1Q48 seeds are added to FRASE assays. We sonicated large preformed Ex1Q48 fibrils for different periods of time and subsequently determined the HSA. We found that seeding activity is high in sonicated Ex1Q48 preparations (FIGS. 8A and 8B), indicating that besides large also small Ex1Q48 fibrils possess HSA. To confirm that indeed small fibrils are produced, we analyzed the generated samples by FRA (Wanker et al., 1999). We detected large Ex1Q48 aggregates in non-sonicated samples (FIG. 8C), while they were not observed in sonicated samples (>30 sec). This suggests that sonication (>30 sec) leads to fibril breakage and the formation of small HTTex1 structures that are no longer retained on filter membranes. Next, the samples were analyzed by dot blot (D B) assays, which allow the identification of protein assemblies on filter membranes independent of their size (Kayed et al., 2003). These experiments revealed Ex1Q48 immunoreactivity in both sonicated and non-sonicated samples (FIG. 8C), confirming the presence of HTT protein in all samples. Finally, we analyzed the generated samples with AFM, confirming that small fibrillar Ex1Q48 structures are produced by sonication (FIG. 8D).

Example 3: FRASE Assays Detect HSA with High Sensitivity and Specificity

To investigate the sensitivity and specificity of FRASE assays, we generated recombinant Ex1Q48 seeds by sonication and analyzed them by blue native PAGE and immunoblotting. We found that sonication for 60 sec leads to the formation of Ex1Q48 structures with an average molecular weight of ~1,250 kDa (~90 mers) (FIG. 2A), while aggregates with a much larger in size were detected in non-sonicated samples.

Next, a large range of concentrations of sonicated Ex1Q48 seeds were analyzed for their activity in FRASE assays. As expected, we observed a dose-dependent shortening of the lag phase when Ex1Q48 structures were added to polymerization reactions (FIGS. 2B and 2C). We determined a threshold of ~60 fM for detecting Ex1Q48 seeds. Furthermore, FRASE assays responded quantitatively to seeds over a dynamic range of 4 orders of magnitude (FIG. 2C). At a concentration of ~560 fM the Z' factor (Zhang et al., 1999) was 0.67 (FIG. 2C).

Finally, we investigated the specificity of the FRASE assay for detecting HTTex1 aggregates. We produced fibrillar α-synuclein, tau, amyloid-β and IAPP aggregates in vitro and subsequently analyzed them in FRASE assays. The unrelated fibrillar aggregates did not significantly influence Ex1Q48-CyPet/-YPet polymerization (FIG. 2D), indicating that the FRASE assay specifically detects amyloidogenic HTTex1 aggregates. AFM analysis confirmed that fibrillar α-synuclein, tau, amyloid-β and IAPP aggregates were added to reactions (FIG. 2E).

Example 4: HSA is Detectable in Brains of HD Mice and Patients

To investigate whether FRASE assays detect HSA in complex biosamples (FIG. 3A), we first assessed brain homogenates prepared from 12-week-old R6/2Q212 transgenic mice (carrying ~212 CAGs) and age-matched controls. R6/2Q212 mice express low levels of the human HTTex1Q212 protein (Sathasivam et al., 2013), show motor abnormalities from 8 weeks of age (Carter et al., 1999) and typical HTTex1 inclusion bodies from 3-4 weeks onwards (Li et al., 1999). We detected high levels of HSA in brain homogenates of R6/2Q212 mice but not in those of age-matched littermate controls (FIGS. 3B and 3C), indicating the presence of seeding-competent HTTex1 structures. Independent control experiments with the non-pathogenic reporter molecules Ex1Q23-CyPet/-YPet did not reveal detectable HSA in R6/2Q212 brain homogenates (FIG. 9A).

Next, we assessed whether HSA is detectable in brain extracts of 12-week-old R6/2Q51 (Larson et al., 2015) mice, which express a mutant HTTex1Q51 fragment. In comparison to R6/2Q212 mice, these mice do not yet have a disease phenotype at 12 weeks of age, suggesting that HSA should be lower. FRASE analysis revealed that brain homogenates of prodromal 12-week-old R6/2Q51 mice do not possess significant HSA (FIG. 9B), while activity was detectable in extracts of very old R6/2Q51 mice (104-105 weeks), which show pathological signs of disease.

We also investigated whether HSA is detectable in the hypothalamus of mouse brains, in which the proteins HTT853-Q79 or HTT853-Q18 were overexpressed for 8 weeks using viral vectors. Previous studies have demonstrated that hypothalamic expression of HTT853-Q79 leads to a gain of body weight and the formation of insoluble HTT protein aggregates (Hult et al., 2011). We found that HTT853-Q79 mice were significantly heavier than control and HTT853-Q18 mice (FIG. 9C). Furthermore, we also observed a significantly higher HSA in brain homogenates of HTT853-Q79 compared to HTT853-Q18 and controls mice (FIG. 9D), indicating that seeding activity and alterations in body weight are associated.

We next examined HSA in brain regions of HD patients. Protein extracts prepared from postmortem tissue (cerebral cortex, caudate nucleus and cerebellum) from HD patients and control individuals were systematically analyzed using the FRASE assay. HSA was invariably detected in HD but not in control samples (FIG. 3D), indicating that the method is suitable to discriminate between patients and healthy individuals. Interestingly, HSA was detectable in the cerebral cortex and the caudate nucleus, which are severely affected in HD patients (Zuccato et al., 2010) while it was not observed in the cerebellum, which is less affected in disease (DiFiglia et al., 1997). Similarly, no HSA was detectable in postmortem brains of patients with Alzheimer's disease (AD) that do not contain abnormal polyQ aggregates (FIG. 9E).

Finally, we investigated whether HSA in biosamples indeed originates from mHTT seeds. We produced brain extracts from symptomatic 12-week-old R6/2Q212 mice and littermate controls and immunodepleted potential seeding-competent mHTTex1 seeds using the monoclonal anti-HTT antibody MW8 (Ko et al., 2001). Then, samples were analyzed using FRASE assays. We observed a dramatic decrease of HSA in MW8-immunodepleted R6/2Q212 brain homogenates but not in homogenates treated with an isotype control antibody (FIGS. 9F and 9G), indicating that antibody treatment removes seeding-competent mHTTex1 aggregates from mouse brain extracts. As expected, we did not detect HSA in crude brain extracts of age-matched wild-type control mice. SDS-PAGE and immunoblotting confirmed depletion of mHTTex1 protein aggregates from brain homogenates by MW8 antibody treatment (FIGS. 9H and 9I).

Example 5: FRASE Assay Detects HSA in Brains of Presymptomatic HD Mice

To address whether HSA is detectable in brains of presymptomatic HD mice, we first analyzed non-sonicated brain homogenates of young R6/2Q212 mice and age-matched controls using the FRASE assay. We detected significant HSA in brain extracts of 2-week-old R6/2Q212 mice (FIG. 3E) that progressively increased over time. A similar result was also obtained with sonicated brain extracts (FIG. 3F). With sonication, significant HSA was already detectable in brains of 1-day-old R6/2Q212 transgenic mice, indicating that seeding-competent mHTTex1 structures are present in brains of R6/2Q212 mice long before inclusion bodies or motor abnormities can be detected (Davies et al., 1997; Zuccato et al., 2010).

Next, we investigated whether HSA is detectable in presymptomatic HdhQ150 knock-in mice that express a full-length HTT protein with a pathogenic polyQ tract of 150 glutamines (Lin et al., 2001). These mice show onset of depressive-like symptoms by 12 months of age (Ciamei et al., 2015) and impairment of motor function at ~18 months of age. Widespread deposition of mHTT aggregates throughout the brain is observed by 8 months of age (Woodman et al., 2007). We systematically analyzed tissue homogenates prepared from cortex, striatum and hippocampus of 2-, 5- and 8-month-old heterozygous HdhQ150 mice and littermate controls using the FRASE assay. We observed progressively increasing HSA in protein extracts from all three brain regions of HdhQ150 but not from control mice (FIG. 3G), confirming that mHTT seeds are detectable in HD mouse brains long before the appearance of neuronal inclusion bodies and motor abnormalities (Woodman et al., 2007).

Example 6: HSA is Detectable in Protein Fractions after Depletion of Large mHTTex1 Aggregates by Centrifugation To investigate whether HSA in HD mouse brains originates predominantly from soluble or insoluble mHTTex1 aggregates, non-sonicated brain homogenates prepared from symptomatic 12-week-old R6/2Q212 mice were centrifuged for 20 min at 2,700×g (low speed) or 18,000×g (medium speed), respectively, and the resulting supernatant and pellet fractions ($S1_{Low}$, P1 Low and $S1_{Med}$, $P1_{Med}$; FIG. 4A) were analyzed with FRASE assays. Interestingly, HSA was high in the parental crude lysate and in the $S1_{Low}$ fraction, while it was relatively low in the $P1_{Low}$ fraction (FIG. 4B), suggesting that it predominantly originates from soluble rather than insoluble mHTTex1 aggregates. A similar result was obtained when the fractions $S1_{Med}$ and $P1_{Med}$ were analyzed (FIG. 4B). However, after medium speed centrifugation HSA in the $P1_{Med}$ fraction was higher than in the $P1_{Low}$ fraction, indicating that mHTTex1 seeds can be removed from supernatant fractions using a higher centrifugation speed. This trend was even more pronounced when the generated $S1_{Med}$ fraction was subjected to a high-speed centrifugation (190,000×g), resulting in the supernatant and pellet fractions S2 and P2 (FIG. 4A). FRASE analysis revealed a significantly higher HSA in the P2 than in the S2 fraction, indicating that small seeding-competent mHTTex1 aggregates can be removed from the soluble $S1_{Med}$ fraction by high-speed centrifugation (FIGS. 4A and B).

To obtain a first hint about the size of the seeding-competent mHTTex1 aggregates in the brains of R6/2Q212 mice, the supernatant and pellet fractions were analyzed by FRA (Wanker et al., 1999). We found mHTTex1 immunoreactivity predominantly in the P1 Low and $P1_{Med}$ fractions. In comparison, weak or no immunoreactivity was detected in the fractions $S1_{Low}$, $S1_{Med}$, P2 and S2 (FIG. 4C), suggesting that HSA in R6/2Q212 mouse brain extracts predominately originates from small rather than large mHTTex1 protein assemblies.

Finally, we used transmission immunoelectron microscopy to assess the size and morphology of mHTTex1 seeds present in P2 fractions. They exhibit high HSA in FRASE assays but does not contain large mHTTex1 aggregates. We detected small, immunoreactive mHTTex1 fibrils with diameters of 10.2±3.6 nm and lengths of 157.8±64.1 nm exclusively in P2 fractions of R6/2Q212 mice (FIG. 4D), suggesting that HSA originates from such structures in P2 fractions.

Example 7: Short-Time Expression of HTTex1Q97 in Adult Neurons Decreases Lifespan and Locomotor Activity of HD Flies We first confirmed that HTTex1 transcripts decline in neurons when HTTex1Q97 (a protein with pathogenic polyQ tracts) expressing elavGS;HTTex1Q97 flies, a newly established inducible HD Drosophila model, are placed back on food without the inducer (FIGS. 10A and 10B).

Next, we investigated whether both long- and short-time expression of HTTex1Q17 or HTTex1Q97 in adult neurons influences survival of HD flies. Starting at an age of 3 days, we treated elavGS;HTTex1Q17 and elavGS;HTTex1Q97 flies either continuously or only for a short time of 3 or 6 days with RU486 (FIG. 5A); survival was measured by counting dead flies. We found that the lifespan of chronically RU486 treated elavGS;HTTex1Q97 flies was significantly reduced in comparison to untreated flies (FIGS. 5B and 5C).

In strong contrast, chronic treatment with RU486 did not shorten the lifespan of elavGS;HTTex1Q17 flies. We calculated a median lifespan of ~30 and ~85 days for treated and untreated elavGS;HTTex1Q97 flies, respectively. Strikingly, median lifespans of short-time (~38 and ~33 days) and chronically treated elavGS;HTTex1Q97 flies was similar.

As a behavioral measure of neuronal dysfunction, locomotor activity of HD flies was assessed using a negative geotaxis (climbing) assay (Latouche et al., 2007). We observed that RU486-treated elavGS;HTTex1Q97 flies show a significant decline in climbing behavior in comparison to untreated controls (FIG. 5D), confirming that both short and long-time expression of HTTex1Q97 in adult neurons induces neurotoxicity in HD flies.

Example 8: Formation of Small, Seeding-Competent HTTex1Q97 Structures in Adult Neurons is Associated with Reduced Survival We first assessed the correlation between the formation of large, SDS-stable HTTex1 aggregates in neurons and the survival of RU486-treated elavGS;HTTex1Q97 flies (FIGS. 5B and 5C). Head lysates were prepared from continuously and short-time (3 and 6 days) RU486-treated and untreated flies (FIG. 10C) and analyzed by FRA using the anti-HTT antibody MW8 (Ko et al., 2001). We found that the abundance of large, SDS-stable HTTex1Q97 aggregates was high in heads of chronically RU486-treated elavGS;HTTex1Q97 flies but relatively low in short-time treated flies (FIG. 5E). A similar result was obtained when the formation of large HTTex1Q97 aggregates in fly heads was quantified by FRAs using the anti-HTT antibody MAB5492 (FIG. 10D). These results indicate that large HTTex1Q97 aggregates detected by FRAs in adult neurons cannot well predict the observed survival phenotypes, which are very similar for short- and long-time RU486-treated flies (FIGS. 5B and 5C).

We next investigated mHTTex1 aggregate formation in brains of hormone-treated elavGS;HTTex1Q97 flies using an immunohistochemical method. We dissected whole brains of short- and long-time treated elavGS;HTTex1Q97 flies (FIG. 10C) and incubated them with the antibody MAB5492. As a control, the brain sections were also immunoassayed with an anti-RBP (RIM-binding protein) antibody, which detects synapses in fly brains (Liu et al., 2011). As expected, we detected high amounts of HTTex1Q97 aggregates (green puncta) in long-time and lower amounts in short-time (3 and 6 days) hormone-treated HD flies (FIG. 10E), confirming the results obtained by FRAs (FIG. 5E). Interestingly, these investigations also revealed very low amounts of HTTex1Q97 aggregates in brains of non-induced elavGS;HTTex1Q97 flies (FIG. 10E), indicating that the elavGS expression system is leaky and very low levels of HTTex1Q97 protein are also produced in the absence of hormone treatment. However, such low expression of HTTex1Q97 was not sufficient to significantly shorten the lifespan of HD flies (FIG. 5C).

Finally, we used the FRASE assay to quantify HSA in head lysates of RU486-treated elavGS;HTTex1Q97 flies. Strikingly, we measured high HSA in protein lysates of both short- and long-time hormone-treated flies (FIGS. 5F and 5G), demonstrating that FRASE assays provide information that is fundamentally different from that obtained by FRAs. As the abundance of large fibrillar aggregates is very low in protein extracts of short-time treated flies (FIGS. 5E and 10D), HSA in these fractions must predominantly result from smaller structures that are not retained by the filter membrane. In contrast to the FRA results (FIGS. 5E and 11D), HSA levels measured with the FRASE assay (FIGS. 5F and 5G) correlate significantly better with the increased mortality of RU486-treated elavGS;HTTex1Q97 flies (FIG. 5H). As expected, HSA was undetectable in head lysates of 27-day-old elav;HTTex1Q17 control flies, which constitutively express the protein HTTex1Q17 in neurons (FIG. 5F).

Example 9: Short-Time Expression of Hsp70 Extends the Lifespan of HD Flies and Decreases HSA in Neurons We hypothesized that co-expression of the molecular chaperone Hsp70 (HSPA1L) (Chan et al., 2000) might influence HSA and neurotoxicity in HD transgenic flies. To address this question, we generated elavGS;HSPA1L; HTTex1Q97 flies, which upon hormone treatment co-produce both Hsp70 and HTTex1Q97 in adult neurons. We first assessed whether in brains of RU486-treated elavGS; HSPA1L;HTTex1Q97 and elavGS;HTTex1Q97 flies similar levels of HTTex1Q97 transcripts are expressed. We treated 3-day-old flies for 6 days with RU486 (400 μM) and subsequently quantified mHTTex1 transcript levels in fly heads by qPCR. Similar HTTex1Q97 transcript levels were observed in both strains, indicating that co-expression of HSPA1L does not significantly influence mHTTex1 expression in elavGS;HSPA1L;HTTex1Q97 flies (FIG. 11A). To confirm the expression of Hsp70 in elavGS;HSPA1L; HTTex1Q97 flies, we also analyzed protein extracts of hormone-treated animals by SDS-PAGE and immunoblotting. As expected, similar Hsp70 protein levels were detectable in head lysates of hormone-treated elavGS;HSPA1L; HTTex1Q97 and elavGS;HSPA1L control flies (FIG. 11B), indicating that HTTex1Q97 co-expression does not significantly influence Hsp70 production in neurons of elavGS; HSPA1L;HTTex1Q97 flies.

Next, we assessed whether short-time co-expression of Hsp70 (for 6 days) in adult neurons influences the survival of elavGS;HSPA1L;HTTex1Q97 HD flies. In control experiments, the survival of short-time RU486-treated elavGS; HTTex1Q97 flies was analyzed. We determined median lifespans of ~39 and ~33 days for RU486 treated elavGS; HSPA1L;HTTex1Q97 and elavGS;HTTex1Q97 flies, respectively, (FIG. 6A-6C), indicating that short-time co-expression of Hsp70 in adult neurons improves the survival of elavGS;HSPA1L;HTTex1Q97 flies. As expected, a median lifespan of ~89 days was observed for non-treated elavGS;HTTex1Q97 flies, confirming our initial results (FIG. 5C).

To examine whether short-time co-expression (6 days) of Hsp70 in adult neurons influences mHTTex1 aggregation, head lysates of 13-day-old RU486-treated elavGS;HSPA1L; HTTex1Q97 and elavGS;HTTex1Q97 flies were analyzed by FRAs and FRASE assays. We found that the abundance of large HTTex1Q97 aggregates and HSA both were significantly decreased in brains of hormone treated elavGS; HSPA1L;HTTex1Q97 flies in comparison to elavGS; HTTex1Q97 flies (FIG. 6D-6F), substantiating our hypotheses that quantification of HSA predicts survival of HD transgenic flies.

Finally, we addressed the question whether the molecular chaperone Hsp70 associates directly with mHTTex1 aggregates in fly neurons. Immunohistochemical investigations of brains prepared from 9-day-old elavGS;HSPA1L; HTTex1Q97 flies treated for 6 days with RU486 revealed partial co-localization of Hsp70 and HTTex1Q97 aggregates (FIG. 6G), supporting previous observations that Hsp70 directly targets aggregation-prone polyQ-containing HTTex1 fragments (Warrick J M, 1999).

Example 10: Depletion of Hsc70 Increases Q35-YFP Seeding Activity in a *C. elegans* Model Our studies in HD flies indicate that short-time overproduction of Hsp70 decreases HSA in neurons (FIG. 6F), suggesting that a decrease of chaperone expression might have the opposite effects. To address this question, we performed RNAi knockdown experiments in transgenic worms that overproduce the aggregation-prone protein Q35-YFP in body wall muscle cells. Previous studies have demonstrated that Q35-YFP aggregation in these cells leads to motor impairment and that this phenotype increases in severity upon knock-down of hsp-1 (Hsc70) gene expression by RNAi (Brehme et al., 2014). We treated Q35-YFP expressing worms with hsp-1 RNAi and assessed their motility at day five. We observed a significant reduction of motility in RNAi-treated in comparison to untreated worms (FIG. 11C), confirming previously published results (Brehme et al., 2014). Furthermore, this phenotypic change was associated with a significant increase in Q35-YFP seeding activity measured by FRASE assays (FIGS. 11D and 11E), supporting our hypothesis that HSA is a marker of dysfunction and toxicity in model systems.

Example 11: Application of the FRASE Assay for the Detection of HSA in Human Brain Tissue Using the FRASE assay, HSA was detectable in brain tissues of various HD mice at symptomatic stage, regardless whether an N-terminal fragment of mutant HTT or the full-length protein was expressed. In addition, HSA was detectable in severely affected brain regions of HD patients but not in control individuals. This suggests that the presence of seeding-competent mHTT aggregates is a general phenomenon in HD models and patients and further implies a potential role of these structures in disease development or progression. However, to be regarded as disease relevant and capable of promoting pathogenesis, such structures would need to be present early in disease development and their abundance in affected tissues should increase with the severity of disease symptoms. Initial experiments using R6/2Q212 and HdhQ150 mice demonstrated that mHTT seeds are detectable in HD mouse brains long before the appearance of inclusion bodies and motor abnormalities and increase in abundance with the development of disease pathology (Woodman et al., 2007). Subsequently, we asked whether similar results can be obtained with brain tissues prepared from HD patients. Based on the temporospatial pattern of degeneration in the striatum, Vonsattel et al. developed a grading system to classify the severity of neuropathological changes into five distinct grades (0-5) (Vonsattel et al., 1985). Longitudinal examination of HD patients prior to death showed significant correlation between clinical features and the neuropathological grade assigned postmortem (Rosenblatt et al., 2003).

Here, we analyzed brain homogenates prepared from the putamen of HD patients and control individuals. Neuropathological changes of HD patients were classified and ranged from grade 2 to grade 4. FRASE analysis demonstrates a significant elevation of HSA in brain tissue with mild neuropathological changes (FIG. 12, Grade 2). With the advancement of neuropathological changes, a successive increase of HSA (FIG. 12, Grade 3 and 4) was observed, indicating that HSA correlates with the severity of neuropathological changes.

Example 12: Application of the FRASE Assay for the Detection of HSA in Human Brain Tissue The FRASE assay could be further optimized regarding its sensitivity. Impeding primary nucleation and thereby delaying spontaneous self-assembly of the reporter proteins might improve the detection limit. Primary nucleation of mHTTex1 depends on the concentration of the protein and the length of the polyQ tract (Li and Li, 1998; Scherzinger et al., 1999). In addition, primary nucleation is greatly influenced by the amino acid sequences flanking the polyQ domain (N17 and PRD domain). Whereas the N17 domain has been reported to facilitate aggregation, the PRD was shown to counteract this process (Bhattacharyya et al., 2006; Crick et al., 2013; Mishra et al., 2012). Therefore, the deletion of the N17 region on the one hand or the expansion of the PRD on the other hand, might be strategies to generate sensor proteins of even higher sensitivity. In addition, minimizing or removing both flanking sequences (N17 and PRD) might generate a generic seeding sensor that can detect seeding-competent aggregates associated to other polyQ diseases.

We generated three additional mHTTex1 based reporter protein pairs. For the constructs GST-K2Q48P6-CyPet/GST-K2Q48P6-YPet the N17 region was replaced by two lysine residues and the proline-rich domain (PRD) was replaced by 6 proline residues. The construct contains, in consecutive order, 2 lysines, 48 glutamines and 6 prolines, and was fused N-terminally to GST and C-terminally to CyPet or YPet (GST-K2Q48P6-CyPet/GST-K2Q48P6-YPet; SEQ ID NOs: 48 and 50).

In order to generate the constructs GST-ΔN17Q48+6PRD-CyPet/GST-ΔN17Q48+6PRD-YPet the N17 region was deleted and the proline rich domain was extended by 6 proline residues. The construct contains, in consecutive order, 48 glutamines and an extended PRD, and was fused N-terminally to GST and C-terminally to CyPet or YPet (GST-ΔN17Q48+6PRD-CyPet/GST-ΔN17Q48+6PRD-YPet; SEQ ID NOs: 52 and 54).

In order to generate the constructs GST-ΔN17Q40+6PRD-CyPet/GST-ΔN17Q40+6PRD-YPet the N17 region was deleted and the proline rich domain was extended by 6 proline residues. The construct contains, in consecutive order, 40 glutamines and an extended PRD, and was fused N-terminally to GST and C-terminally to CyPet or YPet (GST-ΔN17Q40+6PRD-CyPet/GST-ΔN17Q40+6PRD-YPet; SEQ ID NOs: 56 and 58).

Using the above fusion proteins, the FRASE assay's sensitivity was improved and thus, its applicability was broadened.

Example 13: Analyzing Compound Effects on Seeded Aggregation and Seed Modulation Within the context of the above-described method for the quantification of seeding activity ($\Delta t_{50}$) of an amyloidogenic aggregate, it is also encompassed by the invention that the preformed aggregate may be used to screen for compounds that influence seeding competence of the aggregate. For example, a given amyloidogenic aggregate C may be pretreated with a compound of interest (D) before being used in the described screening method. Then, seeding activity is determined once with a sample containing aggregate C without pretreatment, and once with a sample containing aggregate C pretreated with the compound D. Compound D may be e.g. a protein, peptide or small molecule as defined herein.

The small molecule O4

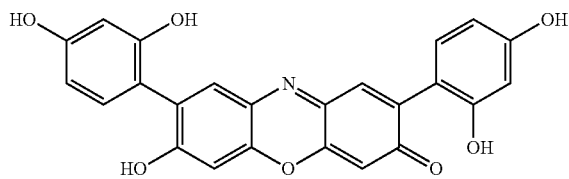 [SMILES: O=c1cc2oc3cc(O)c(-c4ccc(O)cc4O)cc3nc-2cc1-c1ccc(O)cc1O]

has previously been shown to interfere with the aggregation of HTTex1Q48 (Wagner et al., 2018), which makes it a promising candidate to modulate preformed aggregates and alter their seeding activity. In order to test this hypothesis we performed proof of principle experiments in which preformed, sonicated HTTex1Q48 aggregates were incubated with O4 in a 200-fold molar excess at 25° C. for 20 hours and subsequently analyzed for their seeding activity using the FRASE assay.

Pre-incubation of seeds with O4 strongly reduces HTTex1Q48 seeding activity in comparison to HTTex1Q48 seeds incubated with DMSO (FIGS. 13 A and B). In order to confirm that the reduction in HSA results from the modification of HTTex1Q48 seed and not from the modulation of sensor protein aggregation by residual O4, sensor proteins were aggregated in the presence of O4 but in the absence of HTTex1Q48 seeds. At this concentration, O4 has no significant effect on sensor protein aggregation, showing the reduction in HSA of pre-incubated seeds originates from the modulation of HTT aggregates.

DISCUSSION

With the described assay in hand, we assessed the potential correlation between HSA in affected tissues and the appearance of disease phenotypes in various HD models (FIGS. 3-6, FIG. 12). We e.g., detected HSA in crude brain extracts of mice weeks before manifestation of disease (FIGS. 3E-3G). Furthermore, we observed an increase of mutant HSA in mouse brain extracts and homogenates prepared from putamen of HD patients concomitantly with the appearance of symptoms, suggesting that it quantitatively tracks disease progression. Finally, mechanistic studies with a newly established inducible *Drosophila* model of HD indicate a correlation between HSA in adult neurons and reduced survival of HD flies, supporting our hypothesis that mHTT seeding is a disease-relevant process. Taken together, these studies indicate that HSA is a valuable early disease marker that can predict severe downstream phenotypic changes in various HD models.

We observed high HSA in soluble fractions of HD mouse brain extracts (FIGS. 4B and 4C), suggesting that seeding activity in transgenic animals predominately originates from small rather than large mHTTex1 aggregates. However, inclusions with insoluble fibrillar HTTex1 aggregates (Bauerlein et al., 2017) may also possess seeding activity. Further studies will be necessary to purify fibrillar HTTex1 structures of different sizes from mouse and fly brains and to compare their specific seeding activity (i.e., seeding activity per unit of protein). Our results are in agreement with previous investigations indicating that small, fibrillar polyQ-containing HTT assemblies are detectable in the cytoplasm of cells besides large inclusions with fibrillar mHTT aggregates (Sahl et al., 2012). They are also consistent with studies demonstrating that proteotoxicity in mammalian cells is associated with small, diffusible HTT oligomers rather than large inclusions (Arrasate et al., 2004; Leitman et al., 2013). However, our present study advances beyond the state-of-the-art. For the first time, we provide experimental evidence that the abundance of small seeding-competent polyQ structures correlates with dysfunction and toxicity in HD transgenic flies and worms (FIGS. 5, 6 and 11).

Together, our investigations suggest that HSA in HD mouse and fly brain extracts is a biological marker of disease long before its onset. Previous studies argue that the abundance of large inclusions with insoluble mHTT aggregates in brains of HD mice and patients is not predictive for the development of symptoms (Kuemmerle et al., 1999). However, neuronal inclusions are commonly detected with immunohistological methods, which fail to identify small, seeding-competent mHTT assemblies in disease brains. The application of the FRASE assay overcomes this important limitation associated with standard histology and is likely to yield new mechanistic insights into the progressive development of HD. We propose that in future drug trials with HD mice HSA could be utilized as an outcome marker to monitor the efficacy of therapeutic molecules in vivo, before and independent of changes in phenotype. As we detected robust HSA in the striatum of 2-month-old HdhQ150 knock-in mice (FIG. 3G), drug treatment could start before that point in time and animals could be assessed for HSA at any later age. Furthermore, we found that the FRASE method can be applied as a drug screening assay to identify therapeutic molecules such as small molecule compounds that directly target mHTT seeding in vitro (FIG. 13). As the assay can monitor mutant HSA in protein extracts from postmortem patient brain and transgenic animals (FIG. 3D-3G, FIG. 12), it seems now feasible to investigate aggregate-targeting therapeutic candidate molecules in assays which contain disease-relevant seeds.

Through the application of FRASE assays, we have demonstrated that HSA is a robust, early disease biomarker in HD transgenic mice and flies. We propose that it also might be of high value for monitoring disease onset and progression in HD patients if HSA could be quantified in biosamples whose collection is technically and ethically possible, like cerebrospinal fluid, blood or muscle tissue. Through the quantification of HSA in patient samples, the optimal time point for the initiation of clinical trials could be determined and the efficacy of therapeutic interventions could be monitored. In this way, our findings may help to develop novel disease-modifying therapeutic strategies for HD and other polyQ diseases.

REFERENCES

Arrasate, M., Mitra, S., Schweitzer, E. S., Segal, M. R., and Finkbeiner, S. (2004). Inclusion body formation reduces levels of mutant huntingtin and the risk of neuronal death. Nature 431, 805-810.

Atarashi, R., Moore, R. A., Sim, V. L., Hughson, A. G., Dorward, D. W., Onwubiko, H. A., Priola, S. A., and Caughey, B. (2007). Ultrasensitive detection of scrapie prion protein using seeded conversion of recombinant prion protein. Nature methods 4, 645-650.

Atarashi, R., Satoh, K., Sano, K., Fuse, T., Yamaguchi, N., Ishibashi, D., Matsubara, T., Nakagaki, T., Yamanaka, H., Shirabe, S., et al. (2011). Ultrasensitive human prion detection in cerebrospinal fluid by real-time quaking-induced conversion. Nature medicine 17, 175-178.

Babcock, D. T., and Ganetzky, B. (2015). Transcellular spreading of huntingtin aggregates in the *Drosophila* brain. Proceedings of the National Academy of Sciences of the United States of America 112, E5427-5433.

Baldo, B., Soylu, R., and Petersen, A. (2013). Maintenance of basal levels of autophagy in Huntington's disease mouse models displaying metabolic dysfunction. PloS one 8, e83050.

Bhattacharyya, A., Thakur, A. K., Chellgren, V. M., Thiagarajan, G., Williams, A. D., Chellgren, B. W., Creamer, T. P., and Wetzel, R. (2006). Oligoproline Effects on Polyglutamine Conformation and Aggregation. Journal of Molecular Biology 355, 524-535.

Biancalana, M., and Koide, S. (2010). Molecular mechanism of Thioflavin-T binding to amyloid fibrils. Biochimica et biophysica acta 1804, 1405-1412.

Brehme, M., Voisine, C., Rolland, T., Wachi, S., Soper, J. H., Zhu, Y., Orton, K., Villella, A., Garza, D., Vidal, M., et al. (2014). A chaperome subnetwork safeguards proteostasis in aging and neurodegenerative disease. Cell reports 9, 1135-1150.

Brundin, P., Melki, R., and Kopito, R. (2010). Prion-like transmission of protein aggregates in neurodegenerative diseases. Nature reviews. Molecular cell biology 11, 301-307.

Carter, R. J., Lione, L. A., Humby, T., Mangiarini, L., Mahal, A., Bates, G. P., Dunnett, S. B., and Morton, A. J. (1999). Characterization of progressive motor deficits in mice transgenic for the human Huntington's disease mutation. The Journal of neuroscience: the official journal of the Society for Neuroscience 19, 3248-3257.

Castilla, J., Saa, P., and Soto, C. (2005). Detection of prions in blood. Nature medicine 11, 982-985.

Chan, H. Y., Warrick, J. M., Gray-Board, G. L., Paulson, H. L., and Bonini, N. M. (2000). Mechanisms of chaperone suppression of polyglutamine disease: selectivity, synergy and modulation of protein solubility in *Drosophila*. Human molecular genetics 9, 2811-2820.

Chiti, F., and Dobson, C. M. (2017). Protein Misfolding, Amyloid Formation, and Human Disease: A Summary of Progress Over the Last Decade. Annu Rev Biochem 86, 27-68.

Ciamei, A., Detloff, P. J., and Morton, A. J. (2015). Progression of behavioural despair in R6/2 and Hdh knock-in mouse models recapitulates depression in Huntington's disease. Behavioural brain research 291, 140-146.

Cohen, S. I., Vendruscolo, M., Dobson, C. M., and Knowles, T. P. (2012). From macroscopic measurements to microscopic mechanisms of protein aggregation. Journal of molecular biology 421, 160-171.

Crick, S. L., Ruff, K. M., Garai, K., Frieden, C., and Pappu, R. V. (2013). Unmasking the roles of N- and C-terminal flanking sequences from exon 1 of huntingtin as modulators of polyglutamine aggregation. Proceedings of the National Academy of Sciences 110, 20075-20080.

Davies, S. W., Turmaine, M., Cozens, B. A., DiFiglia, M., Sharp, A. H., Ross, C. A., Scherzinger, E., Wanker, E. E., Mangiarini, L., and Bates, G. P. (1997). Formation of neuronal intranuclear inclusions underlies the neurological dysfunction in mice transgenic for the HD mutation. Cell 90, 537-548.

DiFiglia, M., Sapp, E., Chase, K. O., Davies, S. W., Bates, G. P., Vonsattel, J. P., and Aronin, N. (1997). Aggregation of huntingtin in neuronal intranuclear inclusions and dystrophic neurites in brain. Science 277, 1990-1993.

Du, D., Murray, A. N., Cohen, E., Kim, H. E., Simkovsky, R., Dillin, A., and Kelly, J. W. (2011). A kinetic aggregation assay allowing selective and sensitive amyloid-beta quantification in cells and tissues. Biochemistry 50, 1607-1617.

Gao, M., Estel, K., Seeliger, J., Friedrich, R. P., Dogan, S., Wanker, E. E., Winter, R., and Ebbinghaus, S. (2015). Modulation of human IAPP fibrillation: cosolutes, crowders and chaperones. Physical chemistry chemical physics PCCP 17, 8338-8348.

Guo, J. L., and Lee, V. M. (2014). Cell-to-cell transmission of pathogenic proteins in neurodegenerative diseases. Nature medicine 20, 130-138.

Gupta, S., Jie, S., and Colby, D. W. (2012). Protein misfolding detected early in pathogenesis of transgenic mouse model of Huntington disease using amyloid seeding assay. The Journal of biological chemistry 287, 9982-9989.

Herva, M. E., Zibaee, S., Fraser, G., Barker, R. A., Goedert, M., and Spillantini, M. G. (2014). Anti-amyloid compounds inhibit alpha-synuclein aggregation induced by protein misfolding cyclic amplification (PMCA). The Journal of biological chemistry 289, 11897-11905.

Hockly, E., Woodman, B., Mahal, A., Lewis, C. M., and Bates, G. (2003). Standardization and statistical approaches to therapeutic trials in the R6/2 mouse. Brain research bulletin 61, 469-479.

Holmes, B. B., Furman, J. L., Mahan, T. E., Yamasaki, T. R., Mirbaha, H., Eades, W. C., Belaygorod, L., Cairns, N.J., Holtzman, D. M., and Diamond, M. I. (2014). Proteopathic tau seeding predicts tauopathy in vivo. Proceedings of the National Academy of Sciences of the United States of America 111, E4376-4385.

Hult, S., Soylu, R., Bjorklund, T., Belgardt, B. F., Mauer, J., Bruning, J. C., Kirik, D., and Petersen, A. (2011). Mutant huntingtin causes metabolic imbalance by disruption of hypothalamic neurocircuits. Cell metabolism 13, 428-439.

Jarrett, J. T., and Lansbury, P. T., Jr. (1993). Seeding "one-dimensional crystallization" of amyloid: a pathogenic mechanism in Alzheimer's disease and scrapie? Cell 73, 1055-1058.

Jeon, I., Cicchetti, F., Cisbani, G., Lee, S., Li, E., Bae, J., Lee, N., Li, L., Im, W., Kim, M., et al. (2016). Human-to-mouse prion-like propagation of mutant huntingtin protein. Acta neuropathologica.

Jiang, X., and Sorkin, A. (2002). Coordinated traffic of Grb2 and Ras during epidermal growth factor receptor endocytosis visualized in living cells. Molecular biology of the cell 13, 1522-1535.

Jucker, M., and Walker, L. C. (2013). Self-propagation of pathogenic protein aggregates in neurodegenerative diseases. Nature 501, 45-51.

Kayed, R., Head, E., Thompson, J. L., McIntire, T. M., Milton, S. C., Cotman, C. W., and Glabe, C. G. (2003). Common structure of soluble amyloid oligomers implies common mechanism of pathogenesis. Science 300, 486-489.

Ko, J., Ou, S., and Patterson, P. H. (2001). New anti-huntingtin monoclonal antibodies: implications for huntingtin conformation and its binding proteins. Brain research bulletin 56, 319-329.

Kuemmerle, S., Gutekunst, C. A., Klein, A. M., Li, X. J., Li, S. H., Beal, M. F., Hersch, S. M., and Ferrante, R. J. (1999). Huntington aggregates may not predict neuronal death in Huntington's disease. Annals of neurology 46, 842-849.

Larson, E., Fyfe, I., Morton, A. J., and Monckton, D. G. (2015). Age-, tissue- and length-dependent bidirectional somatic CAG*CTG repeat instability in an allelic series of R6/2 Huntington disease mice. Neurobiology of disease 76, 98-111.

Latouche, M., Lasbleiz, C., Martin, E., Monnier, V., Debeir, T., Mouatt-Prigent, A., Muriel, M. P., Morel, L., Ruberg, M., Brice, A., et al. (2007). A conditional pan-neuronal *Drosophila* model of spinocerebellar ataxia 7 with a reversible adult phenotype suitable for identifying modifier genes. The Journal of neuroscience: the official journal of the Society for Neuroscience 27, 2483-2492.

Laue, M. (2010). Electron microscopy of viruses. Methods in cell biology 96, 1-20.

Leitman, J., Ulrich Hartl, F., and Lederkremer, G. Z. (2013). Soluble forms of polyQ-expanded huntingtin rather than large aggregates cause endoplasmic reticulum stress. Nature communications 4, 2753.

LeVine, H., 3rd (1993). Thioflavine T interaction with synthetic Alzheimer's disease beta-amyloid peptides: detection of amyloid aggregation in solution. Protein science: a publication of the Protein Society 2, 404-410.

Li, S.-H., and Li, X.-J. (1998). Aggregation of N-Terminal Huntingtin is Dependent on the Length of Its Glutamine Repeats. Human Molecular Genetics 7, 777-782.

Li, H., Li, S. H., Cheng, A. L., Mangiarini, L., Bates, G. P., and Li, X. J. (1999). Ultrastructural localization and progressive formation of neuropil aggregates in Huntington's disease transgenic mice. Human molecular genetics 8, 1227-1236.

Lin, C. H., Tallaksen-Greene, S., Chien, W. M., Cearley, J. A., Jackson, W. S., Crouse, A. B., Ren, S., Li, X. J., Albin, R. L., and Detloff, P. J. (2001). Neurological abnormalities in a knock-in mouse model of Huntington's disease. Human molecular genetics 10, 137-144.

Liu, K. S. Y., Siebert, M., Mertel, S., Knoche, E., Wegener, S., Wichmann, C., Matkovic, T., Muhammad, K., Depner, H., Mettke, C., et al. (2011). RIM-Binding Protein, a Central Part of the Active Zone, Is Essential for Neurotransmitter Release. Science 334, 1565-1569.

Mangiarini, L., Sathasivam, K., Seller, M., Cozens, B., Harper, A., Hetherington, C., Lawton, M., Trottier, Y., Lehrach, H., Davies, S. W., et al. (1996). Exon 1 of the HD gene with an expanded CAG repeat is sufficient to cause a progressive neurological phenotype in transgenic mice. Cell 87, 493-506.

Mishra, R., Jayaraman, M., Roland, B. P., Landrum, E., Fullam, T., Kodali, R., Thakur, A. K., Arduini, I., and Wetzel, R. (2012). Inhibiting the Nucleation of Amyloid Structure in a Huntingtin Fragment by Targeting α-Helix-Rich Oligomeric Intermediates. Journal of Molecular Biology 415, 900-917.

Nguyen, A. W., and Daugherty, P. S. (2005). Evolutionary optimization of fluorescent proteins for intracellular FRET. Nature biotechnology 23, 355-360.

Nucifora, L. G., Burke, K. A., Feng, X., Arbez, N., Zhu, S., Miller, J., Yang, G., Ratovitski, T., Delannoy, M., Muchowski, P. J., et al. (2012). Identification of novel potentially toxic oligomers formed in vitro from mammalian-derived expanded huntingtin exon-1 protein. The Journal of biological chemistry 287, 16017-16028.

Osterwalder, T., Yoon, K. S., White, B. H., and Keshishian, H. (2001). A conditional tissue-specific transgene expression system using inducible GAL4. Proceedings of the National Academy of Sciences of the United States of America 98, 12596-12601.

Pecho-Vrieseling, E., Rieker, C., Fuchs, S., Bleckmann, D., Esposito, M. S., Botta, P., Goldstein, C., Bernhard, M., Galimberti, I., Muller, M., et al. (2014). Transneuronal propagation of mutant huntingtin contributes to non-cell autonomous pathology in neurons. Nature neuroscience 17, 1064-1072.

Pieri, L., Madiona, K., Bousset, L., and Melki, R. (2012). Fibrillar alpha-synuclein and huntingtin exon 1 assemblies are toxic to the cells. Biophysical journal 102, 2894-2905.

Rosenblatt, A., Abbott, M. H., Gourley, L. M., Troncoso, J. C., Margolis, R. L., Brandt, J., and Ross, C. A. (2003). Predictors of neuropathological severity in 100 patients with Huntington's disease. Ann Neurol 54, 488-493.

Saborio, G. P., Permanne, B., and Soto, C. (2001). Sensitive detection of pathological prion protein by cyclic amplification of protein misfolding. Nature 411, 810-813.

Sahl, S. J., Weiss, L. E., Duim, W. C., Frydman, J., and Moerner, W. E. (2012). Cellular inclusion bodies of mutant huntingtin exon 1 obscure small fibrillar aggregate species. Scientific reports 2, 895.

Sathasivam, K., Neueder, A., Gipson, T. A., Landles, C., Benjamin, A. C., Bondulich, M. K., Smith, D. L., Faull, R. L., Roos, R. A., Howland, D., et al. (2013). Aberrant splicing of HTT generates the pathogenic exon 1 protein in Huntington disease. Proceedings of the National Academy of Sciences of the United States of America 110, 2366-2370.

Scherzinger, E., Lurz, R., Turmaine, M., Mangiarini, L., Hollenbach, B., Hasenbank, R., Bates, G. P., Davies, S. W., Lehrach, H., and Wanker, E. E. (1997). Huntingtin-encoded polyglutamine expansions form amyloid-like protein aggregates in vitro and in vivo. Cell 90, 549-558.

Scherzinger, E., Sittler, A., Schweiger, K., Heiser, V., Lurz, R., Hasenbank, R., Bates, G. P., Lehrach, H., and Wanker, E. E. (1999). Self-assembly of polyglutamine-containing huntingtin fragments into amyloid-like fibrils: implications for Huntington's disease pathology. Proceedings of the National Academy of Sciences of the United States of America 96, 4604-4609.

Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nature methods 9, 676-682.

Stewart, B. A., Atwood, H. L., Renger, J. J., Wang, J., and Wu, C. F. (1994). Improved Stability of *Drosophila* Larval Neuromuscular Preparations in Hemolymph-Like Physiological Solutions. J Comp Physiol A 175, 179-191.

Tan, Z., Dai, W., van Erp, T. G., Overman, J., Demuro, A., Digman, M. A., Hatami, A., Albay, R., Sontag, E. M., Potkin, K. T., et al. (2015). Huntington's disease cerebrospinal fluid seeds aggregation of mutant huntingtin. Molecular psychiatry 20, 1286-1293.

Theillet, F. X., Binolfi, A., Bekei, B., Martorana, A., Rose, H. M., Stuiver, M., Verzini, S., Lorenz, D., van Rossum, M., Goldfarb, D., et al. (2016). Structural disorder of monomeric alpha-synuclein persists in mammalian cells. Nature 530, 45-50.

Vonsattel, J. P., Myers, R. H., Stevens, T. J., Ferrante, R. J., Bird, E. D., and Richardson, E. P., Jr. (1985). Neuropathological classification of Huntington's disease. Journal of neuropathology and experimental neurology 44, 559-577.

Wagner, A. S., Politi, A. Z., Ast, A., Bravo-Rodriguez, K., Baum, K., Buntru, A., Strempel, N. U., Brusendorf, L., Hanig, C., Boeddrich, A., et al. (2018). Self-assembly of Mutant Huntingtin Exon-1 Fragments into Large Complex Fibrillar Structures Involves Nucleated Branching. Journal of molecular biology 430, 1725-1744.

Wanker, E. E., Scherzinger, E., Heiser, V., Sittler, A., Eickhoff, H., and Lehrach, H. (1999). Membrane filter assay for detection of amyloid-like polyglutamine-containing protein aggregates. Methods in enzymology 309, 375-386.

Warrick J M, C. H., Gray-Board G L, Chai Y, Paulson H L, Bonini N M. (1999). Suppression of polyglutamine-mediated neurodegeneration in *Drosophila* by the molecular chaperone HSP70. Nat Genet.

Woodman, B., Butler, R., Landles, C., Lupton, M. K., Tse, J., Hockly, E., Moffitt, H., Sathasivam, K., and Bates, G. P. (2007). The Hdh(Q150/Q150) knock-in mouse model of HD and the R6/2 exon 1 model develop comparable and widespread molecular phenotypes. Brain research bulletin 72, 83-97.

Zhang, J. H., Chung, T. D., and Oldenburg, K. R. (1999). A Simple Statistical Parameter for Use in Evaluation and Validation of High Throughput Screening Assays. Journal of biomolecular screening 4, 67-73.

Zuccato, C., Valenza, M., and Cattaneo, E. (2010). Molecular mechanisms and potential therapeutic targets in Huntington's disease. Physiological reviews 90, 905-981.

The invention claimed is:

1. A method for quantifying seeding activity ($\Delta t_{50}$) of an amyloidogenic aggregate, comprising the steps of:
   (i) providing, in a solution, a mixture of an amyloidogenic protein A which is N-terminally or C-terminally fused to a donor fluorophore molecule and an amyloidogenic protein B which is N-terminally or C-terminally fused to an acceptor fluorophore molecule, wherein the donor fluorophore molecule and the acceptor fluorophore molecule are capable of Förster Resonance Energy Transfer (FRET) if they are in close proximity to each other;
   (ii) adding a sample containing an amyloidogenic protein aggregate C to the mixture of step (i);
   (iii) shaking the mixture of step (ii);
   (iv) measuring fluorescence signals in the donor channel, the acceptor channel, and the Förster Resonance Energy Transfer (FRET) channel at predetermined intervals after completion of step (iii);
   (v) calculating FRET efficiency (E) from the signals obtained in step (iv); and
   (vi) quantifying seeding activity ($\Delta t_{50}$) by subtracting the time at half-maximal FRET efficiency of the sample ($t_{50}(S)$) from the time at half-maximal FRET efficiency of a negative control ($t_{50}(0)$).

2. The method of claim 1, wherein the amyloidogenic proteins A and B are polyQ proteins.

3. The method of claim 2, wherein a mutant form of an amyloidogenic protein A or B is characterized by an increased number of glutamine residues as compared to a corresponding wild-type form and by an increased number of proline residues as compared to the corresponding wild-type form.

4. The method of claim 1, wherein the amyloidogenic protein aggregate C consists of amyloidogenic proteins A and/or B.

5. The method of claim 1, wherein the sample containing aggregate C is selected from the group consisting of an optionally pretreated tissue sample, an optionally pretreated body fluid sample and an optionally pretreated cell culture sample.

6. A method for assessing risk for development of a polyglutamine (polyQ) disease in a subject, comprising
   (i) quantification of seeding activity ($\Delta t_{50}$) of a polyQ-containing protein in a sample, comprising the steps of:
      (a) providing, in a solution, a mixture of a first polyQ-containing protein which is C-terminally fused to a donor fluorophore molecule and a second polyQ-containing protein which is C-terminally fused to an acceptor fluorophore molecule, wherein the first and second proteins are the same polyQ-containing protein and wherein the donor fluorophore molecule and the acceptor fluorophore molecule are capable of FRET if they are in close proximity to each other;
      (b) adding a sample collected from the subject to the mixture of step (a);
      (c) shaking the mixture of step (b);
      (d) measuring fluorescence signals in the donor channel, the acceptor channel, and the FRET channel at predetermined intervals after completion of step (c);
      (e) calculating FRET efficiency (E) from the signals obtained in step (d); and
      (f) quantifying seeding activity ($\Delta t_{50}$) by subtracting the time at half-maximal FRET efficiency of a sample ($t_{50}(S)$) from the time at half-maximal FRET efficiency of a reference ($t_{50}(0)$); and
   (ii) correlating that the subject is at risk for development of the polyQ disease when the seeding activity in the sample is increased as compared to the reference sample.

7. A method for predicting onset of a polyglutamine (polyQ) disease in a subject, comprising
   (i) quantification of seeding activity ($\Delta t_{50}$) of a polyQ-containing protein in a sample, comprising the steps of:
      (a) providing, in a solution, a mixture of a first polyQ-containing protein which is C-terminally fused to a donor fluorophore molecule and a second polyQ-containing protein which is C-terminally fused to an acceptor fluorophore molecule, wherein the first and second proteins are the same polyQ-containing protein and wherein the donor fluorophore molecule and the acceptor fluorophore molecule are capable of FRET if they are in close proximity to each other;
      (b) adding a sample collected from the subject to the mixture of step (a);
      (c) shaking the mixture of step (b);
      (d) measuring fluorescence signals in the donor channel, the acceptor channel, and the FRET channel at predetermined intervals after completion of step (c);
      (e) calculating FRET efficiency (E) from the signals obtained in step (d); and
      (f) quantifying seeding activity ($\Delta t_{50}$) by subtracting the time at half-maximal FRET efficiency of a sample ($t_{50}(S)$) from the time at half-maximal FRET efficiency of a reference ($t_{50}(0)$); and
   (ii) correlating that the onset of the polyQ disease has occurred or will occur soon when the seeding activity in the sample is increased as compared to the reference sample.

8. A method for assessing progression of a polyglutamine (polyQ) disease in a subject, comprising
   (i) quantification of seeding activity ($\Delta t_{50}$) of a polyQ-containing protein in a sample collected at a timepoint $t_1$, comprising the steps of:

(a) providing, in a solution, a mixture of a first polyQ-containing protein which is C-terminally fused to a donor fluorophore molecule and a second polyQ-containing protein which is C-terminally fused to an acceptor fluorophore molecule, wherein the first and second proteins are the same polyQ-containing protein and wherein the donor fluorophore molecule and the acceptor fluorophore molecule are capable of FRET if they are in close proximity to each other;
(b) adding a sample collected from the subject to the mixture of step (a);
(c) shaking the mixture of step (b);
(d) measuring fluorescence signals in the donor channel, the acceptor channel, and the FRET channel at predetermined intervals after completion of step (c);
(e) calculating FRET efficiency (E) from the signals obtained in step (d);
(f) quantifying seeding activity ($\Delta t_{50}$) by subtracting the time at half-maximal FRET efficiency of a sample ($t_{50}(S)$) from the time at half-maximal FRET efficiency of a negative control ($t_{50}(0)$);
(ii) quantification of seeding activity ($\Delta t_{50}$) of a polyQ-containing protein in a sample collected at a timepoint $t_2$, wherein $t_2$ is later than $t_1$, comprising the steps (a) to (f) as defined in (i); and
(iii) correlating that the polyQ disease has progressed when the seeding activity in the sample taken at $t_2$ is increased as compared to the sample taken at $t_1$.

9. The method of claim 1, wherein the acceptor fluorophore molecule is a yellow fluorescent protein (YFP).

10. The method of claim 1, wherein the donor fluorophore molecule is a cyan fluorescent protein (CFP).

11. The method of claim 1, wherein the donor fluorophore molecule is a CFP and wherein the acceptor fluorophore molecule is a YFP.

12. The method of claim 1, wherein the protein fused to the donor fluorophore molecule and the protein fused to the acceptor fluorophore molecule are provided in a ratio ranging from 2:3 to 3:2.

13. The method of claim 1, wherein FRET efficiency (E) is calculated according to formula (1)

$$E=(DA-c_D \cdot DD-c_A \cdot AA)/AA \qquad (1),$$

wherein
DA is the FRET channel signal
$c_D$ is the donor bleed-through
DD is the donor channel signal
$c_A$ is the acceptor cross-excitation
AA is the acceptor channel signal.

14. The method of claim 8, wherein the first polyQ-containing protein is-a soluble glutathione S-transferase HTT exon-1 fusion protein comprising from about 35 to about 75 glutamine residues and wherein the second polyQ-containing protein is a soluble glutathione S-transferase HTT exon-1 fusion protein comprising from about 35 to about 75 glutamine residues.

15. The method of claim 8, wherein the first poly Q-containing protein is a soluble HTT exon-1 fusion protein comprising from about 35 to about 75 glutamine residues and wherein the second polyQ-containing protein is a soluble HTT exon-1 fusion protein comprising from about 35 to about 75 residues.

16. The method of claim 1, wherein the amyloidogenic proteins A and B are the same protein.

17. The method of claim 2, wherein the polyQ proteins are wild-type or mutant forms of the group consisting of huntingtin (HTT), androgen receptor (AR), atrophin 1 (ATN1), ataxin 1, ataxin 2, ataxin 3, ataxin 7, TATA-box binding protein (TBP), $\alpha_{1A}$-voltage dependent calcium channel subunit (CACNA1A), and polyglutamine repeat containing fragments thereof.

18. The method of claim 7, wherein the donor fluorophore molecule is a cyan fluorescent protein (CFP) and the acceptor fluorophore molecule is a yellow fluorescent protein (YFP).

19. The method of claim 9, wherein the yellow fluorescent protein (YFP) is enhanced YFP (EYFP), Venus, Citrine, or yellow fluorescent protein for energy transfer (YPet).

20. The method of claim 10, wherein the cyan fluorescent protein (CFP) is enhanced CFP (ECFP), split CFP (SCFP), Cerulean, Turquoise, and cyan fluorescent protein for energy transfer (CyPet).

21. The method of claim 10, wherein the CFP is cyan fluorescent protein for energy transfer (CyPet).

\* \* \* \* \*

SEQUENCE LISTING

```
<160> NUMBER OF SEQ ID NOS: 73

<210> SEQ ID NO 1
<211> LENGTH: 3142
<212> TYPE: PRT
<213> ORGANISM: Homo sapiens

<400> SEQUENCE: 1

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
                20                  25                  30

Gln Gln Gln Gln Gln Gln Pro Pro Pro Pro Pro Pro Pro Pro Pro Pro
            35                  40                  45

Pro Gln Leu Pro Gln Pro Pro Pro Gln Ala Gln Pro Leu Leu Pro Gln
    50                  55                  60

Pro Gln Pro Pro Pro Pro Pro Pro Pro Pro Gly Pro Ala Val
65                  70                  75                  80

Ala Glu Glu Pro Leu His Arg Pro Lys Lys Glu Leu Ser Ala Thr Lys
                85                  90                  95

Lys Asp Arg Val Asn His Cys Leu Thr Ile Cys Glu Asn Ile Val Ala
                100                 105                 110

Gln Ser Val Arg Asn Ser Pro Glu Phe Gln Lys Leu Leu Gly Ile Ala
            115                 120                 125

Met Glu Leu Phe Leu Leu Cys Ser Asp Asp Ala Glu Ser Asp Val Arg
        130                 135                 140

Met Val Ala Asp Glu Cys Leu Asn Lys Val Ile Lys Ala Leu Met Asp
145                 150                 155                 160

Ser Asn Leu Pro Arg Leu Gln Leu Glu Leu Tyr Lys Glu Ile Lys Lys
                165                 170                 175

Asn Gly Ala Pro Arg Ser Leu Arg Ala Ala Leu Trp Arg Phe Ala Glu
                180                 185                 190

Leu Ala His Leu Val Arg Pro Gln Lys Cys Arg Pro Tyr Leu Val Asn
            195                 200                 205

Leu Leu Pro Cys Leu Thr Arg Thr Ser Lys Arg Pro Glu Glu Ser Val
        210                 215                 220

Gln Glu Thr Leu Ala Ala Ala Val Pro Lys Ile Met Ala Ser Phe Gly
225                 230                 235                 240

Asn Phe Ala Asn Asp Asn Glu Ile Lys Val Leu Leu Lys Ala Phe Ile
                245                 250                 255

Ala Asn Leu Lys Ser Ser Pro Thr Ile Arg Arg Thr Ala Ala Gly
                260                 265                 270

Ser Ala Val Ser Ile Cys Gln His Ser Arg Arg Thr Gln Tyr Phe Tyr
```

```
            275                 280                 285
Ser Trp Leu Leu Asn Val Leu Gly Leu Val Pro Val Glu Asp
290                 295                 300
Glu His Ser Thr Leu Leu Ile Leu Gly Val Leu Leu Thr Leu Arg Tyr
305                 310                 315                 320
Leu Val Pro Leu Leu Gln Gln Gln Val Lys Asp Thr Ser Leu Lys Gly
                    325                 330                 335
Ser Phe Gly Val Thr Arg Lys Glu Met Glu Val Ser Pro Ser Ala Glu
                340                 345                 350
Gln Leu Val Gln Val Tyr Glu Leu Thr Leu His His Thr Gln His Gln
                355                 360                 365
Asp His Asn Val Val Thr Gly Ala Leu Glu Leu Leu Gln Gln Leu Phe
            370                 375                 380
Arg Thr Pro Pro Pro Glu Leu Leu Gln Thr Leu Thr Ala Val Gly Gly
385                 390                 395                 400
Ile Gly Gln Leu Thr Ala Ala Lys Glu Glu Ser Gly Gly Arg Ser Arg
                    405                 410                 415
Ser Gly Ser Ile Val Glu Leu Ile Ala Gly Gly Ser Ser Cys Ser
                420                 425                 430
Pro Val Leu Ser Arg Lys Gln Lys Gly Lys Val Leu Leu Gly Glu Glu
                435                 440                 445
Glu Ala Leu Glu Asp Asp Ser Glu Ser Arg Ser Asp Val Ser Ser Ser
450                 455                 460
Ala Leu Thr Ala Ser Val Lys Asp Glu Ile Ser Gly Glu Leu Ala Ala
465                 470                 475                 480
Ser Ser Gly Val Ser Thr Pro Gly Ser Ala Gly His Asp Ile Ile Thr
                    485                 490                 495
Glu Gln Pro Arg Ser Gln His Thr Leu Gln Ala Asp Ser Val Asp Leu
                500                 505                 510
Ala Ser Cys Asp Leu Thr Ser Ser Ala Thr Asp Gly Asp Glu Glu Asp
                515                 520                 525
Ile Leu Ser His Ser Ser Ser Gln Val Ser Ala Val Pro Ser Asp Pro
            530                 535                 540
Ala Met Asp Leu Asn Asp Gly Thr Gln Ala Ser Ser Pro Ile Ser Asp
545                 550                 555                 560
Ser Ser Gln Thr Thr Thr Glu Gly Pro Asp Ser Ala Val Thr Pro Ser
                    565                 570                 575
Asp Ser Ser Glu Ile Val Leu Asp Gly Thr Asp Asn Gln Tyr Leu Gly
                580                 585                 590
Leu Gln Ile Gly Gln Pro Gln Asp Glu Asp Glu Glu Ala Thr Gly Ile
                595                 600                 605
Leu Pro Asp Glu Ala Ser Glu Ala Phe Arg Asn Ser Ser Met Ala Leu
            610                 615                 620
Gln Gln Ala His Leu Leu Lys Asn Met Ser His Cys Arg Gln Pro Ser
625                 630                 635                 640
Asp Ser Ser Val Asp Lys Phe Val Leu Arg Asp Glu Ala Thr Glu Pro
                    645                 650                 655
Gly Asp Gln Glu Asn Lys Pro Cys Arg Ile Lys Gly Asp Ile Gly Gln
                660                 665                 670
Ser Thr Asp Asp Asp Ser Ala Pro Leu Val His Cys Val Arg Leu Leu
            675                 680                 685
Ser Ala Ser Phe Leu Leu Thr Gly Gly Lys Asn Val Leu Val Pro Asp
            690                 695                 700
```

-continued

```
Arg Asp Val Arg Val Ser Val Lys Ala Leu Ala Leu Ser Cys Val Gly
705                 710                 715                 720

Ala Ala Val Ala Leu His Pro Glu Ser Phe Phe Ser Lys Leu Tyr Lys
                725                 730                 735

Val Pro Leu Asp Thr Thr Glu Tyr Pro Glu Glu Gln Tyr Val Ser Asp
            740                 745                 750

Ile Leu Asn Tyr Ile Asp His Gly Asp Pro Gln Val Arg Gly Ala Thr
                755                 760                 765

Ala Ile Leu Cys Gly Thr Leu Ile Cys Ser Ile Leu Ser Arg Ser Arg
770                 775                 780

Phe His Val Gly Asp Trp Met Gly Thr Ile Arg Thr Leu Thr Gly Asn
785                 790                 795                 800

Thr Phe Ser Leu Ala Asp Cys Ile Pro Leu Leu Arg Lys Thr Leu Lys
                805                 810                 815

Asp Glu Ser Ser Val Thr Cys Lys Leu Ala Cys Thr Ala Val Arg Asn
                820                 825                 830

Cys Val Met Ser Leu Cys Ser Ser Tyr Ser Glu Leu Gly Leu Gln
                835                 840                 845

Leu Ile Ile Asp Val Leu Thr Leu Arg Asn Ser Ser Tyr Trp Leu Val
850                 855                 860

Arg Thr Glu Leu Leu Glu Thr Leu Ala Glu Ile Asp Phe Arg Leu Val
865                 870                 875                 880

Ser Phe Leu Glu Ala Lys Ala Glu Asn Leu His Arg Gly Ala His His
                885                 890                 895

Tyr Thr Gly Leu Leu Lys Leu Gln Glu Arg Val Leu Asn Asn Val Val
                900                 905                 910

Ile His Leu Leu Gly Asp Glu Asp Pro Arg Val Arg His Val Ala Ala
                915                 920                 925

Ala Ser Leu Ile Arg Leu Val Pro Lys Leu Phe Tyr Lys Cys Asp Gln
                930                 935                 940

Gly Gln Ala Asp Pro Val Val Ala Val Ala Arg Asp Gln Ser Ser Val
945                 950                 955                 960

Tyr Leu Lys Leu Leu Met His Glu Thr Gln Pro Pro Ser His Phe Ser
                965                 970                 975

Val Ser Thr Ile Thr Arg Ile Tyr Arg Gly Tyr Asn Leu Leu Pro Ser
                980                 985                 990

Ile Thr Asp Val Thr Met Glu Asn Asn Leu Ser Arg Val Ile Ala Ala
                995                 1000                1005

Val Ser His Glu Leu Ile Thr Ser Thr Thr Arg Ala Leu Thr Phe
    1010                1015                1020

Gly Cys Cys Glu Ala Leu Cys Leu Leu Ser Thr Ala Phe Pro Val
    1025                1030                1035

Cys Ile Trp Ser Leu Gly Trp His Cys Gly Val Pro Pro Leu Ser
    1040                1045                1050

Ala Ser Asp Glu Ser Arg Lys Ser Cys Thr Val Gly Met Ala Thr
    1055                1060                1065

Met Ile Leu Thr Leu Leu Ser Ala Trp Phe Pro Leu Asp Leu
    1070                1075                1080

Ser Ala His Gln Asp Ala Leu Ile Leu Ala Gly Asn Leu Leu Ala
    1085                1090                1095

Ala Ser Ala Pro Lys Ser Leu Arg Ser Ser Trp Ala Ser Glu Glu
    1100                1105                1110
```

```
Glu Ala Asn Pro Ala Ala Thr Lys Gln Glu Glu Val Trp Pro Ala
1115                1120                1125

Leu Gly Asp Arg Ala Leu Val Pro Met Val Glu Gln Leu Phe Ser
1130                1135                1140

His Leu Leu Lys Val Ile Asn Ile Cys Ala His Val Leu Asp Asp
1145                1150                1155

Val Ala Pro Gly Pro Ala Ile Lys Ala Ala Leu Pro Ser Leu Thr
1160                1165                1170

Asn Pro Pro Ser Leu Ser Pro Ile Arg Arg Lys Gly Lys Glu Lys
1175                1180                1185

Glu Pro Gly Glu Gln Ala Ser Val Pro Leu Ser Pro Lys Lys Gly
1190                1195                1200

Ser Glu Ala Ser Ala Ala Ser Arg Gln Ser Asp Thr Ser Gly Pro
1205                1210                1215

Val Thr Thr Ser Lys Ser Ser Ser Leu Gly Ser Phe Tyr His Leu
1220                1225                1230

Pro Ser Tyr Leu Lys Leu His Asp Val Leu Lys Ala Thr His Ala
1235                1240                1245

Asn Tyr Lys Val Thr Leu Asp Leu Gln Asn Ser Thr Glu Lys Phe
1250                1255                1260

Gly Gly Phe Leu Arg Ser Ala Leu Asp Val Leu Ser Gln Ile Leu
1265                1270                1275

Glu Leu Ala Thr Leu Gln Asp Ile Gly Lys Cys Val Glu Glu Ile
1280                1285                1290

Leu Gly Tyr Leu Lys Ser Cys Phe Ser Arg Glu Pro Met Met Ala
1295                1300                1305

Thr Val Cys Val Gln Gln Leu Leu Lys Thr Leu Phe Gly Thr Asn
1310                1315                1320

Leu Ala Ser Gln Phe Asp Gly Leu Ser Ser Asn Pro Ser Lys Ser
1325                1330                1335

Gln Gly Arg Ala Gln Arg Leu Gly Ser Ser Ser Val Arg Pro Gly
1340                1345                1350

Leu Tyr His Tyr Cys Phe Met Ala Pro Tyr Thr His Phe Thr Gln
1355                1360                1365

Ala Leu Ala Asp Ala Ser Leu Arg Asn Met Val Gln Ala Glu Gln
1370                1375                1380

Glu Asn Asp Thr Ser Gly Trp Phe Asp Val Leu Gln Lys Val Ser
1385                1390                1395

Thr Gln Leu Lys Thr Asn Leu Thr Ser Val Thr Lys Asn Arg Ala
1400                1405                1410

Asp Lys Asn Ala Ile His Asn His Ile Arg Leu Phe Glu Pro Leu
1415                1420                1425

Val Ile Lys Ala Leu Lys Gln Tyr Thr Thr Thr Thr Cys Val Gln
1430                1435                1440

Leu Gln Lys Gln Val Leu Asp Leu Leu Ala Gln Leu Val Gln Leu
1445                1450                1455

Arg Val Asn Tyr Cys Leu Leu Asp Ser Asp Gln Val Phe Ile Gly
1460                1465                1470

Phe Val Leu Lys Gln Phe Glu Tyr Ile Glu Val Gly Gln Phe Arg
1475                1480                1485

Glu Ser Glu Ala Ile Ile Pro Asn Ile Phe Phe Phe Leu Val Leu
1490                1495                1500

Leu Ser Tyr Glu Arg Tyr His Ser Lys Gln Ile Ile Gly Ile Pro
```

```
            1505                1510                1515
Lys Ile Ile Gln Leu Cys Asp Gly Ile Met Ala Ser Gly Arg Lys
    1520                1525                1530

Ala Val Thr His Ala Ile Pro Ala Leu Gln Pro Ile Val His Asp
    1535                1540                1545

Leu Phe Val Leu Arg Gly Thr Asn Lys Ala Asp Ala Gly Lys Glu
    1550                1555                1560

Leu Glu Thr Gln Lys Glu Val Val Ser Met Leu Leu Arg Leu
    1565                1570                1575

Ile Gln Tyr His Gln Val Leu Glu Met Phe Ile Leu Val Leu Gln
    1580                1585                1590

Gln Cys His Lys Glu Asn Glu Asp Lys Trp Lys Arg Leu Ser Arg
    1595                1600                1605

Gln Ile Ala Asp Ile Ile Leu Pro Met Leu Ala Lys Gln Gln Met
    1610                1615                1620

His Ile Asp Ser His Glu Ala Leu Gly Val Leu Asn Thr Leu Phe
    1625                1630                1635

Glu Ile Leu Ala Pro Ser Ser Leu Arg Pro Val Asp Met Leu Leu
    1640                1645                1650

Arg Ser Met Phe Val Thr Pro Asn Thr Met Ala Ser Val Ser Thr
    1655                1660                1665

Val Gln Leu Trp Ile Ser Gly Ile Leu Ala Ile Leu Arg Val Leu
    1670                1675                1680

Ile Ser Gln Ser Thr Glu Asp Ile Val Leu Ser Arg Ile Gln Glu
    1685                1690                1695

Leu Ser Phe Ser Pro Tyr Leu Ile Ser Cys Thr Val Ile Asn Arg
    1700                1705                1710

Leu Arg Asp Gly Asp Ser Thr Ser Thr Leu Glu Glu His Ser Glu
    1715                1720                1725

Gly Lys Gln Ile Lys Asn Leu Pro Glu Glu Thr Phe Ser Arg Phe
    1730                1735                1740

Leu Leu Gln Leu Val Gly Ile Leu Leu Glu Asp Ile Val Thr Lys
    1745                1750                1755

Gln Leu Lys Val Glu Met Ser Glu Gln Gln His Thr Phe Tyr Cys
    1760                1765                1770

Gln Glu Leu Gly Thr Leu Leu Met Cys Leu Ile His Ile Phe Lys
    1775                1780                1785

Ser Gly Met Phe Arg Arg Ile Thr Ala Ala Ala Thr Arg Leu Phe
    1790                1795                1800

Arg Ser Asp Gly Cys Gly Gly Ser Phe Tyr Thr Leu Asp Ser Leu
    1805                1810                1815

Asn Leu Arg Ala Arg Ser Met Ile Thr Thr His Pro Ala Leu Val
    1820                1825                1830

Leu Leu Trp Cys Gln Ile Leu Leu Leu Val Asn His Thr Asp Tyr
    1835                1840                1845

Arg Trp Trp Ala Glu Val Gln Gln Thr Pro Lys Arg His Ser Leu
    1850                1855                1860

Ser Ser Thr Lys Leu Leu Ser Pro Gln Met Ser Gly Glu Glu Glu
    1865                1870                1875

Asp Ser Asp Leu Ala Ala Lys Leu Gly Met Cys Asn Arg Glu Ile
    1880                1885                1890

Val Arg Arg Gly Ala Leu Ile Leu Phe Cys Asp Tyr Val Cys Gln
    1895                1900                1905
```

-continued

Asn Leu His Asp Ser Glu His Leu Thr Trp Leu Ile Val Asn His
1910                    1915                    1920

Ile Gln Asp Leu Ile Ser Leu Ser His Glu Pro Pro Val Gln Asp
1925                    1930                    1935

Phe Ile Ser Ala Val His Arg Asn Ser Ala Ala Ser Gly Leu Phe
1940                    1945                    1950

Ile Gln Ala Ile Gln Ser Arg Cys Glu Asn Leu Ser Thr Pro Thr
1955                    1960                    1965

Met Leu Lys Lys Thr Leu Gln Cys Leu Glu Gly Ile His Leu Ser
1970                    1975                    1980

Gln Ser Gly Ala Val Leu Thr Leu Tyr Val Asp Arg Leu Leu Cys
1985                    1990                    1995

Thr Pro Phe Arg Val Leu Ala Arg Met Val Asp Ile Leu Ala Cys
2000                    2005                    2010

Arg Arg Val Glu Met Leu Leu Ala Ala Asn Leu Gln Ser Ser Met
2015                    2020                    2025

Ala Gln Leu Pro Met Glu Glu Leu Asn Arg Ile Gln Glu Tyr Leu
2030                    2035                    2040

Gln Ser Ser Gly Leu Ala Gln Arg His Gln Arg Leu Tyr Ser Leu
2045                    2050                    2055

Leu Asp Arg Phe Arg Leu Ser Thr Met Gln Asp Ser Leu Ser Pro
2060                    2065                    2070

Ser Pro Pro Val Ser Ser His Pro Leu Asp Gly Asp Gly His Val
2075                    2080                    2085

Ser Leu Glu Thr Val Ser Pro Asp Lys Asp Trp Tyr Val His Leu
2090                    2095                    2100

Val Lys Ser Gln Cys Trp Thr Arg Ser Asp Ser Ala Leu Leu Glu
2105                    2110                    2115

Gly Ala Glu Leu Val Asn Arg Ile Pro Ala Glu Asp Met Asn Ala
2120                    2125                    2130

Phe Met Met Asn Ser Glu Phe Asn Leu Ser Leu Leu Ala Pro Cys
2135                    2140                    2145

Leu Ser Leu Gly Met Ser Glu Ile Ser Gly Gly Gln Lys Ser Ala
2150                    2155                    2160

Leu Phe Glu Ala Ala Arg Glu Val Thr Leu Ala Arg Val Ser Gly
2165                    2170                    2175

Thr Val Gln Gln Leu Pro Ala Val His His Val Phe Gln Pro Glu
2180                    2185                    2190

Leu Pro Ala Glu Pro Ala Ala Tyr Trp Ser Lys Leu Asn Asp Leu
2195                    2200                    2205

Phe Gly Asp Ala Ala Leu Tyr Gln Ser Leu Pro Thr Leu Ala Arg
2210                    2215                    2220

Ala Leu Ala Gln Tyr Leu Val Val Ser Lys Leu Pro Ser His
2225                    2230                    2235

Leu His Leu Pro Pro Glu Lys Glu Lys Asp Ile Val Lys Phe Val
2240                    2245                    2250

Val Ala Thr Leu Glu Ala Leu Ser Trp His Leu Ile His Glu Gln
2255                    2260                    2265

Ile Pro Leu Ser Leu Asp Leu Gln Ala Gly Leu Asp Cys Cys Cys
2270                    2275                    2280

Leu Ala Leu Gln Leu Pro Gly Leu Trp Ser Val Val Ser Ser Thr
2285                    2290                    2295

```
Glu Phe Val Thr His Ala Cys Ser Leu Ile Tyr Cys Val His Phe
2300                2305                2310

Ile Leu Glu Ala Val Ala Val Gln Pro Gly Glu Gln Leu Leu Ser
2315                2320                2325

Pro Glu Arg Arg Thr Asn Thr Pro Lys Ala Ile Ser Glu Glu Glu
2330                2335                2340

Glu Glu Val Asp Pro Asn Thr Gln Asn Pro Lys Tyr Ile Thr Ala
2345                2350                2355

Ala Cys Glu Met Val Ala Glu Met Val Glu Ser Leu Gln Ser Val
2360                2365                2370

Leu Ala Leu Gly His Lys Arg Asn Ser Gly Val Pro Ala Phe Leu
2375                2380                2385

Thr Pro Leu Leu Arg Asn Ile Ile Ile Ser Leu Ala Arg Leu Pro
2390                2395                2400

Leu Val Asn Ser Tyr Thr Arg Val Pro Pro Leu Val Trp Lys Leu
2405                2410                2415

Gly Trp Ser Pro Lys Pro Gly Gly Asp Phe Gly Thr Ala Phe Pro
2420                2425                2430

Glu Ile Pro Val Glu Phe Leu Gln Glu Lys Glu Val Phe Lys Glu
2435                2440                2445

Phe Ile Tyr Arg Ile Asn Thr Leu Gly Trp Thr Ser Arg Thr Gln
2450                2455                2460

Phe Glu Glu Thr Trp Ala Thr Leu Leu Gly Val Leu Val Thr Gln
2465                2470                2475

Pro Leu Val Met Glu Gln Glu Glu Ser Pro Pro Glu Glu Asp Thr
2480                2485                2490

Glu Arg Thr Gln Ile Asn Val Leu Ala Val Gln Ala Ile Thr Ser
2495                2500                2505

Leu Val Leu Ser Ala Met Thr Val Pro Val Ala Gly Asn Pro Ala
2510                2515                2520

Val Ser Cys Leu Glu Gln Gln Pro Arg Asn Lys Pro Leu Lys Ala
2525                2530                2535

Leu Asp Thr Arg Phe Gly Arg Lys Leu Ser Ile Ile Arg Gly Ile
2540                2545                2550

Val Glu Gln Glu Ile Gln Ala Met Val Ser Lys Arg Glu Asn Ile
2555                2560                2565

Ala Thr His His Leu Tyr Gln Ala Trp Asp Pro Val Pro Ser Leu
2570                2575                2580

Ser Pro Ala Thr Thr Gly Ala Leu Ile Ser His Glu Lys Leu Leu
2585                2590                2595

Leu Gln Ile Asn Pro Glu Arg Glu Leu Gly Ser Met Ser Tyr Lys
2600                2605                2610

Leu Gly Gln Val Ser Ile His Ser Val Trp Leu Gly Asn Ser Ile
2615                2620                2625

Thr Pro Leu Arg Glu Glu Glu Trp Asp Glu Glu Glu Glu Glu Glu
2630                2635                2640

Ala Asp Ala Pro Ala Pro Ser Ser Pro Pro Thr Ser Pro Val Asn
2645                2650                2655

Ser Arg Lys His Arg Ala Gly Val Asp Ile His Ser Cys Ser Gln
2660                2665                2670

Phe Leu Leu Glu Leu Tyr Ser Arg Trp Ile Leu Pro Ser Ser Ser
2675                2680                2685

Ala Arg Arg Thr Pro Ala Ile Leu Ile Ser Glu Val Val Arg Ser
```

-continued

```
                2690                2695                2700
Leu Leu Val Val Ser Asp Leu Phe Thr Glu Arg Asn Gln Phe Glu
        2705                2710                2715
Leu Met Tyr Val Thr Leu Thr Glu Leu Arg Arg Val His Pro Ser
        2720                2725                2730
Glu Asp Glu Ile Leu Ala Gln Tyr Leu Val Pro Ala Thr Cys Lys
        2735                2740                2745
Ala Ala Ala Val Leu Gly Met Asp Lys Ala Val Ala Glu Pro Val
        2750                2755                2760
Ser Arg Leu Leu Glu Ser Thr Leu Arg Ser Ser His Leu Pro Ser
        2765                2770                2775
Arg Val Gly Ala Leu His Gly Val Leu Tyr Val Leu Glu Cys Asp
        2780                2785                2790
Leu Leu Asp Asp Thr Ala Lys Gln Leu Ile Pro Val Ile Ser Asp
        2795                2800                2805
Tyr Leu Leu Ser Asn Leu Lys Gly Ile Ala His Cys Val Asn Ile
        2810                2815                2820
His Ser Gln Gln His Val Leu Val Met Cys Ala Thr Ala Phe Tyr
        2825                2830                2835
Leu Ile Glu Asn Tyr Pro Leu Asp Val Gly Pro Glu Phe Ser Ala
        2840                2845                2850
Ser Ile Ile Gln Met Cys Gly Val Met Leu Ser Gly Ser Glu Glu
        2855                2860                2865
Ser Thr Pro Ser Ile Ile Tyr His Cys Ala Leu Arg Gly Leu Glu
        2870                2875                2880
Arg Leu Leu Leu Ser Glu Gln Leu Ser Arg Leu Asp Ala Glu Ser
        2885                2890                2895
Leu Val Lys Leu Ser Val Asp Arg Val Asn Val His Ser Pro His
        2900                2905                2910
Arg Ala Met Ala Ala Leu Gly Leu Met Leu Thr Cys Met Tyr Thr
        2915                2920                2925
Gly Lys Glu Lys Val Ser Pro Gly Arg Thr Ser Asp Pro Asn Pro
        2930                2935                2940
Ala Ala Pro Asp Ser Glu Ser Val Ile Val Ala Met Glu Arg Val
        2945                2950                2955
Ser Val Leu Phe Asp Arg Ile Arg Lys Gly Phe Pro Cys Glu Ala
        2960                2965                2970
Arg Val Val Ala Arg Ile Leu Pro Gln Phe Leu Asp Asp Phe Phe
        2975                2980                2985
Pro Pro Gln Asp Ile Met Asn Lys Val Ile Gly Glu Phe Leu Ser
        2990                2995                3000
Asn Gln Gln Pro Tyr Pro Gln Phe Met Ala Thr Val Val Tyr Lys
        3005                3010                3015
Val Phe Gln Thr Leu His Ser Thr Gly Gln Ser Ser Met Val Arg
        3020                3025                3030
Asp Trp Val Met Leu Ser Leu Ser Asn Phe Thr Gln Arg Ala Pro
        3035                3040                3045
Val Ala Met Ala Thr Trp Ser Leu Ser Cys Phe Phe Val Ser Ala
        3050                3055                3060
Ser Thr Ser Pro Trp Val Ala Ala Ile Leu Pro His Val Ile Ser
        3065                3070                3075
Arg Met Gly Lys Leu Glu Gln Val Asp Val Asn Leu Phe Cys Leu
        3080                3085                3090
```

Val Ala Thr Asp Phe Tyr Arg His Gln Ile Glu Glu Glu Leu Asp
   3095                3100                3105

Arg Arg Ala Phe Gln Ser Val Leu Glu Val Val Ala Ala Pro Gly
   3110                3115                3120

Ser Pro Tyr His Arg Leu Leu Thr Cys Leu Arg Asn Val His Lys
   3125                3130                3135

Val Thr Thr Cys
   3140

<210> SEQ ID NO 2
<211> LENGTH: 115
<212> TYPE: PRT
<213> ORGANISM: Homo sapiens

<400> SEQUENCE: 2

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln
                20                  25                  30

Gln Gln Gln Gln Gln Gln Gln Gln Gln Gln Gln Gln Gln Gln
        35                  40                      45

Gln Gln Gln Gln Gln Gln Gln Gln Gln Gln Gln Gln Gln
    50                  55                      60

Gln Pro Pro Pro Pro Pro Pro Pro Pro Gln Leu Pro Gln
65                  70                  75                  80

Pro Pro Pro Gln Ala Gln Pro Leu Leu Pro Gln Leu Gln Pro Pro Pro
                85                  90                  95

Pro Pro Pro Pro Pro Pro Pro Gly Pro Ala Ala Ala Glu Glu Pro Leu
                100                 105                 110

His Arg Pro
    115

<210> SEQ ID NO 3
<211> LENGTH: 345
<212> TYPE: DNA
<213> ORGANISM: Homo sapiens

<400> SEQUENCE: 3
atggcgaccc tggaaaagct gatgaaggcc ttcgagtccc tcaagtcctt ccagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc aacagccgcc accgccgccg ccgccgccgc cgcctcctca gcttcctcag     240
ccgccgccgc aggcacagcc gctgctgcct cagctgcagc cgccccgcc gccgcccccg      300 ccgccacccg gcccggccgc ggctgaggag ccgctgcacc gacca                     345

<210> SEQ ID NO 4
<211> LENGTH: 116
<212> TYPE: PRT
<213> ORGANISM: Homo sapiens

<400> SEQUENCE: 4

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln
                20                  25                  30

```
Gln Gln Gln Gln Gln Gln Gln Gln Gln Gln Gln Gln Gln
        35                  40                  45

Gln Gln Gln Gln Gln Gln Gln Gln Gln Gln Gln Gln Gln
    50                  55                  60

Gln Gln Pro Pro Pro Pro Pro Pro Pro Pro Pro Gln Leu Pro
65              70                  75                  80

Gln Pro Pro Pro Gln Ala Gln Pro Leu Leu Pro Gln Leu Gln Pro Pro
                85                  90                  95

Pro Pro Pro Pro Pro Pro Pro Gly Pro Ala Ala Ala Glu Glu Pro
            100                 105                 110

Leu His Arg Pro
        115

<210> SEQ ID NO 5
<211> LENGTH: 348
<212> TYPE: DNA
<213> ORGANISM: Homo sapiens

<400> SEQUENCE: 5
atggcgaccc tggaaaagct gatgaaggcc ttcgagtccc tcaagtcctt ccagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcaacagcc gccaccgccg ccgccgccgc cgccgcctcc tcagcttcct     240
cagccgccgc cgcaggcaca gccgctgctg cctcagctgc agccgccccc gccgccgccc     300
ccgccgccac ccggcccggc cgcggctgag gagccgctgc accgacca                  348

<210> SEQ ID NO 6
<211> LENGTH: 218
<212> TYPE: PRT
<213> ORGANISM: Artificial Sequence
<220> FEATURE:
<223> OTHER INFORMATION: cloned glutathione-S-transferase

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65              70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
```

```
              165                 170                 175
Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys
        210                 215

<210> SEQ ID NO 7
<211> LENGTH: 654
<212> TYPE: DNA
<213> ORGANISM: Artificial Sequence
<220> FEATURE:
<223> OTHER INFORMATION: cloned glutathione-S-transferase

<400> SEQUENCE: 7 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg agtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg atgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaa          654

<210> SEQ ID NO 8
<211> LENGTH: 8
<212> TYPE: PRT
<213> ORGANISM: Artificial Sequence
<220> FEATURE:
<223> OTHER INFORMATION: protease recognition sequence

<400> SEQUENCE: 8

Leu Glu Val Leu Phe Gln Gly Pro
1               5

<210> SEQ ID NO 9
<211> LENGTH: 349
<212> TYPE: PRT
<213> ORGANISM: Artificial Sequence
<220> FEATURE:
<223> OTHER INFORMATION: mHTT GST-Ex1Q48

<400> SEQUENCE: 9

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
```

65                  70                  75                  80
        Met Leu Gly Gly Cys Pro Lys Glu Arg Ala Glu Ile Ser Met Leu Glu
                        85                  90                  95

Gly Ala Val Leu Asp Ile Arg Tyr Gly Val Ser Arg Ile Ala Tyr Ser
                        100                 105                 110

Lys Asp Phe Glu Thr Leu Lys Val Asp Phe Leu Ser Lys Leu Pro Glu
                        115                 120                 125

Met Leu Lys Met Phe Glu Asp Arg Leu Cys His Lys Thr Tyr Leu Asn
                        130                 135                 140

Gly Asp His Val Thr His Pro Asp Phe Met Leu Tyr Asp Ala Leu Asp
        145                 150                 155                 160

Val Val Leu Tyr Met Asp Pro Met Cys Leu Asp Ala Phe Pro Lys Leu
                        165                 170                 175

Val Cys Phe Lys Lys Arg Ile Glu Ala Ile Pro Gln Ile Asp Lys Tyr
                        180                 185                 190

Leu Lys Ser Ser Lys Tyr Ile Ala Trp Pro Leu Gln Gly Trp Gln Ala
                        195                 200                 205

Thr Phe Gly Gly Gly Asp His Pro Pro Lys Ser Asp Leu Glu Val Leu
                        210                 215                 220

Phe Gln Gly Pro Leu Gly Ser Pro Glu Phe Met Ala Thr Leu Glu Lys
        225                 230                 235                 240

Leu Met Lys Ala Phe Glu Ser Leu Lys Ser Phe Gln Gln Gln Gln Gln
                        245                 250                 255

Gln Gln Gln Gln Gln Gln Gln Gln Gln Gln Gln Gln Gln Gln Gln Gln
                        260                 265                 270

Gln Gln Gln Gln Gln Gln Gln Gln Gln Gln Gln Gln Gln Gln Gln Gln
                        275                 280                 285

Gln Gln Gln Gln Gln Gln Gln Gln Gln Pro Pro Pro Pro Pro Pro Pro
                        290                 295                 300

Pro Pro Pro Pro Pro Gln Leu Pro Gln Pro Pro Pro Gln Ala Gln Pro
        305                 310                 315                 320

Pro Leu Leu Pro Gln Leu Gln Pro Pro Pro Pro Pro Pro Pro Pro Pro
                        325                 330                 335

Pro Gly Pro Ala Ala Ala Glu Glu Pro Leu His Arg Pro
                        340                 345

<210> SEQ ID NO 10
<211> LENGTH: 1047
<212> TYPE: DNA
<213> ORGANISM: Artificial Sequence
<220> FEATURE:
<223> OTHER INFORMATION: mHTT GST-Ex1Q48

<400> SEQUENCE: 10 atgtcccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg agtttcccca tcttccttta ttatattgat   180
ggtgatgtta aattaacaca gtctatggcc atcatacgtt atatagctga caagcacaac   240
atgttgggtg ttgtccaaa agagcgtgca gagatttcaa tgcttgaagg agcggttttg   300
gatattagat acgtgttttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca gttgtatga cgctcttgat   480

-continued

```
gttgttttat acatggaccc aatgtgcctg gatgcgttcc caaaattagt ttgttttaaa      540
aaacgtattg aagctatccc acaaattgat aagtacttga aatccagcaa gtatatagca      600
tggcctttgc agggctggca agccacgttt ggtggtggcg accatcctcc aaaatcggat      660
ctggaagttc tgttccaggg gcccctggga tccccggaat tcatggcgac cctggaaaag      720
ctgatgaagg ccttcgagtc cctcaagtcc ttccagcagc agcagcagca gcagcagcag      780
cagcagcagc agcagcagca gcagcagcag cagcagcagc agcagcagca gcagcagcag      840
cagcagcagc agcagcagca gcagcagcag cagcagcagc agcagcagca gcaacagccg      900
ccaccgccgc cgccgccgcc gccgcctcct cagcttcctc agccgccgcc gcaggcacag      960
ccgctgctgc ctcagctgca gccgcccccg ccgccgcccc cgccgccacc cggcccggcc     1020
gcggctgagg agccgctgca ccgacca                                         1047
```

```
<210> SEQ ID NO 11
<211> LENGTH: 350
<212> TYPE: PRT
<213> ORGANISM: Artificial Sequence
<220> FEATURE:
<223> OTHER INFORMATION: mHTT GST-Ex1Q49

<400> SEQUENCE: 11

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Pro Glu Phe Met Ala Thr Leu Glu Lys
225                 230                 235                 240

Leu Met Lys Ala Phe Glu Ser Leu Lys Ser Phe Gln Gln Gln Gln Gln
                245                 250                 255

Gln Gln Gln Gln Gln Gln Gln Gln Gln Gln Gln Gln Gln Gln Gln Gln
```

```
              260                 265                 270
Gln Gln Gln Gln Gln Gln Gln Gln Gln Gln Gln Gln Gln Gln Gln
        275                 280                 285
Gln Gln Gln Gln Gln Gln Gln Gln Gln Gln Gln Pro Pro Pro
        290                 295                 300
Pro Pro Pro Pro Pro Pro Gln Leu Pro Gln Pro Pro Pro Gln Ala
305                 310                 315                 320
Gln Pro Leu Leu Pro Gln Leu Gln Pro Pro Pro Pro Pro Pro Pro
                325                 330                 335
Pro Pro Gly Pro Ala Ala Ala Glu Glu Pro Leu His Arg Pro
                340                 345                 350

<210> SEQ ID NO 12
<211> LENGTH: 1050
<212> TYPE: DNA
<213> ORGANISM: Artificial Sequence
<220> FEATURE:
<223> OTHER INFORMATION: mHTT GST-Ex1Q49

<400> SEQUENCE: 12
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600
tggcctttgc agggctggca agccacgttt ggtggtggcg accatcctcc aaaatcggat     660
ctggaagttc tgttccaggg gcccctggga tccccggaat tcatggcgac cctggaaaag     720
ctgatgaagg ccttcgagtc cctcaagtcc ttccagcagc agcagcagca gcagcagcag     780
cagcagcagc agcagcagca gcagcagcag cagcagcagc agcagcagca gcagcagcag     840
cagcagcagc agcagcagca gcagcagcag cagcagcagc agcagcagca gcagcaacag     900
ccgccaccgc cgccgccgcc gccgccgcct cctcagcttc ctcagccgcc gccgcaggca     960
cagccgctgc tgcctcagct gcagccgccc ccgccgccgc cccgccgcc acccggcccg    1020
gccgcggctg aggagccgct gcaccgacca                                    1050

<210> SEQ ID NO 13
<211> LENGTH: 360
<212> TYPE: PRT
<213> ORGANISM: Artificial Sequence
<220> FEATURE:
<223> OTHER INFORMATION: mHTT Ex1Q48-YPet

<400> SEQUENCE: 13

Met Ala Thr Leu Glu Lys Leu Met Lys Ala Phe Glu Ser Leu Lys Ser
1               5                   10                  15
Phe Gln Gln Gln Gln Gln Gln Gln Gln Gln Gln Gln Gln Gln Gln
            20                  25                  30
```

Gln Gln Gln Gln Gln Gln Gln Gln Gln Gln Gln Gln Gln
         35                  40                  45
Gln Gln Gln Gln Gln Gln Gln Gln Gln Gln Gln Gln Gln
 50                  55                  60
Gln Pro Pro Pro Pro Pro Pro Pro Pro Pro Gln Leu Pro Gln
 65                  70                  75                  80
Pro Pro Pro Gln Ala Gln Pro Leu Leu Pro Gln Leu Pro Pro
                 85                  90                  95
Pro Pro Pro Pro Pro Pro Gly Pro Ala Ala Ala Glu Pro Leu
            100                 105                 110
His Arg Pro Leu Glu Gly Gly Gly Gly Met Ser Lys Gly Glu Glu
            115                 120                 125
Leu Phe Thr Gly Val Val Pro Ile Leu Val Glu Leu Asp Gly Asp Val
         130                 135                 140
Asn Gly His Lys Phe Ser Val Ser Gly Glu Gly Glu Gly Asp Ala Thr
145                 150                 155                 160
Tyr Gly Lys Leu Thr Leu Lys Leu Leu Cys Thr Thr Gly Lys Leu Pro
                 165                 170                 175
Val Pro Trp Pro Thr Leu Val Thr Thr Leu Gly Tyr Gly Val Gln Cys
            180                 185                 190
Phe Ala Arg Tyr Pro Asp His Met Lys Gln His Asp Phe Phe Lys Ser
         195                 200                 205
Ala Met Pro Glu Gly Tyr Val Gln Glu Arg Thr Ile Phe Phe Lys Asp
210                 215                 220
Asp Gly Asn Tyr Lys Thr Arg Ala Glu Val Lys Phe Glu Gly Asp Thr
225                 230                 235                 240
Leu Val Asn Arg Ile Glu Leu Lys Gly Ile Asp Phe Lys Glu Asp Gly
                 245                 250                 255
Asn Ile Leu Gly His Lys Leu Glu Tyr Asn Tyr Asn Ser His Asn Val
            260                 265                 270
Tyr Ile Thr Ala Asp Lys Gln Lys Asn Gly Ile Lys Ala Asn Phe Lys
         275                 280                 285
Ile Arg His Asn Ile Glu Asp Gly Gly Val Gln Leu Ala Asp His Tyr
290                 295                 300
Gln Gln Asn Thr Pro Ile Gly Asp Gly Pro Val Leu Leu Pro Asp Asn
305                 310                 315                 320
His Tyr Leu Ser Tyr Gln Ser Ala Leu Phe Lys Asp Pro Asn Glu Lys
                 325                 330                 335
Arg Asp His Met Val Leu Leu Glu Phe Leu Thr Ala Ala Gly Ile Thr
            340                 345                 350
Glu Gly Met Asn Glu Leu Tyr Lys
         355                 360

<210> SEQ ID NO 14
<211> LENGTH: 1080
<212> TYPE: DNA
<213> ORGANISM: Artificial Sequence
<220> FEATURE:
<223> OTHER INFORMATION: mHTT Ex1Q48-YPet

<400> SEQUENCE: 14
atggcgaccc tggaaaagct gatgaaggcc ttcgagtccc tcaagtcctt ccagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180

```
cagcagcagc aacagccgcc accgccgccg ccgccgccgc cgcctcctca gcttcctcag    240
ccgccgccgc aggcacagcc gctgctgcct cagctgcagc cgcccccgcc gccgcccccg    300
ccgccacccg gcccggccgc ggctgaggag ccgctgcacc gaccactcga gggtggcggt    360
ggcggtatgt ctaaaggtga agaattattc actggtgttg tcccaatttt ggttgaatta    420
gatggtgatg ttaatggtca caaatttct gtctccggtg aaggtgaagg tgatgctacg    480
tacggtaaat tgaccttaaa attactctgt actactggta aattgccagt tccatggcca    540
accttagtca ctactttagg ttatggtgtt caatgttttg ctagataccc agatcatatg    600
aaacaacatg acttttcaa gtctgccatg ccagaaggtt atgttcaaga agaactatt     660 ttttcaaag atgacggtaa ctacaagacc agagctgaag tcaagtttga aggtgatacc    720
ttagttaata gaatcgaatt aaaaggtatt gattttaaag aagatggtaa cattttaggt    780
cacaaattgg aatacaacta taactctcac aatgtttaca tcactgctga caaacaaaag    840
aatggtatca agctaacctt caaaattaga cacaacattg aagatggtgg tgttcaatta    900
gctgaccatt atcaacaaaa tactccaatt ggtgatggtc cagtcttgtt accagacaac    960
cattacttat cctatcaatc tgccttattc aaagatccaa cgaaaagag agaccacatg    1020 gtcttgttag aattttgac tgctgctggt attaccgagg gtatgaatga attgtacaaa    1080
```

<210> SEQ ID NO 15
<211> LENGTH: 360
<212> TYPE: PRT
<213> ORGANISM: Artificial Sequence
<220> FEATURE:
<223> OTHER INFORMATION: mHTT Ex1Q48-CyPet

<400> SEQUENCE: 15

```
Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Gln
    50                  55                  60

Gln Pro Pro Pro Pro Pro Pro Pro Pro Pro Gln Leu Pro Gln
65                  70                  75                  80

Pro Pro Pro Gln Ala Gln Pro Leu Leu Pro Gln Leu Gln Pro Pro Pro
                85                  90                  95

Pro Pro Pro Pro Pro Pro Gly Pro Ala Ala Ala Glu Glu Pro Leu
            100                 105                 110

His Arg Pro Leu Glu Gly Gly Gly Gly Met Ser Lys Gly Glu Glu
            115                 120                 125

Leu Phe Gly Gly Ile Val Pro Ile Leu Val Glu Leu Glu Gly Asp Val
130                 135                 140

Asn Gly His Lys Phe Ser Val Ser Gly Glu Gly Glu Gly Asp Ala Thr
145                 150                 155                 160

Tyr Gly Lys Leu Thr Leu Lys Phe Ile Cys Thr Thr Gly Lys Leu Pro
            165                 170                 175

Val Pro Trp Pro Thr Leu Val Thr Thr Leu Thr Trp Gly Val Gln Cys
            180                 185                 190

Phe Ser Arg Tyr Pro Asp His Met Lys Gln His Asp Phe Phe Lys Ser
            195                 200                 205
```

Val Met Pro Glu Gly Tyr Val Gln Glu Arg Thr Ile Phe Phe Lys Asp
    210                 215                 220

Asp Gly Asn Tyr Lys Thr Arg Ala Glu Val Lys Phe Glu Gly Asp Thr
225                 230                 235                 240

Leu Val Asn Arg Ile Glu Leu Lys Gly Ile Asp Phe Lys Glu Asp Gly
                245                 250                 255

Asn Ile Leu Gly His Lys Leu Glu Tyr Asn Tyr Ile Ser His Asn Val
            260                 265                 270

Tyr Ile Thr Ala Asp Lys Gln Lys Asn Gly Ile Lys Ala Asn Phe Lys
        275                 280                 285

Ala Arg His Asn Ile Thr Asp Gly Ser Val Gln Leu Ala Asp His Tyr
290                 295                 300

Gln Gln Asn Thr Pro Ile Gly Asp Gly Pro Val Ile Leu Pro Asp Asn
305                 310                 315                 320

His Tyr Leu Ser Thr Gln Ser Ala Leu Ser Lys Asp Pro Asn Glu Lys
                325                 330                 335

Arg Asp His Met Val Leu Leu Glu Phe Val Thr Ala Ala Gly Ile Thr
            340                 345                 350

His Gly Met Asp Glu Leu Tyr Lys
        355                 360

<210> SEQ ID NO 16
<211> LENGTH: 1080
<212> TYPE: DNA
<213> ORGANISM: Artificial Sequence
<220> FEATURE:
<223> OTHER INFORMATION: mHTT Ex1Q48-CyPet

<400> SEQUENCE: 16
atggcgaccc tggaaaagct gatgaaggcc ttcgagtccc tcaagtcctt ccagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc aacagccgcc accgccgccg ccccccgccg cgcctcctca gcttcctcag     240
ccgccgccgc aggcacagcc gctgctgcct cagctgcagc cgccccccgcc gccgccccccg     300
ccgccacccg gcccggccgc ggctgaggag ccgctgcacc gaccactcga gggtggcggt     360
ggcggtatgt ctaaaggtga agaattattc ggcggtatcg tcccaatttt agttgaatta     420
gagggtgatg ttaatggtca aaattttct gtctccggtg aaggtgaagg tgatgctacg     480
tacggtaaat tgaccttaaa atttatttgt actactggta aattgccagt tccatggcca     540
accttagtca ctactctgac ttggggtgtt caatgttttt ctagataccc agatcatatg     600
aaacaacatg acttttttcaa gtctgtcatg ccagaaggtt atgttcaaga agaactatat     660
tttttcaaag atgacggtaa ctacaagacc agagctgaag tcaagtttga aggtgatacc     720
ttagttaata gaatcgaatt aaaaggtatt gatttaaag aagatggtaa cattttaggt     780
cacaaattgg aatacaacta tatctctcac aatgtttaca tcaccgctga caaacaaaag     840
aatggtatca agctaacttc caaagccaga cacaacatta ccgatggttc tgttcaatta     900
gctgaccatt atcaacaaaa tactccaatt ggtgatggtc cagtcatctt gccagacaac     960
cattacttat ccactcaatc tgccttatct aaagatccaa acgaaaagag agaccacatg    1020
gtcttgctcg aatttgttac tgctgctggt attacccatg gtatggatga attgtacaaa    1080

<210> SEQ ID NO 17
<211> LENGTH: 594

```
<212> TYPE: PRT
<213> ORGANISM: Artificial Sequence
<220> FEATURE:
<223> OTHER INFORMATION: mHTT GST-Ex1Q48-YPet

<400> SEQUENCE: 17
```

| | | | | | | | | | | | | | | |
|---|---|---|---|---|---|---|---|---|---|---|---|---|---|---|
| Met | Ser | Pro | Ile | Leu | Gly | Tyr | Trp | Lys | Ile | Lys | Gly | Leu | Val | Gln | Pro |
| 1 | | | | 5 | | | | | 10 | | | | | 15 | |
| Thr | Arg | Leu | Leu | Leu | Glu | Tyr | Leu | Glu | Glu | Lys | Tyr | Glu | Glu | His | Leu |
| | | | 20 | | | | | 25 | | | | | 30 | | |
| Tyr | Glu | Arg | Asp | Glu | Gly | Asp | Lys | Trp | Arg | Asn | Lys | Lys | Phe | Glu | Leu |
| | | 35 | | | | | 40 | | | | | 45 | | | |
| Gly | Leu | Glu | Phe | Pro | Asn | Leu | Pro | Tyr | Tyr | Ile | Asp | Gly | Asp | Val | Lys |
| | 50 | | | | | 55 | | | | | 60 | | | | |
| Leu | Thr | Gln | Ser | Met | Ala | Ile | Ile | Arg | Tyr | Ile | Ala | Asp | Lys | His | Asn |
| 65 | | | | 70 | | | | | 75 | | | | | 80 | |
| Met | Leu | Gly | Gly | Cys | Pro | Lys | Glu | Arg | Ala | Glu | Ile | Ser | Met | Leu | Glu |
| | | | | 85 | | | | | 90 | | | | | 95 | |
| Gly | Ala | Val | Leu | Asp | Ile | Arg | Tyr | Gly | Val | Ser | Arg | Ile | Ala | Tyr | Ser |
| | | | 100 | | | | | 105 | | | | | 110 | | |
| Lys | Asp | Phe | Glu | Thr | Leu | Lys | Val | Asp | Phe | Leu | Ser | Lys | Leu | Pro | Glu |
| | | 115 | | | | | 120 | | | | | 125 | | | |
| Met | Leu | Lys | Met | Phe | Glu | Asp | Arg | Leu | Cys | His | Lys | Thr | Tyr | Leu | Asn |
| 130 | | | | | 135 | | | | | 140 | | | | | |
| Gly | Asp | His | Val | Thr | His | Pro | Asp | Phe | Met | Leu | Tyr | Asp | Ala | Leu | Asp |
| 145 | | | | | 150 | | | | | 155 | | | | | 160 |
| Val | Val | Leu | Tyr | Met | Asp | Pro | Met | Cys | Leu | Asp | Ala | Phe | Pro | Lys | Leu |
| | | | | 165 | | | | | 170 | | | | | 175 | |
| Val | Cys | Phe | Lys | Lys | Arg | Ile | Glu | Ala | Ile | Pro | Gln | Ile | Asp | Lys | Tyr |
| | | | 180 | | | | | 185 | | | | | 190 | | |
| Leu | Lys | Ser | Ser | Lys | Tyr | Ile | Ala | Trp | Pro | Leu | Gln | Gly | Trp | Gln | Ala |
| | | | 195 | | | | | 200 | | | | | 205 | | |
| Thr | Phe | Gly | Gly | Gly | Asp | His | Pro | Pro | Lys | Ser | Asp | Leu | Glu | Val | Leu |
| | 210 | | | | | 215 | | | | | 220 | | | | |
| Phe | Gln | Gly | Pro | Leu | Gly | Ser | Pro | Glu | Phe | Met | Ala | Thr | Leu | Glu | Lys |
| 225 | | | | | 230 | | | | | 235 | | | | | 240 |
| Leu | Met | Lys | Ala | Phe | Glu | Ser | Leu | Lys | Ser | Phe | Gln | Gln | Gln | Gln | Gln |
| | | | | 245 | | | | | 250 | | | | | 255 | |
| Gln | Gln | Gln | Gln | Gln | Gln | Gln | Gln | Gln | Gln | Gln | Gln | Gln | Gln | Gln | Gln |
| | | | 260 | | | | | 265 | | | | | 270 | | |
| Gln | Gln | Gln | Gln | Gln | Gln | Gln | Gln | Gln | Gln | Gln | Gln | Gln | Gln | Gln | Gln |
| | | 275 | | | | | 280 | | | | | 285 | | | |
| Gln | Gln | Gln | Gln | Gln | Gln | Gln | Gln | Gln | Gln | Pro | Pro | Pro | Pro |
| | 290 | | | | | 295 | | | | | 300 | | | |
| Pro | Pro | Pro | Pro | Pro | Gln | Leu | Pro | Gln | Pro | Pro | Pro | Gln | Ala | Gln |
| 305 | | | | | 310 | | | | | 315 | | | | | 320 |
| Pro | Leu | Leu | Pro | Gln | Pro | Gln | Pro | Pro | Pro | Pro | Pro | Pro | Pro | Pro | Pro |
| | | | | 325 | | | | | 330 | | | | | 335 | |
| Pro | Gly | Pro | Ala | Ala | Ala | Glu | Glu | Pro | Leu | His | Arg | Pro | Leu | Glu | Gly |
| | | | 340 | | | | | 345 | | | | | 350 | | |
| Gly | Gly | Gly | Gly | Met | Ser | Lys | Gly | Glu | Glu | Leu | Phe | Thr | Gly | Val | Val |
| | | 355 | | | | | 360 | | | | | 365 | | | |
| Pro | Ile | Leu | Val | Glu | Leu | Asp | Gly | Asp | Val | Asn | Gly | His | Lys | Phe | Ser |
| | 370 | | | | | 375 | | | | | 380 | | | | |

Val Ser Gly Glu Gly Glu Gly Asp Ala Thr Tyr Gly Lys Leu Thr Leu
385             390                 395                 400

Lys Leu Leu Cys Thr Thr Gly Lys Leu Pro Val Pro Trp Pro Thr Leu
            405                 410                 415

Val Thr Thr Leu Gly Tyr Gly Val Gln Cys Phe Ala Arg Tyr Pro Asp
            420                 425                 430

His Met Lys Gln His Asp Phe Phe Lys Ser Ala Met Pro Glu Gly Tyr
        435                 440                 445

Val Gln Glu Arg Thr Ile Phe Phe Lys Asp Gly Asn Tyr Lys Thr
    450                 455                 460

Arg Ala Glu Val Lys Phe Glu Gly Asp Thr Leu Val Asn Arg Ile Glu
465                 470                 475                 480

Leu Lys Gly Ile Asp Phe Lys Glu Asp Gly Asn Ile Leu Gly His Lys
                485                 490                 495

Leu Glu Tyr Asn Tyr Asn Ser His Asn Val Tyr Ile Thr Ala Asp Lys
            500                 505                 510

Gln Lys Asn Gly Ile Lys Ala Asn Phe Lys Ile Arg His Asn Ile Glu
        515                 520                 525

Asp Gly Gly Val Gln Leu Ala Asp His Tyr Gln Gln Asn Thr Pro Ile
530                 535                 540

Gly Asp Gly Pro Val Leu Leu Pro Asp Asn His Tyr Leu Ser Tyr Gln
545                 550                 555                 560

Ser Ala Leu Phe Lys Asp Pro Asn Glu Lys Arg Asp His Met Val Leu
                565                 570                 575

Leu Glu Phe Leu Thr Ala Ala Gly Ile Thr Glu Gly Met Asn Glu Leu
            580                 585                 590

Tyr Lys

<210> SEQ ID NO 18
<211> LENGTH: 1782
<212> TYPE: DNA
<213> ORGANISM: Artificial Sequence
<220> FEATURE:
<223> OTHER INFORMATION: mHTT GST-Ex1Q48-YPet

<400> SEQUENCE: 18 atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300 gatattgat acggtgtttc gagaattgca tatagtaaag actttgaaac tctcaaagtt     360
gattttctta gcaagctacc tgaaatgctg aaaatgttcg aagatcgttt atgtcataaa     420 acatattaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600 tggccttgc agggctggca agccacgttt ggtggtggcg accatcctcc aaaatcggat     660
ctggaagttc tgttccaggg gcccctggga tccccggaat tcatggcgac cctggaaaag     720
ctgatgaagg ccttcgagtc cctcaagtcc ttccagcagc agcagcagca gcagcagcag     780
cagcagcagc agcagcagca gcagcagcag cagcagcagc agcagcagca gcagcagcag     840

```
cagcagcagc agcagcagca gcagcagcag cagcagcagc agcagcagca gcaacagccg    900
ccaccgccgc cgccgccgcc gccgcctcct cagcttcctc agccgccgcc gcaggcacag    960
ccgctgctgc ctcagctgca gccgcccccg ccgccgcccc cgccgccacc cggcccggcc   1020
gcggctgagg agccgctgca ccgaccactc gagggtggcg gtggcggtat gtctaaaggt   1080
gaagaattat tcactggtgt tgtcccaatt ttggttgaat tagatggtga tgttaatggt   1140
cacaaatttt ctgtctccgg tgaaggtgaa ggtgatgcta cgtacggtaa attgacctta   1200
aaattactct gtactactgg taaattgcca gttccatggc caaccttagt cactacttta   1260
ggttatggtg ttcaatgttt tgctagatac ccagatcata tgaaacaaca tgactttttc   1320
aagtctgcca tgccagaagg ttatgttcaa gaaagaacta ttttttttcaa agatgacggt   1380 aactacaaga ccagagctga agtcaagttt gaaggtgata ccttagttaa tagaatcgaa   1440
ttaaaaggta ttgattttaa agaagatggt aacattttag gtcacaaatt ggaatacaac   1500
tataactctc acaatgttta catcactgct gacaaacaaa agaatggtat caaagctaac   1560
ttcaaaatta gacacaacat tgaagatggt ggtgttcaat tagctgacca ttatcaacaa   1620
aatactccaa ttggtgatgg tccagtcttg ttaccagaca accattactt atcctatcaa   1680
tctgccttat tcaaagatcc aaacgaaaag agagaccaca tggtcttgtt agaattttg   1740 actgctgctg gtattaccga gggtatgaat gaattgtaca aa                      1782
```

<210> SEQ ID NO 19
<211> LENGTH: 594
<212> TYPE: PRT
<213> ORGANISM: Artificial Sequence
<220> FEATURE:
<223> OTHER INFORMATION: mHTT GST-Ex1Q48-CyPet

<400> SEQUENCE: 19

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
```

```
                        195                 200                 205
Thr Phe Gly Gly Gly Asp His Pro Pro Lys Ser Asp Leu Glu Val Leu
210                 215                 220
Phe Gln Gly Pro Leu Gly Ser Pro Glu Phe Met Ala Thr Leu Glu Lys
225                 230                 235                 240
Leu Met Lys Ala Phe Glu Ser Leu Lys Ser Phe Gln Gln Gln Gln Gln
                245                 250                 255
Gln Gln Gln Gln Gln Gln Gln Gln Gln Gln Gln Gln Gln Gln Gln Gln
                260                 265                 270
Gln Gln Gln Gln Gln Gln Gln Gln Gln Gln Gln Gln Gln Gln Gln Gln
                275                 280                 285
Gln Gln Gln Gln Gln Gln Gln Gln Gln Gln Pro Pro Pro Pro Pro Pro
290                 295                 300
Pro Pro Pro Pro Pro Gln Leu Pro Gln Pro Pro Pro Gln Ala Gln
305                 310                 315                 320
Pro Leu Leu Pro Gln Leu Gln Pro Pro Pro Pro Pro Pro Pro Pro Pro
                325                 330                 335
Pro Gly Pro Ala Ala Ala Glu Glu Pro Leu His Arg Pro Leu Glu Gly
                340                 345                 350
Gly Gly Gly Gly Met Ser Lys Gly Glu Glu Leu Phe Gly Gly Ile Val
                355                 360                 365
Pro Ile Leu Val Glu Leu Glu Gly Asp Val Asn Gly His Lys Phe Ser
370                 375                 380
Val Ser Gly Glu Gly Glu Gly Asp Ala Thr Tyr Gly Lys Leu Thr Leu
385                 390                 395                 400
Lys Phe Ile Cys Thr Thr Gly Lys Leu Pro Val Pro Trp Pro Thr Leu
                405                 410                 415
Val Thr Thr Leu Thr Trp Gly Val Gln Cys Phe Ser Arg Tyr Pro Asp
                420                 425                 430
His Met Lys Gln His Asp Phe Phe Lys Ser Val Met Pro Glu Gly Tyr
                435                 440                 445
Val Gln Glu Arg Thr Ile Phe Phe Lys Asp Asp Gly Asn Tyr Lys Thr
450                 455                 460
Arg Ala Glu Val Lys Phe Glu Gly Asp Thr Leu Val Asn Arg Ile Glu
465                 470                 475                 480
Leu Lys Gly Ile Asp Phe Lys Glu Asp Gly Asn Ile Leu Gly His Lys
                485                 490                 495
Leu Glu Tyr Asn Tyr Ile Ser His Asn Val Tyr Ile Thr Ala Asp Lys
                500                 505                 510
Gln Lys Asn Gly Ile Lys Ala Asn Phe Lys Ala Arg His Asn Ile Thr
                515                 520                 525
Asp Gly Ser Val Gln Leu Ala Asp His Tyr Gln Gln Asn Thr Pro Ile
530                 535                 540
Gly Asp Gly Pro Val Ile Leu Pro Asp Asn His Tyr Leu Ser Thr Gln
545                 550                 555                 560
Ser Ala Leu Ser Lys Asp Pro Asn Glu Lys Arg Asp His Met Val Leu
                565                 570                 575
Leu Glu Phe Val Thr Ala Ala Gly Ile Thr His Gly Met Asp Glu Leu
                580                 585                 590
Tyr Lys

<210> SEQ ID NO 20
<211> LENGTH: 1782
```

```
<212> TYPE: DNA
<213> ORGANISM: Artificial Sequence
<220> FEATURE:
<223> OTHER INFORMATION: mHTT GST-Ex1Q48-CyPet

<400> SEQUENCE: 20 atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggtttg      300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg atgcgttcc caaaattagt tgtttttaaa      540
aaacgtattg aagctatccc acaaattgat aagtacttga atccagcaa gtatatagca     600
tggcctttgc agggctggca agccacgttt ggtggtggcg accatcctcc aaaatcggat     660
ctggaagttc tgttccaggg gcccctggga tccccggaat tcatggcgac cctggaaaag    720
ctgatgaagg ccttcgagtc cctcaagtcc ttccagcagc agcagcagca gcagcagcag     780
cagcagcagc agcagcagca gcagcagcag cagcagcagc agcagcagca gcagcagcag     840
cagcagcagc agcagcagca gcagcagcag cagcagcagc agcagcagca gcaacagccg     900
ccaccgccgc cgccccgcc gccgcctcct cagcttcctc agccgccgcc gcaggcacag     960
ccgctgctgc ctcagctgca gccgcccccg ccgccgcccc cgccgccacc cggcccggcc    1020
gcggctgagg agccgctgca ccgaccactc gagggtggcg gtggcggtat gtctaaaggt    1080
gaagaattat tcggcggtat cgtcccaatt ttagttgaat tagagggtga tgttaatggt    1140
cacaaatttt ctgtctccgg tgaaggtgaa ggtgatgcta cgtacggtaa attgaccta     1200
aaatttattt gtactactgg taaattgcca gttccatggc caaccttagt cactactctg    1260
acttggggtg ttcaatgttt ttctagatac ccagatcata tgaaacaaca tgactttttc    1320
aagtctgtca tgccagaagg ttatgttcaa gaaagaacta tttttttcaa agatgacggt    1380
aactacaaga ccagagctga agtcaagttt gaaggtgata ccttagttaa tagaatcgaa    1440
ttaaaggta ttgattttaa agaagatggt aacattttag gtcacaaatt ggaatacaac    1500
tatatctctc acaatgttta catcaccgct gacaaacaaa agaatggtat caaagctaac    1560
ttcaaagcca gacacaacat taccgatggt tctgttcaat agctgacca ttatcaacaa    1620
aatactccaa ttggtgatgg tccagtcatc ttgccagaca accattactt atccactcaa    1680
tctgccttat ctaaagatcc aaacgaaaag agagaccaca tggtcttgct cgaatttgtt    1740
actgctgctg gtattaccca tggtatggat gaattgtaca aa                      1782

<210> SEQ ID NO 21
<211> LENGTH: 238
<212> TYPE: PRT
<213> ORGANISM: Artificial Sequence
<220> FEATURE:
<223> OTHER INFORMATION: YPet

<400> SEQUENCE: 21

Met Ser Lys Gly Glu Glu Leu Phe Thr Gly Val Val Pro Ile Leu Val
1               5                   10                  15
```

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Leu Leu Cys
        35                  40                  45

Thr Thr Gly Lys Leu Pro Val Pro Trp Pro Thr Leu Val Thr Thr Leu
    50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Phe
        195                 200                 205

Lys Asp Pro Asn Glu Lys Arg Asp His Met Val Leu Leu Glu Phe Leu
    210                 215                 220

Thr Ala Ala Gly Ile Thr Glu Gly Met Asn Glu Leu Tyr Lys
225                 230                 235

<210> SEQ ID NO 22
<211> LENGTH: 714
<212> TYPE: DNA
<213> ORGANISM: Artificial Sequence
<220> FEATURE:
<223> OTHER INFORMATION: YPet

<400> SEQUENCE: 22
atgtctaaag gtgaagaatt attcactggt gttgtcccaa ttttggttga attagatggt      60
gatgttaatg gtcacaaatt ttctgtctcc ggtgaaggtg aaggtgatgc tacgtacggt     120
aaattgacct aaaattact ctgtactact ggtaaattgc agttccatg gccaacctta      180 gtcactactt taggttatgg tgttcaatgt tttgctagat acccagatca tatgaaacaa    240
catgactttt tcaagtctgc catgccagaa ggttatgttc agaaagaac tattttttc     300 aaagatgacg gtaactacaa gaccagagct gaagtcaagt ttgaaggtga taccttagtt    360
aatagaatcg aattaaaagg tattgatttt aagaagatg gtaacatttt aggtcacaaa    420
ttggaataca actataactc tcacaatgtt tacatcactg ctgacaaaca aaagaatggt    480
atcaaagcta acttcaaaat tagacacaac attgaagatg gtggtgttca attagctgac    540
cattatcaac aaaatactcc aattggtgat ggtccagtct tgttaccaga caaccattac    600
ttatcctatc aatctgcctt attcaaagat ccaaacgaaa agagagacca catggtcttg    660
ttagaatttt tgactgctgc tggtattacc gagggtatga atgaattgta caaa           714

<210> SEQ ID NO 23

```
<211> LENGTH: 238
<212> TYPE: PRT
<213> ORGANISM: Artificial Sequence
<220> FEATURE:
<223> OTHER INFORMATION: CyPet

<400> SEQUENCE: 23

Met Ser Lys Gly Glu Glu Leu Phe Gly Gly Ile Val Pro Ile Leu Val
1               5                   10                  15

Glu Leu Glu Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Trp Gly Val Gln Cys Phe Ser Arg Tyr Pro Asp His Met Lys Gln
65                  70                  75                  80

His Asp Phe Phe Lys Ser Val Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Ile Ser His Asn Val Tyr Ile Thr Ala Asp Lys Gln Lys Asn Gly
145                 150                 155                 160

Ile Lys Ala Asn Phe Lys Ala Arg His Asn Ile Thr Asp Gly Ser Val
                165                 170                 175

Gln Leu Ala Asp His Tyr Gln Gln Asn Thr Pro Ile Gly Asp Gly Pro
            180                 185                 190

Val Ile Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 24
<211> LENGTH: 714
<212> TYPE: DNA
<213> ORGANISM: Artificial Sequence
<220> FEATURE:
<223> OTHER INFORMATION: CyPet

<400> SEQUENCE: 24
atgtctaaag gtgaagaatt attcggcggt atcgtcccaa ttttagttga attagagggt      60
gatgttaatg gtcacaaatt ttctgtctcc ggtgaaggtg aaggtgatgc tacgtacggt     120
aaattgacct taaaatttat ttgtactact ggtaaattgc cagttccatg gccaacctta     180
gtcactactc tgacttgggg tgttcaatgt ttttctagat acccagatca tatgaaacaa     240
catgactttt tcaagtctgt catgccagaa ggttatgttc aagaaagaac tatttttttc     300
aaagatgacg gtaactacaa gaccagagct gaagtcaagt ttgaaggtga tactttagtt     360
aatagaatcg aattaaaagg tattgatttt aagaagatg gtaacatttt aggtcacaaa      420
ttggaataca actatatctc tcacaatgtt tacatcaccg ctgacaaaca aaagaatggt     480
```

```
atcaaagcta acttcaaagc cagacacaac attaccgatg gttctgttca attagctgac    540
cattatcaac aaaatactcc aattggtgat ggtccagtca tcttgccaga caaccattac    600
ttatccactc aatctgcctt atctaaagat ccaaacgaaa agagagacca catggtcttg    660
ctcgaatttg ttactgctgc tggtattacc catggtatgg atgaattgta caaa          714
```

```
<210> SEQ ID NO 25
<211> LENGTH: 90
<212> TYPE: PRT
<213> ORGANISM: Homo sapiens

<400> SEQUENCE: 25
```

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
                20                  25                  30

Gln Gln Gln Gln Gln Gln Gln Pro Pro Pro Pro Pro Pro Pro
            35                  40                  45

Pro Pro Pro Gln Leu Pro Gln Pro Pro Pro Gln Ala Gln Pro Leu Leu
50                  55                  60

Pro Gln Pro Gln Pro Pro Pro Pro Pro Pro Pro Pro Pro Gly Pro
65                  70                  75                  80

Ala Val Ala Glu Glu Pro Leu His Arg Pro
                85                  90

```
<210> SEQ ID NO 26
<211> LENGTH: 270
<212> TYPE: DNA
<213> ORGANISM: Homo sapiens

<400> SEQUENCE: 26
atggcgaccc tggaaaagct gatgaaggcc ttcgagtccc tcaagtcctt ccagcagcag    60
cagcagcagc agcagcagca gcagcagcag cagcagcagc agcagcagca gcagcaacag    120
ccgccaccgc cgccgccgcc gccgccgcct cctcagcttc ctcagccgcc gccgcaggca    180
cagccgctgc tgcctcagcc gcagccgccc ccgccgccgc cccgccgcc acccggcccg    240 gctgtggctg aggagccgct gcaccgacca                                    270
```

```
<210> SEQ ID NO 27
<211> LENGTH: 324
<212> TYPE: PRT
<213> ORGANISM: Artificial Sequence
<220> FEATURE:
<223> OTHER INFORMATION: GST-Ex1Q23

<400> SEQUENCE: 27
```

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Leu Glu Val Leu
210                 215                 220

Phe Gln Gly Pro Leu Gly Ser Pro Glu Phe Met Ala Thr Leu Glu Lys
225                 230                 235                 240

Leu Met Lys Ala Phe Glu Ser Leu Lys Ser Phe Gln Gln Gln Gln
            245                 250                 255

Gln Gln Gln Gln Gln Gln Gln Gln Gln Gln Gln Gln Gln Gln Gln
            260                 265                 270

Gln Gln Pro Pro Pro Pro Pro Pro Pro Pro Pro Gln Leu Pro
        275                 280                 285

Gln Pro Pro Gln Ala Gln Pro Leu Leu Pro Gln Pro Gln Pro Pro
290                 295                 300

Pro Pro Pro Pro Pro Pro Pro Gly Pro Ala Val Ala Glu Glu Pro
305                 310                 315                 320

Leu His Arg Pro

<210> SEQ ID NO 28
<211> LENGTH: 972
<212> TYPE: DNA
<213> ORGANISM: Artificial Sequence
<220> FEATURE:
<223> OTHER INFORMATION: GST-Ex1Q23

<400> SEQUENCE: 28 atgtcccta tactaggtta ttggaaaatt aagggccttg tgcaacccac tcgacttctt     60
ttggaatatc ttgaagaaaa atatgaagag catttgtatg agcgcgatga aggtgataaa    120
tggcgaaaca aaaagtttga attgggtttg agtttcccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg    300 gatattgat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gccccctggga tccccggaat tcatggcgac cctggaaaag    720

```
ctgatgaagg ccttcgagtc cctcaagtcc ttccagcagc agcagcagca gcagcagcag    780
cagcagcagc agcagcagca gcagcagcag cagcagcaac agccgccacc gccgccgccg    840
ccgccgccgc tcctcagct  tcctcagccg ccgccgcagg cacagccgct gctgcctcag    900
ccgcagccgc ccccgccgcc gccccgccg  ccacccggcc cggctgtggc tgaggagccg    960
ctgcaccgac ca                                                        972
```

<210> SEQ ID NO 29
<211> LENGTH: 569
<212> TYPE: PRT
<213> ORGANISM: Artificial Sequence
<220> FEATURE:
<223> OTHER INFORMATION: GST-Ex1Q23-YPet

<400> SEQUENCE: 29

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Pro Glu Phe Met Ala Thr Leu Glu Lys
225                 230                 235                 240

Leu Met Lys Ala Phe Glu Ser Leu Lys Ser Phe Gln Gln Gln Gln
                245                 250                 255

Gln Gln Gln Gln Gln Gln Gln Gln Gln Gln Gln Gln Gln Gln Gln
            260                 265                 270

Gln Gln Pro Pro Pro Pro Pro Pro Pro Pro Pro Gln Leu Pro
        275                 280                 285

Gln Pro Pro Pro Gln Ala Gln Pro Leu Leu Pro Gln Pro Gln Pro Pro
    290                 295                 300

Pro Pro Pro Pro Pro Pro Pro Gly Pro Ala Val Ala Glu Glu Pro
305                 310                 315                 320
```

-continued

```
Leu His Arg Pro Leu Glu Gly Gly Gly Gly Met Ser Lys Gly Glu
                325                 330                 335
Glu Leu Phe Thr Gly Val Val Pro Ile Leu Val Glu Leu Asp Gly Asp
            340                 345                 350
Val Asn Gly His Lys Phe Ser Val Ser Gly Glu Gly Glu Gly Asp Ala
        355                 360                 365
Thr Tyr Gly Lys Leu Thr Leu Lys Leu Leu Cys Thr Thr Gly Lys Leu
    370                 375                 380
Pro Val Pro Trp Pro Thr Leu Val Thr Thr Leu Gly Tyr Gly Val Gln
385                 390                 395                 400
Cys Phe Ala Arg Tyr Pro Asp His Met Lys Gln His Asp Phe Phe Lys
                405                 410                 415
Ser Ala Met Pro Glu Gly Tyr Val Gln Glu Arg Thr Ile Phe Phe Lys
            420                 425                 430
Asp Asp Gly Asn Tyr Lys Thr Arg Ala Glu Val Lys Phe Glu Gly Asp
        435                 440                 445
Thr Leu Val Asn Arg Ile Glu Leu Lys Gly Ile Asp Phe Lys Glu Asp
    450                 455                 460
Gly Asn Ile Leu Gly His Lys Leu Glu Tyr Asn Tyr Asn Ser His Asn
465                 470                 475                 480
Val Tyr Ile Thr Ala Asp Lys Gln Lys Asn Gly Ile Lys Ala Asn Phe
                485                 490                 495
Lys Ile Arg His Asn Ile Glu Asp Gly Gly Val Gln Leu Ala Asp His
            500                 505                 510
Tyr Gln Gln Asn Thr Pro Ile Gly Asp Gly Pro Val Leu Leu Pro Asp
        515                 520                 525
Asn His Tyr Leu Ser Tyr Gln Ser Ala Leu Phe Lys Asp Pro Asn Glu
    530                 535                 540
Lys Arg Asp His Met Val Leu Leu Glu Phe Leu Thr Ala Ala Gly Ile
545                 550                 555                 560
Thr Glu Gly Met Asn Glu Leu Tyr Lys
                565
```

<210> SEQ ID NO 30
<211> LENGTH: 1707
<212> TYPE: DNA
<213> ORGANISM: Artificial Sequence
<220> FEATURE:
<223> OTHER INFORMATION: GST-Ex1Q23-YPet

<400> SEQUENCE: 30

| | | |
|---|---|---|
| atgtcccta tactaggtta ttggaaaatt aagggccttg tgcaacccac tcgacttctt | 60 |
| ttggaatatc ttgaagaaaa atatgaagag catttgtatg agcgcgatga aggtgataaa | 120 |
| tggcgaaaca aaaagtttga attgggtttg agtttcccca atcttcctta ttatattgat | 180 |
| ggtgatgtta aattaacaca gtctatggcc atcatacgtt atagctga caagcacaac | 240 |
| atgttgggtg ttgtccaaa agagcgtgca gagatttcaa tgcttgaagg agcggttttg | 300 |
| gatattagat acggtgtttc gagaattgca tatagtaaag actttgaaac tctcaaagtt | 360 |
| gattttctta gcaagctacc tgaaatgctg aaaatgttcg aagatcgttt atgtcataaa | 420 |
| acatatttaa atggtgatca tgtaacccat cctgacttca tgttgtatga cgctcttgat | 480 |
| gttgttttat acatggaccc aatgtgcctg gatgcgttcc caaaattagt ttgttttaaa | 540 |
| aaacgtattg aagctatccc acaaattgat aagtacttga atccagcaa gtatatagca | 600 |

```
tggcctttgc agggctggca agccacgttt ggtggtggcg accatcctcc aaaatcggat    660
ctggaagttc tgttccaggg gcccctggga tccccggaat tcatggcgac cctggaaaag    720
ctgatgaagg ccttcgagtc cctcaagtcc ttccagcagc agcagcagca gcagcagcag    780
cagcagcagc agcagcagca gcagcagcag cagcagcaac agccgccacc gccgccgccg    840
ccgccgccgc ctcctcagct tcctcagccg ccgccgcagg cacagccgct gctgcctcag    900
ccgcagccgc ccccgccgcc gccccgccg ccacccggcc cggctgtggc tgaggagccg    960
ctgcaccgac cactcgaggg tggcggtggc ggtatgtcta aaggtgaaga attattcact   1020
ggtgttgtcc caattttggt tgaattagat ggtgatgtta atggtcacaa atttctgtc   1080 tccggtgaag gtgaaggtga tgctacgtac ggtaaattga ccttaaaatt actctgtact   1140
actggtaaat tgccagttcc atggccaacc ttagtcacta ctttaggtta tggtgttcaa   1200
tgttttgcta gatacccaga tcatatgaaa caacatgact ttttcaagtc tgccatgcca   1260
gaaggttatg ttcaagaaag aactattttt tcaaagatg acggtaacta caagaccaga   1320
gctgaagtca agtttgaagg tgataccttgtta gttaatagaa tcgaattaaa aggtattgat   1380
tttaaagaag atggtaacat tttaggtcac aaattggaat acaactataa ctctcacaat   1440
gtttacatca ctgctgacaa acaaaagaat ggtatcaaag ctaacttcaa aattagacac   1500
aacattgaag atggtggtgt tcaattagct gaccattatc aacaaaatac tccaattggt   1560
gatggtccag tcttgttacc agacaaccat tacttatcct atcaatctgc cttattcaaa   1620
gatccaaacg aaagagaga ccacatggtc ttgttagaat ttttgactgc tgctggtatt   1680
accgagggta tgaatgaatt gtacaaa                                      1707
```

<210> SEQ ID NO 31
<211> LENGTH: 569
<212> TYPE: PRT
<213> ORGANISM: Artificial Sequence
<220> FEATURE:
<223> OTHER INFORMATION: GST-Ex1Q23-CyPet

<400> SEQUENCE: 31

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
```

```
            165                 170                 175
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Glu Val Leu
            210                 215                 220

Phe Gln Gly Pro Leu Gly Ser Pro Glu Phe Met Ala Thr Leu Glu Lys
225                 230                 235                 240

Leu Met Lys Ala Phe Glu Ser Leu Lys Ser Phe Gln Gln Gln Gln
            245                 250                 255

Gln Gln Gln Gln Gln Gln Gln Gln Gln Gln Gln Gln Gln Gln Gln
            260                 265                 270

Gln Gln Pro Pro Pro Pro Pro Pro Pro Pro Gln Leu Pro
            275                 280                 285

Gln Pro Pro Pro Gln Ala Gln Pro Leu Leu Pro Gln Pro Gln Pro Pro
290                 295                 300

Pro Pro Pro Pro Pro Pro Gly Pro Ala Val Ala Glu Glu Pro
305                 310                 315                 320

Leu His Arg Pro Leu Glu Gly Gly Gly Gly Met Ser Lys Gly Glu
            325                 330                 335

Glu Leu Phe Gly Gly Ile Val Pro Ile Leu Val Glu Leu Glu Gly Asp
            340                 345                 350

Val Asn Gly His Lys Phe Ser Val Ser Gly Glu Gly Glu Gly Asp Ala
            355                 360                 365

Thr Tyr Gly Lys Leu Thr Leu Lys Phe Ile Cys Thr Thr Gly Lys Leu
            370                 375                 380

Pro Val Pro Trp Pro Thr Leu Val Thr Thr Leu Thr Trp Gly Val Gln
385                 390                 395                 400

Cys Phe Ser Arg Tyr Pro Asp His Met Lys Gln His Asp Phe Phe Lys
            405                 410                 415

Ser Val Met Pro Glu Gly Tyr Val Gln Glu Arg Thr Ile Phe Phe Lys
            420                 425                 430

Asp Asp Gly Asn Tyr Lys Thr Arg Ala Glu Val Lys Phe Glu Gly Asp
            435                 440                 445

Thr Leu Val Asn Arg Ile Glu Leu Lys Gly Ile Asp Phe Lys Glu Asp
            450                 455                 460

Gly Asn Ile Leu Gly His Lys Leu Glu Tyr Asn Tyr Ile Ser His Asn
465                 470                 475                 480

Val Tyr Ile Thr Ala Asp Lys Gln Lys Asn Gly Ile Lys Ala Asn Phe
            485                 490                 495

Lys Ala Arg His Asn Ile Thr Asp Gly Ser Val Gln Leu Ala Asp His
            500                 505                 510

Tyr Gln Gln Asn Thr Pro Ile Gly Asp Gly Pro Val Ile Leu Pro Asp
            515                 520                 525

Asn His Tyr Leu Ser Thr Gln Ser Ala Leu Ser Lys Asp Pro Asn Glu
            530                 535                 540

Lys Arg Asp His Met Val Leu Leu Glu Phe Val Thr Ala Ala Gly Ile
545                 550                 555                 560

Thr His Gly Met Asp Glu Leu Tyr Lys
            565

<210> SEQ ID NO 32
```

<211> LENGTH: 1707
<212> TYPE: DNA
<213> ORGANISM: Artificial Sequence
<220> FEATURE:
<223> OTHER INFORMATION: GST-Ex1Q23-CyPet

<400> SEQUENCE: 32

| | | | | | |
|---|---|---|---|---|---|
| atgtcccta | tactaggtta | ttggaaaatt | aagggccttg | tgcaacccac | tcgacttctt | 60 |
| ttggaatatc | ttgaagaaaa | atatgaagag | catttgtatg | agcgcgatga | aggtgataaa | 120 |
| tggcgaaaca | aaaagtttga | attgggtttg | gagtttccca | atcttcctta | ttatattgat | 180 |
| ggtgatgtta | aattaacaca | gtctatggcc | atcatacgtt | atatagctga | caagcacaac | 240 |
| atgttgggtg | gttgtccaaa | agagcgtgca | gagatttcaa | tgcttgaagg | agcggttttg | 300 |
| gatattagat | acggtgtttc | gagaattgca | tatagtaaag | actttgaaac | tctcaaagtt | 360 |
| gattttctta | gcaagctacc | tgaaatgctg | aaaatgttcg | aagatcgttt | atgtcataaa | 420 |
| acatatttaa | atggtgatca | tgtaacccat | cctgacttca | tgttgtatga | cgctcttgat | 480 |
| gttgttttat | acatggaccc | aatgtgcctg | gatgcgttcc | caaaattagt | ttgttttaaa | 540 |
| aaacgtattg | aagctatccc | acaaattgat | aagtacttga | atccagcaa | gtatatagca | 600 |
| tggccttgc | agggctggca | agccacgttt | ggtggtggcg | accatcctcc | aaaatcggat | 660 |
| ctggaagttc | tgttccaggg | gccccgggga | tccccggaat | tcatggcgac | cctggaaaag | 720 |
| ctgatgaagg | ccttcgagtc | cctcaagtcc | ttccagcagc | agcagcagca | gcagcagcag | 780 |
| cagcagcagc | agcagcagca | gcagcagcag | cagcagcaac | agccgccacc | gccgccgccg | 840 |
| ccgccgccgc | ctcctcagct | tcctcagccg | ccgccgcagg | cacagccgct | gctgcctcag | 900 |
| ccgcagccgc | cccgccgcc | gccccgccg | ccacccggcc | cggctgtggc | tgaggagccg | 960 |
| ctgcaccgac | cactcgaggg | tggcggtggc | ggtatgtcta | aaggtgaaga | attattcggc | 1020 |
| ggtatcgtcc | caattttagt | tgaattagag | ggtgatgtta | atggtcacaa | attttctgtc | 1080 |
| tccggtgaag | gtgaaggtga | tgctacgtac | ggtaaattga | ccttaaaatt | tatttgtact | 1140 |
| actggtaaat | tgccagttcc | atggccaacc | ttagtcacta | ctctgacttg | ggtgttcaa | 1200 |
| tgttttctcta | gatacccaga | tcatatgaaa | caacatgact | ttttcaagtc | tgtcatgcca | 1260 |
| gaaggttatg | ttcaagaaag | aactattttt | ttcaaagatg | acggtaacta | caagaccaga | 1320 |
| gctgaagtca | agtttgaagg | tgatacctta | gttaatagaa | tcgaattaaa | aggtattgat | 1380 |
| tttaagaag | atggtaacat | tttaggtcac | aaattggaat | acaactatat | ctctcacaat | 1440 |
| gtttacatca | ccgctgacaa | acaaaagaat | ggtatcaaag | ctaacttcaa | agccagacac | 1500 |
| aacattaccg | atggttctgt | tcaattagct | gaccattatc | aacaaaatac | tccaattggt | 1560 |
| gatggtccag | tcatcttgcc | agacaaccat | tacttatcca | ctcaatctgc | cttatctaaa | 1620 |
| gatccaaacg | aaaagagaga | ccacatggtc | ttgctcgaat | tgttactgc | tgctggtatt | 1680 |
| acccatggta | tggatgaatt | gtacaaa | | | | 1707 |

<210> SEQ ID NO 33
<211> LENGTH: 335
<212> TYPE: PRT
<213> ORGANISM: Artificial Sequence
<220> FEATURE:
<223> OTHER INFORMATION: Ex1Q23-YPet

<400> SEQUENCE: 33

Met Ala Thr Leu Glu Lys Leu Met Lys Ala Phe Glu Ser Leu Lys Ser
1               5                   10                  15

| | | | | | | | | | | | | |
|---|---|---|---|---|---|---|---|---|---|---|---|---|
|Phe|Gln|Gln|Gln|Gln|Gln|Gln|Gln|Gln|Gln|Gln|Gln|Gln|
| | |20| | | |25| | | |30| | |
|Gln|Gln|Gln|Gln|Gln|Gln|Gln|Pro|Pro|Pro|Pro|Pro|Pro|
| | |35| | | |40| | | |45| | |
|Pro|Pro|Pro|Gln|Leu|Pro|Gln|Pro|Pro|Gln|Ala|Gln|Pro|Leu|Leu|
| |50| | | | |55| | | |60| | |
|Pro|Gln|Pro|Gln|Pro|Pro|Pro|Pro|Pro|Pro|Pro|Pro|Gly|Pro|
|65| | | |70| | | |75| | | |80|
|Ala|Val|Ala|Glu|Glu|Pro|Leu|His|Arg|Pro|Leu|Glu|Gly|Gly|Gly|
| | | | |85| | | |90| | | |95|
|Gly|Met|Ser|Lys|Gly|Glu|Glu|Leu|Phe|Thr|Gly|Val|Val|Pro|Ile|Leu|
| | | |100| | | |105| | | |110| |
|Val|Glu|Leu|Asp|Gly|Asp|Val|Asn|Gly|His|Lys|Phe|Ser|Val|Ser|Gly|
| | | |115| | | |120| | | |125| |
|Glu|Gly|Glu|Gly|Asp|Ala|Thr|Tyr|Gly|Lys|Leu|Thr|Leu|Lys|Leu|Leu|
| | | |130| | | |135| | | |140| |
|Cys|Thr|Thr|Gly|Lys|Leu|Pro|Val|Pro|Trp|Pro|Thr|Leu|Val|Thr|Thr|
|145| | | | |150| | | |155| | | |160|
|Leu|Gly|Tyr|Gly|Val|Gln|Cys|Phe|Ala|Arg|Tyr|Pro|Asp|His|Met|Lys|
| | | |165| | | |170| | | |175| |
|Gln|His|Asp|Phe|Phe|Lys|Ser|Ala|Met|Pro|Glu|Gly|Tyr|Val|Gln|Glu|
| | | |180| | | |185| | | |190| |
|Arg|Thr|Ile|Phe|Phe|Lys|Asp|Asp|Gly|Asn|Tyr|Lys|Thr|Arg|Ala|Glu|
| | | |195| | | |200| | | |205| |
|Val|Lys|Phe|Glu|Gly|Asp|Thr|Leu|Val|Asn|Arg|Ile|Glu|Leu|Lys|Gly|
| | |210| | | |215| | | |220| | |
|Ile|Asp|Phe|Lys|Glu|Asp|Gly|Asn|Ile|Leu|Gly|His|Lys|Leu|Glu|Tyr|
|225| | | |230| | | |235| | | |240|
|Asn|Tyr|Asn|Ser|His|Asn|Val|Tyr|Ile|Thr|Ala|Asp|Lys|Gln|Lys|Asn|
| | | |245| | | |250| | | |255| |
|Gly|Ile|Lys|Ala|Asn|Phe|Lys|Ile|Arg|His|Asn|Ile|Glu|Asp|Gly|Gly|
| | | |260| | | |265| | | |270| |
|Val|Gln|Leu|Ala|Asp|His|Tyr|Gln|Gln|Asn|Thr|Pro|Ile|Gly|Asp|Gly|
| | |275| | | |280| | | |285| | |
|Pro|Val|Leu|Leu|Pro|Asp|Asn|His|Tyr|Leu|Ser|Tyr|Gln|Ser|Ala|Leu|
| |290| | | | |295| | | |300| | |
|Phe|Lys|Asp|Pro|Asn|Glu|Lys|Arg|Asp|His|Met|Val|Leu|Leu|Glu|Phe|
|305| | | |310| | | |315| | | |320|
|Leu|Thr|Ala|Ala|Gly|Ile|Thr|Glu|Gly|Met|Asn|Glu|Leu|Tyr|Lys|
| | | |325| | | |330| | | |335|

<210> SEQ ID NO 34
<211> LENGTH: 1005
<212> TYPE: DNA
<213> ORGANISM: Artificial Sequence
<220> FEATURE:
<223> OTHER INFORMATION: Ex1Q23-YPet

<400> SEQUENCE: 34

```
atggcgaccc tggaaaagct gatgaaggcc ttcgagtccc tcaagtcctt ccagcagcag    60
cagcagcagc agcagcagca gcagcagcag cagcagcagc agcagcagca gcagcaacag   120
ccgccaccgc cgccgccgcc gccgccgcct cctcagcttc ctcagccgcc gccgcaggca   180
cagccgctgc tgcctcagcc gcagccgccc cgccgccgc ccccgccgcc acccggcccg   240
gctgtggctg aggagccgct gcaccgacca ctcgagggtg gcggtggcgg tatgtctaaa   300
```

-continued

```
ggtgaagaat tattcactgg tgttgtccca attttggttg aattagatgg tgatgttaat      360
ggtcacaaat tttctgtctc cggtgaaggt gaaggtgatg ctacgtacgg taaattgacc      420
ttaaaattac tctgtactac tggtaaattg ccagttccat ggccaacctt agtcactact      480
ttaggttatg gtgttcaatg ttttgctaga tacccagatc atatgaaaca acatgacttt      540
ttcaagtctg ccatgccaga aggttatgtt caagaaagaa ctattttttt caaagatgac      600
ggtaactaca agaccagagc tgaagtcaag tttgaaggtg ataccttagt aatagaatc       660 gaattaaaag gtattgattt taaagaagat ggtaacattt aggtcacaa attggaatac       720 aactataact ctcacaatgt ttacatcact gctgacaaac aaaagaatgg tatcaaagct      780
aacttcaaaa ttagacacaa cattgaagat ggtggtgttc aattagctga ccattatcaa      840
caaaatactc caattggtga tggtccagtc ttgttaccag acaaccatta cttatcctat      900
caatctgcct tattcaaaga tccaaacgaa aagagagacc acatggtctt gttagaattt      960
ttgactgctg ctggtattac cgagggtatg aatgaattgt acaaa                     1005
```

<210> SEQ ID NO 35
<211> LENGTH: 335
<212> TYPE: PRT
<213> ORGANISM: Artificial Sequence
<220> FEATURE:
<223> OTHER INFORMATION: Ex1Q23-CyPet

<400> SEQUENCE: 35

```
Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln
                20                  25                  30

Gln Gln Gln Gln Gln Gln Gln Pro Pro Pro Pro Pro Pro Pro
            35                  40                  45

Pro Pro Pro Gln Leu Pro Gln Pro Pro Pro Gln Ala Gln Pro Leu Leu
50                  55                  60

Pro Gln Pro Gln Pro Pro Pro Pro Pro Pro Pro Pro Pro Gly Pro
65                  70                  75                  80

Ala Val Ala Glu Glu Pro Leu His Arg Pro Leu Glu Gly Gly Gly
                85                  90                  95

Gly Met Ser Lys Gly Glu Glu Leu Phe Gly Gly Ile Val Pro Ile Leu
            100                 105                 110

Val Glu Leu Glu Gly Asp Val Asn Gly His Lys Phe Ser Val Ser Gly
        115                 120                 125

Glu Gly Glu Gly Asp Ala Thr Tyr Gly Lys Leu Thr Leu Lys Phe Ile
    130                 135                 140

Cys Thr Thr Gly Lys Leu Pro Val Pro Trp Pro Thr Leu Val Thr Thr
145                 150                 155                 160

Leu Thr Trp Gly Val Gln Cys Phe Ser Arg Tyr Pro Asp His Met Lys
                165                 170                 175

Gln His Asp Phe Phe Lys Ser Val Met Pro Glu Gly Tyr Val Gln Glu
            180                 185                 190

Arg Thr Ile Phe Phe Lys Asp Asp Gly Asn Tyr Lys Thr Arg Ala Glu
        195                 200                 205

Val Lys Phe Glu Gly Asp Thr Leu Val Asn Arg Ile Glu Leu Lys Gly
    210                 215                 220

Ile Asp Phe Lys Glu Asp Gly Asn Ile Leu Gly His Lys Leu Glu Tyr
225                 230                 235                 240
```

Asn Tyr Ile Ser His Asn Val Tyr Ile Thr Ala Asp Lys Gln Lys Asn
            245                 250                 255

Gly Ile Lys Ala Asn Phe Lys Ala Arg His Asn Ile Thr Asp Gly Ser
        260                 265                 270

Val Gln Leu Ala Asp His Tyr Gln Gln Asn Thr Pro Ile Gly Asp Gly
    275                 280                 285

Pro Val Ile Leu Pro Asp Asn His Tyr Leu Ser Thr Gln Ser Ala Leu
290                 295                 300

Ser Lys Asp Pro Asn Glu Lys Arg Asp His Met Val Leu Leu Glu Phe
305                 310                 315                 320

Val Thr Ala Ala Gly Ile Thr His Gly Met Asp Glu Leu Tyr Lys
                325                 330                 335

<210> SEQ ID NO 36
<211> LENGTH: 1005
<212> TYPE: DNA
<213> ORGANISM: Artificial Sequence
<220> FEATURE:
<223> OTHER INFORMATION: Ex1Q23-YPet

<400> SEQUENCE: 36
atggcgaccc tggaaaagct gatgaaggcc ttcgagtccc tcaagtcctt ccagcagcag      60
cagcagcagc agcagcagca gcagcagcag cagcagcagc agcagcagca gcagcaacag     120
ccgccaccgc cgccgccgcc gccgccgcct cctcagcttc ctcagccgcc gccgcaggca     180
cagccgctgc tgcctcagcc gcagccgccc cgccgccgc ccccgccgcc acccggcccg      240
gctgtggctg aggagccgct gcaccgacca ctcgagggtg gcggtggcgg tatgtctaaa     300
ggtgaagaat tattcggcgg tatcgtccca attttagttg aattagaggg tgatgttaat     360
ggtcacaaat tttctgtctc cggtgaaggt gaaggtgatg ctacgtacgg taaattgacc     420
ttaaaattta tttgtactac tggtaaattg ccagttccat ggccaacctt agtcactact     480
ctgacttggg gtgttcaatg ttttctaga tacccagatc atatgaaaca acatgacttt     540
ttcaagtctg tcatgccaga aggttatgtt caagaaagaa ctatttttt caaagatgac     600 ggtaactaca agaccagagc tgaagtcaag tttgaaggtg ataccttagt taatagaatc     660
gaattaaaag gtattgattt taaagaagat ggtaacattt taggtcacaa attggaatac     720
aactatatct ctcacaatgt ttacatcacc gctgacaaac aaaagaatgg tatcaaagct     780
aacttcaaag ccagacacaa cattaccgat ggttctgttc aattagctga ccattatcaa     840
caaaatactc caattggtga tggtccagtc atcttgccag acaaccatta cttatccact     900
caatctgcct atctaaaga tccaaacgaa agagagacc acatggtctt gctcgaattt      960
gttactgctg ctggtattac ccatggtatg gatgaattgt acaaa                    1005

<210> SEQ ID NO 37
<211> LENGTH: 24
<212> TYPE: DNA
<213> ORGANISM: Artificial Sequence
<220> FEATURE:
<223> OTHER INFORMATION: primer HTTEx1Q48 fw

<400> SEQUENCE: 37
gacgacgaat tcatggcgac cctg      24

<210> SEQ ID NO 38
<211> LENGTH: 27
<212> TYPE: DNA

```
<213> ORGANISM: Artificial Sequence
<220> FEATURE:
<223> OTHER INFORMATION: primer HTTEx1Q48 rev

<400> SEQUENCE: 38
gacgacctcg agtggtcggt gcagcgg                                              27

<210> SEQ ID NO 39
<211> LENGTH: 52
<212> TYPE: DNA
<213> ORGANISM: Artificial Sequence
<220> FEATURE:
<223> OTHER INFORMATION: primer CyPet fw

<400> SEQUENCE: 39
acgacctcga gggtggcggt ggcggtatgt ctaaaggtga agaattattc gg                  52

<210> SEQ ID NO 40
<211> LENGTH: 41
<212> TYPE: DNA
<213> ORGANISM: Artificial Sequence
<220> FEATURE:
<223> OTHER INFORMATION: primer CyPet rev

<400> SEQUENCE: 40
gacgacgcgg ccgcttattt gtacaattca tccataccat g                             41

<210> SEQ ID NO 41
<211> LENGTH: 56
<212> TYPE: DNA
<213> ORGANISM: Artificial Sequence
<220> FEATURE:
<223> OTHER INFORMATION: primer YPet fw

<400> SEQUENCE: 41
gacgacctcg agggtggcgg tggcggtatg tctaaaggtg aagaattatt cactgg             56

<210> SEQ ID NO 42
<211> LENGTH: 42
<212> TYPE: DNA
<213> ORGANISM: Artificial Sequence
<220> FEATURE:
<223> OTHER INFORMATION: primer YPet rev

<400> SEQUENCE: 42
gacgacgcgg ccgcttattt gtacaattca ttcataccct cg                            42

<210> SEQ ID NO 43
<211> LENGTH: 24
<212> TYPE: DNA
<213> ORGANISM: Artificial Sequence
<220> FEATURE:
<223> OTHER INFORMATION: primer HTTEx1Q23 fw1

<400> SEQUENCE: 43
gacgacgaat tcatggcgac cctg                                                24

<210> SEQ ID NO 44
<211> LENGTH: 35
<212> TYPE: DNA
<213> ORGANISM: Artificial Sequence
<220> FEATURE:
<223> OTHER INFORMATION: primer HTTEx1Q23 rev1

<400> SEQUENCE: 44
gacgacgcgg ccgcctcgag tggtcggtgc agcgg                                    35
```

<210> SEQ ID NO 45
<211> LENGTH: 24
<212> TYPE: DNA
<213> ORGANISM: Artificial Sequence
<220> FEATURE:
<223> OTHER INFORMATION: primer HTTEx1Q23 fw2

<400> SEQUENCE: 45
gacgacgaat tcatggcgac cctg					24

<210> SEQ ID NO 46
<211> LENGTH: 38
<212> TYPE: DNA
<213> ORGANISM: Artificial Sequence
<220> FEATURE:
<223> OTHER INFORMATION: primer HTTEx1Q23 rev2

<400> SEQUENCE: 46
gacgacgcgg ccgcctcgag ttatggtcgg tgcagcgg			38

<210> SEQ ID NO 47
<211> LENGTH: 1599
<212> TYPE: DNA
<213> ORGANISM: Artificial Sequence
<220> FEATURE:
<223> OTHER INFORMATION: GST-K2Q48P6-CYPET

<400> SEQUENCE: 47 atgtcccta tactaggtta ttggaaaatt aagggccttg tgcaacccac tcgacttctt		60 ttggaatatc ttgaagaaaa atatgaagag catttgtatg agcgcgatga aggtgataaa		120 tggcgaaaca aaaagtttga attgggtttg gagtttccca atcttcctta ttatattgat		180 ggtgatgtta aattaacaca gtctatggcc atcatacgtt atatagctga caagcacaac		240 atgttgggtg gttgtccaaa agagcgtgca gagatttcaa tgcttgaagg agcggttttg		300 gatattagat acggtgtttc gagaattgca tatagtaaag actttgaaac tctcaaagtt		360 gattttctta gcaagctacc tgaaatgctg aaaatgttcg aagatcgttt atgtcataaa		420 acatatttaa atggtgatca tgtaacccat cctgacttca tgttgtatga cgctcttgat		480 gttgttttat acatggaccc aatgtgcctg gatgcgttcc caaaattagt ttgttttaaa		540 aaacgtattg aagctatccc acaaattgat aagtacttga atccagcaa gtatatagca		600 tggccttttgc agggctggca agccacgttt ggtggtggcg accatcctcc aaaatcggat		660 ctggaagttc tgttccaggg gccccctggga tccaaaaaac agcagcagca acaacagcag		720 caacagcaac aacaacaaca gcagcagcaa cagcaacagc agcagcagca acaacaacag		780 caacaacagc aacagcagca acagcagcag cagcagcaac agcaacaaca gcagcaacag		840 cagcctccgc ctccgcctcc tctcgagggt ggcggtggcg gtatgtctaa aggtgaagaa		900 ttattcggcg gtatcgtccc aattttagtt gaattagagg gtgatgttaa tggtcacaaa		960 ttttctgtct ccggtgaagg tgaaggtgat gctacgtacg gtaaattgac cttaaaattt		1020 atttgtacta ctggtaaatt gccagttcca tggccaacct tagtcactac tctgacttgg		1080 ggtgttcaat gttttctag atacccagat catatgaaac aacatgactt tttcaagtct		1140 gtcatgccag aaggttatgt tcaagaaaga actattttttt tcaaagatga cggtaactac		1200 aagaccagag ctgaagtcaa gtttgaaggt gataccttag ttaatagaat cgaattaaaa		1260 ggtattgatt ttaaagaaga tggtaacatt ttaggtcaca aattggaata caactatatc		1320

```
tctcacaatg tttacatcac cgctgacaaa caaaagaatg gtatcaaagc taacttcaaa    1380
gccagacaca acattaccga tggttctgtt caattagctg accattatca acaaaatact    1440
ccaattggtg atggtccagt catcttgcca gacaaccatt actatccac tcaatctgcc     1500 ttatctaaag atccaaacga aaagagagac cacatggtct tgctcgaatt tgttactgct    1560
gctggtatta cccatgggtat ggatgaattg tacaaataa                          1599
```

<210> SEQ ID NO 48
<211> LENGTH: 532
<212> TYPE: PRT
<213> ORGANISM: Artificial Sequence
<220> FEATURE:
<223> OTHER INFORMATION: GST-K2Q48P6-CYPET AA

<400> SEQUENCE: 48

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Lys Lys Gln Gln Gln Gln Gln Gln Gln
225                 230                 235                 240

Gln Gln Gln Gln Gln Gln Gln Gln Gln Gln Gln Gln Gln Gln Gln Gln
                245                 250                 255

Gln Gln Gln Gln Gln Gln Gln Gln Gln Gln Gln Gln Gln Gln Gln Gln
            260                 265                 270

Gln Gln Gln Gln Gln Gln Gln Gln Pro Pro Pro Pro Leu
        275                 280                 285

Glu Gly Gly Gly Gly Met Ser Lys Gly Glu Glu Leu Phe Gly Gly
    290                 295                 300

Ile Val Pro Ile Leu Val Glu Leu Glu Gly Asp Val Asn Gly His Lys
305                 310                 315                 320
```

```
Phe Ser Val Ser Gly Glu Gly Asp Ala Thr Tyr Gly Lys Leu
            325                 330                 335

Thr Leu Lys Phe Ile Cys Thr Thr Gly Lys Leu Pro Val Pro Trp Pro
        340                 345                 350

Thr Leu Val Thr Thr Leu Thr Trp Gly Val Gln Cys Phe Ser Arg Tyr
        355                 360                 365

Pro Asp His Met Lys Gln His Asp Phe Phe Lys Ser Val Met Pro Glu
    370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Asp Phe Lys Glu Asp Gly Asn Ile Leu Gly
                420                 425                 430

His Lys Leu Glu Tyr Asn Tyr Ile Ser His Asn Val Tyr Ile Thr Ala
            435                 440                 445

Asp Lys Gln Lys Asn Gly Ile Lys Ala Asn Phe Lys Ala Arg His Asn
    450                 455                 460

Ile Thr Asp Gly Ser Val Gln Leu Ala Asp His Tyr Gln Gln Asn Thr
465                 470                 475                 480

Pro Ile Gly Asp Gly Pro Val Ile Leu Pro Asp Asn His Tyr Leu Ser
                485                 490                 495

Thr Gln Ser Ala Leu Ser Lys Asp Pro Asn Glu Lys Arg Asp His Met
            500                 505                 510

Val Leu Leu Glu Phe Val Thr Ala Ala Gly Ile Thr His Gly Met Asp
        515                 520                 525

Glu Leu Tyr Lys
    530

<210> SEQ ID NO 49
<211> LENGTH: 1599
<212> TYPE: DNA
<213> ORGANISM: Artificial Sequence
<220> FEATURE:
<223> OTHER INFORMATION: GST-K2Q48P6-YPET

<400> SEQUENCE: 49 atgtcccta  tactaggtta  ttggaaaatt  aagggccttg  tgcaacccac  tcgacttctt      60
ttggaatatc  ttgaagaaaa  atatgaagag  catttgtatg  agcgcgatga  aggtgataaa     120
tggcgaaaca  aaaagtttga  attgggtttg  gagtttccca  atcttcctta  ttatattgat     180
ggtgatgtta  aattaacaca  gtctatggcc  atcatacgtt  atatagctga  caagcacaac     240
atgttgggtg  ttgtccaaa  agagcgtgca  gagatttcaa  tgcttgaagg  agcggttttg     300
gatattagat  acgtgtttc  gagaattgca  tatagtaaag  actttgaaac  tctcaaagtt     360
gattttctta  gcaagctacc  tgaaatgctg  aaaatgttcg  aagatcgttt  atgtcataaa     420
acatatttaa  atggtgatca  tgtaacccat  cctgacttca  tgttgtatga  cgctcttgat     480
gttgttttat  acatggaccc  aatgtgcctg  atgcgttcc  caaaattagt  ttgttttaaa     540
aaacgtattg  aagctatccc  acaaattgat  aagtacttga  atccagcaa  gtatatagca     600 tggcctttgc  agggctggca  agccacgttt  ggtggtggcg  accatcctcc  aaaatcggat     660
ctggaagttc  tgttccaggg  gccctggga  tccaaaaaac  agcagcagca  acaacagcag     720
caacagcaac  aacaacaaca  gcagcagcaa  cagcaacagc  agcagcagca  acaacaacag     780
```

```
caacaacagc aacagcagca acagcagcag cagcagcaac agcaacaaca gcagcaacag    840
cagcctccgc ctccgcctcc tctcgagggt ggcggtggcg gtatgtctaa aggtgaagaa    900
ttattcactg gtgttgtccc aattttggtt gaattagatg gtgatgttaa tggtcacaaa    960
ttttctgtct ccggtgaagg tgaaggtgat gctacgtacg gtaaattgac cttaaaatta   1020
ctctgtacta ctggtaaatt gccagttcca tggccaacct tagtcactac tttaggttat   1080
ggtgttcaat gttttgctag atacccagat catatgaaac aacatgactt tttcaagtct   1140
gccatgccag aaggttatgt tcaagaaaga actatttttt tcaaagatga cggtaactac   1200
aagaccagag ctgaagtcaa gtttgaaggt gataccttag ttaatagaat cgaattaaaa   1260
ggtattgatt ttaaagaaga tggtaacatt ttaggtcaca aattggaata caactataac   1320
tctcacaatg tttacatcac tgctgacaaa caaaagaatg gtatcaaagc taacttcaaa   1380
attagacaca acattgaaga tggtggtgtt caattagctg accattatca acaaaatact   1440
ccaattggtg atggtccagt cttgttacca gacaaccatt acttatccta tcaatctgcc   1500
ttattcaaag atccaaacga aaagagagac cacatggtct tgttagaatt tttgactgct   1560
gctggtatta ccgagggtat gatgaattg tacaaataa                            1599
```

<210> SEQ ID NO 50
<211> LENGTH: 532
<212> TYPE: PRT
<213> ORGANISM: Artificial Sequence
<220> FEATURE:
<223> OTHER INFORMATION: GST-K2Q48P6-YPET

<400> SEQUENCE: 50

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220
```

-continued

Phe Gln Gly Pro Leu Gly Ser Lys Lys Gln Gln Gln Gln Gln Gln Gln
225                 230                 235                 240

Gln Gln Gln Gln Gln Gln Gln Gln Gln Gln Gln Gln Gln Gln Gln Gln
            245                 250                 255

Gln Gln Gln Gln Gln Gln Gln Gln Gln Gln Gln Gln Gln Gln Gln Gln
        260                 265                 270

Gln Gln Gln Gln Gln Gln Gln Gln Pro Pro Pro Pro Pro Leu
    275                 280                 285

Glu Gly Gly Gly Gly Met Ser Lys Gly Glu Glu Leu Phe Thr Gly
290                 295                 300

Val Val Pro Ile Leu Val Glu Leu Asp Gly Asp Val Asn Gly His Lys
305                 310                 315                 320

Phe Ser Val Ser Gly Glu Gly Glu Gly Asp Ala Thr Tyr Gly Lys Leu
                325                 330                 335

Thr Leu Lys Leu Leu Cys Thr Thr Gly Lys Leu Pro Val Pro Trp Pro
            340                 345                 350

Thr Leu Val Thr Thr Leu Gly Tyr Gly Val Gln Cys Phe Ala Arg Tyr
        355                 360                 365

Pro Asp His Met Lys Gln His Asp Phe Phe Lys Ser Ala Met Pro Glu
370                 375                 380

Gly Tyr Val Gln Glu Arg Thr Ile Phe Phe Lys Asp Asp Gly Asn Tyr
385                 390                 395                 400

Lys Thr Arg Ala Glu Val Lys Phe Glu Gly Asp Thr Leu Val Asn Arg
                405                 410                 415

Ile Glu Leu Lys Gly Ile Asp Phe Lys Glu Asp Gly Asn Ile Leu Gly
            420                 425                 430

His Lys Leu Glu Tyr Asn Tyr Asn Ser His Asn Val Tyr Ile Thr Ala
        435                 440                 445

Asp Lys Gln Lys Asn Gly Ile Lys Ala Asn Phe Lys Ile Arg His Asn
450                 455                 460

Ile Glu Asp Gly Gly Val Gln Leu Ala Asp His Tyr Gln Gln Asn Thr
465                 470                 475                 480

Pro Ile Gly Asp Gly Pro Val Leu Leu Pro Asp Asn His Tyr Leu Ser
                485                 490                 495

Tyr Gln Ser Ala Leu Phe Lys Asp Pro Asn Glu Lys Arg Asp His Met
            500                 505                 510

Val Leu Leu Glu Phe Leu Thr Ala Ala Gly Ile Thr Glu Gly Met Asn
        515                 520                 525

Glu Leu Tyr Lys
    530

<210> SEQ ID NO 51
<211> LENGTH: 1743
<212> TYPE: DNA
<213> ORGANISM: Artificial Sequence
<220> FEATURE:
<223> OTHER INFORMATION: GST-deltaN17Q48+6PRD-CYPET

<400> SEQUENCE: 51
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240

```
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gcccctggga tcccagcagc agcaacaaca gcagcaacag    720
caacagcagc agcagcagca acaacagcag cagcaacagc aacaacaaca acaacagcag    780
caacaacagc aacagcagca acagcaacag cagcaacaac aacagcaaca acagcagcct    840
ccgcctccgc cacctcctcc acctccgcct ccaccgccac cgcctcctca gttacctcag    900
cctcctccgc aggcacagcc gctgctgccg cagttacagc ctccaccacc acctccgccg    960
cctccacctg tcctgcagc agcagaagaa ccgctgcatc gtccgctcga gggtggcggt   1020
ggcggtatgt ctaaaggtga agaattattc ggcggtatcg tcccaatttt agttgaatta   1080
gagggtgatg ttaatggtca caattttct gtctccggtg aaggtgaagg tgatgctacg   1140
tacggtaaat tgaccttaaa atttatttgt actactggta aattgccagt tccatggcca   1200
accttagtca ctactctgac ttggggtgtt caatgttttt ctagatacc agatcatatg   1260 aaacaacatg acttttcaa gtctgtcatg ccagaaggtt atgttcaaga agaactatt   1320 tttttcaaag atgacggtaa ctacaagacc agagctgaag tcaagtttga aggtgatacc   1380
ttagttaata gaatcgaatt aaaaggtatt gattttaaag aagatggtaa catttaggt    1440 cacaaattgg aatacaacta tctctctcac aatgtttaca tcaccgctga caacaaaag    1500 aatggtatca agctaactt caaagccaga cacaacatta ccgatggttc tgttcaatta   1560
gctgaccatt atcaacaaaa tactccaatt ggtgatggtc cagtcatctt gccagacaac   1620
cattacttat ccactcaatc tgccttatct aaagatccaa acgaaagag agaccacatg   1680 gtcttgctcg aatttgttac tgctgctggt attacccatg gtatggatga attgtacaaa   1740
taa                                                                 1743
```

<210> SEQ ID NO 52
<211> LENGTH: 580
<212> TYPE: PRT
<213> ORGANISM: Artificial Sequence
<220> FEATURE:
<223> OTHER INFORMATION: GST-deltaN17Q48+6PRD-CYPET AA

<400> SEQUENCE: 52

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95
```

```
Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Glu Val Leu
    210                 215                 220

Phe Gln Gly Pro Leu Gly Ser Gln Gln Gln Gln Gln Gln Gln Gln Gln
225                 230                 235                 240

Gln Gln Gln Gln Gln Gln Gln Gln Gln Gln Gln Gln Gln Gln Gln Gln
            245                 250                 255

Gln Gln Gln Gln Gln Gln Gln Gln Gln Gln Gln Gln Gln Gln Gln Gln
            260                 265                 270

Gln Gln Gln Gln Gln Gln Gln Pro Pro Pro Pro Pro Pro Pro Pro Pro
            275                 280                 285

Pro Pro Pro Pro Pro Pro Pro Gln Leu Pro Gln Pro Pro Pro Gln
    290                 295                 300

Ala Gln Pro Leu Leu Pro Gln Leu Gln Pro Pro Pro Pro Pro Pro Pro
305                 310                 315                 320

Pro Pro Pro Gly Pro Ala Ala Ala Glu Glu Pro Leu His Arg Pro Leu
            325                 330                 335

Glu Gly Gly Gly Gly Met Ser Lys Gly Glu Glu Leu Phe Gly Gly
                340                 345                 350

Ile Val Pro Ile Leu Val Glu Leu Glu Gly Asp Val Asn Gly His Lys
            355                 360                 365

Phe Ser Val Ser Gly Glu Gly Glu Gly Asp Ala Thr Tyr Gly Lys Leu
    370                 375                 380

Thr Leu Lys Phe Ile Cys Thr Thr Gly Lys Leu Pro Val Pro Trp Pro
385                 390                 395                 400

Thr Leu Val Thr Thr Leu Thr Trp Gly Val Gln Cys Phe Ser Arg Tyr
                405                 410                 415

Pro Asp His Met Lys Gln His Asp Phe Phe Lys Ser Val Met Pro Glu
            420                 425                 430

Gly Tyr Val Gln Glu Arg Thr Ile Phe Phe Lys Asp Asp Gly Asn Tyr
    435                 440                 445

Lys Thr Arg Ala Glu Val Lys Phe Glu Gly Asp Thr Leu Val Asn Arg
            450                 455                 460

Ile Glu Leu Lys Gly Ile Asp Phe Lys Glu Asp Gly Asn Ile Leu Gly
465                 470                 475                 480

His Lys Leu Glu Tyr Asn Tyr Ile Ser His Asn Val Tyr Ile Thr Ala
                485                 490                 495

Asp Lys Gln Lys Asn Gly Ile Lys Ala Asn Phe Lys Ala Arg His Asn
            500                 505                 510
```

```
Ile Thr Asp Gly Ser Val Gln Leu Ala Asp His Tyr Gln Gln Asn Thr
            515                 520                 525

Pro Ile Gly Asp Gly Pro Val Ile Leu Pro Asp Asn His Tyr Leu Ser
        530                 535                 540

Thr Gln Ser Ala Leu Ser Lys Asp Pro Asn Glu Lys Arg Asp His Met
545                 550                 555                 560

Val Leu Leu Glu Phe Val Thr Ala Ala Gly Ile Thr His Gly Met Asp
                565                 570                 575

Glu Leu Tyr Lys
            580

<210> SEQ ID NO 53
<211> LENGTH: 1743
<212> TYPE: DNA
<213> ORGANISM: Artificial Sequence
<220> FEATURE:
<223> OTHER INFORMATION: GST-deltaN17Q48+6PRD-YPET

<400> SEQUENCE: 53 atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acgtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gcccctggga tcccagcagc agcaacaaca gcagcaacag    720
caacagcagc agcagcagca acaacagcag cagcaacagc aacaacaaca acaacagcag    780
caacaacagc aacagcagca acagcaacag cagcaacaac aacagcaaca acagcagcct    840
ccgcctccgc cacctcctcc acctccgcct ccaccgccac cgcctcctca gttacctcag    900
cctcctccgc aggcacagcc gctgctgccg cagttacagc ctccaccacc acctccgccg    960
cctccacctg tcctgcagc agcagaagaa ccgctgcatc gtccgctcga gggtggcggt   1020
ggcggtatgt ctaaaggtga agaattattc actggtgttg tcccaatttt ggttgaatta   1080
gatggtgatg ttaatggtca caaattttct gtctccggtg aaggtgaagg tgatgctacg   1140
tacggtaaat tgaccttaaa attactctgt actactggta aattgccagt tccatggcca   1200
accttagtca ctactttagg ttatggtgtt caatgttttg ctagataccc agatcatatg   1260
aaacaacatg actttttcaa gtctgccatg ccagaaggtt atgttcaaga agaactatt    1320 ttttttcaaag atgacggtaa ctacaagacc agagctgaag tcaagtttga aggtgatacc   1380
ttagttaata gaatcgaatt aaaaggtatt gatttaaag aagatggtaa cattttaggt    1440
cacaaattgg aatacaacta taactctcac aatgtttaca tcactgctga caacaaaag    1500 aatggtatca agctaactt caaaattaga cacaacattg aagatggtgg tgttcaatta   1560
gctgaccatt atcaacaaaa tactccaatt ggtgatggtc cagtcttgtt accagacaac   1620
```

```
cattacttat cctatcaatc tgccttattc aaagatccaa acgaaaagag agaccacatg    1680
gtcttgttag aattttttgac tgctgctggt attaccgagg gtatgaatga attgtacaaa   1740
taa                                                                 1743
```

<210> SEQ ID NO 54
<211> LENGTH: 580
<212> TYPE: PRT
<213> ORGANISM: Artificial Sequence
<220> FEATURE:
<223> OTHER INFORMATION: GST-deltaN17Q48+6PRD-YPET AA

<400> SEQUENCE: 54

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Gln Gln Gln Gln Gln Gln Gln Gln Gln
225                 230                 235                 240

Gln Gln Gln Gln Gln Gln Gln Gln Gln Gln Gln Gln Gln Gln Gln Gln
                245                 250                 255

Gln Gln Gln Gln Gln Gln Gln Gln Gln Gln Gln Gln Gln Gln Gln Gln
            260                 265                 270

Gln Gln Gln Gln Gln Gln Pro Pro Pro Pro Pro Pro
        275                 280                 285

Pro Pro Pro Pro Pro Pro Pro Gln Leu Pro Gln Pro Pro Pro Gln
    290                 295                 300

Ala Gln Pro Leu Leu Pro Gln Leu Gln Pro Pro Pro Pro Pro Pro
305                 310                 315                 320

Pro Pro Pro Gly Pro Ala Ala Ala Glu Glu Pro Leu His Arg Pro Leu
                325                 330                 335
```

Glu Gly Gly Gly Gly Gly Met Ser Lys Gly Glu Leu Phe Thr Gly
                340                 345                 350

Val Val Pro Ile Leu Val Glu Leu Asp Gly Asp Val Asn Gly His Lys
            355                 360                 365

Phe Ser Val Ser Gly Glu Gly Glu Gly Asp Ala Thr Tyr Gly Lys Leu
        370                 375                 380

Thr Leu Lys Leu Leu Cys Thr Thr Gly Lys Leu Pro Val Pro Trp Pro
385                 390                 395                 400

Thr Leu Val Thr Thr Leu Gly Tyr Gly Val Gln Cys Phe Ala Arg Tyr
                405                 410                 415

Pro Asp His Met Lys Gln His Asp Phe Phe Lys Ser Ala Met Pro Glu
            420                 425                 430

Gly Tyr Val Gln Glu Arg Thr Ile Phe Phe Lys Asp Asp Gly Asn Tyr
        435                 440                 445

Lys Thr Arg Ala Glu Val Lys Phe Glu Gly Asp Thr Leu Val Asn Arg
    450                 455                 460

Ile Glu Leu Lys Gly Ile Asp Phe Lys Glu Asp Gly Asn Ile Leu Gly
465                 470                 475                 480

His Lys Leu Glu Tyr Asn Tyr Asn Ser His Asn Val Tyr Ile Thr Ala
                485                 490                 495

Asp Lys Gln Lys Asn Gly Ile Lys Ala Asn Phe Lys Ile Arg His Asn
            500                 505                 510

Ile Glu Asp Gly Gly Val Gln Leu Ala Asp His Tyr Gln Gln Asn Thr
        515                 520                 525

Pro Ile Gly Asp Gly Pro Val Leu Leu Pro Asp Asn His Tyr Leu Ser
    530                 535                 540

Tyr Gln Ser Ala Leu Phe Lys Asp Pro Asn Glu Lys Arg Asp His Met
545                 550                 555                 560

Val Leu Leu Glu Phe Leu Thr Ala Ala Gly Ile Thr Glu Gly Met Asn
                565                 570                 575

Glu Leu Tyr Lys
        580

<210> SEQ ID NO 55
<211> LENGTH: 1719
<212> TYPE: DNA
<213> ORGANISM: Artificial Sequence
<220> FEATURE:
<223> OTHER INFORMATION: GST-deltaN17Q40+6PRD-CYPET

<400> SEQUENCE: 55 atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atagctga caagcacaac      240 atgttgggtg ttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt tgtttttaaa     540
aaacgtattg aagctatccc acaaattgat aagtacttga atccagcaa gtatatagca     600 tggcctttgc agggctggca agccacgttt ggtggtggcg accatcctcc aaaatcggat     660

```
ctggaagttc tgttccaggg gcccctggga tcccagcagc agcaacaaca gcagcaacag    720
caacagcagc agcagcagca acaacagcag cagcaacagc aacaacaaca acaacagcag    780
caacaacagc aacagcagca acaacaacag caaccgcctc cgcctccgcc acctcctcca    840
ccaccaccgc cacctccgcc tccacagtta cctcagcctc cgcctcaggc acagccgctg    900
ctgccgcagt tacagcctcc tcctcccccct ccacctcctc cgccaggtcc tgcagcagca    960
gaagaaccgc tgcatcgtcc gctcgagggt ggcggtggcg gtatgtctaa aggtgaagaa   1020
ttattcggcg gtatcgtccc aattttagtt gaattagagg gtgatgttaa tggtcacaaa   1080
ttttctgtct ccggtgaagg tgaaggtgat gctacgtacg gtaaattgac cttaaaattt   1140
atttgtacta ctggtaaaatt gccagttcca tggccaacct tagtcactac tctgacttgg   1200
ggtgttcaat gttttctag ataccagat catatgaaac aacatgactt tttcaagtct   1260
gtcatgccag aaggttatgt tcaagaaaga actatttttt tcaaagatga cggtaactac   1320
aagaccagag ctgaagtcaa gtttgaaggt gataccttag ttaatagaat cgaattaaaa   1380
ggtattgatt ttaaagaaga tggtaacatt ttaggtcaca aattggaata caactatatc   1440
tctcacaatg tttacatcac cgctgacaaa caaaagaatg gtatcaaagc taacttcaaa   1500
gccagacaca acattaccga tggttctgtt caattagctg accattatca acaaaatact   1560
ccaattggtg atggtccagt catcttgcca gacaaccatt acttatccac tcaatctgcc   1620
ttatctaaag atccaaacga aaagagagac cacatggtct tgctcgaatt tgttactgct   1680
gctggtatta cccatggtat ggatgaattg tacaaataa                          1719
```

<210> SEQ ID NO 56  
<211> LENGTH: 572  
<212> TYPE: PRT  
<213> ORGANISM: Artificial Sequence  
<220> FEATURE:  
<223> OTHER INFORMATION: GST-deltaN17Q40+6PRD-CYPET AA

<400> SEQUENCE: 56

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Glu Val Leu
210                 215                 220

Phe Gln Gly Pro Leu Gly Ser Gln Gln Gln Gln Gln Gln Gln Gln Gln
225                 230                 235                 240

Gln Gln Gln Gln Gln Gln Gln Gln Gln Gln Gln Gln Gln Gln Gln Gln
            245                 250                 255

Gln Gln Gln Gln Gln Gln Gln Gln Gln Gln Gln Gln Gln Gln Gln Pro
            260                 265                 270

Pro Pro Pro Pro Pro Pro Pro Pro Pro Pro Pro Pro Pro Pro Pro Pro
            275                 280                 285

Gln Leu Pro Gln Pro Pro Pro Gln Ala Gln Pro Leu Leu Pro Gln Leu
            290                 295                 300

Gln Pro Pro Pro Pro Pro Pro Pro Pro Pro Gly Pro Ala Ala Ala
305                 310                 315                 320

Glu Glu Pro Leu His Arg Pro Leu Glu Gly Gly Gly Gly Met Ser
            325                 330                 335

Lys Gly Glu Glu Leu Phe Gly Gly Ile Val Pro Ile Leu Val Glu Leu
            340                 345                 350

Glu Gly Asp Val Asn Gly His Lys Phe Ser Val Ser Gly Glu Gly Glu
            355                 360                 365

Gly Asp Ala Thr Tyr Gly Lys Leu Thr Leu Lys Phe Ile Cys Thr Thr
370                 375                 380

Gly Lys Leu Pro Val Pro Trp Pro Thr Leu Val Thr Thr Leu Thr Trp
385                 390                 395                 400

Gly Val Gln Cys Phe Ser Arg Tyr Pro Asp His Met Lys Gln His Asp
                405                 410                 415

Phe Phe Lys Ser Val Met Pro Glu Gly Tyr Val Gln Glu Arg Thr Ile
                420                 425                 430

Phe Phe Lys Asp Asp Gly Asn Tyr Lys Thr Arg Ala Glu Val Lys Phe
                435                 440                 445

Glu Gly Asp Thr Leu Val Asn Arg Ile Glu Leu Lys Gly Ile Asp Phe
450                 455                 460

Lys Glu Asp Gly Asn Ile Leu Gly His Lys Leu Glu Tyr Asn Tyr Ile
465                 470                 475                 480

Ser His Asn Val Tyr Ile Thr Ala Asp Lys Gln Lys Asn Gly Ile Lys
                485                 490                 495

Ala Asn Phe Lys Ala Arg His Asn Ile Thr Asp Gly Ser Val Gln Leu
                500                 505                 510

Ala Asp His Tyr Gln Gln Asn Thr Pro Ile Gly Asp Gly Pro Val Ile
                515                 520                 525

Leu Pro Asp Asn His Tyr Leu Ser Thr Gln Ser Ala Leu Ser Lys Asp
            530                 535                 540

Pro Asn Glu Lys Arg Asp His Met Val Leu Leu Glu Phe Val Thr Ala
545                 550                 555                 560

Ala Gly Ile Thr His Gly Met Asp Glu Leu Tyr Lys
            565                 570

<210> SEQ ID NO 57
<211> LENGTH: 1719
```

<212> TYPE: DNA
<213> ORGANISM: Artificial Sequence
<220> FEATURE:
<223> OTHER INFORMATION: GST-deltaN17Q40+6PRD-YPET

<400> SEQUENCE: 57

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt tgttttttaaa    540
aaacgtattg aagctatccc acaaattgat aagtacttga atccagcaa gtatatagca    600
tggcctttgc agggctggca agccacgttt ggtggtggcg accatcctcc aaaatcggat    660
ctggaagttc tgttccaggg gcccctggga tcccagcagc agcaacaaca gcagcaacag    720
caacagcagc agcagcagca acaacagcag cagcaacagc aacaacaaca acaacagcag    780
caacaacagc aacagcagca acaacaacag caaccgcctc cgcctccgcc acctcctcca    840
ccaccaccgc cacctccgcc tccacagtta cctcagcctc cgcctcaggc acagccgctg    900
ctgccgcagt tacagcctcc tcctccccct ccacctcctc cgccaggtcc tgcagcagca    960
gaagaaccgc tgcatcgtcc gctcgagggt ggcggtggcg gtatgtctaa aggtgaagaa   1020
ttattcactg gtgttgtccc aattttggtt gaattagatg gtgatgttaa tggtcacaaa   1080
ttttctgtct ccggtgaagg tgaaggtgat gctacgtacg gtaaattgac cttaaaatta   1140
ctctgtacta ctggtaaatt gccagttcca tggccaacct tagtcactac tttaggttat   1200
ggtgttcaat gttttgctag atacccagat catatgaaac aacatgactt tttcaagtct   1260
gccatgccag aaggttatgt tcaagaaaga actatttttt tcaaagatga cggtaactac   1320
aagaccagag ctgaagtcaa gtttgaaggt gataccttag ttaatagaat cgaattaaaa   1380
ggtattgatt taaagaaga tggtaacatt ttaggtcaca aattggaata caactataac   1440
tctcacaatg tttacatcac tgctgacaaa caaaagaatg gtatcaaagc taacttcaaa   1500
attagacaca acattgaaga tggtggtgtt caattagctg accattatca acaaaatact   1560
ccaattggtg atggtccagt cttgttacca gacaaccatt acttatccta tcaatctgcc   1620
ttattcaaag atccaaacga aaagagagac cacatggtct tgttagaatt tttgactgct   1680
gctggtatta ccgagggtat gaatgaattg tacaaataa                         1719
```

<210> SEQ ID NO 58
<211> LENGTH: 572
<212> TYPE: PRT
<213> ORGANISM: Artificial Sequence
<220> FEATURE:
<223> OTHER INFORMATION: GST-deltaN17Q40+6PRD-YPET AA

<400> SEQUENCE: 58

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
```

```
                20                  25                  30
Tyr Glu Arg Asp Glu Gly Asp Lys Trp Arg Asn Lys Lys Phe Glu Leu
            35                  40                  45
Gly Leu Glu Phe Pro Asn Leu Pro Tyr Tyr Ile Asp Gly Asp Val Lys
        50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
        115                 120                 125
Met Leu Lys Met Phe Glu Asp Arg Leu Cys His Lys Thr Tyr Leu Asn
        130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
        195                 200                 205
Thr Phe Gly Gly Gly Asp His Pro Pro Lys Ser Asp Leu Glu Val Leu
        210                 215                 220
Phe Gln Gly Pro Leu Gly Ser Gln Gln Gln Gln Gln Gln Gln Gln Gln
225                 230                 235                 240
Gln Gln Gln Gln Gln Gln Gln Gln Gln Gln Gln Gln Gln Gln Gln Gln
                245                 250                 255
Gln Gln Gln Gln Gln Gln Gln Gln Gln Gln Gln Gln Gln Gln Gln Pro
            260                 265                 270
Pro Pro Pro Pro Pro Pro Pro Pro Pro Pro Pro Pro Pro Pro Pro Pro
        275                 280                 285
Gln Leu Pro Gln Pro Pro Pro Gln Ala Gln Pro Leu Leu Pro Gln Leu
        290                 295                 300
Gln Pro Pro Pro Pro Pro Pro Pro Pro Gly Pro Ala Ala Ala
305                 310                 315                 320
Glu Glu Pro Leu His Arg Pro Leu Glu Gly Gly Gly Gly Met Ser
                325                 330                 335
Lys Gly Glu Glu Leu Phe Thr Gly Val Val Pro Ile Leu Val Glu Leu
            340                 345                 350
Asp Gly Asp Val Asn Gly His Lys Phe Ser Val Ser Gly Glu Gly Glu
        355                 360                 365
Gly Asp Ala Thr Tyr Gly Lys Leu Thr Leu Lys Leu Leu Cys Thr Thr
        370                 375                 380
Gly Lys Leu Pro Val Pro Trp Pro Thr Leu Val Thr Thr Leu Gly Tyr
385                 390                 395                 400
Gly Val Gln Cys Phe Ala Arg Tyr Pro Asp His Met Lys Gln His Asp
                405                 410                 415
Phe Phe Lys Ser Ala Met Pro Glu Gly Tyr Val Gln Glu Arg Thr Ile
            420                 425                 430
Phe Phe Lys Asp Asp Gly Asn Tyr Lys Thr Arg Ala Glu Val Lys Phe
        435                 440                 445
```

-continued

```
Glu Gly Asp Thr Leu Val Asn Arg Ile Glu Leu Lys Gly Ile Asp Phe
    450                 455                 460

Lys Glu Asp Gly Asn Ile Leu Gly His Lys Leu Glu Tyr Asn Tyr Asn
465                 470                 475                 480

Ser His Asn Val Tyr Ile Thr Ala Asp Lys Gln Lys Asn Gly Ile Lys
                485                 490                 495

Ala Asn Phe Lys Ile Arg His Asn Ile Glu Asp Gly Gly Val Gln Leu
            500                 505                 510

Ala Asp His Tyr Gln Gln Asn Thr Pro Ile Gly Asp Gly Pro Val Leu
        515                 520                 525

Leu Pro Asp Asn His Tyr Leu Ser Tyr Gln Ser Ala Leu Phe Lys Asp
    530                 535                 540

Pro Asn Glu Lys Arg Asp His Met Val Leu Leu Glu Phe Leu Thr Ala
545                 550                 555                 560

Ala Gly Ile Thr Glu Gly Met Asn Glu Leu Tyr Lys
                565                 570
```

<210> SEQ ID NO 59
<211> LENGTH: 861
<212> TYPE: DNA
<213> ORGANISM: Artificial Sequence
<220> FEATURE:
<223> OTHER INFORMATION: GST-K2Q48P6

<400> SEQUENCE: 59

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagattcaa tgcttgaagg agcggttttg     300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca     600
tggcctttgc agggctggca agccacgttt ggtggtggcg accatcctcc aaaatcggat    660
ctggaagttc tgttccaggg gcccctggga tccaaaaaac agcagcagca acaacagcag    720
caacagcaac aacaacaaca gcagcagcaa cagcaacagc agcagcagca acaacaacag    780
caacaacagc aacagcagca acagcagcag cagcagcaac agcaacaaca gcagcaacag    840
cagcctccgc ctccgcctcc t                                               861
```

<210> SEQ ID NO 60
<211> LENGTH: 287
<212> TYPE: PRT
<213> ORGANISM: Artificial Sequence
<220> FEATURE:
<223> OTHER INFORMATION: GST-K2Q48P6 AA

<400> SEQUENCE: 60

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
```

```
                20                  25                  30
Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
             100                 105                 110

Lys Asp Phe Glu Thr Leu Lys Val Asp Phe Leu Ser Lys Leu Pro Glu
         115                 120                 125

Met Leu Lys Met Phe Glu Asp Arg Leu Cys His Lys Thr Tyr Leu Asn
 130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                 165                 170                 175

Val Cys Phe Lys Lys Arg Ile Glu Ala Ile Pro Gln Ile Asp Lys Tyr
             180                 185                 190

Leu Lys Ser Ser Lys Tyr Ile Ala Trp Pro Leu Gln Gly Trp Gln Ala
         195                 200                 205

Thr Phe Gly Gly Gly Asp His Pro Pro Lys Ser Asp Leu Glu Val Leu
 210                 215                 220

Phe Gln Gly Pro Leu Gly Ser Lys Lys Gln Gln Gln Gln Gln Gln Gln
225                 230                 235                 240

Gln Gln Gln Gln Gln Gln Gln Gln Gln Gln Gln Gln Gln Gln Gln Gln
                 245                 250                 255

Gln Gln Gln Gln Gln Gln Gln Gln Gln Gln Gln Gln Gln Gln Gln Gln
             260                 265                 270

Gln Gln Gln Gln Gln Gln Gln Gln Gln Pro Pro Pro Pro Pro
         275                 280                 285

<210> SEQ ID NO 61
<211> LENGTH: 1005
<212> TYPE: DNA
<213> ORGANISM: Artificial Sequence
<220> FEATURE:
<223> OTHER INFORMATION: GST-deltaN17Q48+6PRD

<400> SEQUENCE: 61 atgtcccta tactaggtta ttggaaaatt aagggccttg tgcaacccac tcgacttctt       60
ttggaatatc ttgaagaaaa atatgaagag catttgtatg agcgcgatga aggtgataaa      120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300 gatattgat acggtgtttc gagaattgca tatagtaaag actttgaaac tctcaaagtt      360
gattttctta gcaagctacc tgaaatgctg aaaatgttcg aagatcgttt atgtcataaa     420
acatatttaa atggtgatca tgtaacccat cctgacttca tgttgtatga cgctcttgat    480
gttgttttat acatggaccc aatgtgcctg gatgcgttcc caaaattagt tgttttaaa     540 aaacgtattg aagctatccc acaaattgat aagtacttga atccagcaa gtatatagca      600
```

```
tggcctttgc agggctggca agccacgttt ggtggtggcg accatcctcc aaaatcggat    660
ctggaagttc tgttccaggg gcccctggga tcccagcagc agcaacaaca gcagcaacag    720
caacagcagc agcagcagca acaacagcag cagcaacagc aacaacaaca acaacagcag    780
caacaacagc aacagcagca acagcaacag cagcaacaac aacagcaaca acagcagcct    840
ccgcctccgc cacctcctcc acctccgcct ccaccgccac cgcctcctca gttacctcag    900
cctcctccgc aggcacagcc gctgctgccg cagttacagc tccaccacc acctccgccg    960 cctccacctg gtcctgcagc agcagaagaa ccgctgcatc gtccg                   1005
```

<210> SEQ ID NO 62
<211> LENGTH: 335
<212> TYPE: PRT
<213> ORGANISM: Artificial Sequence
<220> FEATURE:
<223> OTHER INFORMATION: GST-deltaN17Q48+6PRD AA

<400> SEQUENCE: 62

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Gln Gln Gln Gln Gln Gln Gln Gln Gln
225                 230                 235                 240

Gln Gln Gln Gln Gln Gln Gln Gln Gln Gln Gln Gln Gln Gln Gln
                245                 250                 255

Gln Gln Gln Gln Gln Gln Gln Gln Gln Gln Gln Gln Gln Gln Gln
            260                 265                 270

Gln Gln Gln Gln Gln Gln Gln Pro Pro Pro Pro Pro Pro Pro Pro
        275                 280                 285
```

```
Pro Pro Pro Pro Pro Pro Pro Gln Leu Pro Gln Pro Pro Gln
    290             295             300

Ala Gln Pro Leu Leu Pro Gln Leu Gln Pro Pro Pro Pro Pro
305             310             315             320

Pro Pro Pro Gly Pro Ala Ala Ala Glu Glu Pro Leu His Arg Pro
            325             330             335
```

<210> SEQ ID NO 63
<211> LENGTH: 981
<212> TYPE: DNA
<213> ORGANISM: Artificial Sequence
<220> FEATURE:
<223> OTHER INFORMATION: GST-deltaN17Q40+6PRD

<400> SEQUENCE: 63

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg agtttcccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg atgcgttcc caaaattagt ttgttttaaa     540
aaacgtattg aagctatccc acaaattgat aagtacttga atccagcaa gtatatagca    600
tggccttttgc agggctggca agccacgttt ggtggtggcg accatcctcc aaaatcggat   660
ctggaagttc tgttccaggg gcccctggga tcccagcagc agcaacaaca gcagcaacag    720
caacagcagc agcagcagca acaacagcag cagcaacagc aacaacaaca acaacagcag    780
caacaacagc aacagcagca acaacaacag caaccgcctc cgcctccgcc acctcctcca    840
ccaccaccgc cacctccgcc tccacagtta cctcagcctc cgcctcaggc acagccgctg    900
ctgccgcagt tacagcctcc tcctccccct ccacctcctc cgccaggtcc tgcagcagca    960
gaagaaccgc tgcatcgtcc g                                              981
```

<210> SEQ ID NO 64
<211> LENGTH: 327
<212> TYPE: PRT
<213> ORGANISM: Artificial Sequence
<220> FEATURE:
<223> OTHER INFORMATION: GST-deltaN17Q40+6PRD AA

<400> SEQUENCE: 64

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
```

```
                85                  90                  95
Gly Ala Val Leu Asp Ile Arg Tyr Gly Val Ser Arg Ile Ala Tyr Ser
            100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
        130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Ser Asp Leu Glu Val Leu
        210                 215                 220
Phe Gln Gly Pro Leu Gly Ser Gln Gln Gln Gln Gln Gln Gln Gln Gln
225                 230                 235                 240
Gln Gln Gln Gln Gln Gln Gln Gln Gln Gln Gln Gln Gln Gln Gln Gln
                245                 250                 255
Gln Gln Gln Gln Gln Gln Gln Gln Gln Gln Gln Gln Gln Gln Gln Pro
            260                 265                 270
Pro Pro Pro Pro Pro Pro Pro Pro Pro Pro Pro Pro Pro Pro Pro Pro
        275                 280                 285
Gln Leu Pro Gln Pro Pro Pro Gln Ala Gln Pro Leu Leu Pro Gln Leu
    290                 295                 300
Gln Pro Pro Pro Pro Pro Pro Pro Pro Gly Pro Ala Ala Ala
305                 310                 315                 320
Glu Glu Pro Leu His Arg Pro
                325

<210> SEQ ID NO 65
<211> LENGTH: 301
<212> TYPE: PRT
<213> ORGANISM: Artificial Sequence
<220> FEATURE:
<223> OTHER INFORMATION: K2Q48P6-CYPET AA

<400> SEQUENCE: 65

Lys Lys Gln Gln Gln Gln Gln Gln Gln Gln Gln Gln Gln Gln Gln Gln
1               5                   10                  15
Gln Gln Gln Gln Gln Gln Gln Gln Gln Gln Gln Gln Gln Gln Gln Gln
                20                  25                  30
Gln Gln Gln Gln Gln Gln Gln Gln Gln Gln Gln Gln Gln Gln Gln Gln
            35                  40                  45
Gln Gln Pro Pro Pro Pro Pro Leu Glu Gly Gly Gly Gly Gly Gly Met
        50                  55                  60
Ser Lys Gly Glu Glu Leu Phe Gly Gly Ile Val Pro Ile Leu Val Glu
65                  70                  75                  80
Leu Glu Gly Asp Val Asn Gly His Lys Phe Ser Val Ser Gly Glu Gly
                85                  90                  95
Glu Gly Asp Ala Thr Tyr Gly Lys Leu Thr Leu Lys Phe Ile Cys Thr
            100                 105                 110
Thr Gly Lys Leu Pro Val Pro Trp Pro Thr Leu Val Thr Thr Leu Thr
```

```
            115                 120                 125
Trp Gly Val Gln Cys Phe Ser Arg Tyr Pro Asp His Met Lys Gln His
    130                 135                 140

Asp Phe Phe Lys Ser Val Met Pro Glu Gly Tyr Val Gln Glu Arg Thr
145                 150                 155                 160

Ile Phe Phe Lys Asp Asp Gly Asn Tyr Lys Thr Arg Ala Glu Val Lys
                165                 170                 175

Phe Glu Gly Asp Thr Leu Val Asn Arg Ile Glu Leu Lys Gly Ile Asp
            180                 185                 190

Phe Lys Glu Asp Gly Asn Ile Leu Gly His Lys Leu Glu Tyr Asn Tyr
        195                 200                 205

Ile Ser His Asn Val Tyr Ile Thr Ala Asp Lys Gln Lys Asn Gly Ile
    210                 215                 220

Lys Ala Asn Phe Lys Ala Arg His Asn Ile Thr Asp Gly Ser Val Gln
225                 230                 235                 240

Leu Ala Asp His Tyr Gln Gln Asn Thr Pro Ile Gly Asp Gly Pro Val
                245                 250                 255

Ile Leu Pro Asp Asn His Tyr Leu Ser Thr Gln Ser Ala Leu Ser Lys
            260                 265                 270

Asp Pro Asn Glu Lys Arg Asp His Met Val Leu Leu Glu Phe Val Thr
        275                 280                 285

Ala Ala Gly Ile Thr His Gly Met Asp Glu Leu Tyr Lys
    290                 295                 300

<210> SEQ ID NO 66
<211> LENGTH: 301
<212> TYPE: PRT
<213> ORGANISM: Artificial Sequence
<220> FEATURE:
<223> OTHER INFORMATION: K2Q48P6-YPET AA

<400> SEQUENCE: 66

Lys Lys Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Pro Pro Pro Pro Pro Leu Glu Gly Gly Gly Gly Met
    50                  55                  60

Ser Lys Gly Glu Glu Leu Phe Thr Gly Val Val Pro Ile Leu Val Glu
65                  70                  75                  80

Leu Asp Gly Asp Val Asn Gly His Lys Phe Ser Val Ser Gly Glu Gly
                85                  90                  95

Glu Gly Asp Ala Thr Tyr Gly Lys Leu Thr Leu Lys Leu Leu Cys Thr
            100                 105                 110

Thr Gly Lys Leu Pro Val Pro Trp Pro Thr Leu Val Thr Thr Leu Gly
        115                 120                 125

Tyr Gly Val Gln Cys Phe Ala Arg Tyr Pro Asp His Met Lys Gln His
    130                 135                 140

Asp Phe Phe Lys Ser Ala Met Pro Glu Gly Tyr Val Gln Glu Arg Thr
145                 150                 155                 160

Ile Phe Phe Lys Asp Asp Gly Asn Tyr Lys Thr Arg Ala Glu Val Lys
                165                 170                 175

Phe Glu Gly Asp Thr Leu Val Asn Arg Ile Glu Leu Lys Gly Ile Asp
```

```
                   180                 185                 190
Phe Lys Glu Asp Gly Asn Ile Leu Gly His Lys Leu Glu Tyr Asn Tyr
            195                 200                 205

Asn Ser His Asn Val Tyr Ile Thr Ala Asp Lys Gln Lys Asn Gly Ile
        210                 215                 220

Lys Ala Asn Phe Lys Ile Arg His Asn Ile Glu Asp Gly Gly Val Gln
225                 230                 235                 240

Leu Ala Asp His Tyr Gln Gln Asn Thr Pro Ile Gly Asp Gly Pro Val
                245                 250                 255

Leu Leu Pro Asp Asn His Tyr Leu Ser Tyr Gln Ser Ala Leu Phe Lys
            260                 265                 270

Asp Pro Asn Glu Lys Arg Asp His Met Val Leu Leu Glu Phe Leu Thr
        275                 280                 285

Ala Ala Gly Ile Thr Glu Gly Met Asn Glu Leu Tyr Lys
    290                 295                 300

<210> SEQ ID NO 67
<211> LENGTH: 349
<212> TYPE: PRT
<213> ORGANISM: Artificial Sequence
<220> FEATURE:
<223> OTHER INFORMATION: deltaN17Q48+6PRD-CYPET AA

<400> SEQUENCE: 67

Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Pro Pro Pro Pro Pro Pro Pro Pro Pro Pro Pro Pro Pro Pro Pro Pro
    50                  55                  60

Pro Gln Leu Pro Gln Pro Pro Pro Gln Ala Gln Pro Leu Leu Pro Gln
65                  70                  75                  80

Leu Gln Pro Pro Pro Pro Pro Pro Pro Pro Pro Gly Pro Ala Ala
                85                  90                  95

Ala Glu Glu Pro Leu His Arg Pro Leu Glu Gly Gly Gly Gly Met
            100                 105                 110

Ser Lys Gly Glu Glu Leu Phe Gly Gly Ile Val Pro Ile Leu Val Glu
        115                 120                 125

Leu Glu Gly Asp Val Asn Gly His Lys Phe Ser Val Ser Gly Glu Gly
    130                 135                 140

Glu Gly Asp Ala Thr Tyr Gly Lys Leu Thr Leu Lys Phe Ile Cys Thr
145                 150                 155                 160

Thr Gly Lys Leu Pro Val Pro Trp Pro Thr Leu Val Thr Thr Leu Thr
                165                 170                 175

Trp Gly Val Gln Cys Phe Ser Arg Tyr Pro Asp His Met Lys Gln His
            180                 185                 190

Asp Phe Phe Lys Ser Val Met Pro Glu Gly Tyr Val Gln Glu Arg Thr
        195                 200                 205

Ile Phe Phe Lys Asp Asp Gly Asn Tyr Lys Thr Arg Ala Glu Val Lys
    210                 215                 220

Phe Glu Gly Asp Thr Leu Val Asn Arg Ile Glu Leu Lys Gly Ile Asp
225                 230                 235                 240

Phe Lys Glu Asp Gly Asn Ile Leu Gly His Lys Leu Glu Tyr Asn Tyr
```

```
                        245                 250                 255

Ile Ser His Asn Val Tyr Ile Thr Ala Asp Lys Gln Lys Asn Gly Ile
                260                 265                 270

Lys Ala Asn Phe Lys Ala Arg His Asn Ile Thr Asp Gly Ser Val Gln
            275                 280                 285

Leu Ala Asp His Tyr Gln Gln Asn Thr Pro Ile Gly Asp Gly Pro Val
        290                 295                 300

Ile Leu Pro Asp Asn His Tyr Leu Ser Thr Gln Ser Ala Leu Ser Lys
305                 310                 315                 320

Asp Pro Asn Glu Lys Arg Asp His Met Val Leu Leu Glu Phe Val Thr
                325                 330                 335

Ala Ala Gly Ile Thr His Gly Met Asp Glu Leu Tyr Lys
            340                 345

<210> SEQ ID NO 68
<211> LENGTH: 349
<212> TYPE: PRT
<213> ORGANISM: Artificial Sequence
<220> FEATURE:
<223> OTHER INFORMATION: deltaN17Q48+6PRD-YPET AA

<400> SEQUENCE: 68

Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
                20                  25                  30

Gln Gln Gln Gln Gln Gln Gln Gln Gln Gln Gln Gln Gln Gln Gln Gln
            35                  40                  45

Pro Pro Pro Pro Pro Pro Pro Pro Pro Pro Pro Pro Pro Pro Pro Pro
        50                  55                  60

Pro Gln Leu Pro Gln Pro Pro Gln Ala Gln Pro Leu Leu Pro Gln
65                  70                  75                  80

Leu Gln Pro Pro Pro Pro Pro Pro Pro Pro Gly Pro Ala Ala
                85                  90                  95

Ala Glu Glu Pro Leu His Arg Pro Leu Glu Gly Gly Gly Gly Met
                100                 105                 110

Ser Lys Gly Glu Glu Leu Phe Thr Gly Val Val Pro Ile Leu Val Glu
            115                 120                 125

Leu Asp Gly Asp Val Asn Gly His Lys Phe Ser Val Ser Gly Glu Gly
        130                 135                 140

Glu Gly Asp Ala Thr Tyr Gly Lys Leu Thr Leu Lys Leu Leu Cys Thr
145                 150                 155                 160

Thr Gly Lys Leu Pro Val Pro Trp Pro Thr Leu Val Thr Thr Leu Gly
                165                 170                 175

Tyr Gly Val Gln Cys Phe Ala Arg Tyr Pro Asp His Met Lys Gln His
            180                 185                 190

Asp Phe Phe Lys Ser Ala Met Pro Glu Gly Tyr Val Gln Glu Arg Thr
        195                 200                 205

Ile Phe Phe Lys Asp Asp Gly Asn Tyr Lys Thr Arg Ala Glu Val Lys
    210                 215                 220

Phe Glu Gly Asp Thr Leu Val Asn Arg Ile Glu Leu Lys Gly Ile Asp
225                 230                 235                 240

Phe Lys Glu Asp Gly Asn Ile Leu Gly His Lys Leu Glu Tyr Asn Tyr
                245                 250                 255

Asn Ser His Asn Val Tyr Ile Thr Ala Asp Lys Gln Lys Asn Gly Ile
```

-continued

```
                260                 265                 270
Lys Ala Asn Phe Lys Ile Arg His Asn Ile Glu Asp Gly Gly Val Gln
            275                 280                 285

Leu Ala Asp His Tyr Gln Gln Asn Thr Pro Ile Gly Asp Gly Pro Val
        290                 295                 300

Leu Leu Pro Asp Asn His Tyr Leu Ser Tyr Gln Ser Ala Leu Phe Lys
305                 310                 315                 320

Asp Pro Asn Glu Lys Arg Asp His Met Val Leu Leu Glu Phe Leu Thr
                325                 330                 335

Ala Ala Gly Ile Thr Glu Gly Met Asn Glu Leu Tyr Lys
            340                 345

<210> SEQ ID NO 69
<211> LENGTH: 341
<212> TYPE: PRT
<213> ORGANISM: Artificial Sequence
<220> FEATURE:
<223> OTHER INFORMATION: deltaN17Q40+6PRD-CYPET AA

<400> SEQUENCE: 69

Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln Gln Pro Pro Pro Pro Pro Pro Pro Pro Pro
        35                  40                  45

Pro Pro Pro Pro Pro Pro Pro Pro Gln Leu Pro Gln Pro Pro Pro Pro
50                  55                  60

Gln Ala Gln Pro Leu Leu Pro Gln Leu Gln Pro Pro Pro Pro Pro Pro
65                  70                  75                  80

Pro Pro Pro Pro Gly Pro Ala Ala Ala Glu Glu Pro Leu His Arg Pro
                85                  90                  95

Leu Glu Gly Gly Gly Gly Met Ser Lys Gly Glu Glu Leu Phe Gly
            100                 105                 110

Gly Ile Val Pro Ile Leu Val Glu Leu Glu Gly Asp Val Asn Gly His
        115                 120                 125

Lys Phe Ser Val Ser Gly Glu Gly Glu Gly Asp Ala Thr Tyr Gly Lys
    130                 135                 140

Leu Thr Leu Lys Phe Ile Cys Thr Thr Gly Lys Leu Pro Val Pro Trp
145                 150                 155                 160

Pro Thr Leu Val Thr Thr Leu Thr Trp Gly Val Gln Cys Phe Ser Arg
                165                 170                 175

Tyr Pro Asp His Met Lys Gln His Asp Phe Phe Lys Ser Val Met Pro
            180                 185                 190

Glu Gly Tyr Val Gln Glu Arg Thr Ile Phe Phe Lys Asp Asp Gly Asn
        195                 200                 205

Tyr Lys Thr Arg Ala Glu Val Lys Phe Glu Gly Asp Thr Leu Val Asn
    210                 215                 220

Arg Ile Glu Leu Lys Gly Ile Asp Phe Lys Glu Asp Gly Asn Ile Leu
225                 230                 235                 240

Gly His Lys Leu Glu Tyr Asn Tyr Ile Ser His Asn Val Tyr Ile Thr
                245                 250                 255

Ala Asp Lys Gln Lys Asn Gly Ile Lys Ala Asn Phe Lys Ala Arg His
            260                 265                 270

Asn Ile Thr Asp Gly Ser Val Gln Leu Ala Asp His Tyr Gln Gln Asn
```

```
                    275                 280                 285
Thr Pro Ile Gly Asp Gly Pro Val Ile Leu Pro Asp Asn His Tyr Leu
        290                 295                 300

Ser Thr Gln Ser Ala Leu Ser Lys Asp Pro Asn Glu Lys Arg Asp His
305                 310                 315                 320

Met Val Leu Leu Glu Phe Val Thr Ala Ala Gly Ile Thr His Gly Met
                325                 330                 335

Asp Glu Leu Tyr Lys
            340

<210> SEQ ID NO 70
<211> LENGTH: 341
<212> TYPE: PRT
<213> ORGANISM: Artificial Sequence
<220> FEATURE:
<223> OTHER INFORMATION: deltaN17Q40+6PRD-YPET AA

<400> SEQUENCE: 70

Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
                20                  25                  30

Gln Gln Gln Gln Gln Gln Gln Pro Pro Pro Pro Pro Pro Pro Pro Pro
            35                  40                  45

Pro Pro Pro Pro Pro Pro Pro Pro Gln Leu Pro Gln Pro Pro Pro Pro
50                  55                  60

Gln Ala Gln Pro Leu Leu Pro Gln Leu Gln Pro Pro Pro Pro Pro Pro
65                  70                  75                  80

Pro Pro Pro Pro Gly Pro Ala Ala Ala Glu Glu Pro Leu His Arg Pro
                85                  90                  95

Leu Glu Gly Gly Gly Gly Met Ser Lys Gly Glu Glu Leu Phe Thr
            100                 105                 110

Gly Val Val Pro Ile Leu Val Glu Leu Asp Gly Asp Val Asn Gly His
                115                 120                 125

Lys Phe Ser Val Ser Gly Glu Gly Glu Gly Asp Ala Thr Tyr Gly Lys
            130                 135                 140

Leu Thr Leu Lys Leu Leu Cys Thr Thr Gly Lys Leu Pro Val Pro Trp
145                 150                 155                 160

Pro Thr Leu Val Thr Thr Leu Gly Tyr Gly Val Gln Cys Phe Ala Arg
                165                 170                 175

Tyr Pro Asp His Met Lys Gln His Asp Phe Phe Lys Ser Ala Met Pro
            180                 185                 190

Glu Gly Tyr Val Gln Glu Arg Thr Ile Phe Phe Lys Asp Asp Gly Asn
        195                 200                 205

Tyr Lys Thr Arg Ala Glu Val Lys Phe Glu Gly Asp Thr Leu Val Asn
    210                 215                 220

Arg Ile Glu Leu Lys Gly Ile Asp Phe Lys Glu Asp Gly Asn Ile Leu
225                 230                 235                 240

Gly His Lys Leu Glu Tyr Asn Tyr Asn Ser His Asn Val Tyr Ile Thr
                245                 250                 255

Ala Asp Lys Gln Lys Asn Gly Ile Lys Ala Asn Phe Lys Ile Arg His
            260                 265                 270

Asn Ile Glu Asp Gly Gly Val Gln Leu Ala Asp His Tyr Gln Gln Asn
        275                 280                 285

Thr Pro Ile Gly Asp Gly Pro Val Leu Leu Pro Asp Asn His Tyr Leu
```

```
                290                 295                 300
Ser Tyr Gln Ser Ala Leu Phe Lys Asp Pro Asn Glu Lys Arg Asp His
305                 310                 315                 320

Met Val Leu Leu Glu Phe Leu Thr Ala Ala Gly Ile Thr Glu Gly Met
                325                 330                 335

Asn Glu Leu Tyr Lys
            340

<210> SEQ ID NO 71
<211> LENGTH: 56
<212> TYPE: PRT
<213> ORGANISM: Artificial Sequence
<220> FEATURE:
<223> OTHER INFORMATION: K2Q48P6 AA

<400> SEQUENCE: 71

Lys Lys Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln
        35                  40                  45

Gln Gln Pro Pro Pro Pro Pro Pro
    50                  55

<210> SEQ ID NO 72
<211> LENGTH: 104
<212> TYPE: PRT
<213> ORGANISM: Artificial Sequence
<220> FEATURE:
<223> OTHER INFORMATION: deltaN17Q48+6PRD AA

<400> SEQUENCE: 72

Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln
        35                  40                  45

Pro Pro Pro Pro Pro Pro Pro Pro Pro Pro Pro Pro Pro Pro Pro Pro
    50                  55                  60

Pro Gln Leu Pro Gln Pro Pro Gln Ala Gln Pro Leu Leu Pro Gln
65                  70                  75                  80

Leu Gln Pro Pro Pro Pro Pro Pro Pro Pro Gly Pro Ala Ala
                85                  90                  95

Ala Glu Glu Pro Leu His Arg Pro
            100

<210> SEQ ID NO 73
<211> LENGTH: 96
<212> TYPE: PRT
<213> ORGANISM: Artificial Sequence
<220> FEATURE:
<223> OTHER INFORMATION: deltaN17Q40+6PRD AA

<400> SEQUENCE: 73

Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln
            20                  25                  30
```

```
Gln Gln Gln Gln Gln Gln Gln Gln Pro Pro Pro Pro Pro Pro Pro Pro
            35                  40                  45

Pro Pro Pro Pro Pro Pro Pro Pro Gln Leu Pro Gln Pro Pro Pro
 50                  55                  60

Gln Ala Gln Pro Leu Leu Pro Gln Leu Gln Pro Pro Pro Pro Pro
65               70                  75                  80

Pro Pro Pro Pro Gly Pro Ala Ala Ala Glu Glu Pro Leu His Arg Pro
                85                  90                  95
```